United States Patent [19]
Heck et al.

[11] Patent Number: 5,985,844
[45] Date of Patent: Nov. 16, 1999

[54] HOMOERYTHROMYCIN A DERIVATIVES MODIFIED AT THE 4"-AND 8A-POSITIONS

[75] Inventors: James V. Heck, Scotch Plains; William J. Leanza, Berkeley Heights; Ronald W. Ratcliffe, Matawan; Thomas N. Salzmann, North Plainfield; Kothandaraman Shankaran, Edison; Michael J. Szymonifka, Clark; Robert R. Wilkening, Maplewood, all of N.J.

[73] Assignee: Merck & Co., Inc., Rahway, N.J.

[21] Appl. No.: 07/855,242

[22] Filed: Mar. 26, 1992

[51] Int. Cl.[6] .................................................. C07H 17/08
[52] U.S. Cl. ............................... 514/29; 536/4.2; 536/7.4
[58] Field of Search .......................... 536/7.2, 7.4; 514/29

[56] References Cited

U.S. PATENT DOCUMENTS

| | | |
|---|---|---|
| 3,869,444 | 3/1975 | Freiberg . |
| 3,979,511 | 9/1976 | Hung et al. . |
| 4,152,424 | 5/1979 | Kierstead et al. . |
| 4,328,334 | 5/1982 | Kobrehel et al. ................ 536/7.4 |
| 4,349,545 | 9/1982 | Gouin d'Ambrieres et al. . |
| 4,464,527 | 8/1984 | Bright ............................... 536/7.4 |
| 4,465,674 | 8/1984 | Bright et al. . |
| 4,474,768 | 10/1984 | Bright ............................... 536/7.4 |
| 4,492,688 | 1/1985 | Bright ............................... 536/7.4 |
| 4,512,982 | 4/1985 | Hauske et al. . |
| 4,517,359 | 5/1985 | Kobrehel et al. . |
| 4,518,590 | 5/1985 | Hauske et al. . |
| 4,526,889 | 7/1985 | Bright . |
| 4,680,386 | 7/1987 | Morimoto et al. . |
| 4,886,792 | 12/1989 | Djokic . |
| 4,921,839 | 5/1990 | Brain et al. . |
| 4,957,905 | 9/1990 | Hunt et al. . |
| 4,990,602 | 2/1991 | Morimoto . |

FOREIGN PATENT DOCUMENTS

| | | |
|---|---|---|
| 0 101 186 | 2/1984 | European Pat. Off. . |
| 0 109 253 | 5/1984 | European Pat. Off. . |
| 0 109 253 A3 | 5/1984 | European Pat. Off. . |
| 0 136 831 | 4/1985 | European Pat. Off. . |
| 0 259 789 | 3/1986 | European Pat. Off. . |
| 0 316 128 | 3/1988 | European Pat. Off. . |
| 0 283 055 | 9/1988 | European Pat. Off. . |
| 0 307 128 | 5/1989 | European Pat. Off. . |
| 0 298 650 | 11/1989 | European Pat. Off. . |
| 0 34 990 | 11/1989 | European Pat. Off. . |

OTHER PUBLICATIONS

Djokic, et al., Erythromycin Series 12; Antibacterial in Vitro Evaluation of 10–Dehydro–11–deoxo–11–azaerythromycin A, Journal of Antibiotics, vol. 40, No. 7, (Jul. 1987) (Cumulative).

Djokic, et al., Erythromycin Series Part II; Ring Expansion of Erythromycin A Oxime by the Beckman Rearrangement. J. Chem. Soc. Perkins Trans.1, pp. 1881–1890 (1986) (Cumulative).

Djokic, et al., Erythromycin Series Part 13; Synthesis and Structure Elucidation of 10–Dihydro–1–Deoxo–11–methyl–11–aza erythromycin A, J. Chem. Research (S), pp. 152–153 (1988) (Cumulative).

Bright, et al., Synthesis, In Vitro And In Vivo Activity of Novel 9–Deoxo–9a–Aza–9a–Homoerythromycin A Derivatives, The Journal of Antibiotics, vol. 61, No. 8, pp. 1029–1047 (1988) (Cumulative).

Massey, et al., Erythromycylamine, Tetrahedron Letters, No. 2, pp. 157–160 (1970) (Cumulative).

Gasc et al., New Ether Oxime Derivatives of Erythromycin A, The Journal of Antibiotics, vol. 44, No. 3, pp. 313–329 (1990) (Cumulative).

Thornsberry, et al., The Macrolide Revival: 35 Years After Erythromycin, Antimicrobic Newsletter, vol. 4, No. 4, pp. 25–36 (1987) (Cumulative).

Egan, et al., Configuration of 9–Imino Derivatives of Erythromycin, J. Org. Chem., vol. 39, pp. 2492–2494, (1974) (Cumulative).

Ser. No. 07/856,267, Mar. 27, 1992, Wilkening.
Ser. No. 07/859,263, Apr. 2, 1992, Wilkening.

Puar, et al., SCH 23831, a Novel macrolide from Micromonospora rosaria, Tetrahedron Letters No. 30, pp. 2767–2770 (1979).

*Primary Examiner*—Marian C. Knode
*Attorney, Agent, or Firm*—Richard C. Billups; David L. Rose

[57] ABSTRACT

Compounds of the formula:

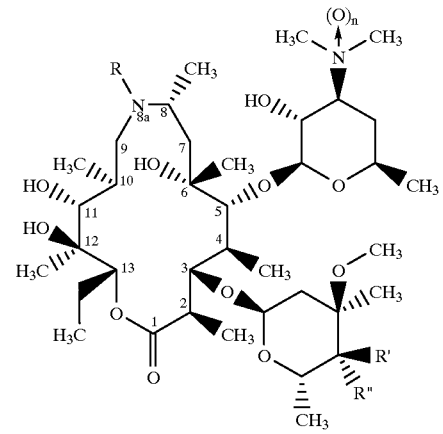

where R is hydrogen, hydroxyl, alkyl or acyl, R' and R" together are oxo, hydroxyimino or alkoxyimino, and R' and R" independently are hydrogen, hydroxyl, acyloxy, or amino substituted by any of hydrogen, alkylcarbonyl, arylcarbonyl, aralkylcarbonyl, alkoxycarbonyl, aralkoxycarbonyl, alkylsulfonyl or arylsulfonyl, and n is 0 or 1, and the pharmaceutically acceptable salts thereof. The compounds are macrolide antibiotics and are also useful as intermediates to the synthesis of other macrolide antibiotics. Pharmaceutical compositions and methods of their use are also provided for.

49 Claims, No Drawings

HOMOERYTHROMYCIN A DERIVATIVES MODIFIED AT THE 4"-AND 8A-POSITIONS

BACKGROUND OF THE INVENTION

The present invention relates to a novel group of chemical compounds having antibacterial activity, which are useful in the therapy of bacterial infections in mammals. More specifically, the invention relates to derivatives of the well-known macrolide antibiotic, erythromycin A, the compound of the structure:

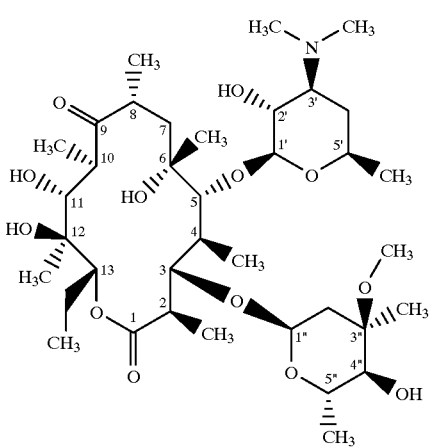

(I)

Even more specifically, the invention relates to the compounds of the structure:

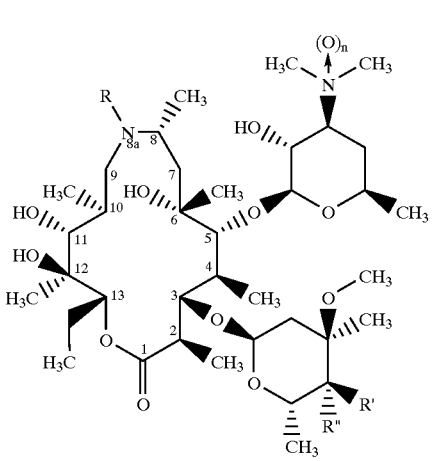

(II)

wherein R is hydrogen, hydroxyl, alkyl or acyl and n is 0 or 1, R' and R" together are oxo, hydroxyimino or alkoxyimimo, and R' and R" independently are hydrogen, hydroxyl, acyloxy, or amino substituted by any of hydrogen, alkycarbonyl, arylcarbonyl, aralkylcarbonyl, alkoxycarbonyl aralkoxycarbonyl, alkylsulfonyl or arylsulfonyl.

The present invention also provides for novel pharmaceutical compositions and methods of their use as antibiotic agents.

SUMMARY OF THE INVENTION

The present invention relates to novel compounds that are macrolides of the following structure:

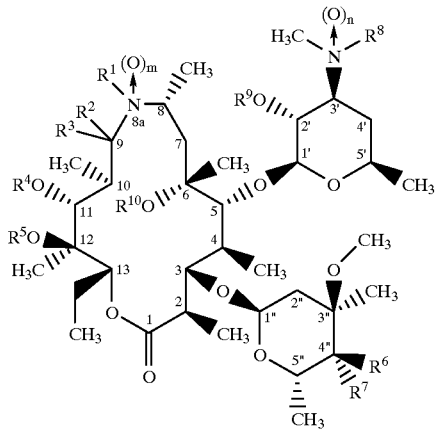

(III)

and the pharmaceutically acceptable salts and esters thereof, and the pharmaceutically acceptable metal complexes thereof, wherein R1 is hydrogen;

hydroxy;

$C_{1-4}$ alkoxy;

formyl;

$C_{1-10}$ alkylcarbonyl, $C_{1-10}$ alkoxycarbonyl, aryloxycarbonyl, $C_{1-10}$ aralkoxycarbonyl, $C_{1-10}$ alkylsulfonyl, or arylsulfonyl wherein said $C_{1-10}$ alkyl group or aryl group is unsubstituted or substituted by 1–3 halo (F, Cl, Br), hydroxy, amino, $C_{1-5}$ acylamino or $C_{1-4}$ alkyl groups; or unsubstituted or substituted $C_{1-10}$ alkyl, $C_{2-10}$ alkenyl or $C_{2-10}$ alkynyl wherein said substituents are independently 1–3 of (a) aryl or heteroaryl optionally substituted by 1–3 halo (F, Cl, Br, I), $C_{1-4}$ alkyl, $C_{1-3}$ alkoxy, amino, $C_{1-4}$ alkylamino, di($C_{1-4}$ alkyl) amino or hydroxy, (b) heterocyclyl optionally substituted by hydroxy, amino, $C_{1-4}$ alkylamino, di($C_{1-4}$ alkyl)amino, $C_{1-4}$ alkylcarbonyloxy or $C_{1-4}$ alkylcarbonylamino, (c) halo (F, Cl, Br or I), (d) hydroxy optionally acylated by a group

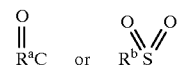

wherein $R^a$ is hydrogen, $C_{1-6}$ alkyl, aryl, heteroaryl, aralkyl, or heteroaralkyl and $R^b$ is $C_{1-6}$ alkyl or aryl, (e) $C_{1-10}$ alkoxy, (f) aryloxy or heteroaryloxy optionally substituted by 1–3 halo, hydroxy, amino or $C_{1-4}$ alkyl groups, (g) amino or $C_{1-10}$ alkylamino optionally acylated by a group

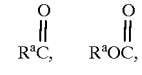

or $R^bSO_2$, (h) di($C_{1-10}$ alkyl)amino, (i) arylamino, heteroarylamino, aralkylamino or heteroaryl-alkylamino wherein said aryl or heteroaryl group is optionally substituted by 1–3 halo, hydroxy, amino or $C_{1-4}$ alkyl groups, (j) mercapto,
(k) $C_{1-10}$ alkylthio, alkylsulfinyl or alkylsulfonyl, arylthio, arylsulfinyl or arylsulfonyl wherein said aryl group is optionally substituted by 1–3 halo, hydroxy, amino or $C_{1-4}$ alkyl groups,
(l) formyl,
(m) $C_{1-10}$ alkylcarbonyl,
(n) arylcarbonyl, heteroarylcarbonyl, aralkylcarbonyl or heteroarylalkylcarbonyl wherein said aryl or heteroaryl group is optionally substituted by 1–3 halo, hydroxy, amino or $C_{1-4}$ alkyl groups,
(o) carboxy,
(p) $C_{1-10}$ alkoxycarbonyl,
(q) aryloxycarbonyl, heteroaryloxycarbonyl, aralkoxycarbonyl or heteroarylalkoxycarbonyl wherein said aryl or heteroaryl group is optionally substituted by 1–3 halo, hydroxy, amino or $C_{1-4}$ alkyl groups,
(r) carbamoyl or sulfamoyl wherein the N-atom is optionally substituted by 1–2 $C_{1-6}$ alkyl groups or by a $C_{4-6}$ alkylene chain,
(s) cyano,
(t) isonitrilo
(u) nitro,
(v) azido,
(w) iminomethyl optionally substituted on nitrogen or carbon with $C_{1-10}$ alkyl,
(x) oxo or
(y) thiono;
wherein said alkyl chain, if more than two carbons in length, can be optionally interrupted by 1–2 oxa, thia or aza (—NR— wherein R is hydrogen or $C_{1-3}$ alkyl) groups.

$R^1$ and $R^{10}$ together are $C_1$–$C_3$ alkylene optionally substituted by an oxo group;
$R^1$ and $R^4$ together are $C_1$–$C_3$ alkylene optionally substituted by an oxo group
$R^2$ and $R^3$ are hydrogen, $C_{1-10}$ alkyl, aryl
$R^2$ and $R^3$ together are oxo and thiono;
$R^4$ and $R^5$ are independently hydrogen and alkylcarbonyl;
$R^4$ and $R^5$ are together carbonyl
$R^6$ and $R^7$ are both hydrogen or one of $R^6$ and $R^7$ is hydrogen and the other is hydroxy, or a series of acyloxy derivatives including, but not limited to, formyloxy, $C_{1-10}$ alkylcarbonyloxy, arylcarbonyloxy and aralkylcarbonyloxy, and —NHR$^{12}$ wherein R$^{12}$ is hydrogen, arylsulfonyl or heteroarylsulfonyl optionally substituted by 1–3 halo or $C_{1-3}$ alkyl groups, alkylsulfonyl, or

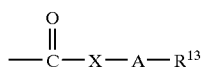

where X is a connecting bond, O or NH, A is a connecting bond or $C_1$–$C_3$ alkylene R$^{13}$ is hydrogen, $C_1$–$C_{10}$ alkyl, aryl, aralkyl, heteroaryl, heterocyclyl, or $C_3$–$C_7$ cycloalkyl, any of which R$^{13}$ groups other than hydrogen can be substituted by one or more of halogen, hydroxyl, $C_1$–$C_3$ alkoxy, cyano, isonitrilo, nitro, amino, mono- or di- ($C_1$–$C_3$) alkylamino, mercapto, $C_1$–$C_3$ alkylthio, $C_1$–$C_3$ alkylsulfinyl, $C_1$–$C_3$ alkylsulfonyl, arylthio, arylsulfinyl, sulfamoyl, arylsulfonyl, carboxy, carbamoyl, $C_1$–$C_3$ alkylcarbonyl, or $C_1$–$C_3$ alkoxycarbonyl;
$R^6$ and $R^7$ are together oxo, hydroxyimino, alkoxyimino, aralkoxyimino or aminoimino;
$R^8$ is methyl, aralkoxycarbonyl, and arylsulfonyl;
$R^9$ is hydrogen, formyl, $C_{1-10}$ alkylcarbonyl, $C_{1-10}$ alkoxycarbonyl, and arylalkoxycarbonyl;

m and n are independently integers of zero or one; and said metal complex is taken from the group consisting of
copper,
zinc,
cobalt,
nickel and
cadmium.

A preferred group of compounds is that of the following formula

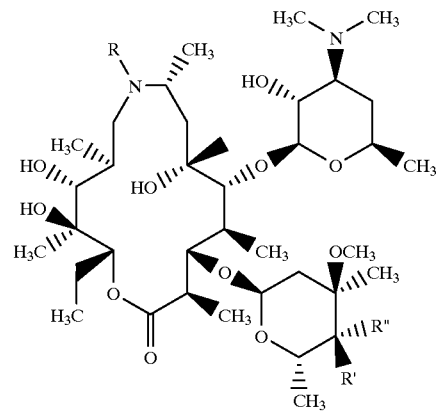

wherein R is hydrogen, substituted or unsubstituted $C_{1-10}$ alkyl, $C_{2-10}$ alkenyl, or arylsulfonyl, and R' and R" together are oxo or hydroxyimino, or one of R' and R" is hydrogen and the other is selected from hydroxyl, aralkylcarbonyloxy, amino, or amino substituted by any of $C_1$–$C_{10}$ alkylcarbonyl, arylcarbonyl, aryl $C_1$–$C_{10}$ alkylcarbonyl, $C_1$–$C_{10}$ alkoxycarbonyl, aryl $C_1$–$C_{10}$ alkoxycarbonyl, heteroarylcarbonyl, heteroarylalkylcarbonyl or arylsulfonyl and the pharmaceutically acceptable salts and esters thereof.

A more preferred group of definitions for R in the structural Formula above is $CH_3$, $CH_3CH_2$, $CH_3CH_2CH_2$, $(CH_3)_2CH$, $CH_2=CHCH_2$, $CH\equiv CCH_2$, $HOCH_2CH_2$, $HOCH_2CH_2CH_2$, $CH_3O_2CCH_2CH_2$, $C_6H_5CH_2O_2CCH_2CH_2$, $NCCH_2$, $H_2NCH_2CH_2$, $(CH_3)_2NCH_2CH_2$, $FCH_2CH_2$, $CH_2=CFCH_2$, $C_6H_5CH_2$, and

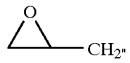

Salt forms are generally prepared as acid addition salts by combining the compound of formula II with one to three equivalents of an appropriate acid in an inert solvent. The salt is then recovered by solvent evaporation or by filtration if the salt precipitates spontaneously, or by precipitation using a co-solvent or a non-polar co-solvent followed by filtration.

Representative salts and esters include the following salts:
Acetate
Benzenesulfonate
Benzoate
Bicarbonate
Bisulfate
Bitartrate
Borate
Bromide
Calcium Edetate
Camsylate
Carbonate Chloride
Clavulanate
Citrate
Dihydrochloride
Edetate
Edisylate
Estolate
Esylate
Ethylsuccinate
Fumarate
Gluceptate
Gluconate
Glutamate
Glycollylarsanilate
Hexylresorcinate
Hydrabamine
Hydrobromide
Hydrochloride
Iodide
Isothionate
Lactate
Lactobionate
Laurate
Malate
Maleate
Mandelate
Mesylate
Methylsulfate
Mucate
Napsylate
Nitrate
Oleate
Oxalate
Pamoate (Embonate)
Palmitate
Pantothenate
Phosphate/diphosphate
Polygalacturonate
Salicylate
Stearate
Subacetate
Succinate
Tannate
Tartrate
Teoclate
Tosylate
Triethiodode
Valerate

DETAILED DESCRIPTION OF THE INVENTION

The term "pharmacologically effective amount" shall mean that amount of a drug or pharmaceutical agent that will elicit the biological or medical response of a tissue, system or animal that is being sought by a researcher or clinician.

The term "antibiotically effective amount" shall mean that amount of an antibiotic compound that will achieve a level of antibacterial activity at the site of infection that is sufficient to inhibit the bacteria in a manner that allows the host organism to overcome the infection.

The term "alkyl" shall mean cyclic or linear straight or branched chain alkane of one to ten carbon atoms unless some specific number is given. The term "alkenyl" shall mean cyclic, linear straight, or branched chain alkane of two to ten carbon atoms with one or more double bonds. The term "alkynyl" shall mean linear straight or branched chain alkane of two to ten carbon atoms with one or more triple bonds.

The term aryl shall include phenyl and napthyl.

The term heteroaryl shall mean mono- or bicyclic unsaturated cyclic structures of 5–12 ring members having one to four heteroatoms which can be O, N or S.

The term heterocyclyl shall mean saturated cyclic structures of 3–7 ring members having one to three heteroatoms which can be O, N or S.

Whenever the terms "alkyl" or "aryl" or either of their prefix roots appear in a name of a substituent (e.g. aralkoxy) they shall be interpreted as including those limitations given above for "alkyl" and "aryl". Designated numbers of carbon atoms (e.g. $C_1$–$C_{10}$ or $C_{3-10}$) shall refer independently to the number of carbon atoms in an alkyl or cyclic alkyl moiety or to the alkyl portion of a larger substituent in which alkyl appears as its prefix root.

The term "substituted" shall be deemed to include multiple degrees of substitution by a named substituent.

Where multiple substituent moieties are disclosed or claimed the substituted compound can be independently substituted by one or more of the disclosed or claimed substituent moieties, singly or plurally.

The compounds of formula II can be prepared readily according to the following detailed descriptions and examples or modifications thereof using readily available starting materials, reagents and conventional synthesis procedures. The overall process is illustrated in the following flow sheets wherein the alkylation steps leading to (X) and (XII) are described. In these reactions, it is also possible to make use of variants which are themselves known to those of ordinary skill in this art, but which are not mentioned in greater detail.

FLOW CHART I
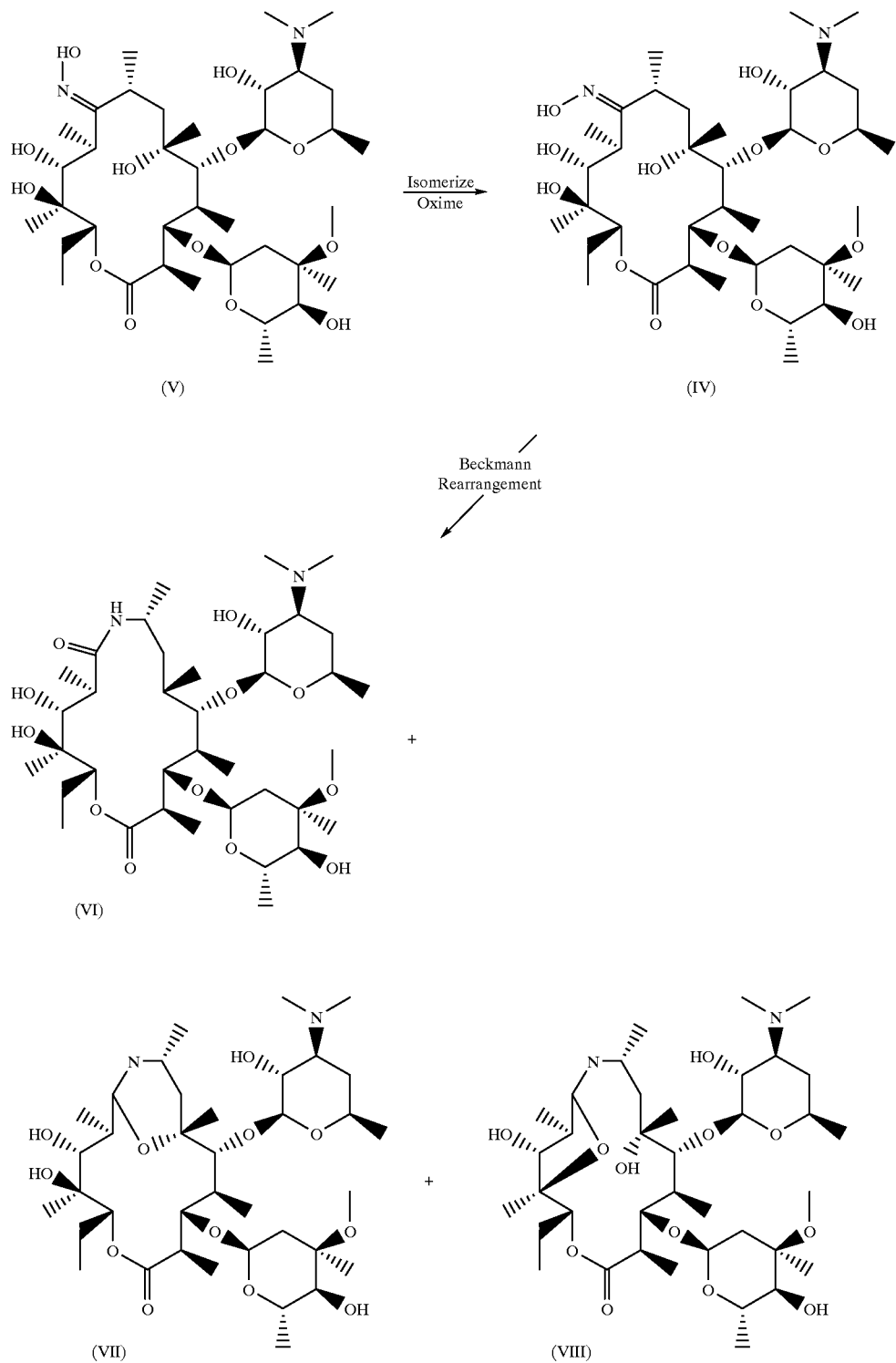

-continued
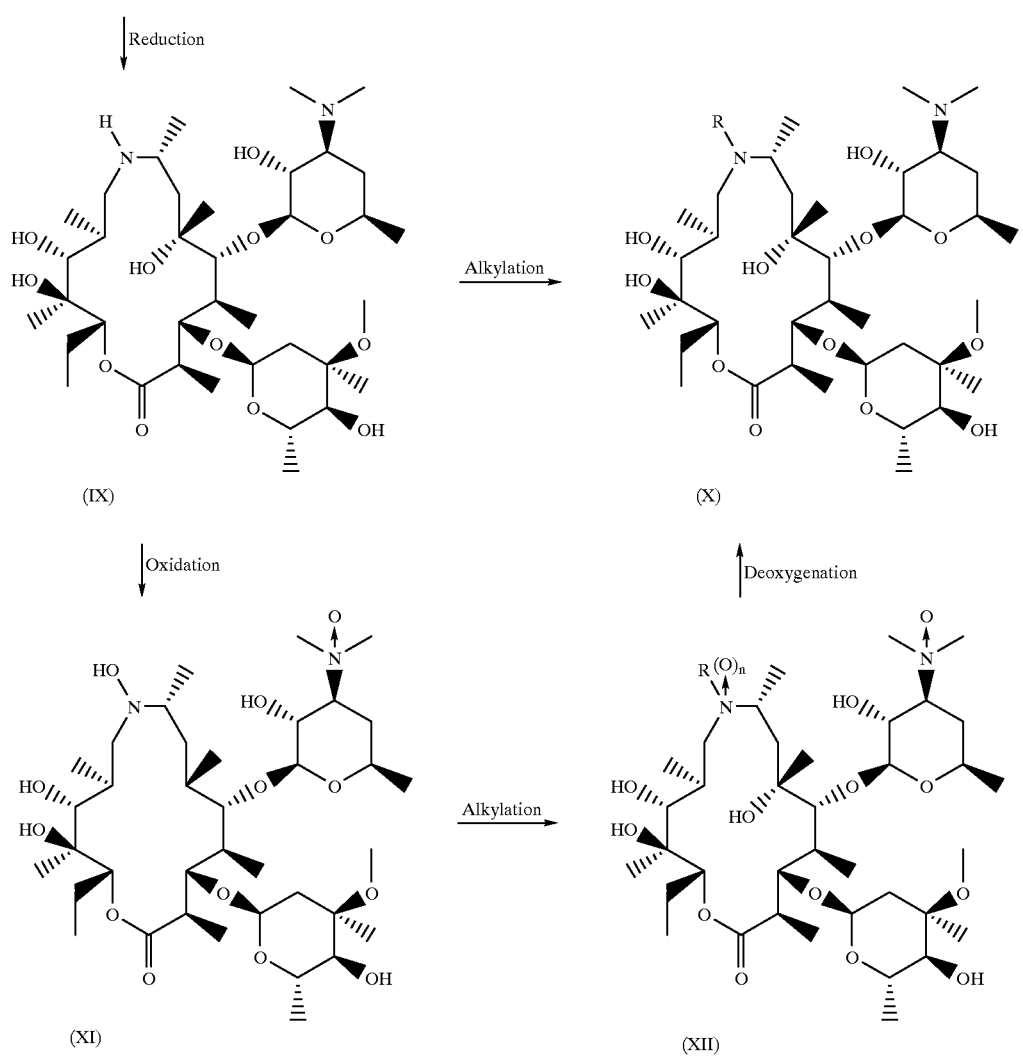

FLOW CHART II
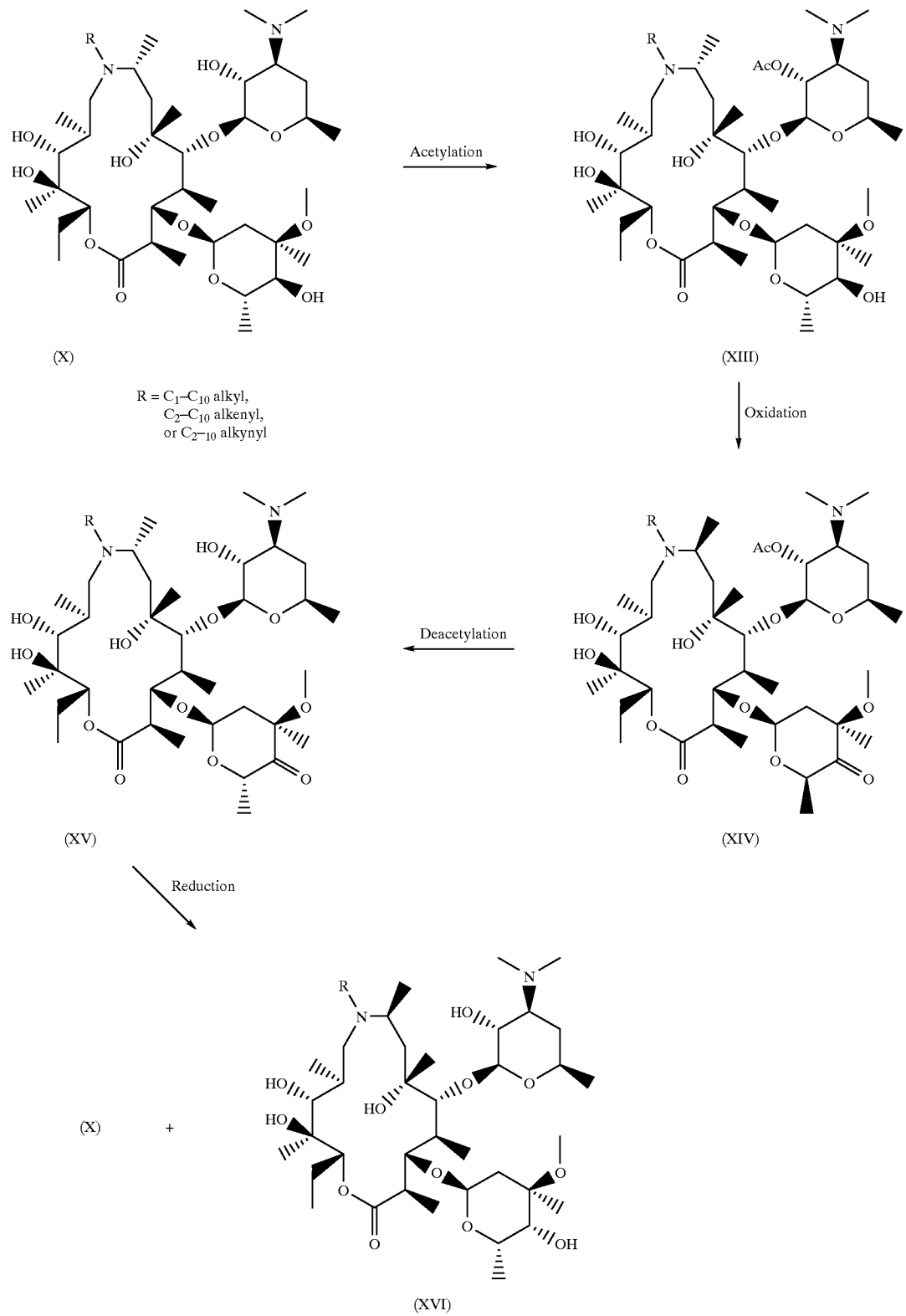

FLOW CHART III

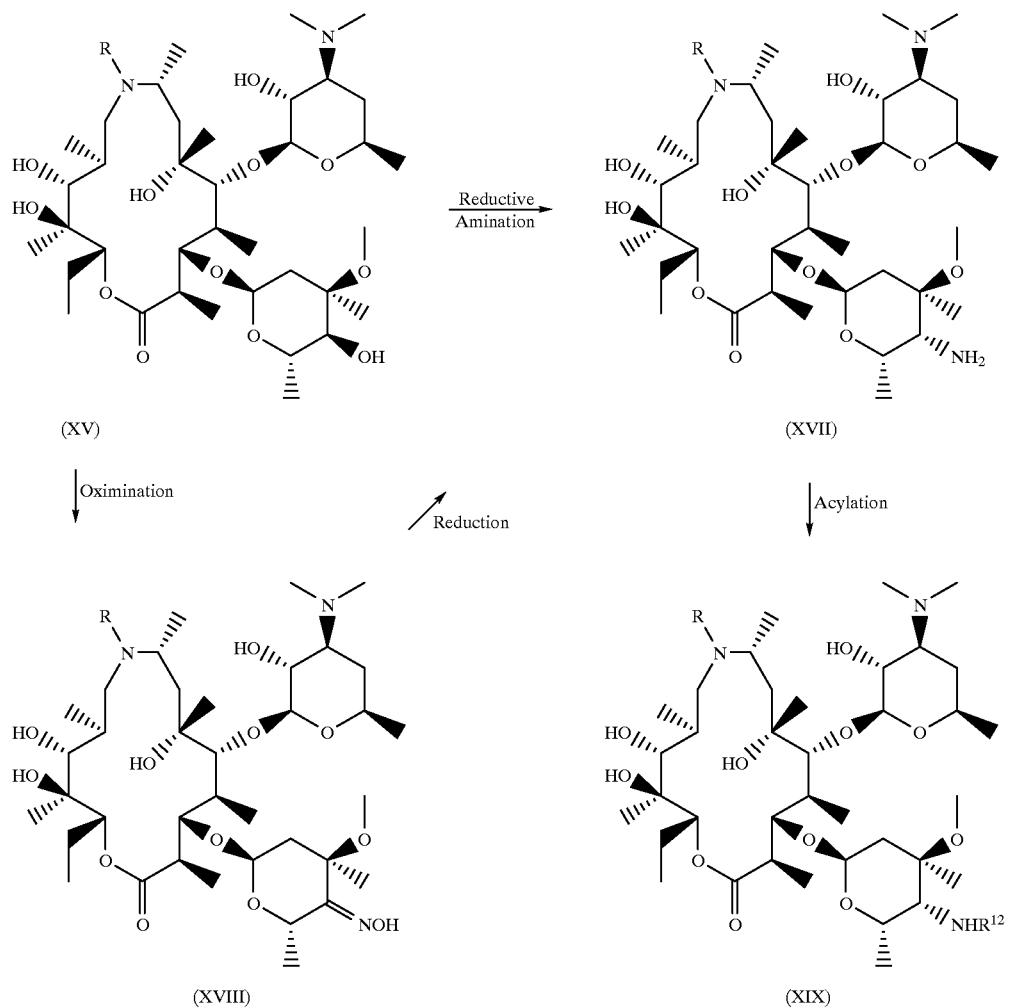

Isomerization of (9E)-9-Deoxo-9-hydroxyiminoerythromycin A to the (9Z) isomer

In a single step procedure, (9Z)-9-deoxo-9hydroxyimininoerythromycin A of the structure:

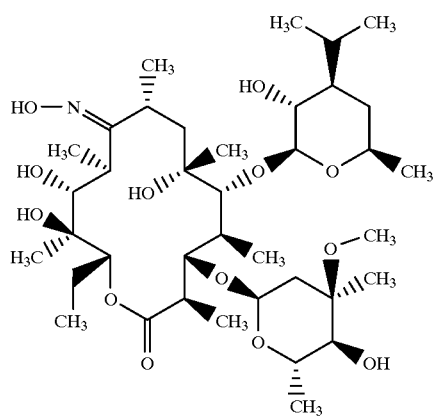

is obtained by reacting (9E)-9-deoxo-9-hydroxyiminoerythromycin A of the structure:

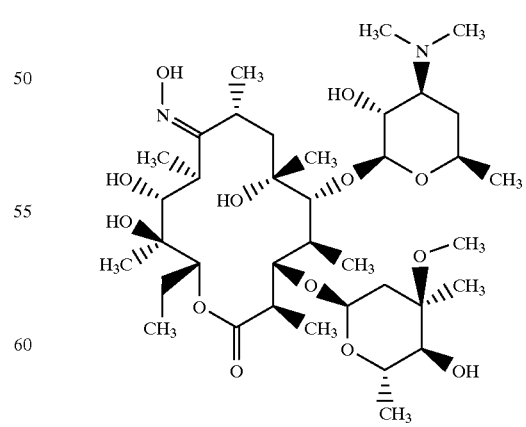

with a base in the presence of a protic or an aprotic solvent. Preferably, the base is an alkali metal hydroxide and the solvent is an alcohol. Most preferably, the base is lithium hydroxide (as the monohydrate) and the solvent is ethanol.

Optimization of the method of the isomerization step requires a ratio of the aforementioned base sufficient to substantially deprotonate the hydroxyimino group of the (E) isomer. Furthermore, the oxime anion must be reasonably stable under the reaction conditions for the time period required to complete the isomerization process.

Upon addition of the base to the (E) isomer, an equilibrium condition is created as shown in the following equation:

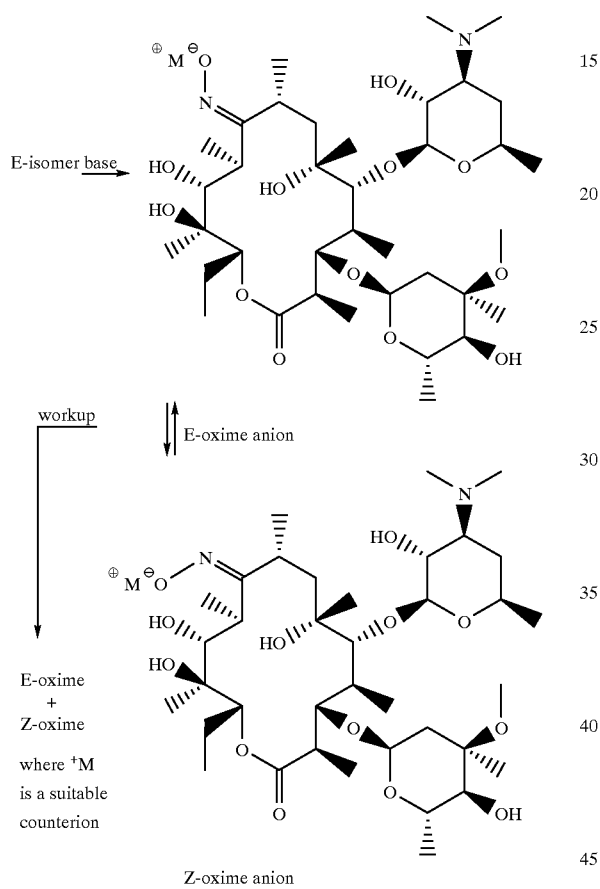

The workup performed on the anions includes protonation of the oxime anions to give the neutral oxime product mixture from which the desired (Z)-isomer is isolated by crystallization or by chromatography followed by crystallization.

The relative amounts of (E) and (Z) oxime anions (and neutral oximes after the workup) in the equilibrium mixture can be controlled and depends on a number of factors. These include (a) the strength and quantity of the base reagent, (b) the size and polarizability of the counterion $M^+$; and (c) the reaction solvent.

Suitable bases include hydroxides, alkoxides, carbonates, amides, amines and hydrides.

The following list of reagents is given to illustrate suitable bases and solvents, although the list is not to be taken as exhaustive and other bases and solvents known to those of ordinary skill in the art are not excluded. Preferred bases and solvents are indicated by one asterisk and most preferred bases are indicated by a dagger.

Bases

1. Hydroxides

| | |
   |---|---|
   | *†LiOH | lithium hydroxide |
   | *†NaOH | sodium hydroxide |
   | *KOH | potassium hydroxide |
   | CsOH | cesium hydroxide |
   | Ca(OH)$_2$ | calcium hydroxide |
   | Mg(OH)$_2$ | magnesium hydroxide |
   | *Me$_4$NOH | tetramethylammonium hydroxide |
   | BnMe$_3$NOH | benzyltrimethylammonium hydroxide |
   | Et$_4$NOH | tetraethylammonium hydroxide |
   | Bu$_4$NOH | tetrabutylammonium hydroxide |

2. Alkoxides

| | |
   |---|---|
   | *†LiOMe | lithium methoxide |
   | *†LiOEt | lithium ethoxide |
   | LiOiPr | lithium isopropoxide |
   | LiOnBu | lithium n-butoxide |
   | LiOsBu | lithium sec-butoxide |
   | *†NaOMe | sodium methoxide |
   | *†NaOEt | sodium ethoxide |
   | NaOPr | sodium n-propoxide |
   | NaOiPr | sodium iso-propoxide |
   | NaOnBu | sodium n-butoxide |
   | NaOsBu | sodium sec-butoxide |
   | NaOtBu | sodium tert-butoxide |
   | NaOSiMe$_3$ | sodium trimethylsilanoate |
   | KOMe | potassium methoxide |
   | *KOEt | potassium ethoxide |
   | KOtBu | potassium tert-butoxide |
   | KOSiMe$_3$ | potassium trimethylsilanoate |
   | KOsBu | potassium sec-butoxide |
   | CsOtBu | cesium tert-butoxide |
   | Ca(OMe)$_2$ | calcium methoxide |
   | *Mg(OEt)$_2$ | magnesium ethoxide |
   | Ti(OEt)$_4$ | titanium (IV) ethoxide |
   | Ti(OiPr)$_4$ | titanium (IV) isopropoxide |
   | BnMe$_3$NOMe | benzyltrimethylammonium-methoxide |

3. Carbonates

| | |
   |---|---|
   | K$_2$CO$_3$ | potassium carbonate |
   | *Cs$_2$CO$_3$ | cesium carbonate |
   | Na$_2$CO$_3$ | sodium carbonate |

4. Amides (for use in aprotic solvents)

| | |
   |---|---|
   | LiNH$_2$ | lithium amide |
   | LiNMe$_2$ | lithium dimethylamide |
   | *LiNiPr$_2$ | lithium diisopropylamide |
   | LiN(C$_6$H$_{11}$)$_2$ | lithium dicyclohexylamide |
   | LiN(SiMe$_3$)$_2$ | lithium bis(trimethylsilyl) amide |
   | NaNH$_2$ | sodium amide |
   | KN(SiMe$_3$)$_2$ | potassium bis(trimethylsilyl) amide |

5. Amines

| | |
   |---|---|
   | *TMG | 1,1,3,3-tetramethyl guanidine |
   | DBU | 1,8-diazabicyclo[5,4,0]undec-7-ene |
   | proton sponge | 1,8-bis(dimethylamino)-naphthalene |

6. Hydrides (for use in aprotic solvents)

| | |
   |---|---|
   | LiH | lithium hydride |
   | *NaH | sodium hydride |
   | KH | potassium hydride |

7. Solvents a. Protic

| | |
   |---|---|
   | H$_2$O (generally used in combination with an alcohol solvent) | |
   | *†MeOH | methanol |
   | *†EtOH | ethanol |
   | *iPrOH | isopropanol |
   | n-BuOH | normal-butanol |

| | |
|---|---|
| s-BuOH | sec-butanol |
| t-BuOH | tert-butanol | b. Aprotic i. Nonpolar (as a group, these are generally used in combination with a protic or polar solvent)

| | |
|---|---|
| Et$_2$O | diethyl ether |
| THF | tetrahydrofuran |
| DME | dimethoxyethane |
| PhMe | toluene |
| CH$_2$Cl$_2$ | dichloromethane |
| CHCl$_3$ | chloroform | ii. Polar

| | |
|---|---|
| *DMF | dimethylformamide |
| DMAC | dimethylacetamide |
| DMI | 1,3-dimethyl-2-imidazolidinone |
| NEP | 1-ethyl-2-pyrrolidinone |
| *NMP | 1-methyl-2-pyrrolidinone |
| HMPA | hexamethylphosphoramide |
| MeNO$_2$ | nitromethane |
| *MeCN | acetonitrile |
| | dioxane |
| | pyridine |
| *DMSO | dimethylsulfoxide |

Preferably, the isomerization reaction is carried out at a concentration of 1–25% w/v of E-oxime to solvent, and most preferably at 10% w/v. The amount of base used is preferably 1.0–10.0 molar equivalents of base, more preferably 1.0–3.0 molar equivalents, and most preferably 2.0 molar equivalents. The reaction is generally run at a temperature of from 0° C. to 80° C., and more preferably at 22–25° C. The reaction can be allowed to run for 0.5 hours to 20 days, but most preferably is carried out over 20–24 hours.

Beckmann Rearrangement of (9Z)-9-Deoxo-9-hydroxyiminoerythromycin A

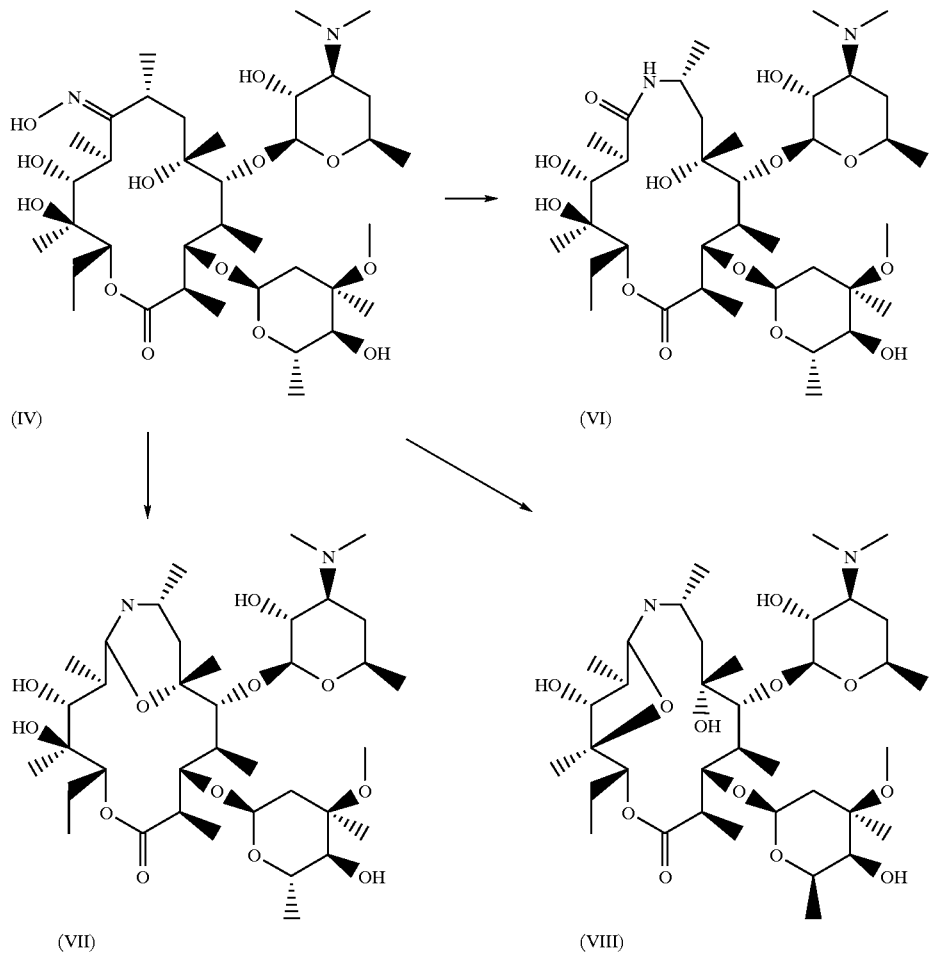

The conversion of (9Z)-9-deoxo-9-hydroxyiminoerythromycin A (IV) to the 8a-aza-8a-homoerythromycin products (VI), (VII) and (VIII) is accomplished by means of the Beckmann rearrangement (see "Comprehensive Organic Chemistry", I. O. Sutherland (Ed.), Pergamon Press, New York, 1979, Vol. 2, pgs. 398–400 and 967–968). In general, the Beckmann rearrangement of ketoximes leads to carboxamides and, in cyclic systems, to ring expanded lactams. The mechanism of the rearrangement involves initial conversion of the oxime hydroxyl group to a leaving group which is then lost with concomitant migration of the oxime carbon substituent that is situated anti to the leaving group. In aqueous media, the intermediate nitrilium cation thus formed usually reacts with water to afford the amide product. The nitrilium intermediate can also be trapped by other suitable nucleophiles thereby leading to imino products such as imidates and amidines.

The Beckmann rearrangement has been accomplished under a variety of acidic, neutral and basic conditions. Common acidic reagents that promote the transformation include concentrated sulfuric acid, polyphosphoric acid, thionyl chloride, phosphorous pentachloride, sulfur dioxide, and formic acid. These reagents are generally not applicable to the rearrangement of oxime (IV) due to the sensitivity of the macrolide molecule, and especially the cladinose sugar residue, to acidic conditions. Efficient Beckmann rearrangement also occurs by heating the oxime with silica gel in xylene or under mildly basic conditions by heating the oxime in hexamethylphosphoramide. These conditions are not particularly valuable for the conversion of (IV) to products (VI), (VII) and (VIII) due to competing isomerization of the oxime function under the reaction conditions.

A preferred method for effecting the Beckmann rearrangement involves initial O-sulfonylation of the oxime group with an alkylsulfonyl halide, arylsulfonyl halide or arylsulfonic anhydride. The intermediate oxime sulfonate thus formed can be isolated or, as more commonly practiced, converted in situ to the rearranged products. The sulfonylation and rearrangement reactions are generally performed in the presence of an organic or inorganic base. This method is particularly valuable for the conversion of oxime (IV) to the rearranged products (VI), (VII), and (VIII).

Preferred sulfonylating reagents for effecting the rearrangement of oxime (IV) include methanesulfonyl chloride, benzenesulfonyl chloride, 4-acetamidobenzenesulfonyl chloride, p-toluenesulfonyl chloride, benzenesulfonic anhydride, and p-toluenesulfonic anhydride. The reaction is carried out in the presence of an inorganic base such as sodium bicarbonate or potassium carbonate, or in the presence of an organic base such as pyridine, 4-dimethylaminopyridine, triethylamine, or N,N-diisopropylethylamine. Suitable solvents include aqueous mixtures such as aqueous acetone or aqueous dioxane and organic solvents such as dichloromethane, chloroform, ethyl acetate, diethyl ether, tetrahydrofuran, toluene, acetonitrile, and pyridine. Mixtures of organic solvents, especially those containing pyridine, are highly useful. The reaction is generally performed using 1–3 molar equivalents of the sulfonylating agent and one or more molar equivalents of base at a reaction temperature of −20° C. to 50° C. Pyridine is often used as both solvent and base.

The distribution of products resulting from Beckmann rearrangement of oxime (IV) depends on the particular reaction conditions employed. For example, when the rearrangement is effected with p-toluenesulfonyl chloride and sodium bicarbonate in aqueous acetone, the major products are the lactam (VI) and the 6,9-bridged iminoether (VII). When the reaction is conducted under anhydrous conditions such as p-toluenesulfonyl chloride in pyridine, the major products are the 6,9-bridged and 9,12-bridged iminoethers (VII) and (VIII). The ratio of products (VII) and (VIII) is also effected by the addition of cosolvents, by temperature, and by the initial oxime concentration. In general, increasing the proportion of pyridine as solvent, increasing the reaction temperature, and decreasing the initial oxime concentration all favor the formation of the 9,12-product (VIII) over that of the 6,9-product (VII).

A particularly preferred method for effecting the Beckmann rearrangement of oxime (IV) involves the addition of a solution of 2.5 molar equivalents of p-toluenesulfonyl chloride in diethyl ether to a solution of the oxime in pyridine at 0–5° C. Oxime O-sulfonylation and subsequent rearrangement occur under the reaction conditions to afford a 1:3 mixture of iminoether products (VII) and (VIII).

The products of the Beckmann rearrangement of oxime (IV) are conveniently purified by chromatographic methods. For example, the lactam (VI) is easily separated from iminoether (VII) using column chromatograhy on silica gel or by reverse phase, high-pressure liquid chromatography. Products (VII) and (VIII) can also be separated by chromatographic methods, and the (VIII) thus obtained can be further purified by crystallization from nitromethane. However, it is generally expedient to simply carry the mixture of (VII) and (VIII) isomers into the subsequent reduction step without further purification.

As previously noted, Beckmann rearrangement of oxime (IV) under anhydrous conditions leads to a product mixture comprised of the 6,9- and 9,12-bridged iminoethers (VII) and (VIII). The 9,12-bridged product, which is formed by stereoselective internal trapping of the intermediate nitrilium species by the hydroxyl group at C-12, is initially isolated as a mixture of major and minor forms that are isomeric about the imino double bond. The initial mixture of isomers equilibrates at room temperature, both in solution or on storing as a crude foam, to approximately a 1:1 mixture of isomers. The first-formed, major isomer can be isolated from the mixture by crystallization from nitromethane solution. However, it should be noted that the equilibration of the 9,12-bridged iminoethers (VIII) is of no consequence to the overall process since both forms are easily reduced in the next step to 9-deoxo-8a-aza-8a-homoerythromycin A.

Reduction of 9-Deoxo-6-deoxy-6,9-epoxy-8a,9-didehydro-8a-aza-8a-homoerythromycin A (VII) and 9-Deoxo-12-deoxy-9,12-epoxy-8a,9-didehydro-8a-aza-8a-homoerythromycin A (VIII)

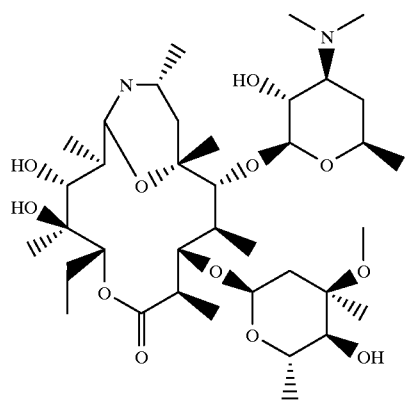

(VII)

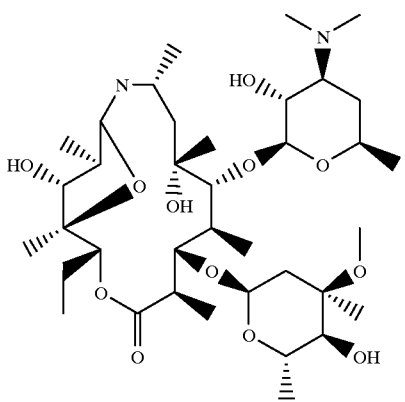

(VIII)

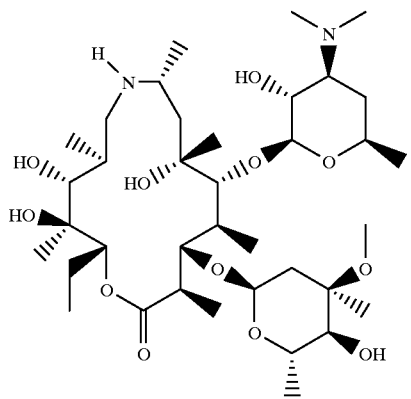

(IX)

Compounds (VII) and (VIII) can be viewed as cyclic imidates (or imidic acid esters) of the macrocyclic lactam (VI). The imidates are formally derived from compound (VI) by transannular addition of the hydroxy groups at positions 6 and 12 to the lactam carbonyl group, followed by elimination of water. However, imidates (VII) and (VIII) most likely arise by intramolecular interception of the Beckmann rearrangement nitrilium intermediate with the 6- and 12-hydroxy groups. In structure (VII), the imidate function (—N=C—O—) lies completely within a 6-membered ring thereby giving rise to a 5,6-dihydro-1,3-oxazine system. By contrast, the second structure (VIII) has the imino nitrogen atom exocyclic to a 5-membered ring containing the oxygen atom thereby giving rise to a 2-iminotetrahydrofuran system.

A number of reagents are known for the reduction of imidates to the corresponding amines (see "The Chemistry of Amidines and Imidates", S. Patai (Ed.), John Wiley and Sons, 1975, pgs. 460–461 and "Comprehensive Organic Chemistry", I. O. Sutherland (Ed.), Pergamon Press, New York, 1979, Vol. 2, pg. 495). These include metal/proton-donor combinations such as sodium amalgam in acid solution or sodium in ethanol or liquid ammonia, catalytic hydrogenation under pressure, and complex metal hydrides such as lithium aluminum hydride and sodium borohydride. The electrochemical reduction of imidates is also reported to give amines in good yield.

A method of choice for reducing the macrocyclic imidates (VII) and (VIII) to the amine (IX) uses a complex metal hydride in an appropriate solvent system. Suitable hydride reagents include lithium aluminum hydride, sodium borohydride, sodium cyanoborohydride, and diisobutyl aluminum hydride. Both lithium aluminum hydride and diisobutyl aluminum hydride require the use of anhydrous solvents such as benzene, toluene, diethyl ether, tetrahydrofuran and dimethoxyethane, whereas sodium borohydride and sodium cyanoborohydride can be used in the presence of water or in alcoholic solvents such as methanol, ethanol, isopropanol, and ethylene glycol. When sodium cyanoborohydride is used the reaction medium is usually acidified by addition of aqueous acid (pH $\geq 3$) or acetic acid. The reaction is generally accomplished by treating the imidate with 1–5 molar equivalents of reductant for 1–20 hours at a temperature ranging from $-20°$ C. to $50°$ C.

A particularly preferred method for reducing imidates (VII) and (VIII) to the amine (IX) employs 2–3 molar equivalents of sodium borohydride in methanol or ethylene glycol at a temperature of $0°$ C. to $25°$ C. Ethylene glycol serves the dual purposes of activating the borohydride agent and of breaking up borate ester complexes of the amine product.

A second method of choice for effecting the reduction of imidates (VII) and (VIII) to the amine (IX) is catalytic hydrogenation at high pressure. The reaction is usually accomplished by shaking a mixture of imidate and catalyst in a suitable solvent such as methanol, ethanol, aqueous dioxane or acetic acid at a hydrogen pressure of 1000–3000 psi for 2-20 hours at ambient temperature. Suitable catalysts include noble metals and their oxidized forms such as platinum on carbon, platinum oxide (Adams' catalyst), palladium on carbon, palladium hydroxide on carbon (Pearlman's catalyst) and rhodium on carbon. An especially preferred method for reducing imidate (VII) uses nearly an equivalent weight of platinum oxide catalyst in acetic acid at 2000 psi hydrogen for 18–20 hours at room temperature. Alkylation of 9-Deoxo-8a-aza-8a-homoerythromycin A Secondary amines such as (IX) can be reductively alkylated to tertiary amines using a number of well known procedures. As illustrated in Flow Chart IA, treatment of (IX) with aldehydes in the presence of a reducing agent leads to compounds of general structure (Xa) wherein $R^a$ is hydrogen, alkyl, aryl or aralkyl. Suitable reductants for this reaction include hydrogen in the presence of a noble metal catalyst, Raney nickel, sodium borohydride, sodium cyanoborohydride, and formic acid. The reaction can be conducted in a number of organic solvents, for example methanol, ethanol, acetonitrile, chloroform, tetrahydrofuran or dioxane, with or without the presence of added water.

Perhaps the most common of these reductive alkylation procedures is Eschweiler-Clarke methylation, which involves the reaction of the amine with formaldehyde in the presence of formic acid. Application of the Eschweiler-Clarke procedure to compound (IX) affords the ring methylated product (Xa) wherein $R^a$ is hydrogen. The reaction is accomplished by treating (IX) with 1–2 molar equivalents of formaldehyde and 2–3 molar equivalents of formic acid in an inert solvent at 20–100° C. A preferred system uses 37% aqueous formaldehyde and formic acid in carbon tetrachloride or chloroform heated at reflux for 1–2 days. The product is conveniently isolated by crystallization from aqueous ethanol.

FLOW CHART IA

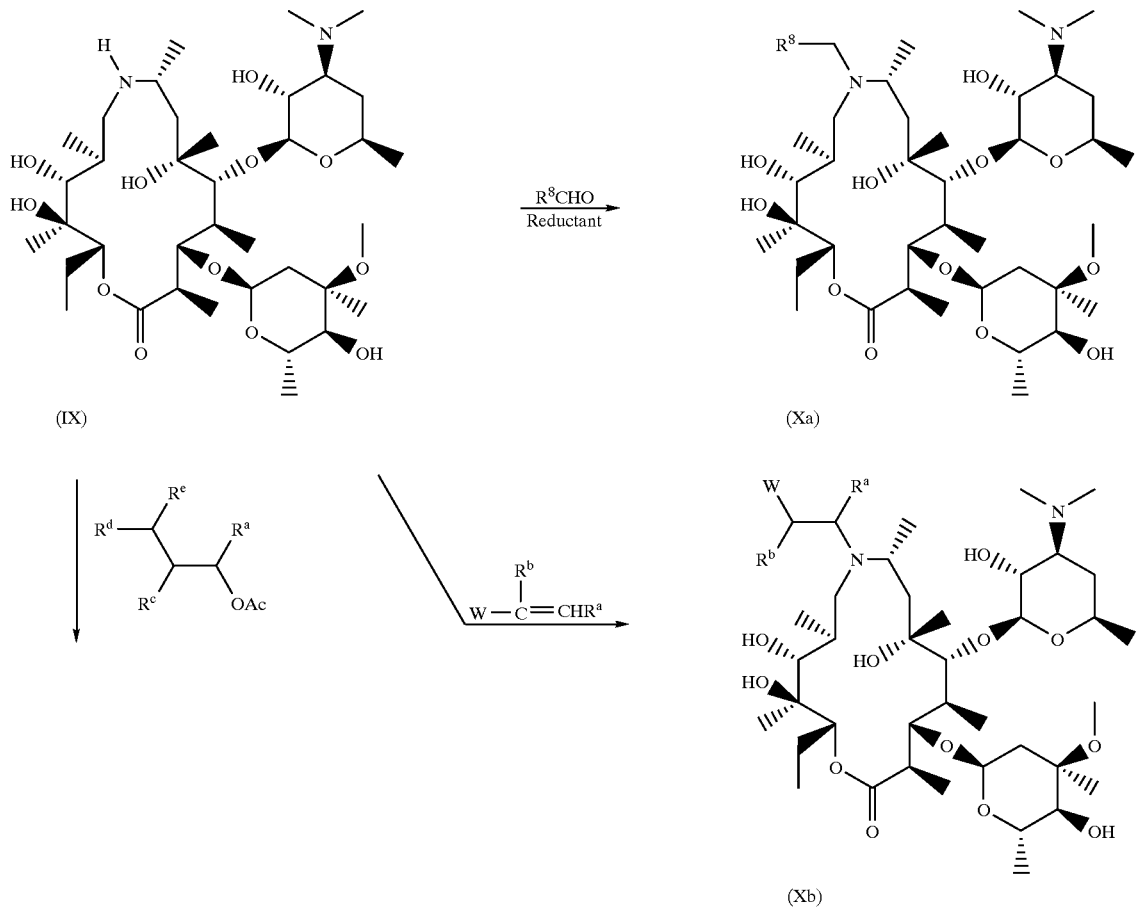

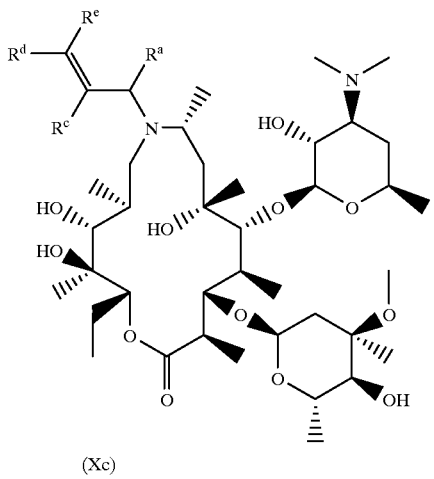

(Xc)

A second method for directly alkylating the aglycone nitrogen of (IX) involves the Michael-type addition of (IX) to a carbon-carbon double bond of the type W—$CR^b$=$CHR^a$ (see Flow Chart IA). For this reaction to be successful, the terminal end of the double bond must contain at least one electron-withdrawing group W of the type CHO, COR, COOR, $CONH_2$, CN, $NO_2$, SOR, or $SO_2R$. The reaction is generally performed using a large excess of alkylating agent (10–120 molar equivalents) in an organic solvent such as methanol or tetrahydrofuran at a temperature of 50–80° C. for 1–18 days. The rate of addition to the double bond can be accelerated by addition of metal salts such as zinc chloride or lanthanum chloride.

A third method for directly alkylating the ring nitrogen of compound (IX) involves a palladium catalyzed allylation reaction leading to alkenyl products of type (Xc) (see, Flow Chart IA). This reaction is usually accomplished with an excess of an allylic acetate and 0.05 to 0.5 equivalents of tetrakis(triphenylphosphine)palladium(O) in an organic solvent such as toluene or tetrahydrofuran containing trietylamine or diisopropylethylamine. A particularly preferred embodiment employs allyl acetate as both alkylating agent and solvent at a temperature of 80° C. for several hours.

The alkylation of the aglycone nitrogen atom of compound (IX) can also be accomplished using reagents of the type RX wherein X is a common leaving group such as chloro, bromo, iodo, iodoso, methanesulfonyloxy, toluensulfonyloxy, or trifluoromethanesulfonyloxy. However, the use of reagents of this type requires prior modification of the desosamine 3'-dimethylamino group to prevent quaternization at that site. Three schemes that employ alkylating reagents of the type RX coupled with protection/deprotection of the 3'-dimethylamino group are outlined in Flow Charts IB, IC and ID.

The first of these methods (see Flow Chart IB) involves a three-step procedure (see G. M. Bright, et al.,J. Antibiotics, 41, 1029 (1988) and U.S. Pat. No. 4,474,768) in which (IX) is first oxidized to the 8a-hydroxy-3'-N-oxide intermediate (XI), then treated with an alkylating agent to afford the intermediate product (XII), and finally deoxygenated to the desired product (X). In this approach, the 3'-N-oxygen serves as a temporary protecting group to prevent quaternization at the desosamine dimethylamino group.

FLOW CHART IB

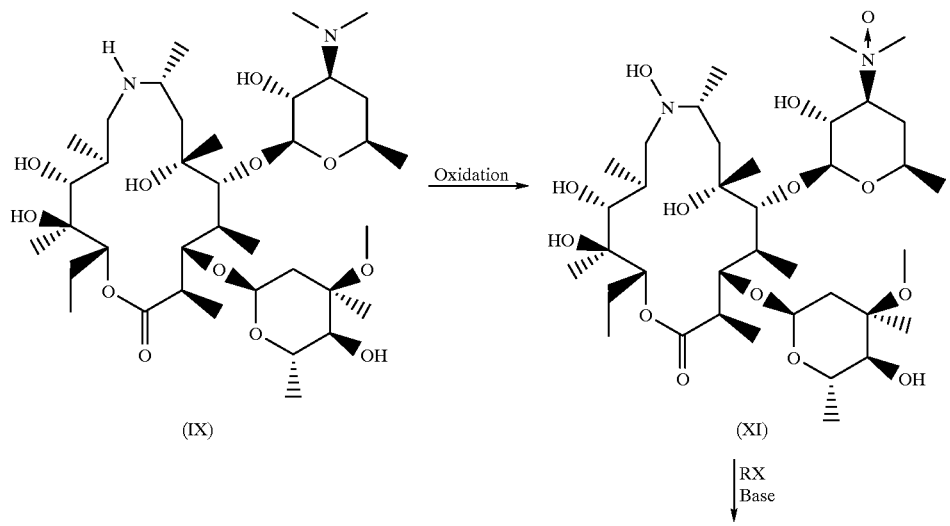

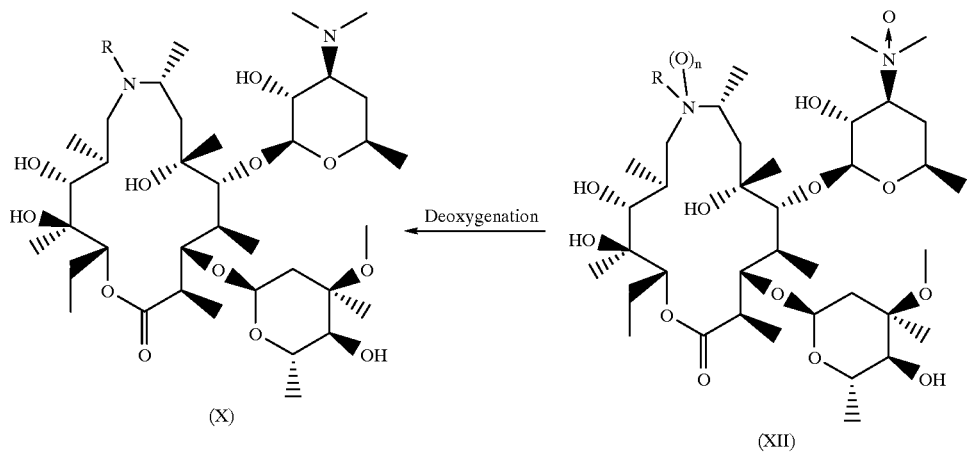

The oxidation step is conducted in an inert solvent using hydrogen peroxide or a peracid such as peracetic acid or 3-chloroperoxybenzoic acid as the oxidant. Suitable solvents for the reaction include dichloromethane, chloroform, tetrahydrofuran, dioxane, methanol, ethanol and acetic acid. In general, a water miscible solvent such as methanol or acetic acid is used with the water-soluble oxidants hydrogen peroxide and peracetic acid, whereas an anhydrous solvent such as dichloromethane or tetrahydrofuran is used with 3-chloroperoxybenzoic acid. The reaction is usually accomplished with an excess of oxidant (2–40 molar equivalents) at a temperature of from 0° C. to 50° C. for up to 24 hours. A particularly preferred embodiment employs excess 30% aqueous hydrogen peroxide as oxidant in methanol solvent at room temperature for 18–20 hours.

Introduction of the ring 8a-alkyl group is accomplished by treating the 8a-hydroxy-3'-N-oxide intermediate (XI) with an alkylating agent in an inert solvent in the presence of an acid acceptor. An inert solvent is defined as one that will not react with the alkylating reagent under the reaction conditions. Suitable solvents include but are not limited to dichloromethane, chloroform, tetrahydrofuran, dimethoxyethane, dimethylformamide, dimethylsulfoxide and toluene. Of the numerous agents that are known to effect alkylation at nitrogen, alkyl chlorides, alkyl iodides, alkyl bromides, dialkylyl sulfates, alkyl mesylates, alkyl tosylates and alkyl trifluoromethanesulfonates are well suited for the present application. The acid acceptor component, which serves to neutralize the acid formed on reaction of the alkylating agent with the ring nitrogen atom, can be an inorganic base such as an alkali metal hydroxide, carbonate or phosphate, or a hindered amine base. Examples of suitable acid acceptors are sodium bicarbonate, potassium carbonate, potassium hydroxide, trisodium phosphate and 2,6-lutidine. The alkylation reaction is generally accomplished using an excess (1.5–75 molar equivalents) of both the alkylating agent and the acid acceptor at a temperature of from 0° C.–100° C. for 1–100 hours. A representative procedure leading to intermediate (XII) wherein R is methyl involves stirring compound (XI) with approximately 40 molar equivalents of methyl iodide and 70 molar equivalents of anhydrous potassium carbonate in dichloromethane at room temperature. The product of the alkylation reaction is usually obtained as a mixture of components (XII, n=0 and 1) wherein the ring nitrogen atom has suffered partial deoxygenation. These components can be separated by chromatography, but are generally used without purification in the following deoxygenation step.

The final step of the sequence, the deoxygenation reaction of (XII) to provide (X), is readily accomplished by catalytic hydrogenation. The hydrogenation reaction is carried out at a temperature of 18° C. to 25° C. and at hydrogen pressures of from 15 psi to 2000 psi in an inert solvent. Suitable catalysts are noble metals and their oxides such as palladium on carbon, palladium hydroxide on carbon, platinum oxide, platinum on carbon, and rhodium on carbon. Representative inert solvents for the catalytic reduction are methanol, ethanol, tetrahydrofuran, dioxane, acetic acid and mixtures thereof. A typical catalytic reduction procedure uses ethanol as solvent, a hydrogen pressure or 45 psi, and 10% palladium on carbon as catalyst at a substrate to catalyst ratio of 1:1 to 1:2.

The reductive deoxygenation of (XII) to (X) can also be accomplished with a number of chemical reductants. Representative reagents of this type include metal hydrides such as sodium borohydride or sodium cyanoborohydride, zinc in acetic acid, and triphenylphosphine.

The 8a-alkylation sequence depicted in Flow Chart IC employs a strategy wherein the desosamine dimethylamino group is first protected by quaternization with a removable protecting group $R^a$. Suitable groups for this purpose include, but are not limited to, benzyl, 4-nitrobenzyl, allyl and trimethylsilylethyl. The protecting group is introduced by selective alkylation at the dimethylamino group using 1.0 to 1.1 molar equivalents of a reagent of the type $R^aX$ where $R^a$ is as defined above and X is a common leaving group. The quaternization reaction is conducted in an inert organic solvent such as dimethylformamide, tetrahydrofuran or methylene chloride at a temperature of 25–80° C. for 0.5 to 2 hours. A typical procedure employs 1.0 equivalents of benzyl bromide in dimethylformamide at 50° C. for 45 minutes. The product of the quaternization reaction (XX) is generally not purified but used directly in the next step.

FLOW CHART IC

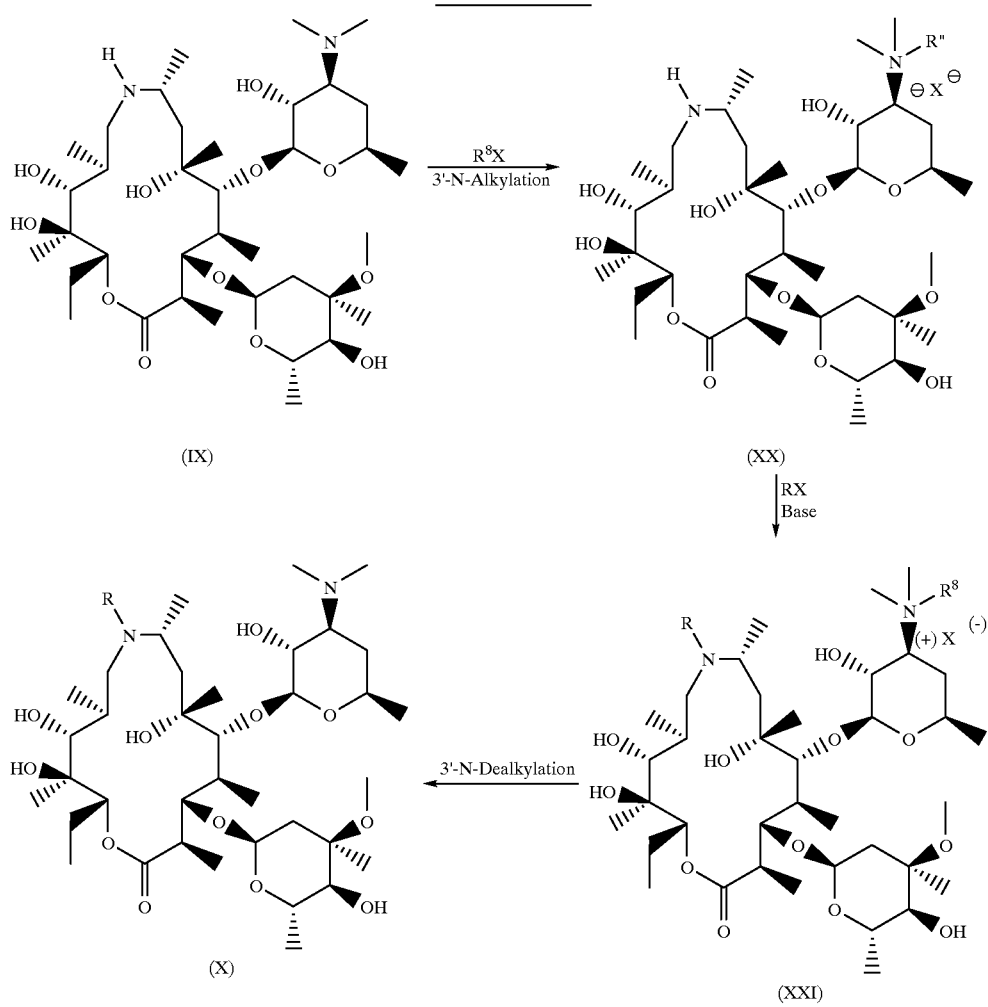

The 8a-alkylation step leading from compound (XX) to compound (XXI) is performed in essentially the same manner as previously described for the alkylation of intermediate (XI) in Flow Chart IB. A preferred procedure uses approximately 5 equivalents of the alkylating agent and 1–2 equivalents of potassium carbonate in dimethylformamide at 50–75° C. for 1–4 days.

The final step of Flow Chart IC involves the restoration of the desosamine dimethylamino group by 3'-N-dealkylation. The exact procedure employed depends on the nature of the protecting group used. For example, when $R^a$ is 4-nitrobenzyl, dequaternization is readily effected by hydrogenation in the presence of palladium on carbon. When $R^a$ is benzyl, the dequaternization reaction is accomplished by using thiophenol and potassium carbonate.

A somewhat longer but preferred method for effecting alkylation at the 8a-position of intermediate (IX) is illustrated in Flow Chart ID. In this approach, the desosamine dimethylamino group is first demethylated to intermediate (XXII) which is subsequently acylated to provide compound (XXIII). Demethylation is accomplished by treating compound (IX) with iodine in buffered methanol at 60° C. The resulting derivative (XXII) is selectively acylated at the 3'-methylamino group with a reagent of the type $R^bX$ in an organic solvent in the presence of an acid acceptor. Suitable acylating reagents include benzenesulfonyl chloride, benzyl chloroformate, allyl chloroformate and trimethylsilylethyl chloroformate. Suitable solvents include but are not limited to dichloromethane, chloroform, tetrahydrofuran and toluene. The acid acceptor can be an inorganic base such as potassium carbonate or an organic base such as triethylamine or diisopropylethylamine. A preferred embodiment of the acylation procedure uses 1.0–1.1 equivalents of benzenesulfonyl chloride and 3 equivalents of triethylamine in dichloromethane at 0–5° C.

FLOW CHART ID

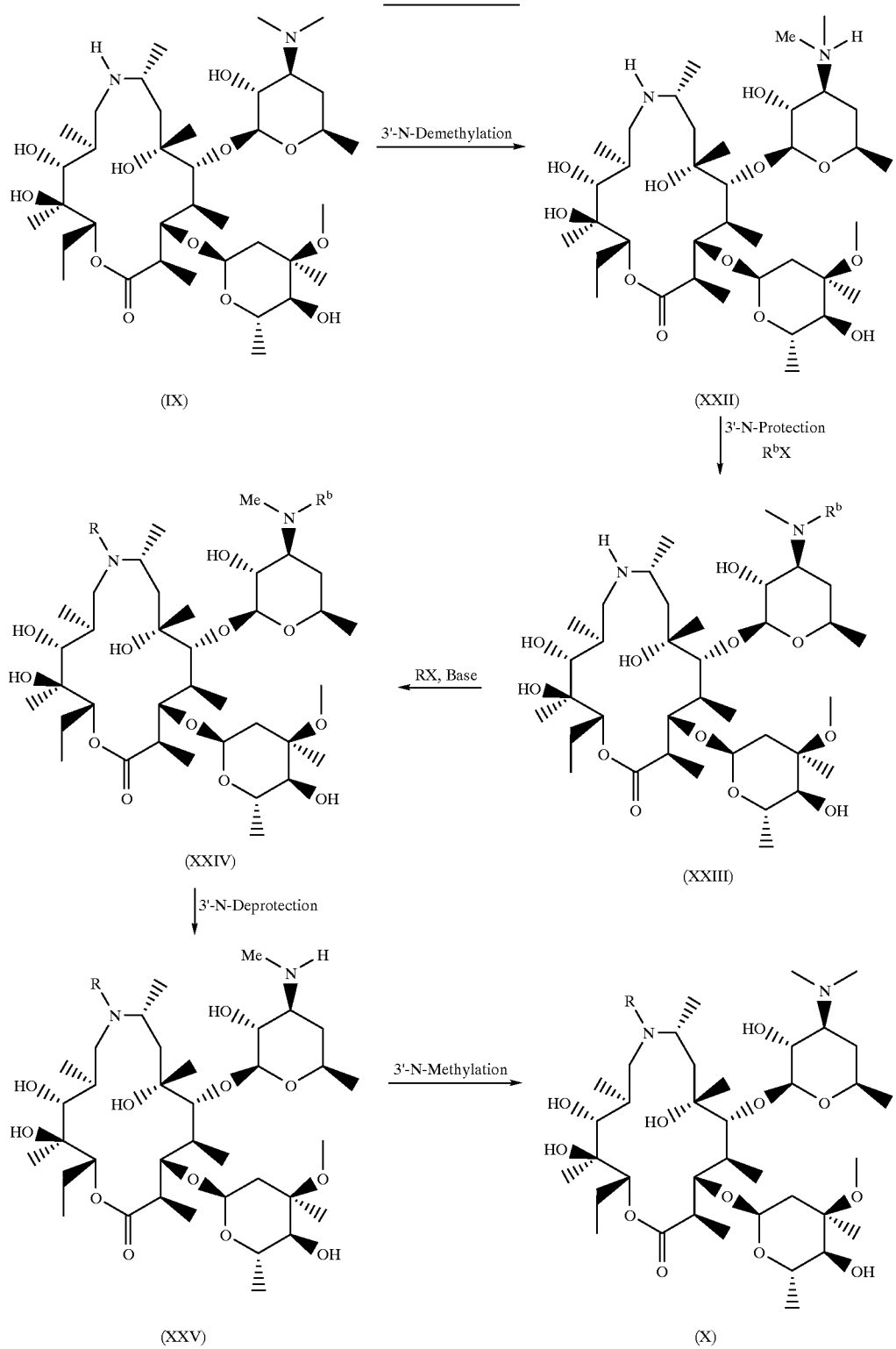

Compound (XXIII) is well suited for 8a-alkylation using essentially the same procedures previously described for alkylating intermediate (XI) in Flow Chart IB. Typical reaction conditions use 1.5–10 equivalents of the alkylating agent RX and 3–10 equivalents of an inorganic base such as sodium bicarbonate or trisodium phosphate in dimethylformamide at 100° C. for 1–7 days. The alkylated product (XXIV) is usually purified by chromatography on silica gel, but can be used in the next step without purification.

The remaining two steps of Flow Chart ID involve restoration of the desosamine 3'-dimethylamino group. The first of these steps involves cleavage of the acyl protecting group $R^b$ in a manner consistent with the exact nature of that group. For example, the benzyloxycarbonyl group is removed by catalytic hydrogenation and the (trimethylsilyl) oxycarbonyl group is removed by treatment with fluoride ion. In the most preferred method, the benzenesulfonyl group is reductively cleaved using excess sodium amalgam in potassium dihydrogen phosphate buffered methanol at −20° C. for 1.5–3 hours. The final step leading to compound (X) involves methylation at the 3'-N-position of intermediate (XXV). This is readily accomplished using the previously described Eschweiler-Clarke procedure.

The sequences outlined in Flow Charts IA–ID provide for the introduction of unsubstituted or substituted alkyl, alkenyl or alkynyl groups at the 8a-position of intermediate (IX). When said group contains one or more functional groups ameneable to chemical manipulation, it should be recognized that additional derivatives are available by suitable chemical modification. This concept is generically illustrated in Flow Chart IE and partially exemplified for the case where R is allyl.

FLOW CHART IE

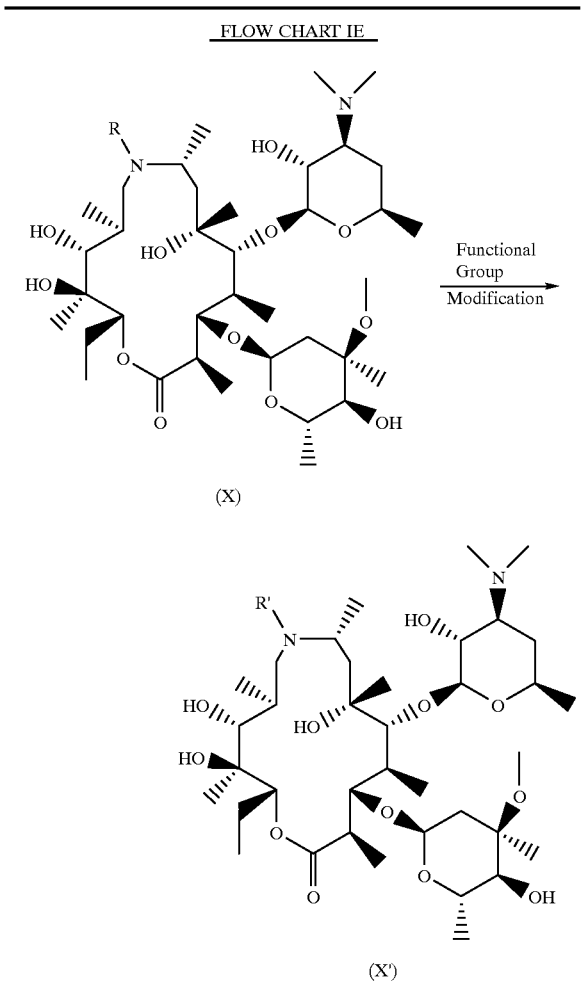

| Example: | R | Modification | R' |
|---|---|---|---|
| | $CH_2$=CHCH$_2$ | Hydrogenation | $CH_3CH_2CH_2$ |

FLOW CHART IE -continued

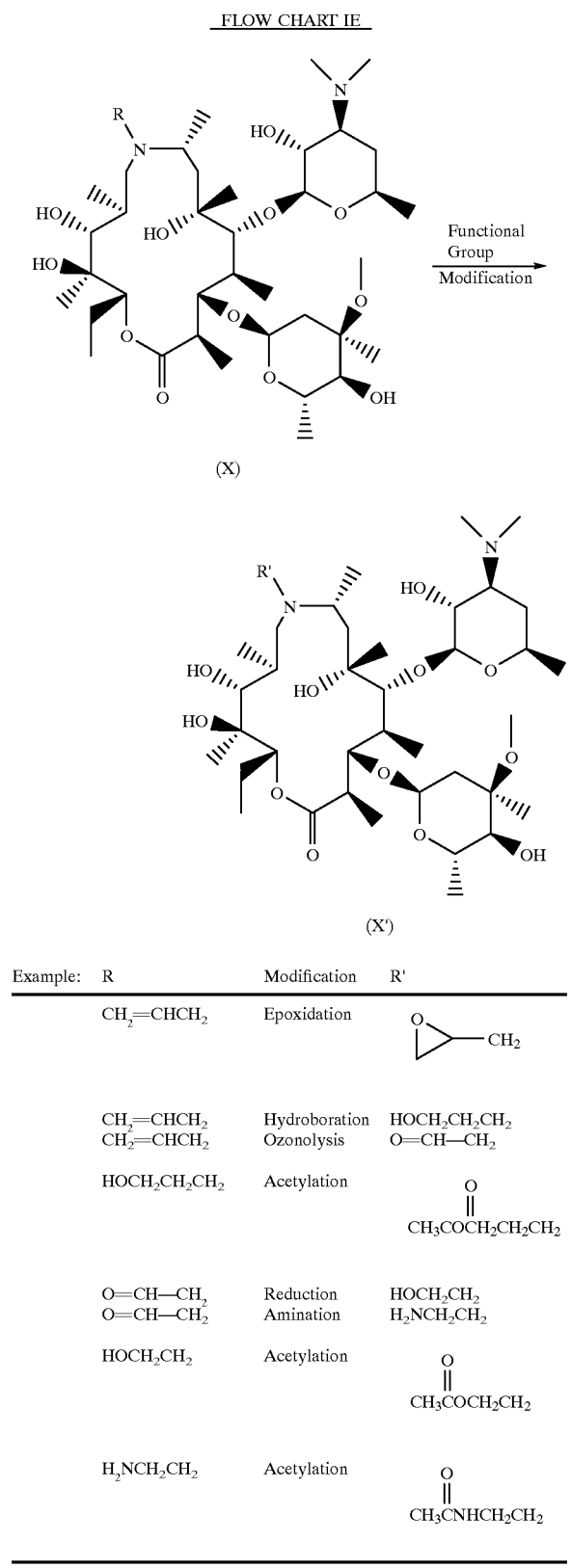

| Example: | R | Modification | R' |
|---|---|---|---|
| | $CH_2$=CHCH$_2$ | Epoxidation | (epoxide)—CH$_2$ |
| | $CH_2$=CHCH$_2$ $CH_2$=CHCH$_2$ | Hydroboration Ozonolysis | HOCH$_2$CH$_2$CH$_2$ O=CH—CH$_2$ |
| | HOCH$_2$CH$_2$CH$_2$ | Acetylation | CH$_3$COCH$_2$CH$_2$CH$_2$ |
| | O=CH—CH$_2$ O=CH—CH$_2$ | Reduction Amination | HOCH$_2$CH$_2$ H$_2$NCH$_2$CH$_2$ |
| | HOCH$_2$CH$_2$ | Acetylation | CH$_3$COCH$_2$CH$_2$ |
| | H$_2$NCH$_2$CH$_2$ | Acetylation | CH$_3$CNHCH$_2$CH$_2$ |

By combining the procedures summarized in the Flow Charts IA–IF, a wide range of 8a-substituents are possible. The following examples, organized according to structural type, are representative of the types of 8a-groups that can be obtained by these methods.

Unsubstituted Alkyl, Alkenyl and Alkynyl Groups

CH₃, CH₃CH₂, CH₃CH₂CH₂, (CH₃)₂CH, CH₃(CH₂)₇,

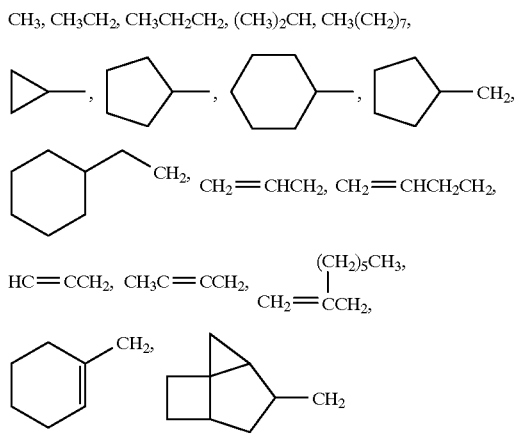

Aralkyl and Aralkenyl Groups

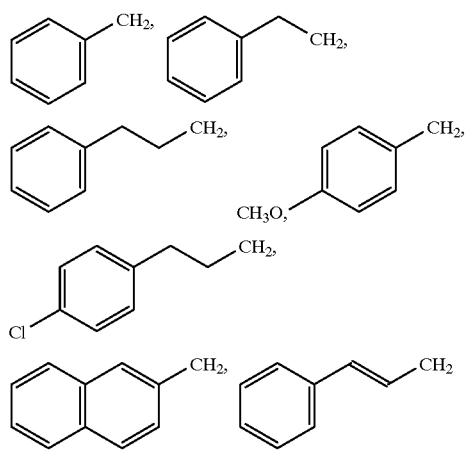

Heteroarylalkyl and Heteroarylalkenyl Groups

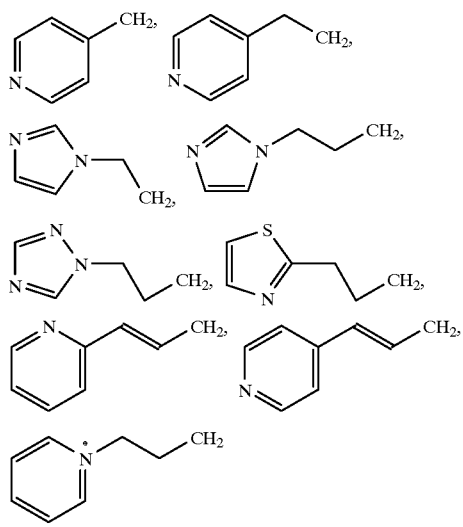

Heterocyclylalkyl and Heterocyclylalkenyl Groups

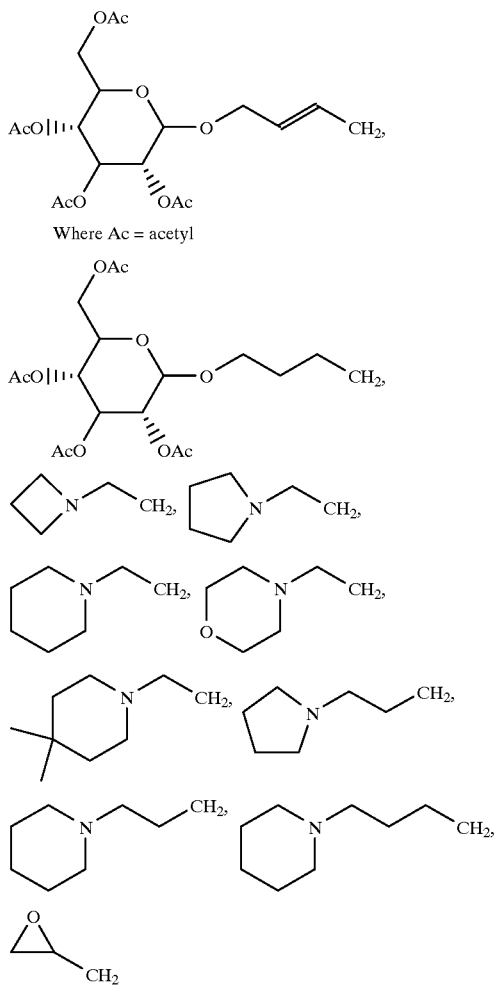

Substituted Alkyl, Alkenyl and Alkynyl Groups

FCH₂CH₂, F₂CHCH₂, CF₃CH₂, FCH₂CH₂CH₂,
CF₃CH₂CH₂CH₂, ClCH₂CH₂CH₂, CH₃SOCH₂CH₂CH₂,

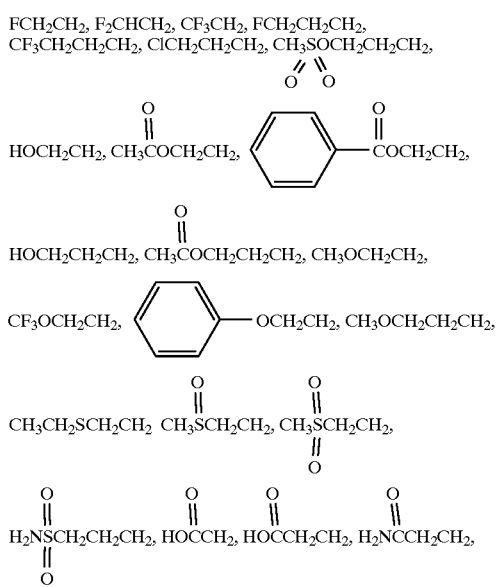

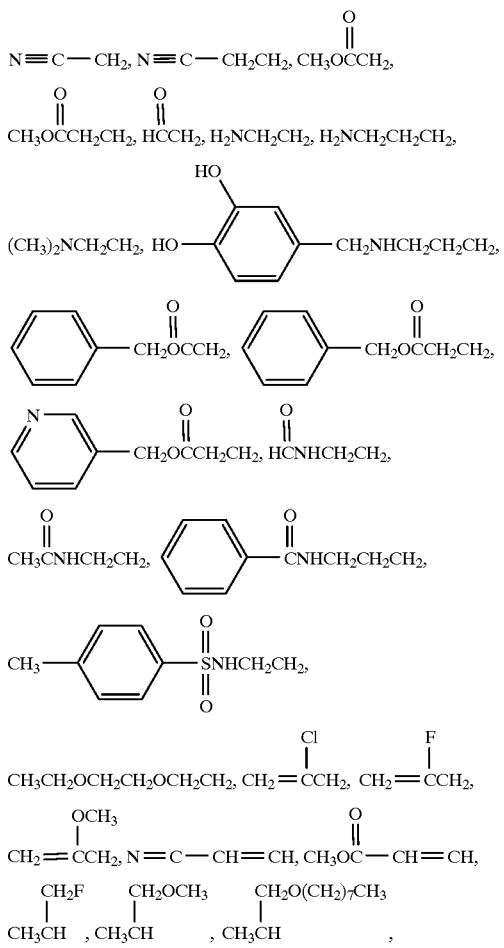

Acylation of 9-Deoxo-8a-aza-8a-homoerythromycin A

The aglycone nitrogen atom of intermediate (IX) can be acylated using a number of procedures generally applicable for the acylation of secondary amines. The process, as outlined in Flow Chart IF, leads to 8a-substituted derivatives of types (Xd) and (Xe) wherein $R^a$ is alkyl or aryl and $R^b$ is hydrogen, alkyl, alkoxy or aralkoxy. The reaction is typically conducted using an excess of an activated sulfonic or carboxylic acid derivative and a base in an organic solvent. Of the numerous acid derivatives available for the conversion of (IX) to (Xd) and (Xe), acid chlorides and acid anhydrides are particularly useful. The added base serves to neutralize the acid HX that is liberated in the acylation reaction, and, in some cases, it also activates the acylating agent. Examples of suitable bases are pyridine, 4-dimethylaminopyridine, triethylamine and diisopropylethylamine. The acylation reaction is typically conducted in an inert organic solvent such dichloromethane, chloroform, dichloroethane, tetrahydrofuran or toluene at a temperature of from 0° C. to 60° C. for 1 to 6 hours. For reactions in which the acylating reagent is a carboxylic acid anhydride, pyridine can serve as both the base and the solvent.

When a carboxylic acid derivative is used as the acylating agent, it is possible to isolate products wherein the 2'-hydroxyl group has also been acylated. The resulting 8a-N,2'-O-diacylated products can be selectively deacylated at the 2'-position by reaction with a lower alcohol. A typical procedure involves stirring the diacyl intermediate with methanol at room temperature for 10–24 hours.

FLOW CHART IF

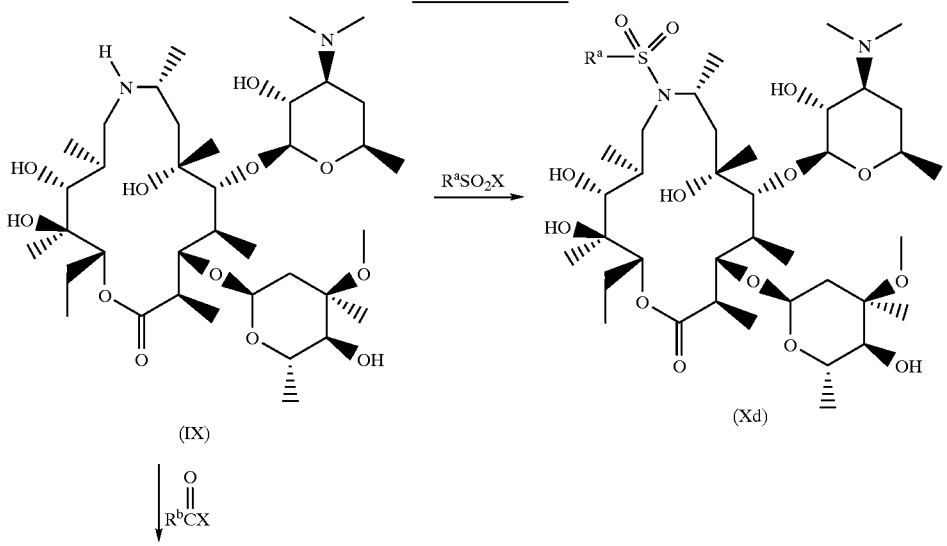

-continued

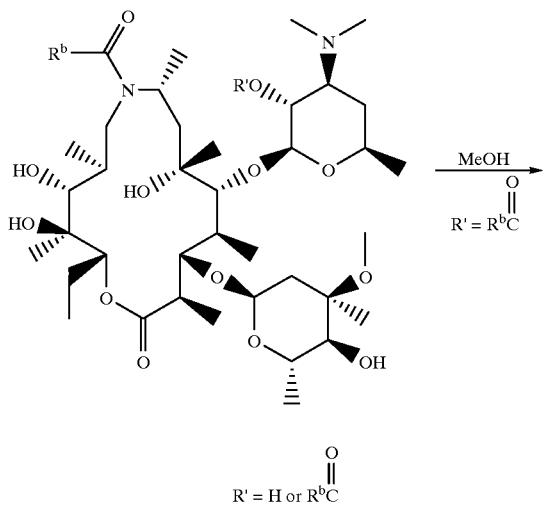

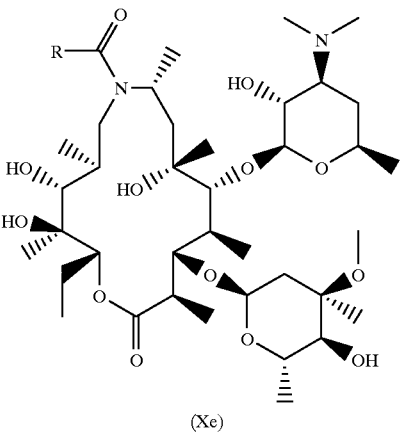

(Xe)

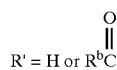

R' = H or R$^b$C

Modifications at the 4"-Position

Turning now to Flow Chart II there is shown in the first step conversion of compounds of formula (X) via acetylation to a protected moiety. Protection of the 2'-hydroxyl group is necessary for the subsequent oxidation step and is generally achievable by use of a lower alkanoyl protecting group such as acetyl or propionyl. Typically, acetic anhydride and pyridine in dichloromethane or acetic anhydride in ethyl acetate will attach the acetyl group to the 2'-hydroxyl when allowed to react at room temperature for several hours.

Next, the 2'-protected intermediate is oxidized at the 4"-hydroxyl substituent to the corresponding 4"-oxo (keto) compound, via treatment with dimethyl sulfoxide and a suitable activating agent in the presence of a base. Typical reaction conditions for the oxidation are either a) Moffatt oxidation which uses N-ethyl-N'-(N,N-dimethylaminopropyl)carbodiimide and dimethylsulfoxide in the presence of pyridinium trifluoroacetate; or b) the Swern oxidation in which oxalyl chloride and dimethylsulfoxide in dichloromethane is followed by the addition of triethylamine or alternatively trifluoroacetic anhydride and dimethylsulfoxide in dichloromethane is followed by the addition of triethylamine.

In the next step, removal of the 2'-protecting group is achieved by solvolysis with methanol at room temperature for 1 to 2 days, followed by in vacuo evaporation of the methanol.

The subsequent reduction step reduces the 4"-oxo group to the 4"-epi isomer of (x) via catalytic hydrogenation, as with Raney nickel and hydrogen. Also, a complex metal hydride such as sodium borohydride in methanol or lithium tri-tert-butoxyaluminohydride in tetrahydrofuran can be used to achieve reduction. To the extent isomeric mixtures at the 4"-position are formed, they are conveniently separated by silica gel column chromatography or by HPLC methods.

Turning now to Flow Chart III, there is shown the reductive amination that directly converts the 4"-oxo to the corresponding 4"-amino. This is accomplished by either a) sodium cyanoborohydride and ammonium acetate in methanolic acetic acid; or b) catalytic hydrogenation in the presence of an ammonia source, such as hydrogen and ammonium acetate in methanol with Raney nickel or 10% palladium on carbon. The resulting amino isomers at the 4"-position can be separated by HPLC or by chromatography on silica gel or alumina.

Alternatively, the 4"-amino derivative can be prepared from the 4"-oxo intermediate via oximation to the corresponding 4"-oxime followed by reduction to the 4"-amine. Oximination is achieved by use of hydroxylamine hydrochloride in pyridine or hydroxylamine hydrochloride and a base such as triethylamine, pyridine or imidazole in methanol. Reduction of the oxime is accomplished by either a) catalytic hydrogenation with hydrogen and Raney nickel in ethanol, b) catalytic hydrogenation with platinum oxide in acetic acid or c) reduction with titanium trichloride and sodium cyanoborohydride in ammonium acetate buffered methanol.

The 4"-amine can be acylated or sulfonylated to the corresponding amide, carbamate, or sulfamate. Suitable reagents for this process include, but are not limited to, a) R"COCl, (R"CO)$_2$O, R"SO$_2$Cl, or (R"SO$_2$)$_2$O, in dichloromethane, ethyl acetate, tetrahydrofuran or dimethylformamide containing triethylamine, where R" is any substituent of interest; b) R"CO$_2$H and dicyclohexylcarbodiimide or diisopropylcarbodiimide in dichloromethane or dimethylformamide; c) R"CO$_2$H and iso-butyl-chloroformate in dichloromethane containing N-methylmorpholine; or d) R"CO$_2$C$_6$F$_5$ in N-methylpyrolidinone.

Structural formula (XIX) shows an N-acyl group, $R^{12}$. $R^{12}$ is preferably either a substituted or unsubstituted $C_1$–$C_{10}$ alkylcarbonyl group, aryl or heteroaryl-carbonyl group, aralkyl or heteroarylalkylcarbonyl group, alkylsulfonyl group or an aryl or heteroaryl-sulfonyl group. These substituents can be 1–3 fluoro, amino, substituted amino wherein said substituent is formyl or $C_1$–$C_{10}$ alkylcarbonyl; cyano, isonitrilo, carboxy, carbamoyl, Br, Cl, disubstituted amino wherein said substituents are $C_1$–$C_{10}$ alkyl; nitro, heterocyclyl, carbamoyl wherein the nitrogen atom is optionally mono or di-substituted with $C_1$–$C_{10}$ alkyl; aryloxy, arylthio, $C_1$–$C_{10}$ alkoxycarbonyl, hydroxy, $C_1$–$C_{10}$ alkoxyl, mercapto, $C_1$–$C_{10}$ alkylthio, $C_1$–$C_{10}$ alkylsulfinyl, $C_1$–$C_{10}$ alkylsulfonyl, sulfamoyl, and unsubstituted or substituted $C_1$–$C_{10}$ alkylamino wherein said substitutent is formyl or $C_1$–$C_{10}$ alkylcarbonyl.

Even more preferably, $R^{12}$ is hydrogen, arylsulfonyl, alkylsulfonyl or

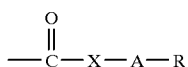

where

X is a connecting bond, O or NH;

A is a connecting bond, or $C_1$–$C_3$ alkylene;

R is hydrogen, $C_1$–$C_{10}$ alkyl, aryl, heteroaryl, aralkyl, heterocyclyl, or $C_3$–$C_7$ cycloalkyl, any of which R groups other than hydrogen can be substituted by one or more of halogen, hydroxyl, $C_1$–$C_3$ alkoxy, cyano, nitro, amino, mono- or di- ($C_1$–$C_3$) alkylamino, mercapto, $C_1$–$C_3$ alkylthio, $C_1$–$C_3$ alkylsulfinyl, $C_1$–$C_3$ alkylsulfonyl, arylthio, arylsulfinyl, sulfamoyl, arylsulfonyl, carboxy, carbamoyl, $C_1$–$C_3$ alkylcarbonyl, or $C_1$–$C_3$ alkoxycarbonyl.

Representative examples of 4"-N-substituents ($R^{12}$) are listed below.

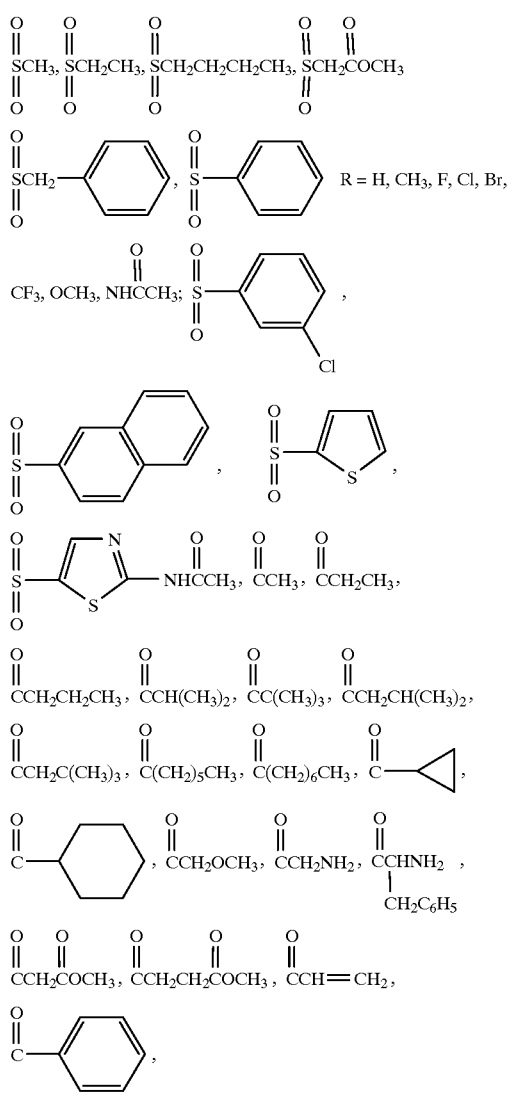

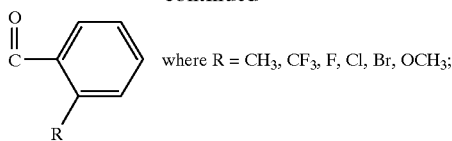
where R = $CH_3$, $CF_3$, F, Cl, Br, $OCH_3$;

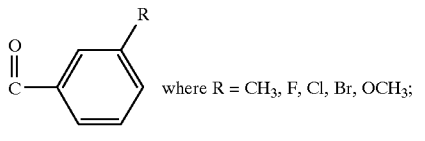
where R = $CH_3$, F, Cl, Br, $OCH_3$;

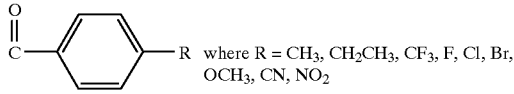
R where R = $CH_3$, $CH_2CH_3$, $CF_3$, F, Cl, Br, $OCH_3$, CN, $NO_2$

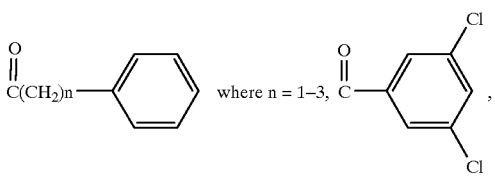
where n = 1–3,

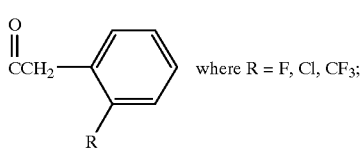
where R = F, Cl, $CF_3$;

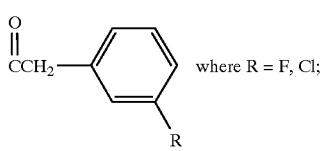
where R = F, Cl;

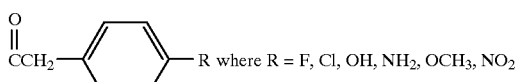
R where R = F, Cl, OH, $NH_2$, $OCH_3$, $NO_2$

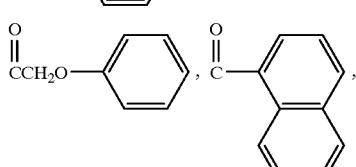

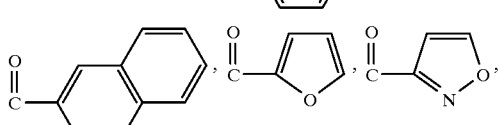

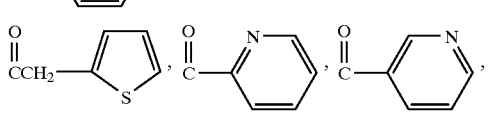

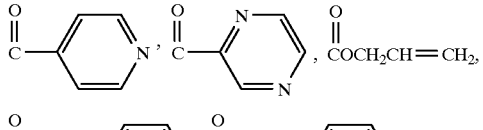

As antibiotics, the compounds of formula (II) can be administered in such oral dosage forms as tablets, capsules, pills, powders, granules, elixirs, tinctures, suspensions, syrups and emulsions. Like-wise, they may also be administered in intravenous, intraperitoneal, subcutaneous or intramuscular form, all using forms well known to those of ordinary skill in the pharmaceutical arts. In general, the preferred form of administration is oral. An effective but non-toxic amount of the compound can be employed as a mammalian antibiotic.

The dosage regimen utilizing the compounds of formula (II) is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Dosages of the compounds of formula (II), when used for the indicated effects, will range between about 0.2 mg per kg of body weight per day (mg/kg/day) to about 120 mg/kg/day and preferably 4–50 mg/kg/day. Advantageously, the compound may be administered in a single daily dose, or the total daily dosage may be administered in divided doses of two, three or four times daily.

Furthermore, the compounds of formula (II) can be administered in topical,otic or ophthalmic form via use of suitable vehicles.

In the methods of using the compounds (II), they can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups, and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol, and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes, and the like. Disintegrators include, without limitation, starch, methyl cellulose, agar, bentonite, xanthan gum, and the like.

The compounds of formula (II) can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (II) may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl residues. Furthermore, the compound of formula (II) may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

EXAMPLE 1

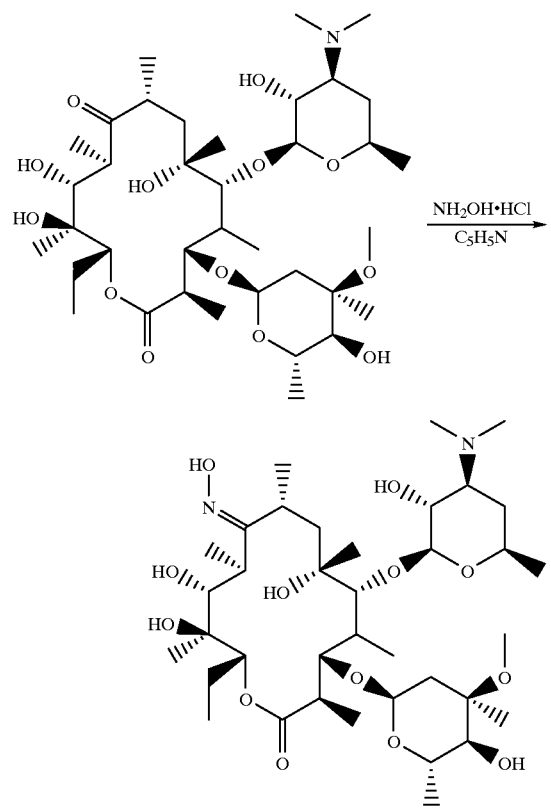

Preparation of (9E)-9-Deoxo-9-hydroxyiminoerythromycin A

Hydroxylamine hydrochloride (224 g, 3.23 mol) was added to a solution of erythromycin A (100 g, ca. 95% pure, 0.129 mol, available from Aldrich Chemical Co., Milwaukee Wis.) in pyridine (500 mL). The resulting mixture was stirred at room temperature for 27 hours, and then concentrated under vacuum at ca. 40° C. The semi-solid residue was kept under high vacuum overnight, then stirred with ethanol (600 mL) for 15 minutes and filtered. The collected solids were washed with hot (50° C.) ethanol. The combined filtrate and washing was evaporated under vacuum to a pale blue foam. The foam was shaken with water (850 mL) to give a thick emulsion which was stirred rapidly at room temperature for 2.5 hours to give a filterable precipitate. The precipitate was collected, washed with water (150 mL), and dried under vacuum to give a white solid (117.7 g).

The crude oxime hydrochloride was suspended in 5% aqueous sodium bicarbonate (1000 mL) and methylene chloride (1000 mL), and the mixture was stirred while the pH was adjusted to 9.5 by addition of 5N aqueous sodium hydroxide. The layers were separated and the aqueous portion was extracted with ethyl acetate (500 mL) and ethyl ether (500 mL). The combined organic layer and extracts were dried over sodium sulfate, filtered, and evaporated under vacuum to a white solid (92.3 g). The solid was dissolved in hot ethyl acetate (250 mL), and the solution diluted with hot hexanes (400 mL) and left overnight in a refrigerator. The crystals of (9E)-9-deoxo-9-hydroxyiminoerythromycin A were collected, washed with ice-cold hexane (250 mL), and dried under vacuum to afford a white solid (88.5 g).

IR (CH$_2$Cl$_2$) 3560, 3400 (br), 2980, 2950, 1735, 1460, 1389, 1165, 1110, 1085, 1050, and 1010 cm$^{-1}$.

$^1$H NMR (CDCl$_3$) δ5.05 (dd, H-13), 4.90 (d, H-1"), 4.38 (d, H-1"), 4.01 (m, H-5"), 3.99 (d, H-3), 3.74 (m, H-8), 3.66 (s, H-11), 3.54 (d, H-5), 3.45 (m, H-5), 3.28 (s, OCH$_3$), 3.23 (dd, H-2'), 2.96 (t, H-4"), 2.87 (m, H-2), 2.64 (q, H-10), 2.43 (m, H-3'), 2.32 (d, H-2" eq), 2.27 (s, N(CH$_3$)$_2$), 1.98 (m, H-4), 1.87 (m, H-14eq), 1.63 (m, H-4'eq), and 1.46 (s, 6-CH$_3$).

$^1$H NMR (CD$_3$OD) δ5.19 (dd, H-13), 4.48 (d, H-1'), 4.15 (dq, H-5"), 3.98 (d, H-3), 3.76 (m, H-8), 3.70 (m, H-5'), 3.67 (s, H-11), 3.58 (d, H-5), 3.33 (s, OCH$_3$), 3.23 (dd, H-2'), 3.01 (d, H-4"), 2.92 (m, H-2), 2.72 (m, H-10), 2.70 (m, H-3'), 2.43 (d, H-2"eq), 2.33 (s, N(CH$_3$)$_2$), 2.01 (m, H-4), 1.88 (m, H-14eq), 1.72 (m, H-4'eq), 1.58 (dd, H-2"ax), 1.48 (m, H-14ax), 1.45 (s, 6-CH$_3$), 1.26 (d, 5"-CH$_3$), 1.23 (s, 3"-CH$_3$), 1.14 (s, 12-CH$_3$), 1.10 (d, 4-CH$_3$), 1.05 (d, 8-CH$_3$), and 0.84 (t, CH$_2$C$\underline{H}_3$).

$^{13}$C NMR (CDCl$_3$) δ175.3, 171.3, 103.1, 96.3, 83.5, 80.3, 78.1, 77.1, 75.1, 74.3, 72.6, 71.2, 70.9, 68.8, 65.4, 65.3, 49.4, 44.6, 40.3, 38.8, 37.8, 35.1, 32.6, 29.2, 27.0, 25.4, 21.5, 21.3, 18.7, 18.6, 16.3, 14.3, 10.6, and 9.3.

$^{13}$C NMR (CD$_3$OD) δ177.5, 171.6, 104.0, 98.0, 84.2, 81.2, 79.3, 78.3, 76.3, 74.2, 72.9, 72.2, 69.0, 66.7, 65.2, 50.0, 46.3, 40.7, 39.3, 36.2, 32.0, 27.4, 26.7, 22.3, 22.0, 21.6, 19.3, 19.1, 17.3, 16.6, 14.8, 11.2, and 10.2.

EI Mass Spectrum, m/z 748, 590, 574, 462, 431, 416, 398, 174, 159, 158, and 116.

EXAMPLE 2

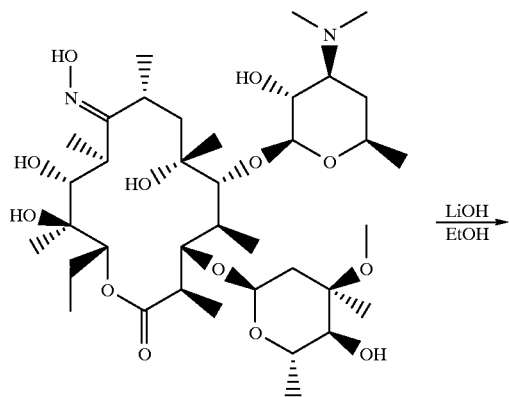

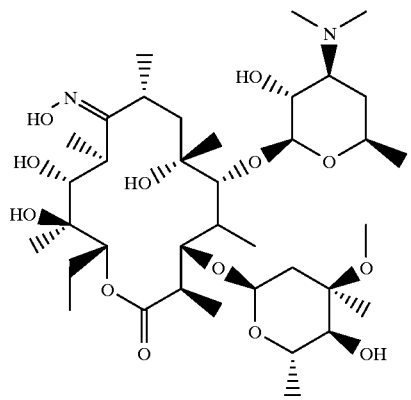

Conversion of (9E)-9-Deoxo-9-hydroxyiminoerythromycin A to (9Z)-9-Deoxo-9-hydroxyiminoerythromycin A Method 1:

(9E)-9-Deoxo-9-hydroxyiminoerythromycin A (20.0 g, 26.7 mMol) was added to a stirred solution of lithium hydroxide monohydrate (2.25 g, 53.5 mMol) in absolute ethanol (200 mL). The solution was blanketed with nitrogen and stirred overnight at room temperature. The solvents were evaporated under vacuum and the residue was partitioned between ethyl acetate (200 mL) and brine (120 mL). The pH of the mixture was adjusted from 11 to 9.3 with 2 N hydrochloric acid. The ethyl acetate was removed and the brine was re-extracted with more ethyl acetate (2×200 mL). The combined ethyl acetate extracts were washed with brine (100 mL), dried with anhydrous magnesium sulfate, filtered and evaporated under vacuum to a foam (ca. 20 g).

The crude oxime mixture was dissolved in methylene chloride (220 mL) and stirred for 1 hour at room temperature to give a filterable, white solid (18.7 g). This material was dissolved in ethyl acetate (100 mL), diluted with nitromethane (100 mL), and 50 mL of solvent was evaporated under vacuum. Additional nitromethane (50 mL) was added and 80 aL of solvent was evaporated under vacuum. The solution was seeded with the (9Z)-isomer and stirred at ambient temperature for 3 hours. The resulting suspension was filtered and the solids were rinsed with nitromethane (20 mL) and dried under a stream of nitrogen to afford (9Z)-9-deoxo-9-hydroxyiminoerythromycin A (14.8 g, 74% yield) as a white solid.

MP 157–164° C.

IR (CHCl$_3$) 3680, 3435 (br), 2970, 2940, 1725, 1455, 1375, 1345, 1165, 1105, 1085, 1045, 1005, and 950 cm$^{-1}$.

$^1$H NMR (CDCl$_3$) δ5.01 (dd, H-13), 4.87 (d, H-1") 4.40 (d, H-1'), 3.98 (m, H-3 and H-5"), 3.80 (s, H-11), 3.49 (m, H-5 and H-5'), 3.27 (s, OCH$_3$), 3.21 (dd, H-2'), 2.99 (m, H-4"), 2.8 (m, H-8, H-2 and H-10), 2.74 (m, H-10), 2.43 (m, H-3'), 2.32 (d, H-2"eq), 2.27 (s, N(CH$_3$)$_2$), 1.91 (m, H-4), 1.87 (m, H-14eq), 1.63 (m, H-4'eq), 1.51 (m, H-2"ax and H-7), 1.42 (m, H-14ax), 1.37 (s, 6-CH$_3$), 1.28 (d, 10-CH$_3$), 1.24 (d, 5"-CH$_3$), 1.19 (s, 3"-CH$_3$), 1.18 (d, 5'-CH$_3$), 1.12 (d, 2-CH$_3$), 1.11 (s, 12-CH$_3$), 1.08 (d, 8-CH$_3$), 1.04 (d, 4-CH$_3$), and 0.79 (t, CH$_2$C$\underline{H}_3$).

$^1$H NMR (CD$_3$OD) δ5.20 (br d, H-13), 4.50 (br d, H-1'), 4.16 (dq, H-5"), 4.02 (d, H-3), 3.70 (m, H-5'), 3.56 (br d, H-5), 3.34 (s, OCH$_3$), 3.25 (dd, H-2'), 3.03 (d, H-4"), 2.87 (m, H-8), 2.84 (m, H-2), 2.73 (m, H-3'), 2.44 (d, H-2"eq), 2.33 (s, N(CH$_3$)$_2$), 1.97 (m, H-4), 1.88 (m, H-14eq), 1.73 (m, H-4'eq), 1.64 (m, H-7), 1.59 (dd, H-2"ax), 1.47 (m, H-14ax), 1.36 (br 8, 6-CH$_3$), 1.28 (d, 5"-CH$_3$), 1.24 (s, 3"-CH$_3$), 1.18 (m, 5'-CH$_3$, 2-CH$_3$, 8-CH$_3$ and 10-CH$_3$)), 1.13 (s, 12-CH$_3$), 1.08 (d, 4-CH$_3$), and 0.86 (t, CH$_2$C$\underline{H}_3$).

$^{13}$C NMR (CDCl$_3$) δ176.2, 168.2, 102.8, 95.9, 83.6 (br), 79.3 (br), 77.9, 77.3, 75.2, 75.1, 72.7, 71.0, 70.9, 68.8, 65.5, 65.3, 49.4, 40.2, 39.9 (br), 37.8 (br), 35.7 (br), 34.9, 34.1 (br), 28.9, 26.0 (br), 21.4, 21.3, 19.8 (br), 18.4, 16.8, 15.3 (br), 10.7, and 9.2.

$^{13}$C NMR (CD$_3$OD) δ177.7, 170.0, 103.9, 97.7, 84.3 (br), 80.7, 79.2, 78.1, 77.0 (br), 76.1, 74.1, 72.8, 71.7 (br), 69.2, 66.7, 65.1, 49.9, 46.2 (br), 41.8 (br), 40.8, 40.5 (br), 36.0, 33.8 (br), 31.9, 26.7 (br), 22.8, 21.8, 21.7 (br), 21.6, 19.1, 17.5, 15.8 (br), 12.2 (br), 11.3, and 10.1.

FAB mass spectrum, m/z 749, 591, 416, 398, 174, 159, 158, and 116.

Elemental Analysis.

Calculated for C$_{37}$H$_{68}$N$_2$O$_{13}$: C, 59.34; H, 9.15; N, 3.74. Found: C, 59.12; H, 8.80; N, 3.82.

Method 2: 1.0 LiOH in EtOH (9E)-9-Deoxo-9-hydroxyiminoerythromycin A (255 mg, 0.34 mmol) was added to a solution of lithium hydroxide monohydrate (14.3 mg, 0.34 mmol) in absolute ethanol (2.55 mL). The resulting solution was stirred at room temperature for 25 hours, and then stored in a freezer at −20° C. for 68 hours. After warming to room temperature, the solution was evaporated under reduced pressure to remove the solvent. The residue was stirred with saturated aqueous sodium chloride (5 mL) and ethyl acetate (5 mL) while the pH was adjusted to 9.2 by addition of dilute hydrochloric acid. After shaking, the phases were separated and the aqueous portion extracted with more ethyl acetate (2×2.5 mL). The combined ethyl acetate extracts were washed with saturated sodium chloride solution (4 mL), dried over magnesium sulfate, filtered and evaporated at reduced pressure to afford a white foam (263 mg). Examination of this material by $^1$H NMR spectroscopy revealed a 31:69 mixture of (9E)-9-deoxo-9-hydroxyiminoerythromycin A and (9Z)-9-deoxo-9-hydroxyiminoerythromycin A.

Method 3: 2.0 LiOH in EtOH (9E)-9-Deoxo-9-hydroxyiminoerythromycin A (291 mg, 0.333 mmol) was added to a solution of lithium hydroxide monohydrate (32.6 mg, 0.776 mmol) in absolute ethanol (2.9 mL). The resulting solution was stirred at room temperature under a nitrogen atmosphere for 22.5 hours. The solvent was evaporated at reduced pressure and the residue stirred with ethyl acetate (5 mL) and saturated aqueous sodium chloride (5 mL) while adjusting the pH to 9 by addition of 2N hydrochloric acid. The mixture was shaken, the phases separated, and the aqueous portion extracted with more ethyl acetate (2×2.5 mL). The combined ethyl acetate extracts were washed with saturated sodium chloride solution (4 mL), dried with magnesium sulfate, filtered and evaporated under vacuum to a white foam (299 mg). This material was shown by $^1$H NMR to be a 21:79 mixture of (9E)-9-deoxo-9-hydroxyiminoerythromycin A and (9Z)-9-deoxo-9-hydroxyiminoerythromycin A.

Method 4: 3.0 LiOH in EtOH (9E)-9-Deoxo-9-hydroxyiminoerythromycin A (239 mg, 0.319 mmol) was added to a mixture of lithium hydroxide monohydrate (40.2 mg, 0.957 mmol) in absolute ethanol (2.4 mL), and the resulting solution was stirred at room temperature under a nitrogen atmosphere for 21.7 hours. Workup as described in method 3 afforded a white foam (236 mg) shown by $^1$H NMR to consist of a 19:81 mixture of (9E)-9-deoxo-9-hydroxyiminoerythromycin A and (9Z)-9-deoxo-9-hydroxyiminoerythromycin A.

Method 5: 2.0 NaOEt in EtOH

Freshly cut sodium metal (48 mg, 2.087 mmol) was dissolved in absolute ethanol (7.8 mL) under a nitrogen atmosphere. (9E)-9-Deoxo-9-hydroxyiminoerythromycin A (782 mg, 1.043 mmol) was added and the resulting solution was stirred at room temperature. A crystalline precipitate, identified as the starting oxime by thin layer chromatography, appeared after a few hours. After stirring overnight, the mixture was once again a clear solution. After 54 hours, approximately half (3.9 mL) of the reaction mixture was removed and evaporated under reduced pressure. The gummy residue was stirred with ethyl acetate (5 mL) and saturated aqueous sodium chloride (5 mL) while the pH was adjusted to 9.2 by addition of dilute hydrochloric acid (2N and 0.2N solutions). The mixture was shaken, the layers separated, and the aqueous portion extracted with more ethyl acetate (2×2.5 mL). The combined ethyl acetate solution was washed with brine (5 mL), dried with magnesium sulfate, filtered and evaporated under reduced pressure to a white foam (361 mg). This material was shown by $^1$H NMR spectroscopy to consist of a 22:78 mixture of the (9E) and (9Z) isomers of 9-deoxo-9-hydroxyiminoerythromycin A.

Method 6: 2.0 NaOH in EtOH

The remaining half of the reaction mixture from method 5 was treated with water (0.0188 mL, 1.04 mmol) to give a solution effectively consisting of sodium hydroxide and oxime in ethanol. The solution was stirred at room temperature for 23 hours, then worked up as described in method 5 to give a white foam (402 mg). This material was shown by $^1$H NMR to consist of a 24:76 mixture of the (9E) and (9Z) isomers of 9-deoxo-9-hydroxyiminoerythromycin A.

Method 7: 2.0 LiOH in MeOH

A solution of lithium hydroxide monohydrate (37 mg, 0.88 mmol), (9E)-9-deoxo-9-hydroxyiminoerythromycin A (330 mg, 0.44 mmol), and methanol (3.3 mL) was stirred at room temperature for 65.5 hours. The solution was then stored at −20° C. for 13 days before warming to room temperature and evaporating the solvent at reduced pressure. The residue was stirred with ethyl acetate (5 mL) and brine (5 mL) while adjusting the pH to 9.2 by successive addition of dilute hydrochloric acid. The mixture was shaken, the layers separated and the aqueous portion extracted with more ethyl acetate (2×2.5 mL). The combined ethyl acetate solution was washed with brine (5 mL), dried with magnesium sulfate, and evaporated under vacuuum to provide a white foam (324 mg). NMR analysis of this material indicated a 45:55 ratio of (9E) to (9Z) 9-deoxo-9-hydroxyiminoerythromycin A products.

Method 8: 2.0 NaOMe in MeOH

A solution of (9E)-9-deoxo-9-hydroxyiminoerythromycin A (375 mg, 0.5 mmol) in anhydrous methanol (3.5 mL) was cooled in an ice bath and stirred under a nitrogen atmosphere while methanolic sodium methoxide (0.23 mL of a 25 wt % solution, 1.01 mmol) was added by syringe. The cooling bath was removed and the solution was stirred at room temperature under a nitrogen atmosphere for 66 hours. The solution was then stored at −20° C. for 13.3 days before being processed to a white foam (329 mg) as described in method 7. The product consisted of a 35:65 mixture of (9E)-9-deoxo-9-hydroxyiminoerythromycin A and (9Z)-9-deoxo-9-hydroxyiminoerythromycin A as determined by $^1$H NMR spectroscopy.

Method 9: 10.0 NaOMe in MeOH

A solution of (9E)-9-deoxo-9-hydroxyiminoerythromycin A (100 mg, 0.134 mmol) in anhydrous methanol (4.70 mL) was treated with sodium methoxide (0.305 mL of a 25 wt.

% solution in methanol, 1.335 mmol) and stirred at room temperature for 74.5 hours. The solvent was evaporated under reduced pressure and the residue stirred with ethyl acetate (5 mL) and brine (5 mL) while adjusting the pH of the aqueous layer to 9.4 with 2N hydrochloric acid. The mixture was shaken, the layers separated and the aqueous portion extracted with more ethyl acetate (2×2.5 mL). The combined ethyl acetate solution was washed with brine (5 mL), dried with magnesium sulfate, filtered and evaporated at reduced pressure to afford a white foam (102 mg). This material was shown by $^1$H NMR spectroscopy to consist of a 26:74 mixture of the (9E) and (9Z) isomers of 9-deoxo-9-hydroxyiminoerythromycin A.

Method 10: 2.0 LiOH in iPrOH (9E)-9-Deoxo-9-hydroxyiminoerythromycin A (279 mg, 0.361 mmol) was added to a partial solution of lithium hydroxide monohydrate (30.3 mg, 0.721 mmol) in isopropanol (2.7 mL), and the mixture was stirred at room temperature in a capped flask. A fine white precipitate formed in a few minutes and, after stiring overnight, the mixture was a hazy suspension. After 21 hours, the mixture was transferred to a freezer at –20° C. and stored there for 15 days. After warming to room temperature, the solvent was evaporated under vacuum and the residue stirred with ethyl acetate (5 mL) and brine (5 mL) while adjusting the pH to 9.2 with dilute hydrochloric acid. The mixture was shaken, the layers separated, and the aqueous phase extracterd with more ethyl acetate (2×2.5 ml). The combined ethyl acetate solution was washed with brine (4 mL), dried with magnesium sulfate, filtered and evaporated under vacuum to afford a white foam (249 mg). The product consisted of a 26:74 mixture of (9E)-9-deoxo-9-hydroxyiminoerythromycin A and (9Z)-9-deoxo-9-hydroxyiminoerythromycin A as determined by $^1$H NMR spectroscopy.

Method 11: 1.0 LiOH in MeCN

A mixture of (9E)-9-deoxo-9-hydroxyiminoerythromycin A (500 mg, 0.668 mmol), lithium hydroxide monohydrate (28 mg, 0.668 mmol), and absolute ethanol (5 mL) was stirred at room temperature for 10 minutes to give a solution. The solution was evaporated under reduced pressure to afford a residue that was twice diluted with ethanol (10 mL) and evaporated at reduced pressure and then suspended in anhydrous acetonitrile (5 mL) and evaporated at reduced pressure. The solid residue was suspended in anhydrous acetonitrile (5 mL) and the mixture was stirred at room temperature for 18 days. The solvent was evaporated under reduced pressure and the residue was stirred with ethyl acetate (5 mL) and saturated aqueous sodium chloride solution (5 mL) while adjusting the pH of the aqueous phase to 9.5 by addition of dilute hydrochloric acid. The mixture was shaken, the layers separated, and the aqueous portion was extracted with additional ethyl acetate (2×2.5 mL). The combined ethyl acetate solution was washed with brine (5 mL), dried over magnesium sulfate, filtered and evaporated under reduced pressure to afford a foam (442 mg). This material was shown by $^1$H NMR spectroscopy to consist of a 44:56 mixture of the (9E) and (9Z) isomers of 9-deoxo-9-hydroxyiminoerythromycin A.

Method 12: 1.0 LiOH in DMF

A mixture of (9E)-9-deoxo-9-hydroxyiminoerythromycin A (500 mg, 0.668 mmol), lithium hydroxide monohydrate (28 mg), and dimethylformamide (5 mL) was stirred at room temperature in a capped flask. After a few hours, the initial suspension gave way to a solution. After stirring for 18 days and 18 hours, the solution was evaporated under reduced pressure and the residue was processed as described in method 11 to afford a foam (402 mg). Analysis of this material by $^1$H NMR spectroscopy indicated a 62:38 mixture of the (9E) and (9Z) isomers of 9-deoxo-9-hydroxyiminoerythromycin A.

Method 13: 1.2 LiN(SiMe$_3$)$_2$ in MECN

A suspension of (9E)-9-deoxo-9-hydroxyiminoerythromycin (500 mg, 0.668 mmol) in anhydrous acetonitrile (4 mL) was treated with lithium hexamethyldisilazide (0.80 mL of a 1M solution in hexane, 0.80 mmol). The resulting suspension rapidly gave way to a solution which reformed a suspension after stirring several days at room temperature. After 18 days and 19 hours, the reaction mixture was worked up as described im method 11 to afford a foam (423 mg). This material was shown by $^1$H NMR spectroscopy to be a 50:50 mixture of (9E)-9-deoxo-9-hydroxyiminoerythromycin A and (9Z)-9-deoxo-9-hydroxyiminoerythromycin A.

EXAMPLE 3

Crystallization of (9Z)-9-Deoxo-9-hydroxyiminoerythromycin A

A 3:1 mixture (30.0 g) of (9Z)-9-deoxo-9-hydroxyiminoerythromycin A and (9E)-9-deoxo-9-hydroxyiminoerythromycin A was added over 2 minutes to well stirred ethyl acetate (60 mL). After obtaining a solution, methylene chloride (120 mL) was rapidly added and the resulting suspension was stirred in an ice bath for one hour. The precipitate was filtered off, washed with methylene chloride (60 mL), and dried under a stream of nitrogen to afford an 86:14 mixture (26.5 g) of (9Z)-9-deoxo-9-hydroxyiminoerythromycin A and (9E)-9-deoxo-9-hydroxyimenoerythromycin A.

A solution of the above solid in ethyl acetate (60 mL) was diluted with methylene chloride (120 mL). The resulting suspension was cooled in an ice bath for one hour and then filtered. The collected solid was rinsed with methylene chloride (60 mL) and dried under a stream of nitrogen to afford a 95:5 mixture (23.4 g) of (9Z)-9-deoxo-9-hydroxyiminoerythromycin A and (9E)-9-deoxo-9-hydroxyiminoerythromycin A.

EXAMPLE 4

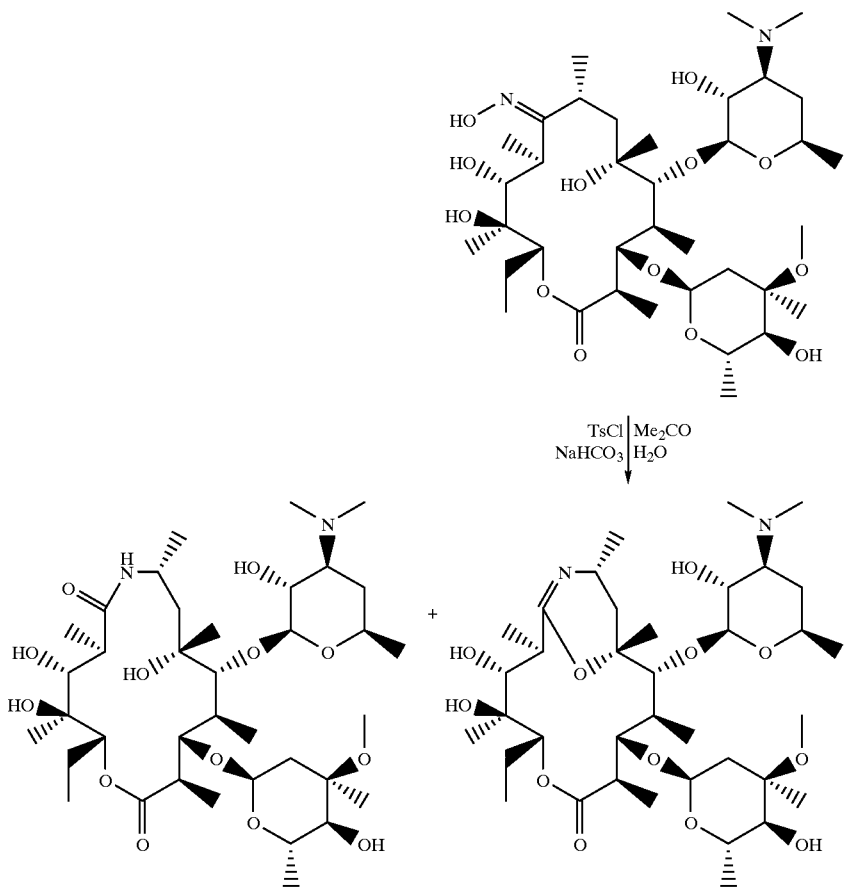

Synthesis of 8a-Aza-8a-homoerythromycin A and 9-Deoxo-6-deoxy-6.9-epoxy-8a,9-didehydro-8a-aza-8a-homoerythromycin A by the Beckmann Rearrangement of (9Z)-9-Deoxo-9-hydroxyiminoerythromycin A Method 1:

(9Z)-9-Deoxo-9-hydroxyiminoerythromycin A (200 mg, 9.27 mMol) was dissolved in acetone (2 mL) and the resulting solution was cooled in an ice-bath and stirred under a nitrogen atmosphere. A solution of sodium bicarbonate (84 mg, 1.0 mMol) in water (2 mL) was added followed by the dropwise addition of an acetone solution (2 mL) of p-toluenesulfonyl chloride (100 mg, 0.53 mMol) over 5 minutes.

After stirring for 1.5 hours at 0–5° C., the mixture was diluted with dichloromethane (10 mL) and water (5 mL), and the pH was adjusted from 10 to 5.5 with 2N HCl. The dichloromethane layer was discarded and the aqueous layer was washed with additional dichloromethane (2×10 mL) which was also discarded. Dichloromethane (10 mL) was added to the aqueous layer and the pH was adjusted to 8.5 with 2.5 N NaOH. The dichloromethane layer was removed and the aqueous layer was extracted with more dichloromethane (2×20 mL). The combined dichloromethane extracts were dried over anhydrous magnesium sulfate, filtered and evaporated under vacuum to give a mixture of the title compounds as a foam (150 mg).

The above mixture was purified by preparative layer chromatography (two 0.1 mm×20×20 cm Analtech silica gel GF plates, developing and eluting with 60:10:1 dichloromethane-methanol concentrated ammonium hydroxide) to afford 8a-aza-8a-homoerythromycin A (95 mg,) and 9-deoxo-6-deoxy-6,9-epoxy-8a,9-didehydro-8a-aza-8a-homoerythromycin A (33 mg).

Method 2:

A solution of p-toluenesulfonyl chloride (1.00 g, 5.2 mmol) in acetone (20 mL) was added to a solution of sodium bicarbonate (0.90 g, 10.7 mmol) in water (20 mL). The resulting suspension was cooled in a −10° C. bath and stirred while a solution of (9Z)-9-deoxo-9-hydroxyiminoerythromycin A (2.00 g, 2.7 mmol) in acetone (20 mL) was added slowly over 75 minutes. The mixture was stirred at −10° C. for 5 hours, then warmed to 0° C. over 10 minutes and stirred at 0–5° C. for 30 minutes. The mixture was evaporated under vacuum to remove the acetone. The aqueous residue was diluted with water (40 mL) and dichloromethane (60 mL) and stirred while the pH was adjusted to 5.5 with dilute hydrochloric acid. The aqueous layer was separated, washed with dichloromethane (60 mL), layered with dichloromethane (60 mL), and stirred while the pH was brought to 9 with dilute aqueous sodium hydroxide. The layers were separated and the aqueous portion extracted with more dichloromethane (2×50 mL). The combined pH 9 extracts were dried over magnesium sulfate, filtered and evaporated under reduced pressure to afford a gum (1.97 g) which was shown by $^1$H NMR spectroscopy to be a 1:1 mixture of 8a-aza-8a-homoerythromycin A and 9-deoxo-6-deoxy-6,9-epoxy-8a,9-didehydro-8a-aza-8a-homoerythromycin A.

The crude product mixture was dissolved in 120:10:1 dichloromethane-methanol-conc. aqueous ammonium hydroxide (5 mL) and loaded onto a column of silica gel (4×16 cm). The column was eluted with 120:10:1 dichloromethane-methanol-ammonium hydroxide. After a 150 mL forerun, 15 mL fractions were collected. Fractions 9–13 were combined and evaporated under vacuum to afford 9-deoxo-6-deoxy-6,9-epoxy-8a,9-didehydro-8a-aza-8a-homoerythromycin A (ca. 500 mg) and fractions 22-26 were combined and evaporated to afford 8a-aza-8a-homoerythromycin A (ca. 500 mg). The later product was crystallized from ether to give the amide (ca. 130 mg) as a white solid.

Physical data for 9-deoxo-6-deoxy-6,9-epoxy-8a,9-didehydro-8a-aza-8a-homoerythromycin A:

IR (CHCl$_3$) 3550, 3440 (br), 2970, 2940, 2880, 1725, 1665, 1455, 1375, 1345, 1325, 1240, 1170, 1105, 1080, 1050, 1015, 995, and 955 cm$^{-1}$.

$^1$H NMR (CDCl$_3$) δ.02 (d, H-1"), 4.90 (dd, H-13), 4.48 (d, H-1'), 4.09 (dq, H-5"), 4.02 (t, H-3), 3.81 (d, H-5), 3.53 (m, H-5'), 3.49 (d, H-11), 3.43 (m, H-8), 3.35 (s, OCH$_3$), 3.20 (dd, H-2'), 3.07 (t, H-4"), 2.75 (dq, H-2), 2.68 dq, H-10), 2.52 (ddd, H-3'), 2.43 (d, H-2"eq), 2.28 (s, N(CH$_3$)$_2$), 1.98 ddq, H-4), 1.91 (m H-14a), 1.90 (dd, H-7a), 1.68 (ddd, H-4'eq), 1.62 (dd, H-2"ax), 1.46 (m, H-14b), 1.39 (s, 6-CH$_3$), 1.32 (d, 5"-CH$_3$), 1.27 (s 3"-CH$_3$), 1.24 (m, H-7b), 1.22 (d, 5'-CH$_3$), 1.21 (m H-4'ax), 1.16 (d, 10-CH$_3$), 1.15 d, 8-CH$_3$), 1.15 (s, 12-CH$_3$), 1.14 (d, 2-CH$_3$), 1.08 (d, 4-CH$_3$), and 0.87 (t, CH$_2$CH$_3$).

$^{13}$C NMR (CDCl$_3$) δ177.6, 160.6, 102.4, 94.6, 80.1, 78.9, 77.9, 77.4, 76.5, 75.7, 73.0, 70.6, 70.0, 68.8, 65.8, 65.6, 49.4, 44.9, 44.0, 42.3, 42.1, 40.3, 34.5, 32.0, 28.5, 23.8, 22.4, 21.5, 21.3, 21.0, 18.2, 17.0, 16.4, 12.5, 10.8, and 8.4.

FAB mass spectrum, m/z 731, 713, 602, 573, 555, 398, 159, 158, and 116.

Physical data for 8a-aza-8a-homoerythromycin A:

MP 170–176° C.

IR (CHCl$_3$) 3500 (br), 3430, 3320, 2970, 2935, 2880, 17730, 1630, 1560, 1525, 1455, 1375, 1325, 1280, 1170, 1160, 1105, 1085, 1045, 1010 and 995 cm$^{-1}$.

$^1$H NMR (CDCl$_3$) δ5.89 (br d, NH), 5.07 (d, H-1"), 4.92 (dd, H-13), 4.43 (d, H-1'), 4.35 (d, H-3), 4.21 (m, H-8), 4.01 (dq, H-5"), 3.58 (d, H-5), 3.50 (m, H-5S), 3.50 (s, H-11), 3.32 (s, OCH$_3$) 3.21 (dd, H-2'), 3.03 (t, H-4"), 2.62 (dq, H-2), 2.54 (m, H-3'), 2.35 (m, H-10), 2.35 (s, N(CH$_3$)$_2$), 2.31 (d, H-2"eq), 1.90 (m, H-4), 1.89 (m, H-14a), 1.75 (br d, H-4'eq), 1.57 (dd, H-2"ax), 1.51 (m, H-7a and H-7b), 1.44 (m, H-14b), 1.43 (s, 6-CH$_3$), 1.30 (d, 5"-CH$_3$), 1.24 (s, 3"-CH$_3$), 1.23 (m, H-4'ax), 1.23 (d, 5'-CH$_3$), 1.20 (d, 8-CH$_3$), 1.19 (d, 10-CH$_3$), 1.18 (d, 2-CH$_3$), 1.09 (s, 12-CH$_3$), 1.05 (d, 4-CH$_3$), and 0.89 (t, CH$_2$CH$_3$).

$^{13}$C NMR (CDCl$_3$) 177.6, 176.6, 102.7, 94.2, 83.0 77.9, 77.0, 76.6, 74.6, 73.7, 72.9, 70.0, 69.8, 68.8, 65.8, 65.2, 49.2, 45.8, 43.2, 42.4, 41.0, 40.4, 40.1, 34.5, 28.3, 27.6, 23.1, 21.7, 21.5, 21.2, 18.0, 16.1, 14.6, 11.2, 10.0, and 9.1

FAB mass spectrum, m/z 749, 731, 591, 589, 573, 416, 174, 159, 158, and 117.

Elemental Analysis.

Calculated for C$_{37}$H$_{68}$N$_2$O$_{13}$: C, 59.31; H, 9.15; N, 3.74. Found: C, 59.24; H, 9.15; N, 3.44 Loss on drying at 120° C., 3.11%.

EXAMPLE 5

Synthesis of 9-Deoxo-6-deoxy-6,9-epoxy-8a,9-didehydro-8a-aza-8a-homoerythromycin A and 9-Deoxo-12-deozy-9,12-epoxy-8a,9-didehydro-8a-aza-8a-homoerythromycin A by Beckmann Rearrangement of (9Z)-9-deoxo-9-hydroxyiminoerythromycin A

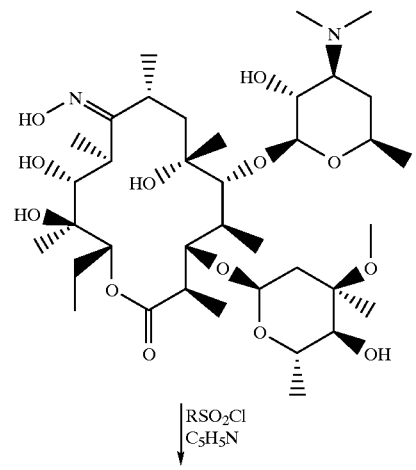

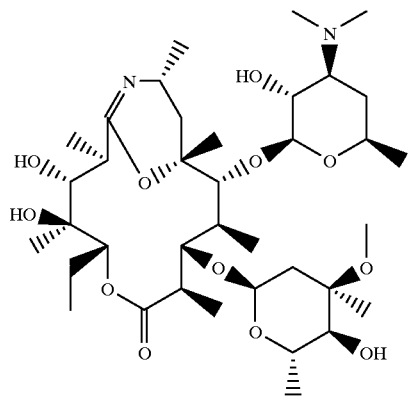 + 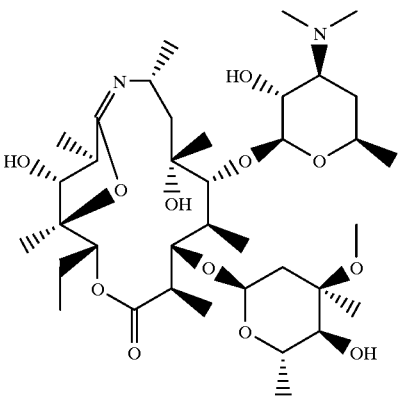

Method 1:

A solution of p-toluenesulfonyl chloride (15.0 g, 0.079 mol) in diethyl ether (50 mL) was added dropwise over 8 minutes to an ice-cold, stirring solution of 9(Z)-9-deoxo-9-hydroxyiminoerythromycin A (23.2 g, 0.031 mol) in pyridine (180 mL). The resulting solution was stirred at 0–5° C. for 2.5 hours, then diluted with dichloromethane (400 mL) and water (500 mL) and basified to pH 9.5 by addition of 5N sodium hydroxide. The layers were separated and the aqueous portion extracted with more dichloromethane (200 mL, 100 mL). The combined dichloromethane extracts were dried over magnesium sulfate, filtered, and evaporated under vacuum to afford an oil. Residual pyridine was removed by twice taking the product up in toluene (100 mL) and evaporating the solvent under vacuum. The resulting foam (21.4 g) was shown by 1H NMR spectroscopy to be a 26:74 mixture of 9-deoxo-6-deoxy-6,9-epoxy-8a,9-didehydro-8a-aza-8a-homoerythromycin A and 9-deoxo-12-deoxy-9,12-epoxy-8a,9-didehydro-8a-aza-8a-homoerythromycin A.

Method 2:

A solution of p-toluenesulfonyl chloride (160 mg, 0.84 mmol) in diethyl ether (0.5 mL) was added rapidly to an ice-cold solution of (9Z)-9-deoxo-9-hydroxyiminoerythromycin A (250 mg. 0.33 mmol) in pyridine (2.0 mL). The resulting solution was stirred at 0–5° C. for 1.5 hours, then diluted with dichloromethane (4 mL) and water (4 mL) and basified to pH 9.5 by addition of 5N sodium hydroxide. The layers were separated and the aqueous portion extracted with more dichloromethane (2×4 mL). The combined dichloromethane extracts were dried over magnesium sulfate, filtered, evaporated under vacuum and stripped with hexane (4×15 mL) to afford a yellow solid (260 mg.) This material was shown by $^1$H NMR spectroscopy to be a 25:75 mixture of 9-deoxo-6-deoxy-6,9-epoxy-8a,9-didehydro-8a-aza-8a-homoerythromycin A and 9-deoxo-12-deoxy-9,12-epoxy-8a,9-didehydro-8a-aza-8a-homoerythromycin A.

Method 3:

A solution of p-toluenesulfonyl chloride (160 mg, 0.84 mmol) in acetonitrile (0.5 mL) was added rapidly to an ice-cold solution of (9Z)-9-deoxo-9-hydroxyiminoerythromycin A (250 mg, 0.33 mmol) in pyridine (2.0 mL). The resulting solution was stirred at 0–5° C. for 80 minutes, then diluted with dichloromethane (4 mL) and water (5 mL) and basified to pH 9.5 by addition of 5N sodium hydroxide. The layers were separated and the aqueous portion extracted with more dichloromethane (2×4 mL). The combined dichloromethane extracts were dried over magnesium sulfate, filtered, and evaporated under vacuum to a foam which was stripped with toluene (2×10 mL) and hexanes (10 mL) to afford a solid (230 mg). This material was shown by $^1$H NMR spectroscopy to be a 33:67 mixture of 9-deoxo-6-deoxy-6,9-epoxy- and 9-deoxo-12-deoxy-9,12-epoxy-8a,9-didehydro-8a-aza-8a-homoerythromycin A.

Method 4:

A solution of p-toluenesfulfonyl chloride (160 mg, 0.84 mmol) in toluene (0.5 mL) was added rapidly to an ice-cold solution of (9Z)-9-deoxo-9-hydroxyiminoerythromycin A (250 mg, 0.33 mmol) in pyridine (2.0 mL). The resulting solution was stirred at 0–5° C. for 90 minutes, then diluted with dichloromethane (4 mL) and water (4 mL) and basified to pH 9.5 by addition of 1N sodium hydroxide. The layers were separated and the aqueous portion extracted with more dichloromethane (3×4 mL). The combined dichloromethane extracts were dried over magnesium sulfate, filtered, and evaporated under vacuum to a solid (250 mg). This material was shown by $^1$H NMR spectroscopy to be a 27:73 mixture of 9-deoxo-6-deoxy-6,9-epoxy- and 9-deoxo-12-deoxy-9,12-epoxy-8a,9-didehydro-8a-aza-8a-homoerythromycin A.

Method 5:

Benzenesulfonyl chloride (0.107 mL, 0.84 mmol) was added by syringe to an ice-cold solution of (9Z)-9-deoxo-9-hydroxyiminoerythromycin A (250 mg, 0.33 mmol) in pyridine (2.0 mL). The resulting solution was stirred at 0–5° C. for 75 minutes, then processed as described above to afford a yellow solid (240 mg). This material was shown by $^1$H NMR spectroscopy to be a 31:69 mixture of 9-deoxo-6-deoxy-6,9-epoxy- and 9-deoxo-12-deoxy-9,12-epoxy-8a,9-didehydro-8a-aza-8a-homoerythromycin A.

Method 6:

Methanesulfonyl chloride (0.065 mL, 0.84 mmol) was added by syringe to an ice-cold solution of (9Z)-9-deoxo-9-hydroxyiminoerythromycin A (250 mg, 0.33 mmol) in pyridine (2.0 mL). The resulting solution was stirred at 0–5° C. for 2 hours, then processed as described above to afford an off-white solid (246 mg). This material was shown by $^1$H NMR spectroscopy to be a 25:70:5 mixture of 9-deoxo-6-deoxy-6,9-epoxy-8a,9-didehydro-8a-aza-8a-homoerythromycin A, 9-deoxo-12-deoxy-9,12-epoxy-8a,9-didehydro-8a-aza-8a-homoerythromycin A, and 9-deoxy-12-deoxy-9,12-epoxy-4"-O-methanesulfonyl-8a,9-didehydro-8a-aza-8a-homoerythromycin A.

Method 7:

A solution of (9Z)-9-deoxo-9-hydroxyiminoerythromycin A (250 mg, 0.33 mmol) in pyridine (2.0 mL) was cooled in a −20° C. bath and treated with methanesulfonyl chloride (0.071 mL, 0.92 mmol). The resulting hazy solution was stirred at −10 to −20° C. for 90 minutes, then processed as described above to afford a yellow solid (254 mg). This material was shown by $^1$H NMR spectroscopy to be a 88:12 mixture of 9-deoxo-6-deoxy-6,9-epoxy-8a,9-didehydro-8a-aza-8a-homoerythromycin A and 9-deoxo-12-deoxy-9,12-epoxy-8a,9-didehydro-8a-aza-8a-homoerythromycin A.
Method 8:

A mixture of (9Z)-9-deoxo-9-hydroxyiminoerythromycin A (0.50 g, 0.67 mmol), p-toluenesulfonyl chloride (318 mg, 1.67 mmol) and pyridine (0.162 mL, 2.0 mmol) in dichloromethane (5.0 mL) was stirred at room temperature for 1.5 hours. The mixture was diluted with water and stirred rapidly while adjusting the pH to 11 with 5N sodium hydroxide. The organic phase was separated, dried with magnesium sulfate, filtered and evaporated under reduced pressure to afford a yellow solid (570 mg.) Analysis of the crude product by $^1$H NMR spectroscopy revealed a 80:20 mixture of 9-deoxo-6-deoxy-6,9-epoxy-8a,9-didehydro-8a-aza-8a-homoerythromycin A and 9-deoxo-12-deoxy-9,12-epoxy-8a,9-didehydro-8a-aza-8a-homoerythromycin A.

EXAMPLE 6

Purification of 9-Deoxo-12-deoxy-9,12-epoxy-8a,9-didehydro-8a-aza-8a-homoerythromycin A by Column Chromatography Although unnecessary for the following reduction step, it is possible to separate the isomeric 6,9-epoxy- and 9,12-epoxy products by silica gel or alumina column chromatography. The following procedure illustrates the purification process for 9-deoxo-12-deoxy-9,12-epoxy-8a,9-didehydro-8a-aza-8a-homoerythromycin A.

The crude products from methods 3 and 4 above were combined, dissolved in 94:5:1 dichloromethane-methanol-triethylamine, and loaded onto a column of silica gel (230–400 mesh, 2.5×24.5 cm, wet packed under 94:5:1 dichloromethane-methanol-triethylamine). The column was eluted with 94:5:1 dichloromethane-methanol-triethylamine, collecting 6 mL fractions. Fractions 15–18 were combined, evaporated under reduced pressure, and the residue twice stripped with toluene to provide 9-deoxo-12-deoxy-9,12-epoxy-8a,9-didehydro-8a-aza-8a-homoerythromycin A (190 mg) as a foam. The product is a mixture of major and minor forms, isomeric about the 8a,9-imino double bond, as ascertained by $^1$H and $^{13}$C NMR spectroscopy.

IR (CHCl$_3$) 3550, 3390 (br), 2975, 2940, 2880, 1735, 1690, 1455, 1375, 1240, 1165, 1085, 1045, 1010, and 970 cm$^{-1}$.

FAB mass spectrum, m/z 731, 713, 602, 573, 556, and 158

EXAMPLE 7

Chromatographic Separation of 9-Deoxo-6-deoxy-6,9-epoxy-8a,9-didehydro-8a-aza-8a-homoerythromycin A and 9-Deoxo-12-deoxy-9,12-epoxy-8a,9-didehydro-8a-aza-8a-homoerythromycin A and Crystallization of 9-Deoxo-12-deoxy-9,12-epoxy-8a,9-didehydro-8a-aza-8a-homoerythromycin A A sample (4.0 g) of the crude product mixture obtained as described in method 1 of Example 5 was dissolved in 60:10:1 dichloromethane-methanol-conc. aqueous ammonium hydroxide (6 mL) and the solution was loaded onto a column of EM silica gel 60 (4.5×18 cm, 230–400 mesh, wet packed under 60:10:1 dichloromethane-methanol-conc. ammonium hydroxide). The column was eluted with 60:10:1 dichloromethane-methanol-conc. aqueous ammonium hydroxide. The fractions collected from 150 mL to 165 mL of eluant were evaporated under vacuum to afford 9-deoxo-6-deoxy-6,9-epoxy-8a,9-didehydro-8a-aza-8a-homoerythromycin A (0.34 g) as a foam. The fractions collected from 185 mL to 285 mL of eluant were combined and evaporated under reduced pressure to afford a mixture of the two isomeric forms of 9-deoxo-12-deoxy-9,12-epoxy-8a,9-didehydro-8a-aza-8a-homoerythromycin A (1.36 g) as a foam.

A solution of the mixture of 9,12-epoxy isomers in nitromethane (2 mL) deposited a large, crystalline mass on standing at room temperature for several days. The mixture was diluted with nitromethane (10 mL) and filtered to remove the solid portion, which was washed with nitromethane (2 mL) and dried under high vacuum. The white solid thus obtained (0.9 g) was shown by $^1$H NMR spectroscopy to be the major 9,12-epoxy isomer which is initially formed in the Beckmann rearrangement reaction. While stable in the solid state, solutions of the crystalline isomer in chloroform-d isomerize at room temperature in several hours to a 1:1 mixture of the two imino double bond isomers of 9-deoxo-12-deoxy-6,9-epoxy-8a,9-didehydro-8a-aza-8a-homoerythromycin A.

Physical data for 9-deoxo-12-deoxy-9.12-epoxy-8a,9-didehydro-8a-aza-8a-homoerythromycin A:
Isomer A (crystalline isomer)
MP 124–130° C. (slowly softens).

IR (CHCl$_3$) 3550, 3380 (br), 2970, 2935, 2875, 1735, 1695, 1560, 1460, 1375, 1250, 1165, 1115, 1058, 1045, 1015, and 975 cm$^{-1}$.

1H NMR (CDCl$_3$) δ5.17 (dd, H-13), 4.73 (d, H-1"), 4.47 (d, H-1'), 4.15 (dq, H-5"), 4.09 (dd, H-3), 3.99 (br s, H-5), 3.81 (t, H-11), 3.68 (m, H-8), 3.65 (m, H-5'), 3.40 (ddd, H-2'), 3.23 (s, OCH$_3$), 2.96 (t, H-4"), 2.70 (O, H-10), 2.68 (m, H-3'), 2.57 (br d, 11-OH), 2.45 (p, H-2), 2.31 (s, N(CH$_3$)$_2$), 2.28 (d, H-2"eq), 2.20 (d, 4"-OH), 2.07 (ddq, H-14a), 1.90 (br d, H-7a), 1.75 (dd, H-7b), 1.74 (m, H-4), 1.70 (m, H-4'eq), 1.69 (m, H-14b), 1.46 (dd, H-2"az), 1.40 (s, 6-CH$_3$), 1.29 (m, H-4'ax), 1.27 (d, 10-CH$_3$), 1.27 (d, 5"-CH$_3$), 1.25 (d, 2-CH$_3$), 1.24 (d, 5'-CH$_3$), 121 (s, 3"-CH$_3$), 1.18 (s, 12-CH$_3$), 1.07 (d, 8-CH$_3$), 1.01 (d, 4-CH$_3$), and 0.86 (t, CH$_2$CH$_3$).

$^{13}$C NMR (CDCl$_3$) δ174.2, 161.3, 106.7, 98.3, 85.4, 84.2, 80.5, 79.8, 77.4, 75.0, 72.3, 70.3, 69.4, 66.3, 63.8, 49.4, 49.2, 49.0, 47.1, 45.4, 43.2, 40.4, 35.0, 29.3, 27.5, 24.6, 24.4, 23.3, 21.4, 21.0, 17.6, 17.2, 16.9, 11.3, and 11.2.

Elemental Analysis. Calculated for $C_{37}H_{66}N_2O_{12}$: C, 60.80; H, 9.10; N, 3.83. Found: C, 60.71; H, 9.38; N, 3.78. Loss on drying at 120° C., 2.82%.
Isomer B
$^1$H NMR (CDCl$_3$) δ5.20 (dd, H-13), 4.74 (d, H-1"), 4.48 (d, H-1'), 4.17 (t, H-3), 4.15 (m H-5"), 4.11 (dd, H-11), 3.97 (m, H-8), 3.71 (d, H-5), 3.62 (m, H-5'), 3.30 (br dd, H-2'), 3.23 (s, OCH$_3$), 2.97 (t, H-4"), 2.88 (d, 11-OH), 2.85 (p, H-10), 2.60 (m, H-3'), 2.46 (p, H-2), 2.28 (s, N(CH$_3$)$_2$), 2.27 (d, H-2"eq), 2.23 (d, 4"-OH), 1.98 (ddq, H-14a), 1.84 (dd, H-7a), 1.77 (m, H-4), 1.76 (m, H-14b), 1.66 (m, H-4'eq), 1.64 (dd, H-7b), 1.49 (dd, H-2"ax), 1.29 (s, 6-CH$_3$), 1.27 (d, 5"-CH$_3$), 1.19 (d, 10-CH$_3$), 1.19 (s, 3"-CH$_3$), 1.14 (s, 12-CH$_3$), 1.09 (d, 8-CH$_3$), 1.09 (d, 4-CH$_3$), and 0.94 (t, CH$_2$CH$_3$).

$^{13}$C NMR (CDCl$_3$) δ174.4, 160.5, 104.6, 97.0, 86.2, 79.1, 78.6, 77 7, 77.4, 75.1, 70.5, 69.4, 66.0, 64.7, 49.4, 48.2, 47.7, 47.4, 42.3, 40.4, 34.9, 29.1, 25.6, 24.0, 23.6, 22.9, 21.5, 21.0, 15.8, 11.7, 10.7, and 9.6.

EXAMPLE 8

Synthesis of 9-Deoxo-8a-aza-8a-homoerythromycin A by Sodium Borohydride Reduction of 9-Deoxo-6-deoxy-6,9-epoxy-8a,9-didehydro-8a-aza-8a-homoerythromycin A and 9-Deoxo-12-deoxy-9,12-epoxy-8a,9-didehydro-8a-aza-8a-homoerythromycin A

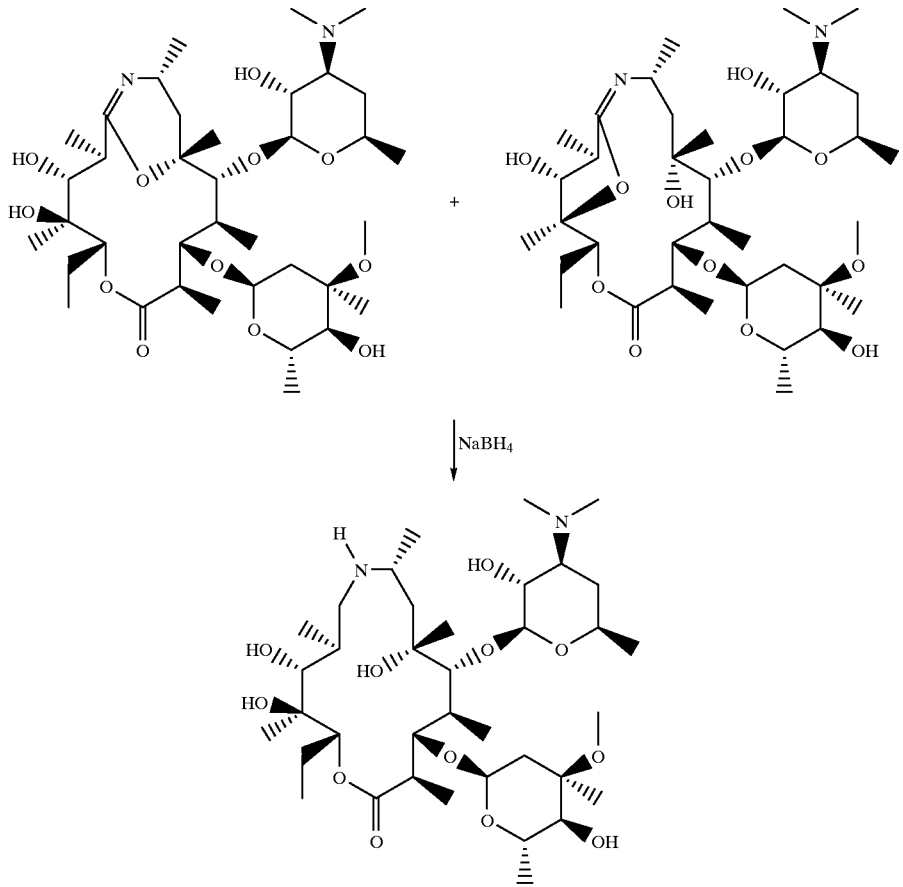

Method 1:

A solution of 9-deoxo-6-deoxy-6,9-epoxy-8a,9-didehydro-8a-aza-8a-homoerythromycin A and 9-deoxo-12-deoxy-9,12-epoxy-8a,9-didehydro-8a-aza-8a homoerythromycin A (22.6 g of a 27:73 mixture, 0.031 mol) in methanol (50 mL) was cooled in an ice bath and stirred under a nitrogen atmosphere. Solid sodium borohydride (3.6 g, 0.093 mol) was added in portions over 3 hours. The resulting, viscous solution was allowed to slowly warm to room temperature and then stirred at room temperature overnight. The solution was diluted with water (50 mL), acidified to pH 2 with 2N hydrochloric acid, and stirred at room temperature for 10 minutes. The solution was diluted with water (150 mL) and dichloromethane (200 mL) and stirred vigorously while the pH was brought to 6.5 by addition of 5N sodium hydroxide. The dichloromethane layer was discarded and the aqueous phase layered with fresh dichloromethane, stirred rapidly and basified to pH 9.5 with 5N sodium hydroxide. The layers were separated and the aqueous portion extracted with more dichloromethane (2×100 mL). The combined pH 9.5 dichloromethane extracts were dried over magnesium sulfate, filtered and evaporated under reduced pressure to a foam (15.4 g).

The crude product was dissolved in 2-propanol (90 mL) and stirred at room temperature to give a crystalline precipitate. This material was collected, washed with cold 2-propanol (20 mL) and dried to afford 9-deoxo-8a-aza-8a-homoerythromycin A (6.0 g) as a white solid.

The mother liquors and washings were evaporated under vacuum to a solid residue. The solid was suspended in water (50 mL), acidified to pH 2, and stirred at room temperature for 30 minutes. The mixture was diluted with water (50 mL) and dichloromethane (100 mL), then stirred vigorously while adjusting the pH to 6.5. The dichloromethane layer was discarded and replaced with fresh dichloromethane (100 mL). The mixture was stirred while the pH was adjusted to 9.5. The layers were separated and the aqueous phase was extracted with more dichloromethane (2×100 mL). The combined basic extracts were dried with magnesium sulfate, filtered and evaporated under vacuum to a foam (6.2 g). This material was dissolved in 2-propanol (30 mL) and the solution cooled in ice to give additional crystalline product. The solid was collected and dried to afford additional 9-deoxo-8a-aza-8a-homoerythromycin A (2.7 g).

MP 177–180° C.

IR (CHCl$_3$) 3540, 3340 (br), 2970, 2930, 2880, 1725, 1450, 1375, 1325, 1125, 1105, 1085, 1065, 1045, 955, and 870 cm$^{-1}$.

$^1$H NMR (CDCl$_3$) δ5.00 (d, H-1"), 4.75 (dd, H-13), 4.48 (br d, H-3), 4.34 (d, H-1'), 4.02 (dq, H-5"), 3.56 (br s, H-11), 3.52 (d, H-5), 3.45 (m, H-5'), 3.31 (s, OCH$_3$), 3.16 (dd, H-2'), 3.01 (br d, H-4"), 2.78 (m, H-8), 2.69 (dq, H-2), 2.59 dd, H-9a), 2.42 (br t, H-9b), 2.30 (d, H-2"eq), 2.26 (s,

N(CH$_3$)$_2$), 1.91 (m, H-14a), 1.77 (br p, H-4), 1.61 (br d, H-4'eq), 1.55 (dd, H-2"ax), 1.44 (m, H-14b), 1.38 (m, H-7), 1.36 (s, 6-CH$_3$), 1.29 (d, 5"-CH$_3$), 1.21 (s, 3"-CH$_3$), 1.20 (d 5'-CH$_3$), 1.18 (d, 2-CH$_3$), 1.10 (d, 8-CH$_3$), 1.06 (s 12-CH$_3$), 1.04 (d, 4-CH$_3$), 0.94 (d, 10-CH$_3$), and 0.86 (t, CH$_2$CH$_3$).

$^{13}$C NMR (CDCl$_3$) δ178.6, 103.4, 94.6, 83.6, 78.1, 77.6, 76.6, 74.9, 72.8, 70.7, 68.9, 66.8, 65.7, 65.2, 49.6, 49.4, 45.5, 43.4, 40.3, 35.3, 34.7, 28.7, 27.6, 21.6, 21.3, 20.8, 18.2, 16.3, 15.1, 12.1, 11.3, and 9.5.

FAB mass spectrum, m/z 735, 577, 559, 402, 159, 158, and 116.

Elemental Analysis. Calculated for C$_{37}$H$_{70}$N$_2$O$_{12}$: C, 60.47; H, 9.60; N. 3.81. Found: C, 59.98; H, 9.46; N, 3.62. Loss on drying at 120° C., 0.33%.

Method 2:

A solution of 9-deoxo-6-deoxy-6,9-epoxy-8a,9-didehydro-8a-aza-8a-homoerythromycin A and 9-deoxo-12-deoxy-9,12-epoxy-8a,9-didehydro-8a-aza-8a-homoerythromycin A (5.0 g of a 1:3 mixture, 6.84 mmol) in ethylene glycol (25 mL) was cooled in an ice bath and stirred under a slow stream of nitrogen. Sodium borohydride (0.60 g, 15.86 mmol) was added in two nearly equal portions spaced one hour apart. Following the borohydride addition, the reaction mixture was stirred at 0–5° C. for 1.5 hours, then warmed to room temperature and stirred at room temperature overnight. The reaction mixture was diluted with water (50 mL) and dichloromethane (25 mL), stirred vigorously, and phases separated. The aqueous portion was extracted with more dichloromethane (4×25 mL). The combined organic extracts were washed with brine (50 mL), dried over magnesium sulfate, filtered and evaporated under reduced pressure to foam (4.0 g).

The crude product was dissolved in 2-propanol (20 mL) and the solution stirred at room temperature to give a crystalline precipitate. The product was collected and dried under a stream of nitrogen to afford 9-deoxo-8a-aza-8a-homoerythromycin A (2.2 g) as a white solid.

EXAMPLE 9

Synthesis of 9-Deoxo-8a-aza-8a-homoerythromycin A by Catalytic Hydrogenation of 9-Deoxo-6-deoxy-6,9-epoxy-8a,9-didehydro-8a-aza-8a-homoerythromycin A

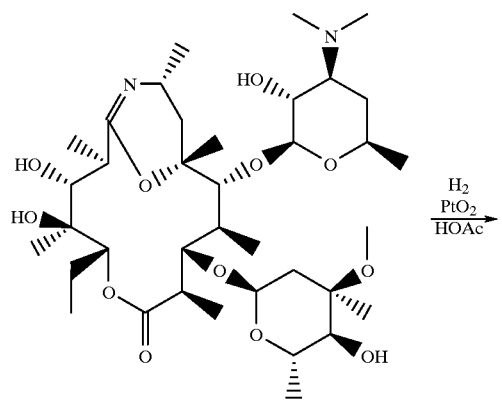

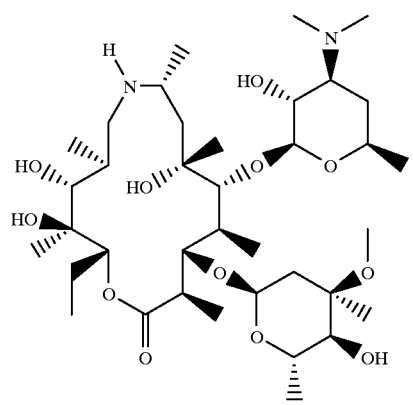

A mixture of 9-deoxo-6-deoxy-6,9-epoxy-8a,9-didehydro-8a-aza-8a-homoerythromycin A (100 mg), acetic acid (4 mL) and platinum oxide (120 mg) was hydrogenated overnight at 2000 psi. The mixture was filtered through celite and the filtrate evaporated under vacuum to a residue that was partitioned between dichloromethane (12 mL) and saturated aqueous sodium bicarbonate (5 mL). The dichloromethane layer was removed and the aqueous layer was extracted with more dichloromethane (2×5 mL). The combined dichloromethane extracts were dried over anhydrous magnesium sulfate, filtered and evaporated under vacuum to a gum (60 mg).

The oil was purified by preparative thin layer chromatography (Analtech 0.1 mm×20×20 cm basic alumina plate, developing and eluting with 5% methanol in dichloromethane) to give the title compound as a white foam (42 mg).

In a manner similar to that described above, a mixture of 9-deoxo-6-deoxy-6,9-epoxy-8a,9-didehydro-8a-aza-8a-homoerythromycin A (400 mg) and platinum oxide (400 mg) in acetic acid (8 mL) was hydrogenated at 2000 psi overnight. Workup provided a foam (372 mg) that was dissolved in 1% methanolic dichloromethane (2 mL) and loaded onto a column of basic alumina (1.75×26 cm, wet packed using 1% methanol in dichloromethane). The column was eluted with 1% methanol in dichloromethane, collecting 6 mL fractions. Fractions 27–42 were combined and evaporated under reduced pressure to afford 9-deoxo-8a-aza-8a-homoerythromycin A (178 mg) as a foam.

EXAMPLE 10

Synthesis of 9-Deoxo-8a-aza-8a-methyl-8a-homoerythromycin A by Methylation of 9-Deoxo-8a-aza-8a-homoerythromycin A

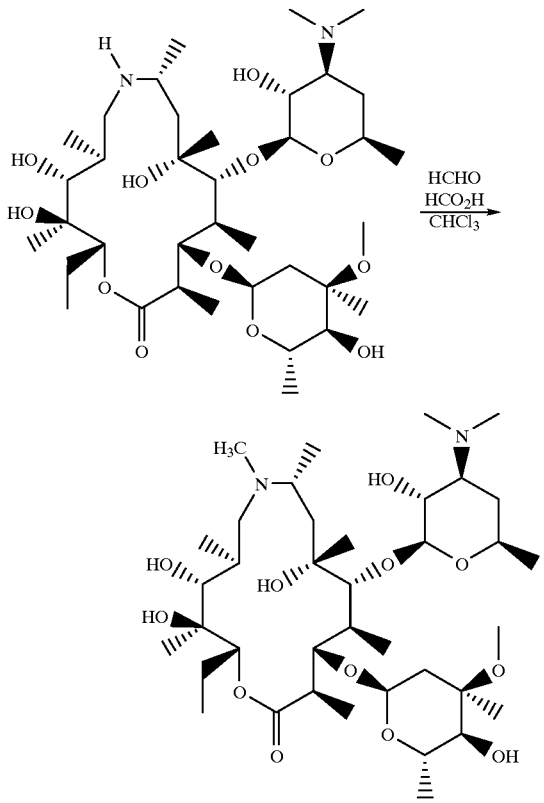

A solution of 9-deoxo-8a-aza-8a-homoerythromycin A (7.30 g, 9.9 mmol) in chloroform (45 mL) was treated with 37% aqueous formaldehyde (0.81 mL, 10.8 mmol) and 98% formic acid (1.08 mL, 28.0 mmol). The resulting mixture was heated at reflux for 25.5 hours, then cooled to room temperature, diluted with dichloromethane (150 mL) and water (120 mL), and stirred vigorously for a few minutes. The dichloromethane layer was discarded and fresh dichloromethane (100 mL) was added. The mixture was stirred rapidly while the pH was adjusted to 9.5 by addition of 5N sodium hydroxide. The dichloromethane layer was removed and the aqueous portion was re-extracted with more dichloromethane (50 mL, 25 mL). The combined dichloromethane extracts were dried over anhydrous magnesium sulfate, filtered and evaporated under vacuum to a foam (7.27 g).

A solution of the foam in warm ethanol (24 mL) was diluted with water (12 mL) and stirred at room temperature for 5 minutes to give a precipitate. The mixture was diluted with more water (12 mL), stirred with ice-bath cooling, and then left in a refrigerator overnight. The mixture was filtered and the collected solid was rinsed with cold 3:1 water-ethanol (12 mL), dried under a stream of nitrogen, and finally dried under vacuum to afford the title compound (6.20 g) as a white solid.

MP 187–188° C.

IR (CHCl$_3$) 3540, 3330 (br), 2970, 2940, 2880, 2830, 1725, 1455, 1375, 1350, 1325, 1275, 1160, 1125, 1105, 1085, 1065, 1045, 995, 975, and 955 cm$^{-1}$.

$^1$H NMR (CDCl$_3$, 55° C.) δ5.10 (d, H-1"), 4.86 (dd, H-13), 4.51 (t, H-3), 4.38 (d, H-1'), 4.04 (dq, H-5"), 3.53 (br s, H-11), 3.52 (d, H-5), 3.51 (m, H-5'), 3.32 (s, OCH$_3$), 3.23 (dd, H-2'), 3.01 (dd, H-4"), 2.99 (m, H-8), 2.81 (dq, H-2), 2.52 (m, H-9a), 2.40 (m, H-3'), 2.34 (s, N(CH$_3$)$_2$), 2.30 (m, H-9b), 2.30 (d, H-2"eq), 2.04 (s, NCH$_3$), 1.99 (m, H-10), 1.92 (m, H-14a), 1.88 (m, H-7a), 1.85 (m, H-4), 1.72 (br d, H-4'eq), 1.55 (dd, H-2"ax), 1.48 (m, H-14b), 1.37 (s, 6-CH$_3$), 1.30 (d, 5"-CH$_3$), 1.24 (d, 5'-CH$_3$), 1.23 (m, H-4'ax), 1.23 (s, 3"-CH$_3$), 1.19 (d, 2-CH$_3$), 1.12 (m, H-7b), 1.10 (d, 4-CH$_3$), 1.10 (s, 12-CH$_3$), 0.96 (d, 10-CH$_3$), 0.94 (d, 8-CH$_3$), and 0.92 (t, CH$_2$CH$_3$).

$^{13}$C NMR (CDCl$_3$, 55° C.) δ178.3, 103.6 94.7, 85.5, 78.4, 77.2, 76.7, 75.9, 74.9, 73.1, 71.0, 69.1, 67.1, 65.8, 65.4, 60.0, 56.7, 49.4, 45.8, 43.5, 40.4, 37.1, 35.1, 30.9, 29.3, 27.8, 22.1, 21.7, 21.3, 18.3, 16.4, 14.3, 12.7, 12.0, 11.4, and 11.3.

FAB mass spectrum, m/z 749, 591, 573, 158, and 116.

Elemental Analysis. Calculated for C$_{38}$H$_{72}$N$_2$O$_{12}$: C, 60.94; H, 9.69; N, 3.74. Found C, 60.87; H, 9.39; N, 3.70. Loss on drying at 120° C., 0.74%.

EXAMPLE 11

Synthesis of 9-Deoxo-8a-aza-8a-methyl-8a-homoerythromycin A by Methylation of 9-Deoxo-8a-aza-8a-hydroxy-8a-homoerythromycin A 3'-N-Oxide

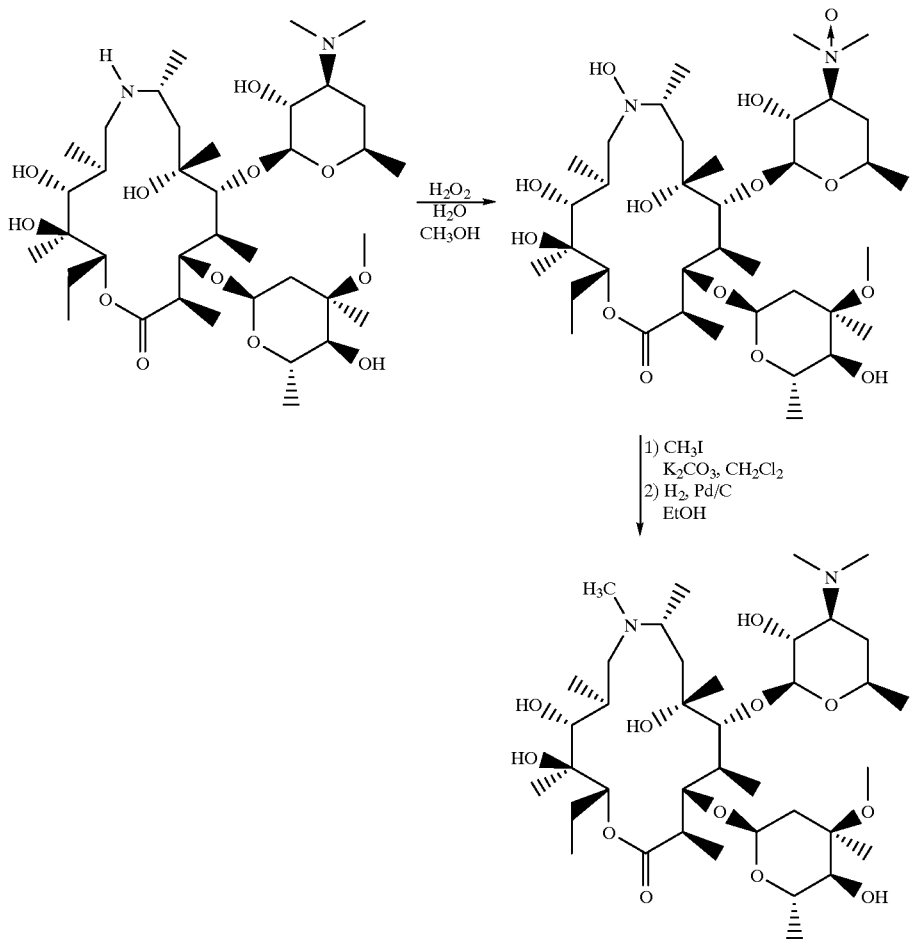

Step 1

9-Deoxo-8a-aza-8a-hydroxy-8a-homoerythromycin A 3'-N-Oxide

9-Deoxo-8a-aza-8a-homoerythromycin A (385 mg, 0.524 mmol) in methanol (1.5 mL) was treated with 30% aqueous hydrogen peroxide (1.9 mL, 18.6 mmol) and the mixture was stirred at room temperature for 24 hours. The mixture was cooled in an ice bath, diluted with dichloromethane (10 mL) and water (8 mL), treated with saturated aqueous sodium sulfite (10 mL), and then stirred for 15 minutes to destroy excess oxidant. The phases were separated and the aqueous portion extracted with more dichloromethane (2×15 mL). The combined organic solution was dried with magnesium sulfate, filtered, and evaporated under reduced pressure to afford crude 9-deoxo-8a-hydroxy-8a-aza-8a-homoerythromycin A 3'-N-oxide (349 mg) as a white solid.

Step 2

9-Deoxo-8a-methyl-8a-aza-8a-homoerythromycin A

A portion of the product from step 1 (150 mg, 0.196 mmol) was dissolved in dichloromethane (3 mL) and the solution was treated with powdered, anhydrous potassium carbonate (2.0 g, 14.5 mmol) and methyl iodide (0.5 mL, 8.0 mmol). The mixture was stirred at room temperature under a nitrogen atmosphere for 3.5 hours. The mixture was filtered and the solids washed with dichloromethane (5 mL). Water (3 mL) was added to the combined filtrate and washings and the mixture was stirred vigorously while the pH was brought to 11 with 1N sodium hydroxide. The dichloromethane phase was dried with magnesium sulfate, filtered and evaporated under reduced pressure to afford a mixture of 9-deoxo-8a-methyl-8a-homoerythromycin A 3'-N-oxide and 9-deoxo-8a-methyl-8a-homoerythromycin A 8a, 3'-N-bisoxide (136 mg) as a foam.

The crude product was dissolved in ethanol (6 mL), treated with 10% palladium on carbon (240 mg), and hydrogenated on a Parr shaker for 75 minutes at 45 psi. The mixture was filtered and the filtrate was evaporated under vacuum. The residue in dichloromethane (20 mL) was washed with saturated aqueous potassium carbonate, dried with magnesium sulfate, filtered, and evaporated under reduced pressure to provide 9-deoxo-8a-methyl-8a-homoerythromycin A (107 mg) as a foam.

$^1$H NMR (400 MHz, CDCl3, at 60° C.) δ5.10 (d, H-1"), 4.82 (dd, H-13), 4.61 (q, H-5"), 4.48 (q, H-3), 4.41 (d, H-1), 3.30 (s, OCH$_3$), 3.16 (dd, H-2'), 2.27 (s, N(CH$_3$)$_2$), 2.01 (s, NCH$_3$).

EXAMPLE 12

Synthesis of 9-Deoxo-8a-aza-8a-ethyl-8a-homoerythromycin A

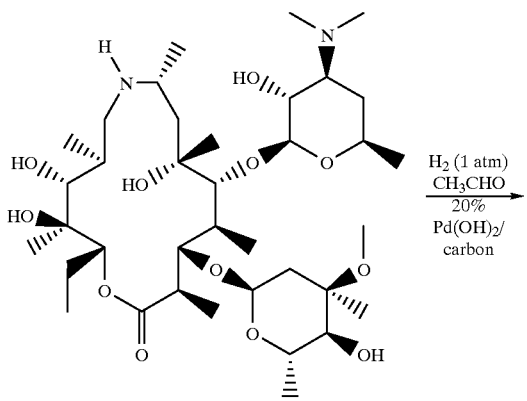

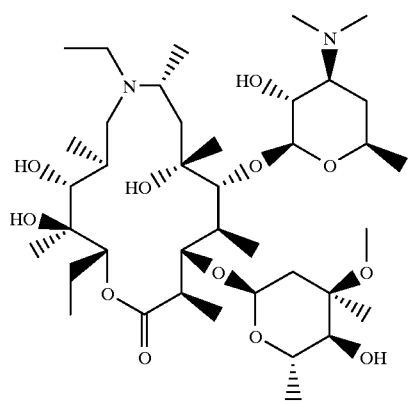

9-Deoxo-8a-aza-8a-homoerythromycin A (1.5grams, 2.4mmol) and acetaldehyde (2mL, 35.8mmol) were dissolved in a mixture of water (1.5mL) and ethanol (12mL), and the solution was hydrogenated for 48 hours at atmospheric pressure in the presence of 20% Palladium hydroxide on carbon (0.5g). The catalyst was filtered, and the filtrate was partitioned between water (100 mL) and methylene chloride (100 mL). The methylene chloride was removed and the aqueous layer was re-extracted with methylene chloride (50 mL). The combined methylene chloride extracts were added to water (100 mL) and the pH of the rapidly stirred mixture was adjusted to 5 with 2N hydrochloric acid. The methylene chloride was removed and more methylene chloride (100 mL) was added. The pH of the mixture was adjusted to 6 with 5N sodium hydroxide, the methylene chloride layer was removed and more methylene chloride was added. The pH of the mixture was adjusted to 8.5 with 5N sodium hydroxide and the methylene chloride layer was removed. The aqueous layer was re-extracted with methylene chloride (50 mL) and the combined pH 8.5 extracts were dried with anhydrous magnesium sulfate, were filtered and evaporated under vacuum to a light yellow foam (0.97 g).

0.5 grams of the above foam was dissolved in 120:10:1 methylene chloride/methanol/conc. ammonium hydroxide and was loaded onto a column of silica gel 60 (2.5×26cm, 230–400 mesh, wet packed with 120:10:1 methylene chloride/methanol/conc. ammonium hydroxide). The column was eluted with 120:10:1 methylene chloride/methanol/conc. ammonium hydroxide and 6 mL fractions were collected. Fractions 33–48 were combined and evaporated to a foam (0.23g).

The foam was dissolved in warm ethanol (10 mL) and the solution was evaporated to approximately 3 mL. Water (1 mL) was added and the turbid solution was stirred for 2 hours in an ice bath. The precipitated solid was filtered, was rinsed with cold 1:1 ethanol/water (2 mL) and dried under vacuum to afford the title compound (130 mg).

MP 193.5–194.5° C.

IR (CHCl3) 3420, 2970, 2940, 2880, 2820, 1725, 1455, 1400, 1372, 1345, 1165, 1120, 1105, 1085, 1045, 1010, 955 cm$^{-1}$.

$^1$H NMR (CDCl$_3$) δ(ppm) 4.98 (m, H-1"+H-13), 4.38 (d, H-1'), 4.05 (br dq, H-5"), 3.27 (8, OCH$_3$), 2.27 (8, N(CH$_3$)$_2$), 0.88 (t, CH$_2$CH$_3$).

FAB mass spectrum, m/z 763, 749, 634, 605, 430, 159, 158 and 116.

Elemental Analysis. Calculated for C$_{39}$H$_{74}$O$_{12}$N$_2$: C, 61.39; H, 9.78; N, 3.67. Found: C, 61.22; H, 9.69; N, 3.42. (Loss on drying at 120° C, 0.607.)

EXAMPLE 13

Synthesis of 8a-(3-phenylpropyl)-8a-aza-9-deoxo-8a-homoerythromycin A by reductive alkylation of 8a-aza-9-deoxo-8a-homoerythromycin A

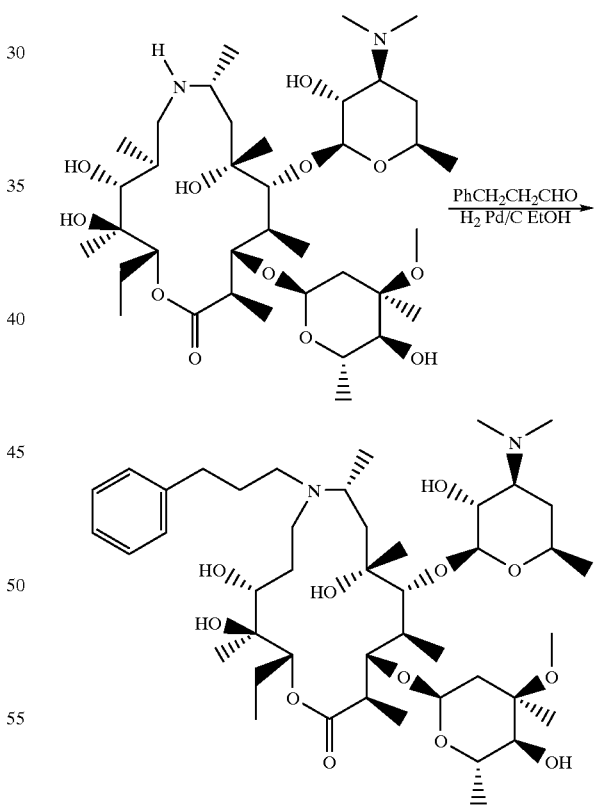

Palladium catalyst (50 mg of 10% Pd/C) was added to a solution of 8a-aza-9-deoxo-8a-homoerythromycin A (250 mg, 0.34 mmol) in 2 mL of hydrocinnamaldehyde. The reaction vessel was evacuated and filled with nitrogen (2X) then evacuated and filled with hydrogen (4X). The resulting mixture was stirred under one atmosphere of hydrogen (balloon) at room temperature for 6 days (hydrogen balloon was refilled as needed). The reaction mixture, which had become very viscous and was no longer stirring, was diluted with ethyl acetate (10 mL) and centrifuged. The supernatant was decanted and the solid residue was washed with ethyl acetate (2×4 mL). The combined supernatants were extracted with 0.5 N aqueous HCl (10 mL). The organic layer was discarded. The pH of the aqueous layer was adjusted to ca. pH 10 by addition of 5 N NaOH then the aqueous layer was extracted with ethyl acetate (3×10 mL). The combined extracts were dried over magnesium sulfate, filtered, and evaporated under vacuum to a colorless oil (174 mg). The crude product was purified by flash chromatography on silica gel (3.0×30 cm column eluted with 92:6.5:1.5 chloroform : methanol saturated methanolic ammonia, collecting 50 mL fractions). Analytical TLC of the fractions indicated that fractions 38–47 contained the desired product ($R_f$ 0.33). These fractions were combined and evaporated under vacuum to afford impure 8a-(3-phenylpropyl)-8a-aza-9-deoxo-8a-homoerythromycin A as a colorless oil (68 mg, approximately 85% pure by $^1$H NMR). This material was further purified by flash chromatography on silica gel (2.0× 27 cm column eluted with 60:40:1.5 ethyl acetate:methanol:saturated methanolic ammonia, collecting 10 mL fractions). Analytical TLC of the fractions indicated that fractions 15–17 contained the desired product ($R_f$ 0.31). These fractions were combined and evaporated under vacuum to afford pure 8a-(3-phenylpropyl)-8a-aza-9-deoxo-8a-homoerythromycin A as a white foam (11 mg).

$^1$H NMR (400 MHz, CDCl$_3$, 53° C.) δ7.27–7.20 (3H, m, Ar—H), 7.18-7.10 (2H, m, Ar—H), 3.28 (3H, s, OCH$_3$), 2.27 (6H, s, N(CH$_3$)$_2$).

FAB-MS m/z 854 (M+H).

EXAMPLE 14

9-Deoxo-8a-aza-8a-allyl-8a-homoerythromycin A

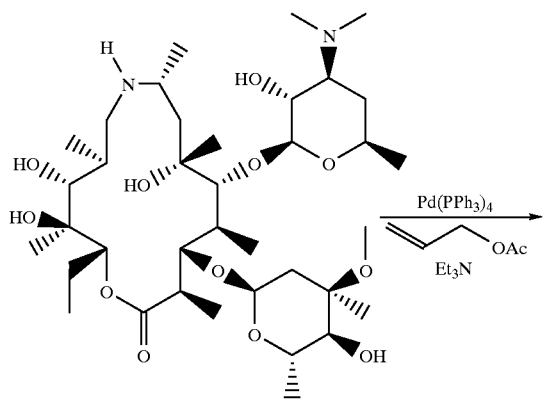

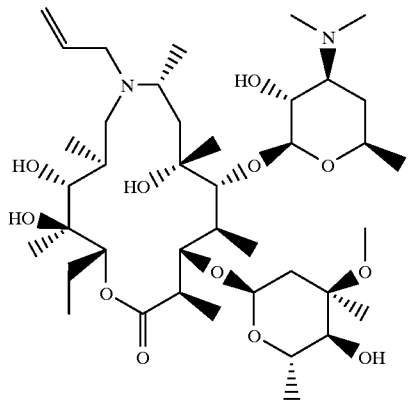

A mixture of 9-deoxo-8a-aza-8a-homoerythromycin A (5.0 g, 6.8 mmol), allyl acetate (35 mL), triethylamine (2.5 mL) and tetrakis(triphenyphosphine)palladium(O) (0.23 g) was stirred and heated in an oil bath at 80° C. for 7 hours. After stirring at room temperature overnight, the mixture was evaporated under vacuum to remove excess allyl acetate. The residue was stirred with dichloromethane (50 mL) and water (50 mL) while the pH was adjusted from 5.6 to 4.0 with 2N hydrochloric acid. The layers were separated and the organic portion was extracted with more water (15 mL). The combined aqueous solution was layered with dichloromethane and stirred while the pH was brought to 9.4 by addition of 5N aqueous sodium hydroxide solution. The layers were separated and the aqueous portion was extracted with additional dichloromethane (50 mL, 25 mL). The combined dichloromethane extracts were dried over magnesium sulfate, filtered and evaporated under vacuum to a foam (4.85 g).

A solution of the foam in 2-propanol (40 mL) deposited crystals on stirring at room temperature. The crystalline product was collected, washed with 2-propanol (3×4 mL) and dried under a nitrogen stream to afford 9-deoxo-8a-aza-8a-allyl-8a-homoerythromycin A (1.8 g ) as a white solid. The mother liquors and washings were evaporated under vacuum and the residue stirred with ethanol (12 mL) to afford a second crop (1.5 g ) of the title compound.

$^1$H NMR (CDCl$_3$) δ5.90 (m, CH=CH$_2$), 5.13 (d, CH=C HaHb), 5.03 (m, CH=CHaHb and H-1"), 4.92 (m, H-13), 4.36 (m, H-3), 4.35 (d, H-1"), 4.03 (m, H-5"), 3.62 (br s, H-11), 3.50 (m, H-5 and H-5'), 3.27 (s, OCH$_3$), 3.24 (m, H-2'), 2.26 (s, N(CH$_3$)$_2$), 1.87 (m, H-14a), 1.65 (m, H-4'eq), 1.53 (dd, H-2"ax), 1.44 (m, H-14b), 1.29 (br s, 6-CH$_3$), 0.87 (t, CH$_2$CH$_3$).

FAB-MS m/z 798 (M+Na), 776 (M+H), 618, 600, 159.

EXAMPLE 15

Synthesis of 9-Deoxo-8a-aza-8a-(prop-1-yl)-8a-homoerythromycin A and 9-Deoxo-8a-aza-8a-homoerythromycin A

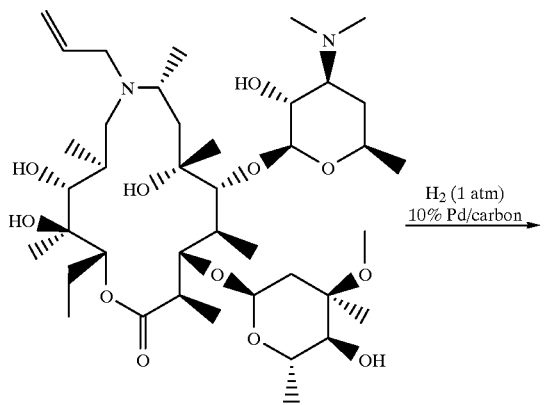

EXAMPLE 16

Synthesis of 9-Deoxo-8a-aza-8a-(prop-1-yloxy)-8a-homoerythromycin A

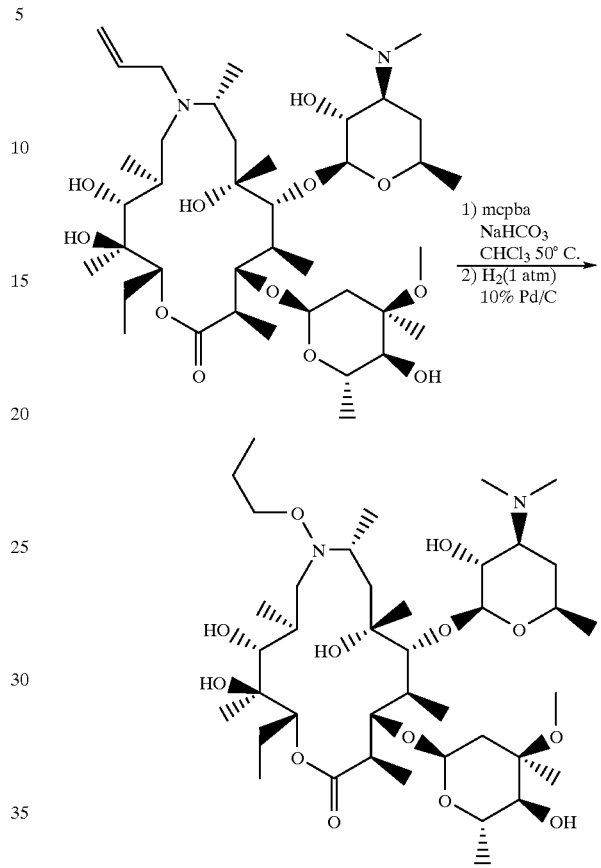

9-Deoxo-8a-aza-8a-(prop-2-en-1-yl)-8a-homoerythromycin A (120 mg, 0.155 mmol) was dissolved in ethanol (2 mL) and was hydrogenated at atmospheric pressure for 3 hours in the presence of 10% Palladium on carbon (40 mg). The mixture was filtered through solka-floc and the filtrate was evaporated to a foam.

The above foam was dissolved in 90:10:1 methylene chloride/methanol/conc. ammonium hydroxide and was loaded onto a column of silica gel 60 (2.5×25.5 cm, 230–400 mesh, wet packed with 90:10:1 methylene chloride/methanol/conc. ammonium hydroxide). The column was eluted with 90:10:1 methylene chloride/methanol/conc. ammonium hydroxide and 8 mL fractions were collected. Fractions 12–15 were combined and evaporated to provide the title compound as a foam (49 mg). Fractions 23–32 were combined and evaporated to provide 9-Deoxo-8a-aza-8a-homoerythromycin A as a foam (50 mg).

IR (CHCl$_3$) 3400, 2950, 2935, 2875, 2830, 1725, 1455, 1395, 1370, 1345, 1325, 1280, 1165, 1100, 1085, 1045, 1010, 995, 975, 950cm$^{-1}$

1H NMR (60° C CDCl$_3$) δ(ppm) 5.0 (br d, H-1") 4.95 (br dd, H-13), 4.38 (d, H-1'), 3.25 (s, OCH$_3$), 2.30 (s, N(CH$_3$)$_2$), 0.85 (t, CH$_2$CH$_3$)

$^{13}$C NMR (CDCl$_3$) δ(ppm) 177.8, 104.5, 95.9, 78.1, 77.0, 75.6, 74.6, 73.0, 70.7, 69.2, 65.8, 65.4, 59.2, 49.4, 46.7, 42.6, 40.5, 35.1, 32.6, 29.8, 26.4, 22.2, 21.6, 21.1, 18.0, 16.3, 14.9, 14.7, 12.8, 12.1, 11.8, 11.3

FAB mass spectrum, m/z 777.8, 761.8, 648.9, 619.6, 601.7, 462.5, 444.5, 430.4, 158.3.

3-chloroperoxybenzoic acid (0.1 g, 0.58 mmol) was added to a mixture of 9-Deoxo-8a-aza-8a-(prop-2 -en-yl)-8a-homoerythromycin A (0.2 g, 0.26 mmol) and sodium bicarbonate (0.065 g, 0.78 mmol) in chloroform (2 mL). The suspension was heated at 50° C. for 20 hours, with a second addition of 3-chloroperoxybenzoic acid (0.05 g, 0.29 mmol) after 5 minutes. The mixture was cooled to room temperature and was partitioned between water (4 mL) and methylene chloride (4 mL). The methylene chloride was removed and the aqueous layer was re-extracted with more methylene chloride (4 mL). The combined extracts were dried with magnesium sulfate, were filtered, and evaporated to a foam (0.21 g).

The above foam was dissolved in a mixture of ethanol (3 mL) and water (1 mL), containing sodium bicarbonate (0.1 g, 1.19 mmol), and was hydrogenated at atmospheric pressure for 105 minutes in the presence of 20% palladium hydroxide on carbon (40 mg). The suspension was filtered through solka-floc and the filtrate was evaporated to an oil. Methylene chloride (4 mL) and water (4 mL) were added and the pH was adjusted to 10 with dilute sodium hydroxide. The methylene chloride was removed and the aqueous layer was re-extracted with more methylene chloride (4 mL). The combined extracts were dried with magnesium sulfate, were filtered and evaporated to a foam (0.17 g).

The foam was dissolved in 90:10:1 methylene chloride/methanol/conc. ammonium hydroxide and was loaded onto a column of silica gel 60 (2.5×18.5 cm, 230–400 mesh, wet packed with 90:10:1 methylene chloride/methanol/conc. ammonium hydroxide). The column was eluted with 90:10:1 methylene chloride/methanol/conc. ammonium hydroxide and 4 mL fractions were collected. Fractions 10–12 were combined and evaporated to give 9-Deoxo-8a-aza-8a-(prop-1-yloxy)-8a-homoerythromycin A as a foam (0.026 g).

IR (CHCl$_3$) 3420, 2970, 2940, 2880, 1725, 1455, 1420, 1400, 1375, 1345, 1280, 1260, 1240, 1165, 1120, 1105, 1085, 1045, 1030, 1005cm$^{-1}$ $^1$H NMR (CDCl$_3$) δ(ppm) 5.00 (br d, H-1"), 4.80 (br dd, H-13), 4.35 (br d, H-1'), 3.26 (br s, OCH$_3$), 2.30 (br s, N(CH$_3$)$_2$), 0.88 (t, CH$_2$CH$_3$)

FAB mass spectrum, m/z 793.8, 617.6, 575.7, 478.5, 460.7, 415.4, 360.4, 286.3, 258.3, 240.3, 172.3, 158.4

EXAMPLE 17

Synthesis of 9-Deoxo-8a-aza-8a-(2-oxoeth-1-yl)-8a-homoerythromycin A

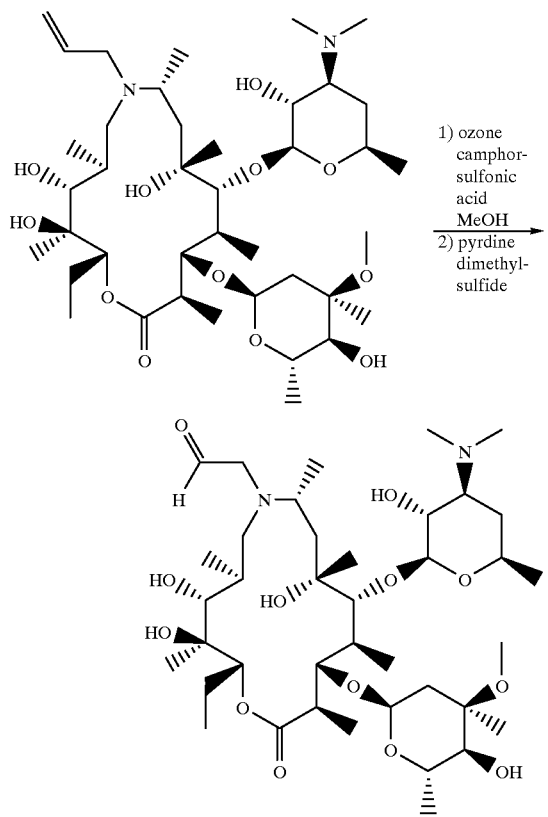

1) ozone camphor-sulfonic acid MeOH
2) pyrdine dimethyl-sulfide dl-10-Camphorsulfonic acid (1.26 g, 5.4 mmol) was added to a solution of 9-Deoxo-8a-aza-8a-(prop-2-en-1-yl)-8a-homoerythromycin A (2 g, 2.6 mmol) in methanol (20 mL). The mixture was cooled in a dry ice/acetone bath, and ozone was bubbled through the solution for 15 minutes. (8 minutes after first observing the appearance of a light blue color.) The solution was bubbled with oxygen for 5 minutes, to remove excess ozone, and dimethyl sulfide (3.2 mL, 43.6 mmol) and pyridine (5 mL, 61.8 mmol) were added. After warming to room temperature, the solution was stirred for 2 hours and was then added to a rapidly stirred mixture of water (60 mL) and methylene chloride (40 mL). The ph was adjusted from 5.4 to 10.5 with dilute sodium hydroxide. The methylene chloride was removed and the aqueous layer was re-extracted with more methylene chloride (4 mL). The combined extracts were dried with magnesium sulfate, were filtered and evaporated to an oil. The oil was twice dissolved in toluene (40 mL) and was evaporated to a foam.

The foam was dissolved in isopropyl alcohol (2 mL) and was stored at room temperature for 18 hours. The precipitate was filtered, was rinsed with isopropyl alcohol (2 mL) and was dried under a stream of nitrogen to give the title compound as a white crystalline solid (1.25 g).

MP Dec.>125° C.

IR (CHCl$_3$) 3400, 2965, 2935, 2875, 2830, 2790, 1720, 1455, 1395, 1375, 1355, 1345, 1330, 1290, 1275, 1180, 1160, 1120, 1100, 1085, 1065, 1045, 1010, 995, 975, 955cm$^{-1}$ $^1$H NMR (60° C. CDCl$_3$) δ(ppm) 9.7 (d, CHO), 5.10 (d, H-1"), 4.90 (dd, H-13), 4.65 (br d, H-1'), 3.27 (s, OCH$_3$), 2.27 (s, N(CH$_3$)$_2$), 0.86 (t, CH$_2$CH$_3$)

FAB mass spectrum Li spike, m/z 810.1, 784.2, 747.9, 736.0, 619.6, 589.9, 571.9

EXAMPLE 18

Synthesis of 9-Deoxo-8a-aza-8a-(2-hydroxyeth-1-yl)-8a-homoerythromycin A

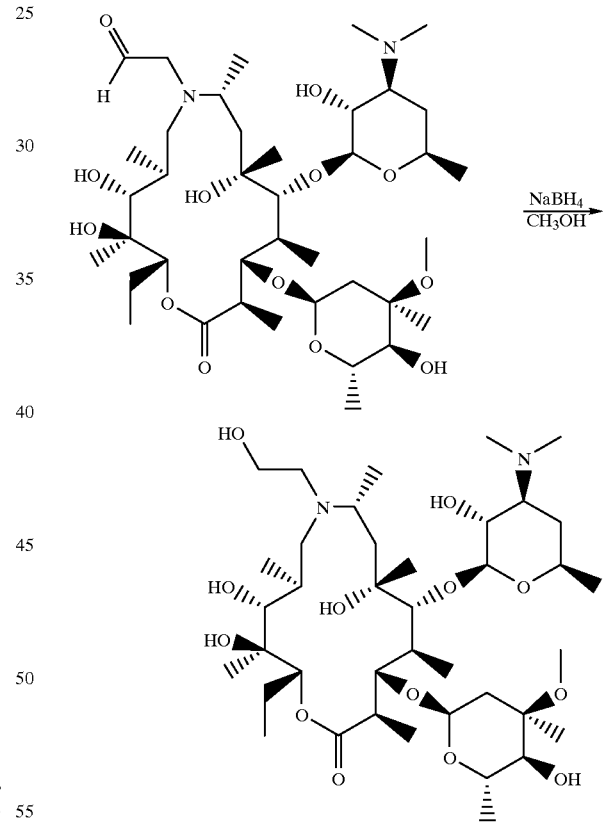

NaBH$_4$ / CH$_3$OH

Sodium borohydride (0.012 g, 0.3 mmol) was added to an ice cooled suspension of 9-Deoxo-8a-aza-8a-(2-oxoeth-1-yl)-8a-homoerythromycin A (0.2 g, 0.26 mmol) in methanol (1 mL). The solid rapidly dissolved and the solution was allowed to warm to room temperature after 1 hour. Dilute hydrochloric acid was added until the apparent pH was 2.35. After 3 minutes, water (5 mL) and methylene chloride (8 mL) were added and the pH was adjusted to 11 with 5N and the aqueous layer was re-extracted with more methylene chloride (4 mL). The combined extracts were dried with magnesium sulfate, were filtered and evaporated to a foam (0.2 g).

The foam was dissolved in 90:10:1 methylene chloride/methanol/conc. ammonium hydroxide and was loaded onto a column of silica gel 60 (2.5×36cm, 230–400 mesh, wet packed with 90:10:1 methylene chloride/methanol/conc. Ammonium hydroxide). The column was eluted with 90:10:1 methylene chloride/methanol/conc. ammonium hydroxide and 3mL fractions were collected. Fractions 29–44 were combined and evaporated to give the title compound as a foam (0.15 g).

IR (CHCl$_3$) 3400, 2970, 2935, 2880, 2830, 2790, 1722, 1455, 1400, 1370, 1355, 1345, 1280, 1260, 1240, 1160, 1105, 1085, 1070, 1045, 1010, 995, 975, 955cm$^{-1}$ $^1$H NMR (60° C. CDCl$_3$) δ(ppm) 4.99 (dd, H-13), 4.92 (d, H-1"), 4.42 (d, H-1'), 3.24 (s, OCH$_3$), 2.33 (s, N(CH$_3$)$_2$), 0.85 (t, CH$_2$CH$_3$)

$^{13}$C NMR (60° C. CDCl$_3$) δ(ppm) 177.0, 104.4, 96.9, 87.9, 78.5, 77.8, 77.2, 75.5, 75.0, 72.8, 70.5, 69.4, 66.0, 64.9, 61.1, 58.1, 58.0, 54.9, 54.2, 54.1, 49.3, 46.9, 42.9(2), 42.2, 40.5, 35.0, 33.6, 30.0, 25.1, 22.0, 21.4, 20.9, 17.7, 16.2, 15.2, 14.0, 13.1, 11.9, 11.1

FAB mass spectrum, m/z 780.4, 748.1, 604.1, 446.5, 159.0, 157.9

EXAMPLE 19

Synthesis of 9-Deoxo-8a-aza-8a-((2,3-epoxy)prop-1-yl)-8a-homoerythromycin A (isomer A) and 9-Deoxo-8a-aza-8a-((2,3-epoxy)prop-1-yl)-8a-homoerythromycin A (isomer B)

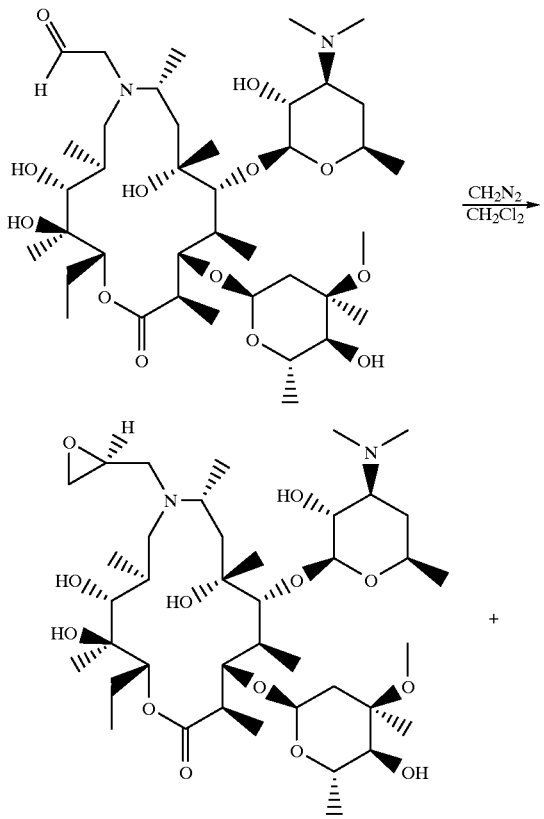

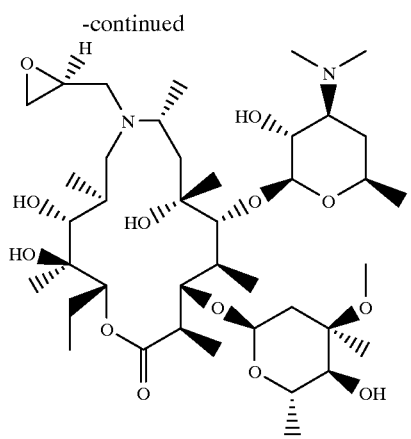

9-Deoxo-8a-aza-8a-(2-oxoeth-1-yl)-8a-homoerythromycin A (0.1 g, 0.128 mmol) was dissolved in anhydrous tetrahydrofuran (1 mL), was cooled in an ice bath and was treated with a large excess of diazomethane in diethyl ether (1.5 mL). After 48 hours the solution was added to a rapidly stirred mixture of water (6 mL) and methylene chloride (6 mL). The ph was adjusted to 6 with dilute hydrochloric acid and the methylene chloride was removed and the aqueous layer was washed with more methylene chloride (4 mL). Methylene chloride (6 mL) was added to the aqueous layer and the pH was adjusted to 10 with dilute sodium hydroxide. The methylene chloride was removed and the aqueous layer was re-extracted with more methylene chloride (4 mL). The combined extracts were dried with magnesium sulfate, were filtered and evaporated to an oil (0.082 g).

The oil was dissolved in 90:10:1 methylene chloride/methanol/conc. ammonium hydroxide and was loaded onto a column of silica gel 60 (2.5×30 cm, 230–400 mesh, wet packed with 90:10:1 methylene chloride/methanol/conc. ammonium hydroxide). The column was eluted with 90:10:1 methylene chloride/methanol/conc. ammonium hydroxide and 3mL fractions were collected. Fractions 34–37 were combined and evaporated to give isomer A as a foam (0.012 g). Fractions 43–48 were combined and evaporated to give isomer B as a foam (0.019g).

Data for isomer A

IR (CHCl$_3$) 3400, 2965, 2935, 2875, 2830, 2790, 1725, 1455, 1375, 1355, 1345, 1160, 1105, 1085, 1065, 1045, 1010, 995, 975, 950cm$^{-1}$ $^1$H NMR (60° C. CDCl$_3$) δ(ppm) 5.05 (d, H-1"), 4.93 (dd, H-13), 4.36 (d, H-1'), 3.28 (s, OCH$_3$), 2.30 (s, N(CH$_3$)$_2$), 0.88 (t, CH$_2$CH$_3$)

FAB mass spectrum Li spike, m/z 792.4, 776.5, 634.7, 615.9, 158.0

Data for isomer B

IR (CHCl$_3$) 3400, 2965, 2935, 2875, 2830, 2790, 1722, 1455, 1395, 1375, 1355, 1345, 1325, 1295, 1275, 1160, 1105, 1085, 1065, 1045, 1010, 995, 975, 950cm$^{-1}$ $^1$H NMR (60° C. CDCl$_3$) δ(ppm) 5.01 (d, H-1"), 4.90 (dd, H-13), 4.34 (d, H-1'), 3.29 (s, OCH$_3$), 2.31 (s, N(CH$_3$)$_2$), 0.89 (t, CH$_2$CH$_3$)

FAB mass spectrum Li spike, m/z 792.3, 748.2, 736.2, 633.6, 615.8, 572.1, 458.5, 157.9

EXAMPLE 20

Synthesis of 9-Deoxo-8a-aza-8a-((1-azetidinyl)-2-eth-1-yl)-8a-homoerythromycin A

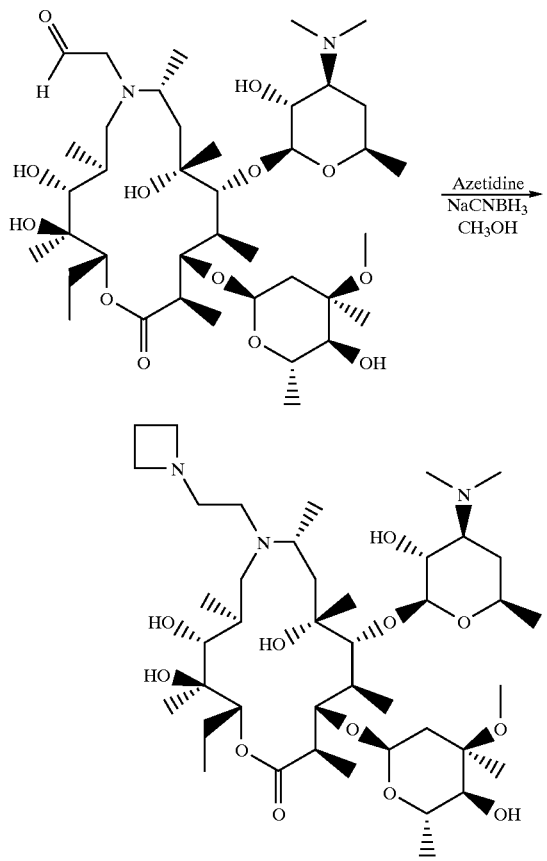

9-Deoxo-8a-aza-8a-(2-oxoeth-1-yl)-8a-homoerythromycin A (0.1 g, 0.129 mmol) was added to a methanol (1 mL) solution of azetidine (0.018 mL, 0.26 mmol). Sodium cyanoborohydride (0.02 g, 0.32 mmol) was added and the pH of the solution was adjusted to 6 with acetic acid. After 27 hours the pH was adjusted to 2.5 with 2N hydrochloric acid. After 5 minutes, water (6 mL) and 5% methanol in methylene chloride (6 mL) were added. The pH of the mixture was adjusted to 10 and the methylene chloride layer was removed and the aqueous layer was re-extracted with 5% methanol in methylene chloride (6 mL). The methylene chloride extracts were dried with anhydrous magnesium sulfate, were filtered and evaporated to a foam (0.11 g).

The foam was dissolved in 90:10:1 methylene chloride/methanol/concentrated ammonium hydroxide and was loaded onto a column of silica gel 60 (2.5×18 cm, 230–400 mesh, wet packed with 90:10;1 methylene chloride/methanol/concentrated ammonium hydroxide). The column was eluted with 9010:1 methylene chloride/methanol/concentrated ammonium hydroxide and 8 mL fractions were collected. Fractions 23–28 were combined and evaporated to give the title compound as a foam (0.070g).

IR (CHCl$_3$) 3440, 2965, 2935, 2875, 2835, 1725, 1455, 1400, 1370, 1355, 1345, 1320, 1275, 1240, 1176, 1165, 1120, 1100, 1080, 1060, 1045, 1010, 950, 895cm$^{-1}$ $^1$H NMR (CDCl$_3$) δ(ppm) 5.07 (dd, H-13), 5.0 (d, H-1"), 4.50 (d, H-1'), 3.32 (s, OCH$_3$), 2.29 (s, N(Me)$_2$), 0.85 (t, H-15)

FAB mass spectrum m/z 818, 747, 735, 660, 589, 577, 485, 158

EXAMPLE 21

Synthesis of 9-Deoxo-8a-aza-8a-((1-pyrrolidinyl)-2-eth-1-yl)-8a-homoerythromycin A

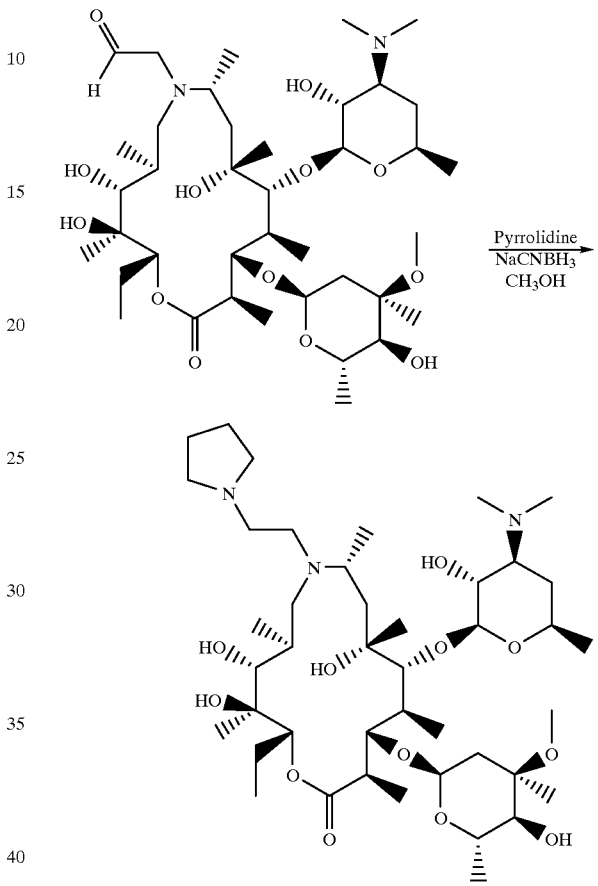

9-Deoxo-8a-aza-8a-(2-oxoeth-1-yl)-8a-homoerythromycin A (0.1 g, 0.129 mmol) was added to a methanol (1 mL) solution of pyrrolidine (0.022 mL, 0.26 mmol). Sodium cyanoborohydride (0.02 g, 0.32 mmol) was added and the pH of the solution was adjusted to 5.5 with acetic acid. After 18 hours the mixture was added to water (6 mL) and 5% methanol in methylene chloride (6 mL). The pH was adjusted to 10 and the methylene chloride layer was removed and the aqueous layer was re-extracted with 5% methanol in methylene chloride (6 mL). The methylene chloride extracts were combined, were filtered and evaporated to a foam (0.12 g).

The foam was dissolved in 90:10:1 methylene chloride/methanol/concentrated ammonium hydroxide and was loaded onto a column of silica gel 60 (2.5×30 cm, 230–400 mesh, wet packed with 90:10:1 methylene chloride/methanol/concentrated ammonium hydroxide). The column was eluted with 90:10:1 methylene chloride/methanol/concentrated ammonium hydroxide and 8 mL fractions were collected. Fractions 37–51 were combined and evaporated to give the title compound as a foam (0.095 g).

IR (CHCl$_3$) 3430, 2965, 2935, 2875, 2830, 1725, 1455, 1400, 1375, 1355, 1345, 1325, 1275, 1240, 1165, 1120, 1105, 1085, 1060, 1045, 1010, 995, 975, 950, 890 cm$^{-1}$

¹H NMR (CDCl₃) δ(ppm) 4.99 (d, H-1"), 4.98 (dd, H-13), 4.45 (d, H-1'), 3.29 (s, OCH₃), 2.27 (s, N(Me)₂), 0.84 (t, H-15)

¹³C NMR (60° C CDCl₃) δ(ppm) 177.0, 103.4, 95.9, 84.4, 78.3, 77.9, 75.0, 74.3, 72.8, 70.8, 69.2, 68.0, 65.8, 65.4, 57.3, 56.5, 54.1, 49.3, 45.9, 43.1, 40.3, 35.0, 33.7, 29.3, 25.3, 23.2, 21.6, 21.5, 21.0, 17.9, 16.4, 14.8, 14.3, 12.4, 10.9, 9.78

FAB mass spectrum m/z 833.5, 748.4, 675.0, 590.3, 159.0, 158.0

EXAMPLE 22

Synthesis of 9-Deoxo-8a-aza-8a-((N-piperidinyl)-2-eth-1-yl)-8a-homoerythromycin A

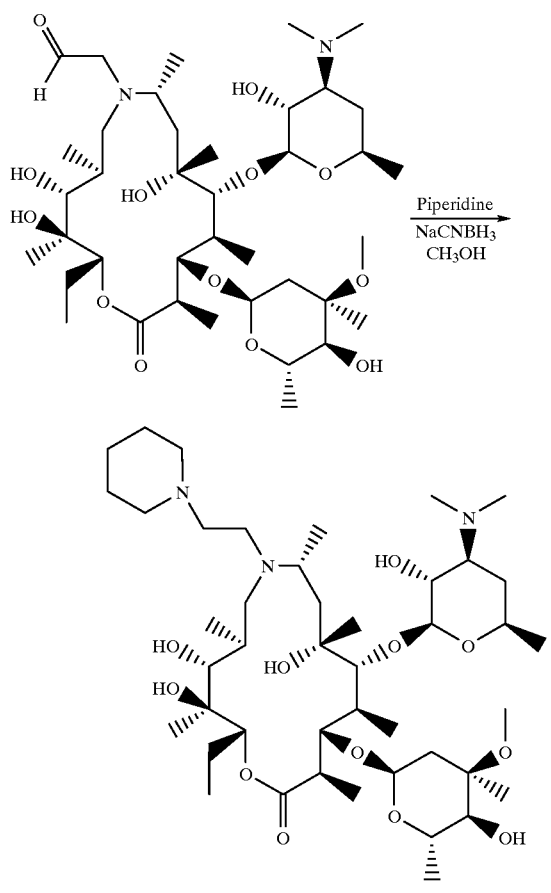

9-Deoxo-8a-aza-8a-(2-oxoeth-1-yl)-8a-homoerythromycin A (0.1 g, 0.129 mmol) was added to a methanol (lmL) solution of piperidine (0.015 mL, 0.15 mmol). Sodium cyanoborohydride (0.03 g, 0.48 mmol) was added and the pH of the solution was adjusted to 5.5 with acetic acid. After 18 hours the mixture was added to water (6 mL) and 5% methanol in methylene chloride (6 mL). The pH was adjusted to 10 and the methylene chloride layer was removed and the aqueous layer was re-extracted with 5% methanol in methylene chloride (6 mL). The methylene chloride extracts were combined, were filtered and evaporated to a foam (0.12 g).

The foam was dissolved in 90:10:1 methylene chloride/methanol/concentrated ammonium hydroxide and was loaded onto a column of silica gel 60 (2.5×15 cm, 230–400 mesh, wet packed with 90:10:1 methylene chloride/methanol/concentrated ammonium hydroxide). The column was eluted with 90:10:1 methylene chloride/methanol/concentrated ammonium hydroxide and 8 mL fractions were collected. Fractions 15–21 were combined and evaporated to give the title compound as a foam (0.05 g).

IR (CHCl₃) 3430, 2970, 2935, 2875, 2830, 2890, 1725, 1455, 1400, 1370, 1350, 1325, 1275, 1160, 1120, 1100, 1085, 1060, 1045, 1010, 995, 950, 890 cm⁻¹

¹H NMR (CDCl₃) δ(ppm) 5.01 (d, H-1"), 5.00 (dd, H-13), 4.48 (d, H-1'), 3.32 (s, OCH₃), 2.29 (s, N(Me)₂), 0.86 (t, H-15)

FAB mass spectrum m/z 847.5, 748.2

EXAMPLE 23

Synthesis of 9-Deoxo-8a-aza-8a-((4-morpholinyl)-2-eth-1-yl)-8a-homoerythromycin A

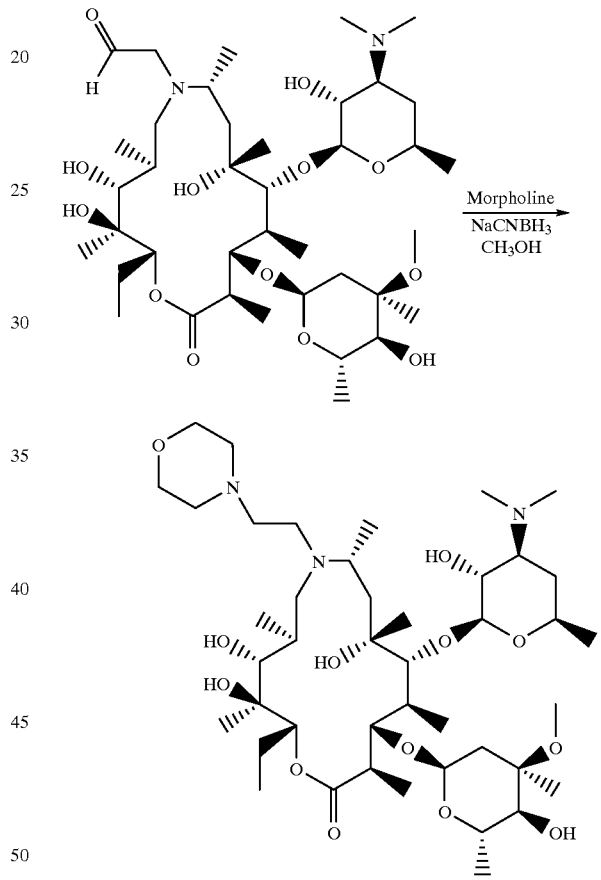

9-Deoxo-8a-aza-8a-(2-oxoeth-1-yl)-8a-homoerythromycin A (0.1 g, 0.13 mmol) was added to a methanol (1 mL) solution of morpholine (0.022 mL, 0.26 mmol). Sodium cyanoborohydride (0.02 g, 0.32 mmol) was added and the pH of the solution was adjusted to 6.0 with acetic acid. After 24 hours the mixture was added to water (6 mL) and methylene chloride (6 mL). The pH was adjusted to 11 and the methylene chloride layer was removed and the aqueous layer was re-extracted with methylene chloride (6 mL). The methylene chloride extracts were dried with magnesium sulfate, were filtered and evaporated to a foam.

The foam was dissolved in 90:10:1 methylene chloride/methanol/concentrated ammonium hydroxide and was loaded onto a column of silica gel 60 (2.5×18.5 cm, 230–400 mesh, wet packed with 90:10:1 methylene chloride/methanol/concentrated ammonium hydroxide). The column was eluted with 90:10:1 methylene chloride/methanol/concentrated ammonium hydroxide and 6 mL fractions were collected. Fractions 13–19 were combined and evaporated to give the title compound as a foam (0.05 g).

IR (CHCl$_3$) 3430, 2965, 2935, 2875, 2830, 2890, 1725, 1455, 1400, 1370, 1355, 1325, 1305, 1275, 1240, 1160, 1135, 1105, 1085, 1065, 1045, 1010, 995, 950, 890 cm$^{-1}$ $^1$H NMR (CDCl$_3$) δ(ppm) 5.02 (d, H-13), 4.98 (dd, H-1"), 4.48 (d, H-1'), 3.31 (s, OCH$_3$), 2.34 (s, N(Me)$_2$), 0.87 (t, H-15)

FAB mass spectrum m/z 849.8, 748.4, 691.2, 590.3

EXAMPLE 24

Synthesis of 9-Deoxo-8a-aza-8a-((2-fluoroeth-1-yl)-2-aminoeth-1-yl)-8a-homoerythromycin A

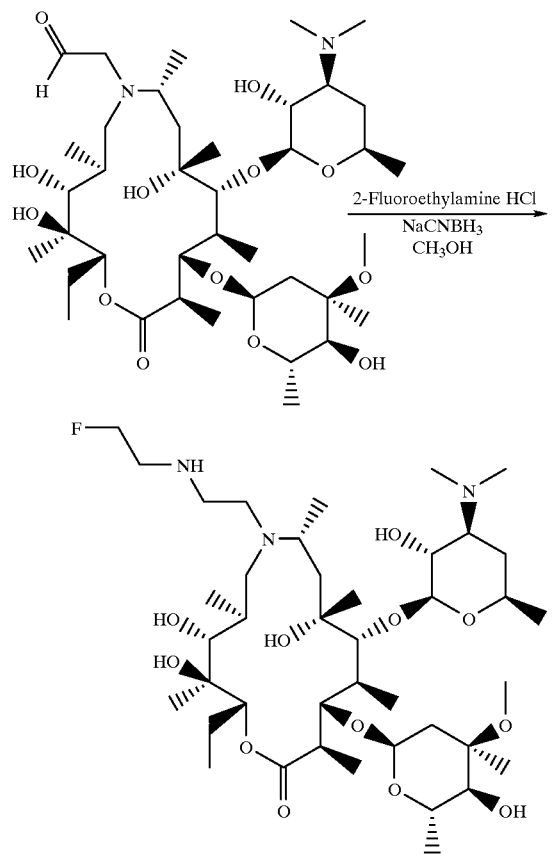

9-Deoxo-8a-aza-8a-(2-oxoeth-1-yl)-8a-homoerythromycin A (0.1 g, 0.13 mmol) was added to a methanol (1 mL) solution of 2-fluoroethylamine hydrochloride (0.038 mg, 0.38 mmol). Sodium cyanoborohydride (0.02 g, 0.32 mmol) was added and the pH of the solution was adjusted to 5.5 with acetic acid. After 24 hours the mixture was added to water (6 mL) and methylene chloride (6 mL). The pH was adjusted to 11 and the methylene chloride layer was removed and the aqueous layer was re-extracted with methylene chloride (6 mL). The methylene chloride extracts were dried with magnesium sulfate, were filtered and evaporated to a foam.

The foam was dissolved in 90:10:1 methylene chloride/methanol/concentrated ammonium hydroxide and was loaded onto a column of silica gel 60 (2.5×30 cm, 230–400 mesh, wet packed with 90:10:1 methylene chloride/methanol/concentrated ammonium hydroxide). The column was eluted with 90:10:1 methylene chloride/methanol/concentrated ammonium hydroxide and 6 mL fractions were collected. Fractions 40–49 were combined and evaporated to give the title compound as a foam (0.02 g).

IR (CHCl$_3$) 3430, 2965, 2935, 2875, 2830, 2890, 1725, 1455, 1400, 1370, 1350, 1345, 1325, 1275, 1240, 1160, 1135, 1105, 1080, 1065, 1045, 1030, 1010, 995, 975, 950, 890 cm$^{-1}$ $^1$H NMR (CDCl$_3$) δ(ppm) 5.02 (d, H-13), 4.99 (dd, H-1"), 4.48 (d, H-1'), 3.31 (s, OCR$_3$), 2.33 (s, N(Me)$_2$), 0.88 (t, H-15)

FAB mass spectrum m/z 825.7, 748.3, 648.6, 590.2, 492.0, 159.0, 157.9

EXAMPLE 25

Synthesis of 8a-(2-chloroallyl)-8a-aza-9-deoxo-8a-homoerythromycin A by palladium catalyzed allylation of 8a-aza-9-deoxo-8a-homoerythromycin A

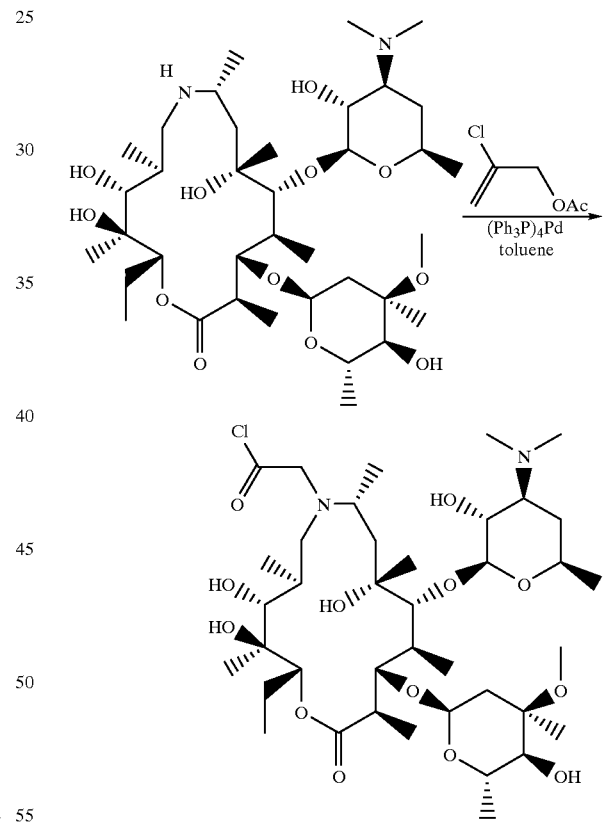

Tetrakis(triphenylphosphine)palladium(O) (98 mg, 0.085 mmol) was added to a solution of triethylamine (0.14 mL, 1.0 mmol), 2-chloroallyl acetate (0.29 mL, 2.4 mmol), and 8a-aza-9-deoxo-8a-homoerythromycin A (250 mg, 0.34 mmol) in 1 mL of toluene. The resulting mixture was stirred at 95° C. for 18 hours. The mixture was cooled to room temperature then diluted with ethyl acetate (3 mL) and filtered. The filtrate was extracted with 0.5 N aqueous HCl (3 mL). The organic layer was discarded. The aqueous layer was washed with ethyl acetate (2 mL) (organic layer discarded) then the pH of the aqueous layer was adjusted to ca. pH 10 by addition of 5 N NaOH. The aqueous layer was then extracted with ethyl acetate (3×3 mL). The combined extracts were dried over magnesium sulfate, filtered, and evaporated under vacuum to a an oil which was purified by flash chromatography on silica gel (3.0×20 cm column eluted with 93:5.5:1.5 chloroform:methanol:saturated methanolic ammonia, collecting 25 mL fractions). Analytical TLC of the fractions indicated that fractions 14–30 contained the desired product ($R_f$ 0.31). These fractions were combined and evaporated under vacuum to afford 8a-(2-chloroallyl)-8a-aza-9-deoxo-8a-homoerythromycin A as an oil (94 mg, 34% yield). An additional higher $R_f$ product ($R_f$ 0.44) was obtained by combining and evaporating fractions 6–8 to afford an oil (61 mg, 21% yield) which was identified as 2'-O-acetyl-8a-(2-chloroallyl)-8a-aza-9-deoxo-8a-homoerythromycin A.

$^1$H NMR (400 MHz, CDCl$_3$, 53° C.) δ5.46 & 5.26 (2×1H, 2 br s, C=CH$_2$), 3.44 & 3.12 (2×1H, 2 d, J=15 Hz, allylic CH$_2$), 3.28 (3H, s, OCH$_3$), 2.30 (6H, s, N(CH$_3$)$_2$).

EXAMPLE 26

Synthesis of 8a-(2-fluoroallyl)-8a-aza-9-deoxo-8a-homoerythromycin A by palladium catalyzed allylation of 8a-aza-9-deoxo-8a-homoerythromycin A

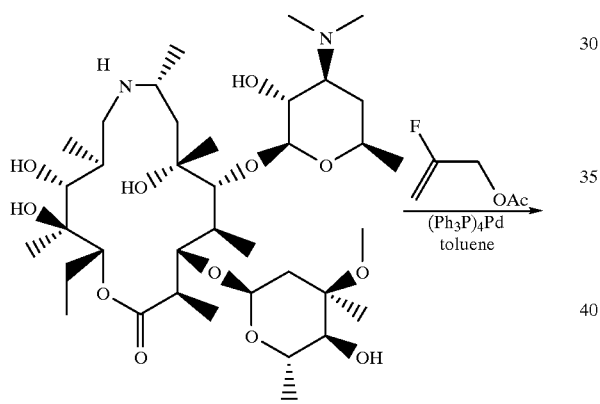

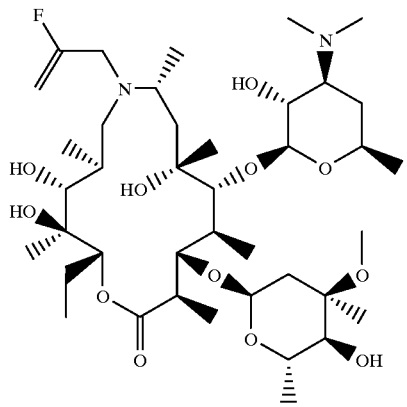

Substitution of 2-fluoroallyl acetate for 2-chloroallyl acetate in the procedure described above for the preparation of 8a-(2-chloroallyl)-8a-aza-9-deoxo-8a-homoerythromycin A affords 8a-(2-fluoroallyl)-8a-aza-9-deoxo-8a-homoerythromycin A.

EXAMPLE 27

Synthesis of 8a-(4-(tetra-O-acetyl-β-D-glucopyranosloxy-but-2-enyl-)-9-deoxo-8a-aza-8a-homoerythromycin A by palladium catalyzed allylation of 8a-aza-9-deoxo-8a-homoerythromycin A.

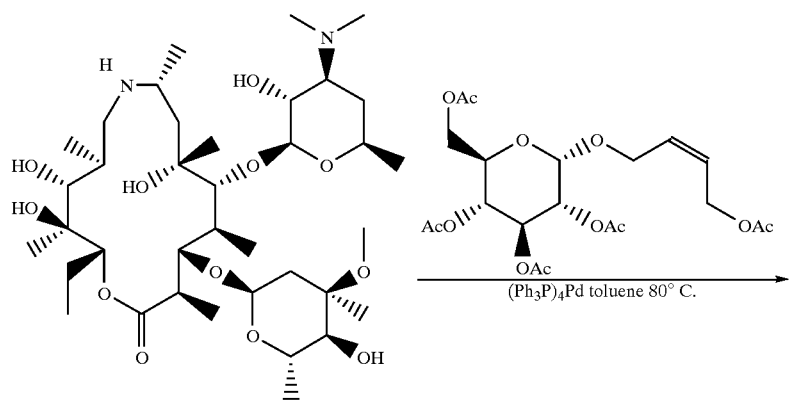

-continued

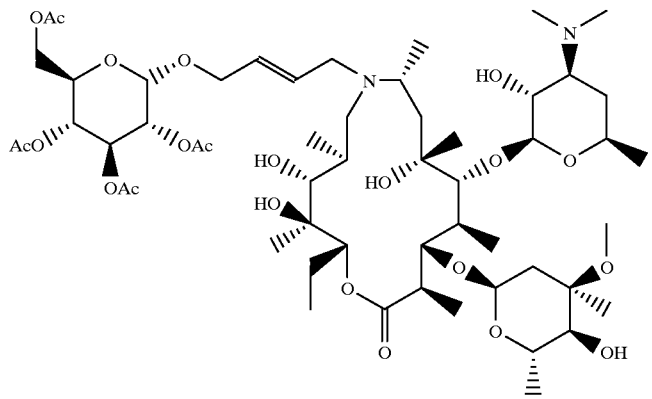

Tetrakis(triphenylphosphine)palladium(O) (79 mg, 0.068 mmol) was added to a solution of triethylamine (0.57 mL, 0.41 mmol), β-(4-acetoxy-but-2-enyl-)-tetra-O-acetyl-glucopyranoside (323 mg, 0.7 mmol), and 8a-aza-9-deoxo-8a-homoerythromycin A (101 mg, 0.14 mmol) in 0.5 mL of toluene. The resulting mixture was stirred at 80° C. for 5 hours. The mixture was cooled to room temperature then diluted with ethyl acetate (2 mL) and filtered. The filtrate was evaporated under vacuum to a an oil which was purified by flash chromatography on silica gel (4.0×24 cm column eluted with 97:3:1.5 chloroform:methanol: saturated methanolic ammonia, collecting 30 mL fractions). Analytical TLC of the fractions indicated that fractions 61–99 contained the desired product ($R_f$ 0.26). These fractions were combined and evaporated under vacuum to afford impure 8a-(4-(tetra-O-acetyl-β-D-glucopyranosloxy-but-2-enyl-))-9-deoxo-8a-aza-8a-homoerythromycin A (53 mg). This material was further purified by flash chromatography on silica gel (1.0× 18 cm column eluted with 60:40:3 acetone:hexane:saturated methanolic ammonia, collecting 5 mL fractions). Fractions 10–16 were combined and evaporated under vacuum to afford 8a-(4-(tetra-O-acetyl-β-D-glucopyranosloxy-but-2-enyl-))-9-deoxo-8a-aza-8a-homoerythromycin A ($R_f$ 0.30, 31 mg, 19% yield).

$^1$H NMR (400 MHz, CD$_3$OD, 53° C.): δ5.86 (1H, dt, J=15, 7 Hz, C=CH), 5.66 (1H, dt, J=15, 6 Hz, HC=C), 4.69 (1H, d, J=8 Hz, H1'''), 3.32 (3H, s, OCH$_3$), 2.31 (6H, br s, N(CH$_3$)$_2$), 2.05 & 2.01 & 1.99 & 1.95 (4×3H, 4 s, 4×OAc).

$^{13}$C NMR (100 MHz, CD$_3$OD) δ179.7, 172.2, 171.7, 171.3, 171.0, 134.8, 128.5, 104.6, 101.2, 96.5.

FAB-MS: m/z 1136 (M+H).

EXAMPLE 27 cont'd.

Synthesis of B-(4-acetoxy-but-2-enyl-)-tetra-O-acetyl-glucopyranoside by condensation of 1.4-butene-diol and acetobromoglucose followed by acetylation

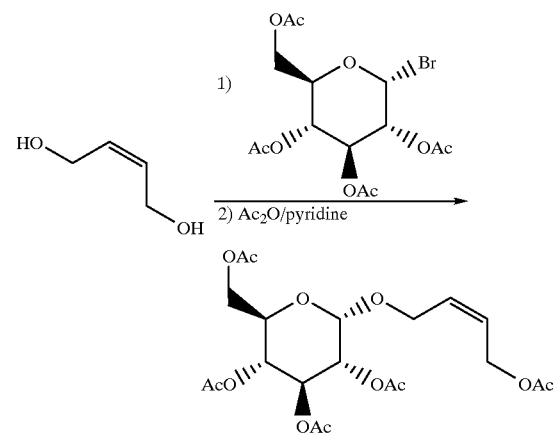

But-2-ene-1,4-diol (2.0 mL, 24.3 mmol) was added to a cooled (ice bath) solution of acetobromo-α-D-glucose (2.0 g, 4.9 mmol) in 10 mL of dry acetonitrile. A solution of silver trifluoromethanesulfonate (1.6 g, 6.3 mmol) in 2 mL of dry acetonitrile was then added dropwise. The resulting solution was stirred at 0° C. in the dark for 4 hours. The reaction mixture was diluted with ethyl acetate and filtered through Celite and the filtrate was washed with 5% aqueous HaHCO$_3$ saturated with NaCl. The aqueous layer was back-extracted with ethyl acetate and the combined organic layers were dried over magnesium sulfate, filtered, and evaporated under vacuum. The residue (5.0 g) was dissolved in 3.9 mL of pyridine and cooled (ice bath) as acetic anhydride (4.6 mL) was added dropwise. The resulting solution was stirred at 0° C. for 4 hours then partitioned between ethyl acetate and aqueous K$_2$CO$_3$ (additional K$_2$CO$_3$ was added as necessary to adjust the PH to 10). The aqueous layer was extracted with ethyl acetate and the combined organic extracts were dried over magnesium sulfate, filtered, and evaporated. The crude porduct was purified by flash chromatography on silica gel (7.0×26 cm column eluted with 3:1 hexane:acetone, collecting 50 mL fractions). Fractions 74–100 were combined and evaporated under vacuum to afford β-(4-acetoxy-but-2-enyl-)-tetra-O-acetyl-glucopyranoside ($R_f$ 0.26, 1.1 g, 49% yield).

$^1$H NMR (400 MHz, CDCl$_3$): δ5.76–5.64 (2H, m, HC=CH), 4.55 (1H, d, J=8 Hz, anomeric H), 2.09 & 2.06 & 2.02 & 2.02 & 2.00 (5×3H, s, 5×OAc).

EXAMPLE 28

Synthesis of 8a-(4-(tetra-O-acetyl-β-D-glucopyranosloxy-butyl-))-9-deoxo-8a-aza-8a-homoerythromycin A by hydrogenation of 8a-(4-(tetra-O-acetyl-β-D-glucopyranosloxy-but-2-enyl-))-9-deoxo-8a-aza-8a-homoerythromycin A

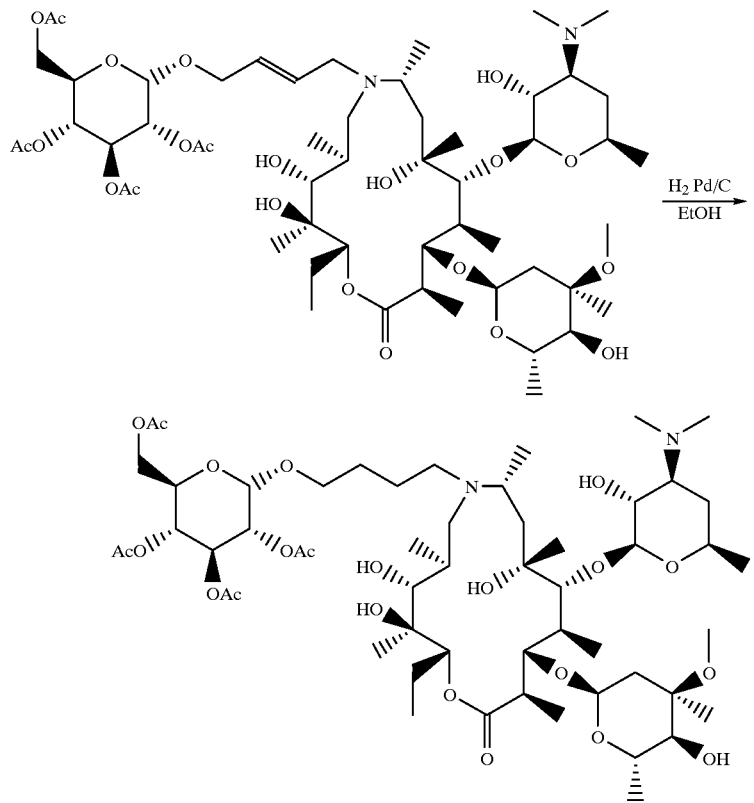

Palladium catalyst (23 mg, 10% Pd/C) was added to a solution of 8a-(4-(tetra-O-acetyl-β-D-glucopyranosloxy-but-2-enyl-))-9-deoxo-8a-aza-8a-homoerythromycin A (20 mg, 0.018 mmol) in 0.5 mL of absolute ethanol. The reaction vessel was flushed and filled with nitrogen then flushed and filled with hydrogen. The reaction mixture was stirred at room temperature under one atmosphere (balloon) of hydrogen for 0.5 hours. The reaction mixture was filtered through Celite and the filtrate was evaporated under vacuum to afford 8a-(4-(tetra-O-acetyl-β-D-glucopyranosloxy-butyl-))-9-deoxo-8a-aza-8a-homoerythromycin A (7 mg, 35% yield).

$^1$H NMR (400 MHz, CDCl$_3$): δ4.47 (1H, d, J=8 Hz, H1'''), 3.31 (3H, s, OCH$_3$), 2.42 (6H, br s, N(CH$_3$)$_2$), 2.07 & 2.03 & 2.01 & 1.99 (4×3H, 4 s, 4×OAc).

FAB-MS: m/z 1138 (M+H).

EXAMPLE 29

Synthesis of 9-Deoxo-8a-aza-8a-((2-cyano)eth-1-yl)-8a-homoerythromycin A

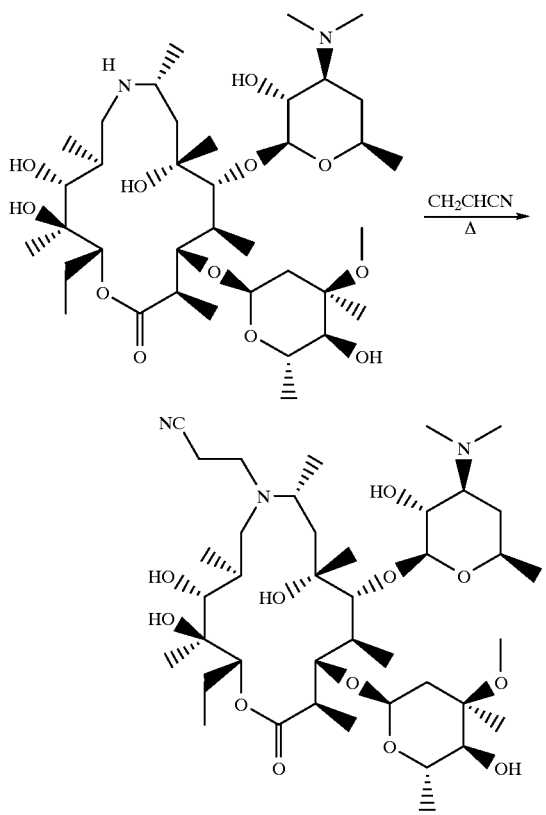

9-Deoxo-8a-aza-8a-homoerythromycin A (4.0 g, 5.5 mmol) was dissolved in acrylonitrile (30 mL, 456 mmol) and the solution was refluxed for 27 hours. The solvent was evaporated under vacuum and the residue was dissolved in isopropyl alcohol (24 mL). After stirring for 1 hour at room temperature and 3 hours in an ice bath, the precipitate was filtered, rinsed with cold isopropyl alcohol (10 mL), and was dried under vacuum to afford the title compound as a white crystalline solid (2.85 g).

MP 173–175° C.

IR (CHCl$_3$) 3540, 3420, 2965, 2935, 2880, 2835, 2790, 2250(w), 1722, 1455, 1405, 1375, 1345, 1330, 1275, 1255, 1245, 1175, 1160, 1120, 1100, 1085, 1070, 1040, 995, 975, 955 cm$^{-1}$ $^1$H NMR (CDCl$_3$) δ(ppm) 4.95 (br d, H-1") 4.90 (br dd, H-13), 4.38 (d, H-1'), 3.22 (s, OCH$_3$), 2.28 (s, N(CH$_3$)$_2$), 0.85 (t, CH$_2$CH$_3$)

FAB mass spectrum, m/z 788.4, 644.2, 630.2, 612.3, 571.3, 158.3

EXAMPLE 30

Synthesis of 9-Deoxo-8a-aza-8a-((3-amino)prop-1-yl)-8a-homoerythromycin A

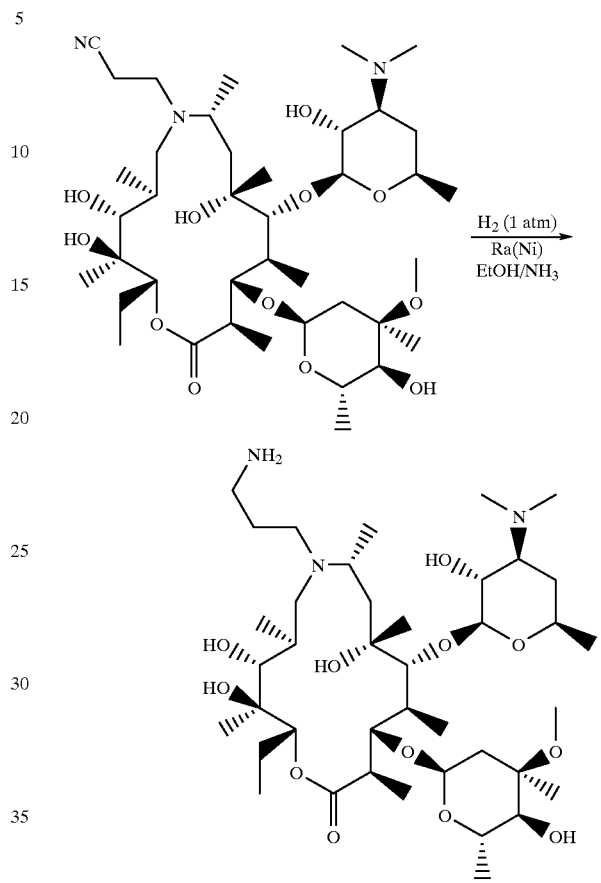

9-Deoxo-8a-aza-8a-((2-cyano)eth-1-yl-8a-homoerythromycin A (0.5 g, 0.635 mmol) was dissolved in ethanol (6 mL) and the solution was saturated with ammonia. Raney nickel (0.5 g) was added and the mixture was hydrogenated at 40 psi for 4 hours, whereupon more Raney nickel (0.5 g) was added and the hydrogenation was continued for an additional 20 hours. The suspension was filtered and the filtrate was evaporated to a light blue foam.

The above foam was dissolved in 60:10:1 methylene chloride/methanol/conc. ammonium hydroxide and was loaded onto a column of silica gel 60 (2.5×14 cm, 230–400 mesh, wet packed with 60:10:1 methylene chloride/methanol/conc. ammonium hydroxide). The column was eluted with 60:10:1 methylene chloride/methanol/conc. ammonium hydroxide and 8 mL fractions were collected. Fractions 12–18 were combined and evaporated to give the title compound as a white foam (0.35 g).

IR (CHCl$_3$) 3400, 2970, 2935, 2875, 2835, 2785, 1725, 1455, 1395, 1370, 1345, 1325, 1275, 1255, 1240, 1160, 1105, 1085, 1045, 1010, 995, 975, 950, 890 cm$^{-1}$ $^1$H NMR (CDCl$_3$) δ(ppm) 4.92 (br d, H-1"+H-13), 4.35 (d, H-1'), 3.25 (8, OCH$_3$), 2.25 (s, N(CH$_3$)$_2$), 0.82 (t, CH$_2$CH$_3$)

$^{13}$C NMR (CDCl$_3$) δ(ppm) 177.0, 104.4, 96.1, 77.8, 77.1, 75.0, 74.4, 72.7, 70.5, 69.2, 69.0, 65.6, 65.0, 63.9, 50.4, 49.3, 46.6, 46.5, 42.2, 40.3, 40.2, 34.9, 32.6, 31.0, 28.9, 26.0, 21.8, 21.5, 21.1, 17.9, 16.2, 15.3, 14.6, 14.5, 13.0, 11.1, 10.7

FAB mass spectrum, m/z 792.5, 616.4

EXAMPLE 31

Synthesis of 9-Deoxo-8a-aza-8a-(((N,N-dimethyl)-3-amino)prop-1-yl)-8a-homoerythromycin A

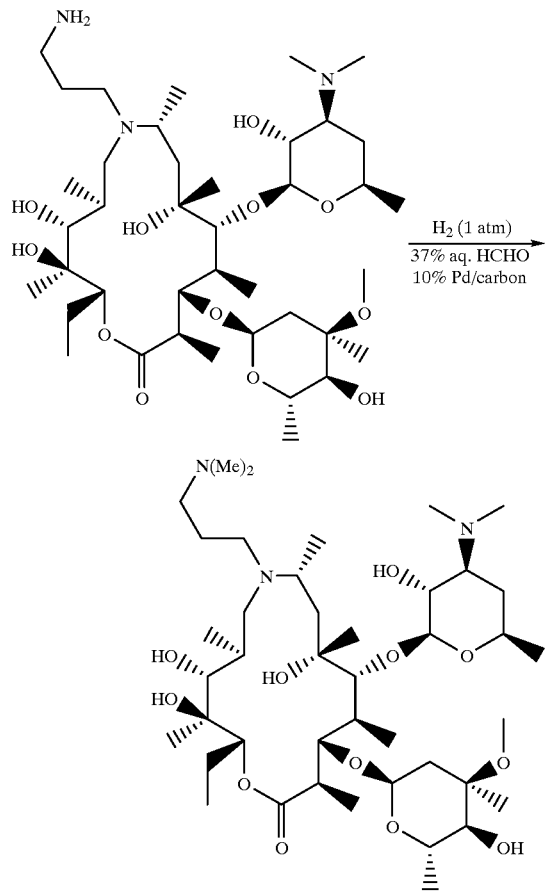

9-Deoxo-8a-aza-8a-((3-amino)prop-1-yl)-8a-homoerythromycin A (100 mg, 0.125 mmol) and formalin (0.12 mL, 1.6 mmol) were dissolved in a mixture of 4:1 ethanol/water (1.2 mL). The solution was hydrogenated at atmospheric pressure for 26 hours in the presence of 10% palladium on carbon (50 mg). The suspension was filtered through solka-floc and the filtrate was evaporated to an oil. The oil was partitioned between water (4 mL) and methylene chloride (4 mL), the pH was adjusted from 7.0 to 11.0, and the methylene chloride layer was removed. The aqueous layer was re-extracted with more methylene chloride (4 mL) and the combined methylene chloride extracts were dried with magnesium sulfate, were filtered and evaporated under vacuum to give an oil (91 mg).

The oil was dissolved in methylene chloride and was placed on a 1000 micron silica preparative thin layer plate. The plate was developed with 90:10:1 methylene chloride/methanol/conc. ammonium hydroxide and the title compound was removed, eluted with 90:10:1 methylene chloride/methanol/conc. ammonium hydroxide, and evaporated to a foam (66 mg).

IR (CHCl$_3$) 3400, 2965, 2935, 2875, 2825, 2780, 1725, 1455, 1395, 1370, 1345, 1325, 1275, 1255, 1240, 1160, 1115, 1100, 1085, 1045, 1010, 975, 950, 890 cm$^{-1}$ $^1$H NMR (CDCl$_3$) δ(ppm) 4.95 (br d+dd, H-1"+H-13), 4.38 (d, H-1'), 3.25 (s, OCH$_3$), 2.28 (s, N(CH$_3$)$_2$), 2.22 (s, N(CH$_3$)$_2$), 0.85 (t, CH$_2$CH$_3$)

FAB mass spectrum, m/z 820.3, 733.3, 662.4, 158.2

EXAMPLE 32

Synthesis of 9-Deoxo-8a-aza-8a-((2-cyanoethyl)-3-aminoprop-1-yl)-8a-homoerythromycin A

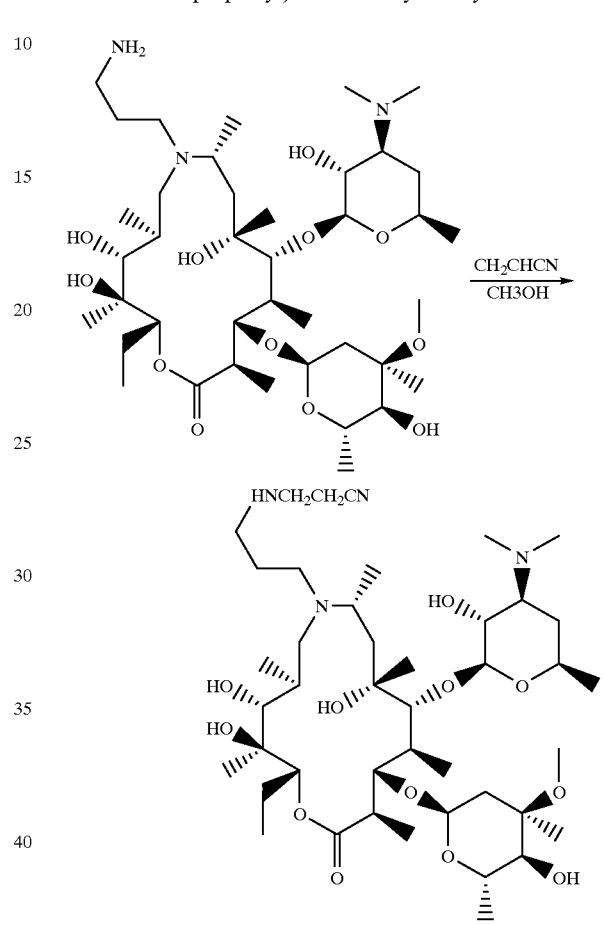

9-Deoxo-8a-aza-8a-((3-amino)prop-1-yl)-8a-homoerythromycin A (200 mg, 0.253 mmol) was dissolved in methanol (0.5 mL) and was treated with acrylonitrile (0.033 mL, 0.50 mmol). The solution was stirred at room temperature for 4 hours and was evaporated to a foam.

The above foam was dissolved in 90:10:1 methylene chloride/methanol/conc. ammonium hydroxide and was loaded onto a column of silica gel 60 (2.5×17.5 cm, 230–400 mesh, wet packed with 90:10:1 methylene chloride/methanol/conc. ammonium hydroxide). The column was eluted with 90:10:1 methylene chloride/methanol/conc. ammonium hydroxide and 8 mL fractions were collected. Fractions 25–37 were combined and evaporated to give the title compound as a white foam (0.17 g).

IR (CHCl$_3$) 3400, 2970, 2935, 2880, 2825, 2455(w), 1725, 1555, 1400, 1375, 1345, 1325, 1280, 1165, 1120, 1105, 1085, 1045, 1010, 995, 975, 955, 900 cm$^{-1}$ $^1$H NMR (60° C. CDCl$_3$) δ(ppm) 4.92 (br d, H-1") 4.89 (dd, H-13), 4.34 (d, H-1'), 3.23 (s, OCH$_3$), 2.28 (s, N(CH$_3$)$_2$), 0.83 (t, CH$_2$CH$_3$)

$^{13}$C NMR (60° C. CHCl$_3$) δ(ppm) 177.0, 118.4, 104.5, 96.3, 87.6, 87.5, 78.7, 77.9, 77.2, 75.3, 74.5, 72.8, 70.6, 69.4, 69.0, 65.7, 65.1, 57.5, 54.5, 49.3, 49.2, 47.1, 46.8, 45.0, 42.3, 41.4, 40.3, 35.0, 32.8, 29.5, 28.7, 26.0, 21.9, 21.4, 21.0, 18.5, 17.9, 16.2, 15.2, 14.4, 13.0, 11.1, 10.7

FAB mass spectrum, m/z 846.9, 793.8, 687.8, 669.7, 513.4, 157.9

EXAMPLE 33

Synthesis of 9-Deoxo-8a-aza-8a-((3,4-dibenzyloxybenzyl)-3-aminoprop-1-yl)-8a-homoerythromycin A

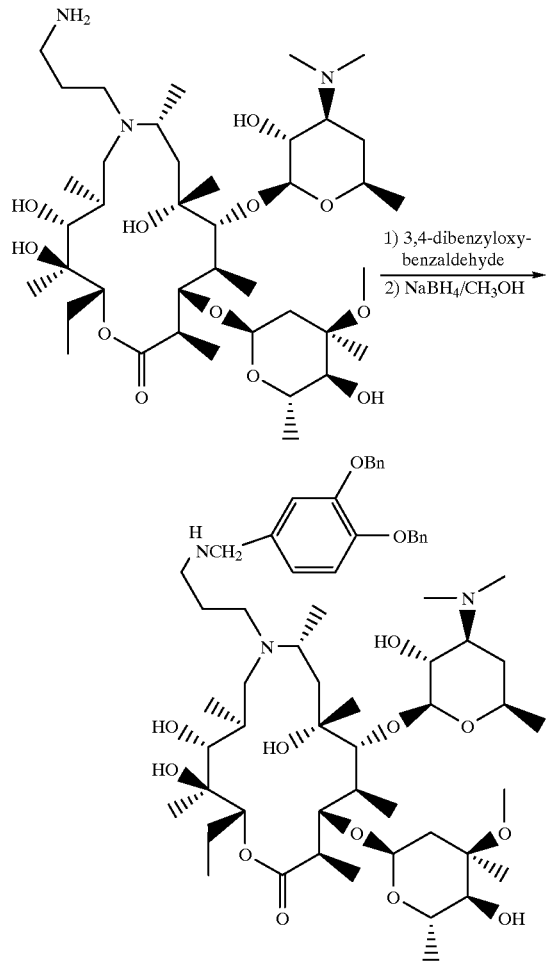

9-Deoxo-8a-aza-8a-((3-amino)prop-1-yl)-8a-homoerythromycin A (100 mg, 0.125 mmol) and 3,4-dibenzyloxybenzaldehyde (44 mg, 0.138 mol) were dissolved in isopropyl alcohol and were heated at 60° C. for 22 hours. The solution was cooled to room temperature and evaporated to a glassy solid. The solid was dissolved in methanol (1 mL) and was treated with sodium borohydride (15 mg, 0.4 mmol). After 0.5 hours, several drops of ethylene glycol were added to break up the borate esters, and the solution was stirred an additional 0.5 hours. The mixture was partitioned between water (4 mL) and methylene chloride (4 mL). The methylene chloride layer was removed and the aqueous layer was re-extracted with more methylene chloride (4 mL). The combined methylene chloride extracts were dried with magnesium sulfate, were filtered and evaporated to a foam.

The foam was dissolved in methylene chloride and was placed on two 1000 micron silica preparative thin layer plates. The plates were developed with 90:10:1 methylene chloride/methanol/conc. ammonium hydroxide and the title compound was removed, eluted with 90:10:1 methylene chloride/methanol/conc. ammonium hydroxide, and evaporated to a foam (54 mg).

$^1$H NMR (CDCl$_3$) δ(ppm) 5.15 (s, CH$_2$Ar), 5.12 (s, CH$_2$Ar), 4.98 (br dd, H-13), 4.90 (dd, H-1"), 4.38 (d, H-1), 3.27 (s, OCH$_3$), 2.28 (s, N(CH$_3$)$_2$), 0.85 (t, CH$_2$CH$_3$)

EXAMPLE 34

Synthesis of 9-Deoxo-8a-aza-8a-((3,4-dihydroxybenzyl)-3-aminoprop-1-yl)-8a-homoerythromycin A

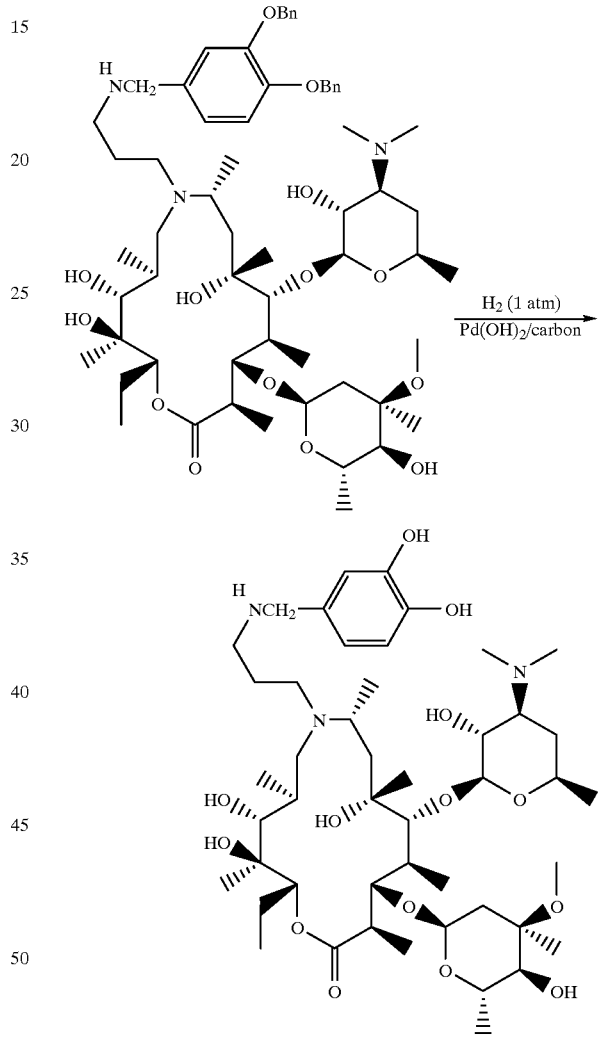

The crude 9-Deoxo-8a-aza-8a-((3,4-dibenzyloxybenzyl)-3-aminoprop-1-yl)-8a-homoerythromycin A was dissolved in ethanol (4 mL), and was hydrogenated at atmospheric pressure for 3 hours in the presence of 20% palladium hydroxide on carbon (48 mg). The suspension was filtered through a 0.45 micron acrodisc and the filtrate was evaporated to give the title compound (40 mg).

$^1$H NMR (CDCl$_3$) δ(ppm) 7.22 (br m, ArH), 6.83 (br m, ArH), 5.12 (br dd, H-13) 4.87 (br d, H-1"), 4.34 (br d, H-1'), 3.25 (s, OCH$_3$), 2.42 (s, N(CH$_3$)$_2$), 0.85 (t, CH$_2$CH$_3$)

IR (nujol) 3360, 2940, 2920, 2850, 1725, 1460, 1450, 1370, 1280, 1175, 1160, 1110, 1070, 1045, 1005, 995, 975, 950, 890 cm$^{-1}$ FAB mass spectrum, m/z 914.5, 820.4, 792.3, 747.2, 178.1, 165.1, 154.0

EXAMPLE 35

Synthesis of 9-Deoxo-8a-aza-8a-(3-acetoxyprop-1-yl)-8a-homoerythromycin A and 9-Deoxo-8a-aza-(8a,6-O-trimethylene)-8a-homoerythromycin A

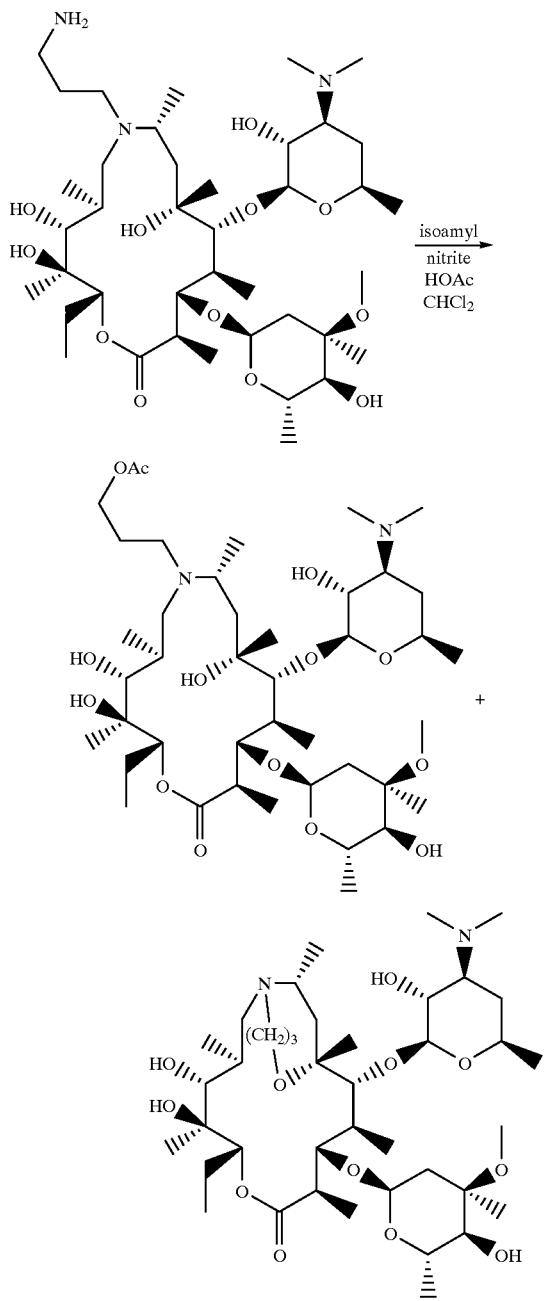

9-Deoxo-8a-aza-8a-((3-amino)prop-1-yl)-8-a-homoerythromycin A (0.38 g, 0.48 mmol) was dissolved in chloroform (6 mL) and was treated with isoamylnitrite (0.072 ml, 0.54mmol) and acetic acid (0.056 mL, 0.98 mmol). The solution was refluxed a total of 2 hours, with an addition of isoamylnitrite (0.036 mL, 0.27 mmol) and acetic acid (0.025 mL, 0.4375 mmol) at 50 minutes. The mixture was cooled to room temperature, water (6 mL) was added and the pH was adjusted to 4 with dilute hydrochloric acid. The methylene chloride layer was removed and additional methylene chloride (6 mL) was added. The pH was adjusted to 11 with dilute sodium hydroxide, the methylene chloride was removed and the aqueous layer was re-extracted with more methylene chloride (4 mL). The combined extracts were dried with magnesium sulfate, were filtered and evaporated to a foam (0.385 g).

The above foam was dissolved in 90:10:1 methylene chloride/methanol/conc. ammonium hydroxide and was loaded onto a column of silica gel 60 (4.25×13 cm, 230–400 mesh, wet packed with 90:10:1 methylene chloride/methanol/conc. ammonium hydroxide). The column was eluted with 90:10:1 methylene chloride/methanol/conc. ammonium hydroxide and 8 mL fractions were collected. Fractions 19–22 were combined and evaporated to give 9-Deoxo-8a-aza-8a-(3-acetoxypropyl)-8a-homoerythromycin A as a white foam (0.17 g). Fractions 25–27 were combined and evaporated to a foam (0.028 g). The foam was dissolved in 90:10:1 methylene chloride/methanol/conc. ammonium hydroxide and was loaded onto a column of silica gel 60 (2.5×27 cm, 230–400 mesh, wet packed with 90:10:1 methylene chloride/methanol/conc. ammonium hydroxide). The column was eluted with 90:10:1 methylene chloride/methanol/conc. ammonium hydroxide and 4mL fractions were collected. Fractions 32–43 were combined and evaporated to give 9-Deoxo-8a-aza-(8a,6-O-trimethylene)-8a-homoerythromycin A as a foam (0.016 g).

Data for 9-Deoxo-8a-aza-8a-(3-acetoxyprop-1-yl)-8a-homoerythromycin A

IR (CHCk$_3$) 3410, 2970, 2935, 2880, 2830, 2785, 1728, 1455, 1395, 1370, 1345, 1325, 1270, 1240, 1160, 1120, 1105, 1085, 1045, 1010, 995, 975, 950 cm$^{-1}$ $^1$H NMR (60° C. CDCl$_3$) δ(ppm) 4.98 (m, H-1"+H-13), 4.38 (d, H-1'), 3.28 (s, OCH$_3$), 2.32 (s, N(CH$_3$)$_2$), 2.02 (s, OAc), 0.89 (t, CH$_2$CH$_3$)

$^{13}$C NMR (60° C. CDCl$_3$) δ(ppm) 177.2, 170.7, 104.7, 96.1, 88.1, 78.0, 77.0, 75.5, 74.4, 72.8, 70.6, 70.5, 69.2, 65.7, 65.2, 62.9, 58.6, 58.6, 49.3, 47.1, 47.0, 46.6, 42.4, 41.2, 40.3, 40.2, 35.0, 32.6, 29.4, 28.0, 22.0, 21.6, 21.5, 21.0, 20.7, 17.9, 16.1, 14.9, 14.6, 12.7, 11.6, 11.2

FAB mass spectrum, m/z 835.6, 677.1, 659.8, 158.4

Data for 9-Deoxo-8a-aza-(8a,6-O-trimethylene)-8a-homoerythromycin A

IR (CHCl$_3$) 3410, 2970, 2935, 2880, 2830, 2785, 1725, 1455, 1395, 1370, 1345, 1275, 1240, 1160, 1110, 1105, 1085, 1045, 1010, 995, 975, 950 cm$^{-1}$ $^1$H NMR (60° C. CDCl$_3$) δ(ppm) 5.19 (d, H-1"), 4.85 (dd, H-13), 4.62 (br d, H-1'), 3.33 (s, OCH$_3$), 2.35 (br s, N(CH$_3$)$_2$), 0.85 (t, CH$_2$CH$_3$)

FAB mass spectrum, m/z 775.5, 759.0, 615.0, 599.3, 500.3, 158.4

EXAMPLE 36

Synthesis of 9-Deoxo-8a-aza-8a-(3-hydroxyprop-1-yl)-8a-homoerythromycin A

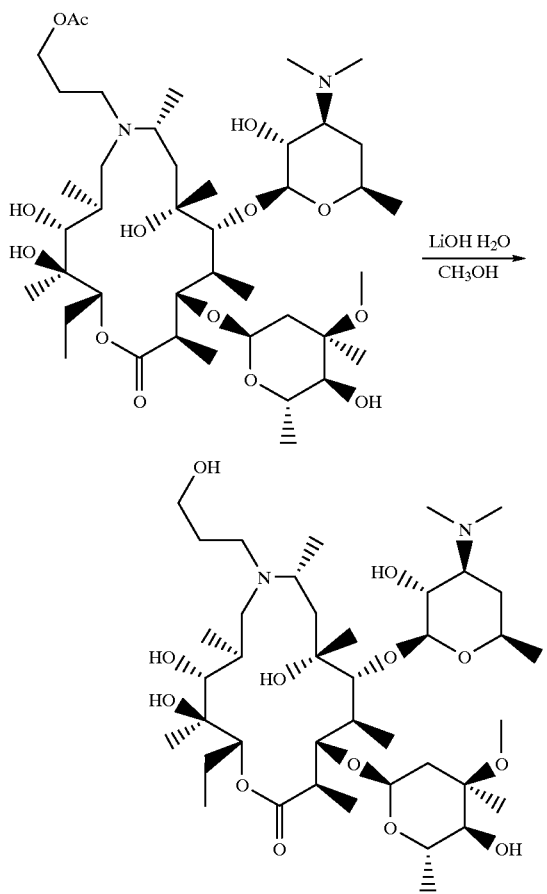

Lithium hydroxide monohydrate (0.005 g, 0.12 mmol) was added to a solution of 9-Deoxo-8a-aza-8a-(3-acetoxyprop-1-yl)-8a-homoerythromycin A (0.098 g, 0.117 mmol) in methanol (1.5 mL), and the solution was heated at 50° C. for 0.5 hours. After cooling to room temperature, the mixture was evaporated and the residue was partitioned between water (4 mL) and methylene chloride (4 mL). The methylene chloride was removed and the aqueous layer was re-extracted with more methylene chloride (4 mL). The combined methylene chloride extracts were dried with magnesium sulfate, were filtered and evaporated to a foam.

The above foam was dissolved in 90:10:1 methylene chloride/methanol/conc. ammonium hydroxide and was loaded onto a column of silica gel 60 (2.5×18cm, 230–400 mesh, wet packed with 90:10:1 methylene chloride/methanol/conc. ammonium hydroxide). The column was eluted with 90:10:1 methylene chloride/methanol/conc. ammonium hydroxide and 8 mL fractions were collected. Fractions 24–27 were combined and evaporated to give the title compound as a foam (0.042 g).

IR (CHCl$_3$) 3405, 2970, 2935, 2875, 2830, 2785, 1722, 1455, 1400, 1375, 1345, 1280, 1160, 1105, 1085, 1045, 1010, 995, 975, 950, 890 cm$^{-1}$ $^1$H NMR (CD$_3$OD) δ(ppm) 5.11 (d, H-1"), 4.98 (dd, H-13), 4.38 (d, H-1'), 3.32 (s, OCH$_3$), 2.32 (s, N(CH$_3$)$_2$), 0.88 (t, CH$_2$CH$_3$)

FAB mass spectrum (Li spike), m/z 799.8, 793.8, 635.6, 617.6, 478.4, 460.5, 172.5, 167.3, 158.3

EXAMPLE 37

9-Deoxo-8a-aza-8a-(3-methoxy-3-oxopropyl)-8a-homoerythromycin A

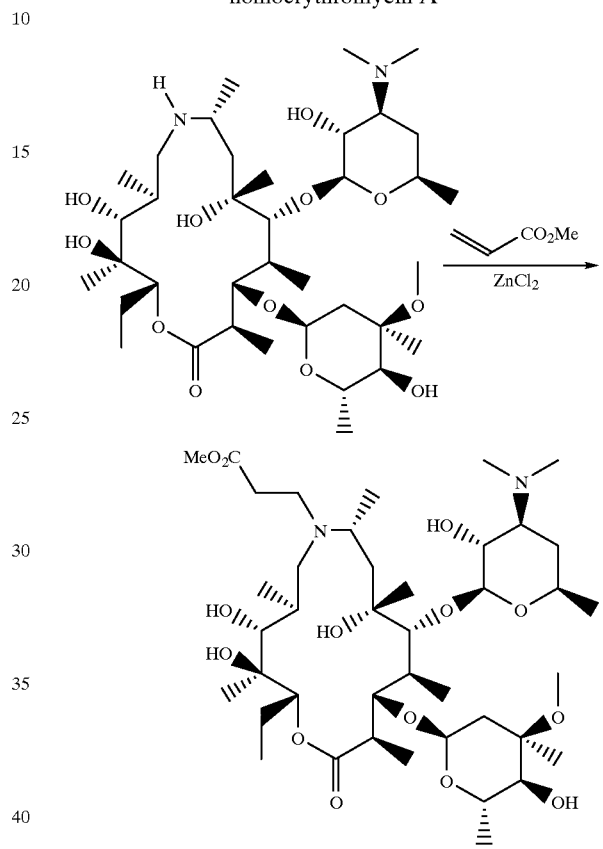

Zinc chloride (215 mg, 1.58 mmol) and methanol (0.11 mL, 2.7 mmol) were added to a mixture of 9-deoxo-8a-aza-8a-homoerythromycin A (2.0 g, 2.7 mmol) and methyl acrylate (30 mL, 333 mmol). The resulting mixture was stirred at 60° C. for 91 hours. The excess methyl acrylate was removed under vacuum leaving a white solid residue. The crude product was purified by flash chromatography on EM silica gel 60 (7.0×30.5 cm, column eluted with 95:5:1 chloroform:methanol:aqueous ammonia collecting 50 mL fractions). Fractions 29–40 were combined and evaporated under vacuum to afford 9-deoxo-8a-aza-8a-(3-methoxy-3-oxopropyl)-8a-homoerythromycin A (1.58 g) as a foam.

$^1$H NMR (400 MHz, CD$_3$OD) δ5.14 (d, H-1"), 4.97 (dd, H-13), 4.42 (br s, H-3), 4.39 (d. H-1'), 4.19 (m, H-5"), 3.67 (s, CO$_2$CH$_3$), 3.64 (m, H-5'), 3.51 (d, H-5), 3.48 (br s, H-11), 3.31 (s, OCH$_3$), 3.27 (dd, H-2'), 3.00 (d, H-4"), 2.36 (s, N(CH$_3$)$_2$), 1.34 (br s, 6-CH$_3$), 1.14 (d, 8-CH$_3$), 1.10 (s, 12-CH$_3$), 1.02 (d, 4-CH$_3$), 0.93 (d, 10-CH$_3$), 0.89 (t, CH$_2$CH$_3$).

FAB-MS, m/z 821 (M+H), 827 (M+Li).

EXAMPLE 38

Synthesis of 8a-(3-octyloxy-3-oxopropyl)-9-deoxo-8a-aza-8a-homoerythromycin A by transesterification of 8a-(3-methoxy-3-oxopropyl)-9-deoxo-8a-aza-8a-homoerythromycin A

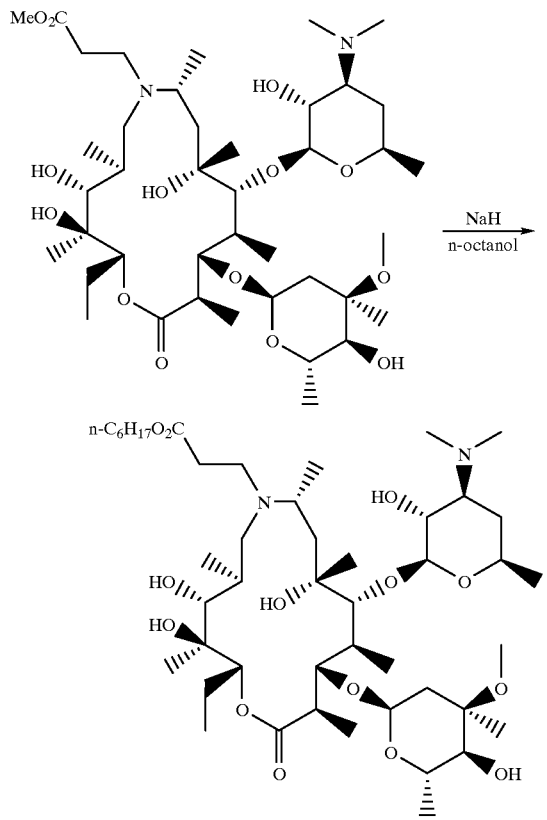

Sodium hydride (6 mg of a 60% oil dispersion, 0.15 mmol) was added to a cooled (ice bath) solution of 8a-(3-methoxy-3-oxopropyl)-9-deoxo-8a-aza-8a-homoerythromycin A (105 mg, 0.13 mmol) in 0.5 mL of n-octanol. A single layer of 3A molecular sieves was then added to the reaction vial and the mixture was stirred at room temperature for 22 hours. The reaction mixture was then filtered through Celite and the filtrate was washed with saturated aqueous NaCl, dried over magnesium sulfate, filtered and evaporated under vacuum. The residue was purified by flash chromatography on silica gel (2.0×30.5 cm column eluted with 95:5:1.5 chloroform:methanol:saturated methanolic ammonia, collecting 10 mL fractions). Fractions 45–56 were combined and evaporated under vacuum to afford 8a-(3-octyloxy-3-oxopropyl)-9-deoxo-8a-aza-8a-homoerythromycin A (48 mg, 41% yield).

$^1$H NMR (400 MHz, CDCl$_3$, 53° C.): δ4.10–4.00 (2H, m, CH$_2$OCO), 3.28 (3H, s, OCH$_3$), 2.32 (6H, br s, N(CH$_3$)$_2$).

EXAMPLE 39

Synthesis of 8a-(3-(2-methoxyethoxy)-3-oxopropyl)-9-deoxo-8a-aza-8a-homoerythromycin A by transesterification of 8a-(3-methoxy-3-oxopropyl)-9-deoxo-8a-aza-8a-homoerythromycin A.

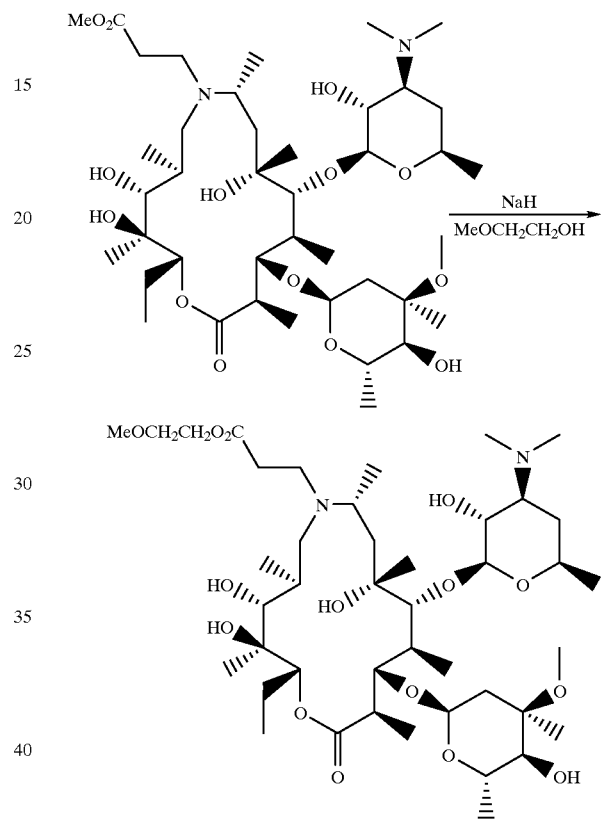

Substitution of 2-methoxyethanol for n-octanol as the solvent in the procedure described above for the preparation of 8a-(3-octyloxy-3-oxopropyl)-9-deoxo-8a-aza-8a-homoerythromycin A afforded 8a-(3-(2-methoxyethoxy)-3-oxopropyl)-9-deoxo-8a-aza-8a-homoerythromycin A (45 mg, 43% yield).

$^1$H NMR (400 MHz, CDCl$_3$, 53° C.): δ4.12–4.04 (2H, m, CH$_2$OCO), 3.38 (3H, s, OCH$_3$), 3.30 (3H, s, OCH$_3$), 2.32 (6H, br s, N(CH$_3$)$_2$).

EXAMPLE 40

Synthesis of 8a-(3-isopropoxy-3-oxopropyl-9-deoxo-8a-aza-8a-homoerythromycin A by transesterification of 8a-(3-methoxy-3-oxopropyl)-9-deoxo-8a-aza-8a-homoerythromycin A

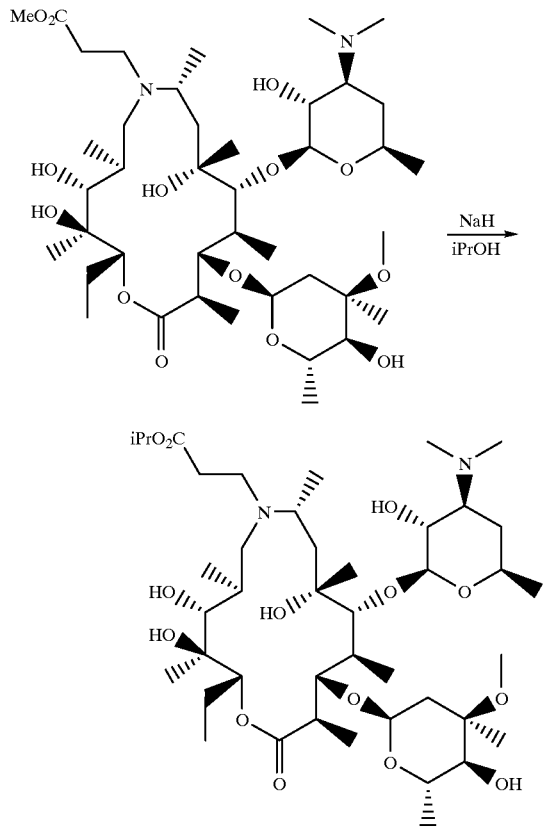

Substitution of isopropanol for n-octanol as the solvent in the procedure described above for the preparation of 8a-(3-octyloxy-3-oxopropyl)-9-deoxo-8a-aza-8a-homoerythromycin A afforded 8a-(3-isopropoxy-3-oxopropyl)-9-deoxo-8a-aza-8a-homoerythromycin A (39 mg, 36% yield).

$^1$H NMR (400 MHz, CDCl$_3$, 53° C): δ4.10–4.02 (1H, m, Me$_2$CHOCO), 3.29 (3H, s, OCH$_3$), 2.32 (6H, br s, N(CH$_3$)$_2$), 1.22 (6H, d, J=7 Hz., C(CH$_3$)$_2$).

FAB MS m/z 850 (M+H).

EXAMPLE 41

Synthesis of 8a-(3-benzyloxy-3-oxopropyl)-9-deoxo-8a-aza-8a-homoerythromycin A by Michael addition of 9-deoxo-8a-aza-8a-homoerythromycin A to benzyl acrylate

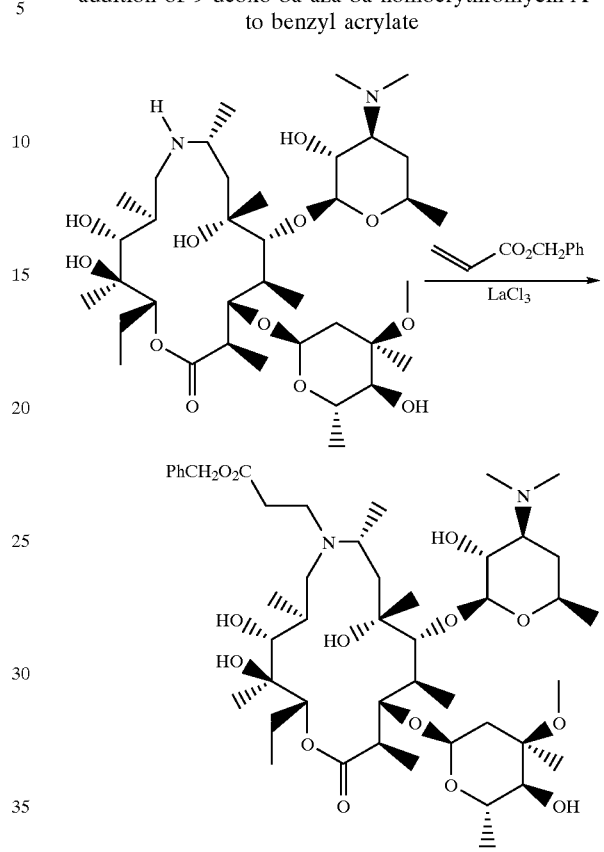

Benzyl acrylate (1.1 g, 6.8 mmol) and lanthanum chloride-hydrate (225 mg, 0.61 mmol) were added to a solution of 9-deoxo-8a-aza-8a-homoerythromycin A (501 mg, 0.68 mmol) in 2 mL of dry THF. The resulting mixture was stirred at 50° C. for 17 days. The excess benzyl acrylate was removed under vacuum and the residue was partitioned between ethyl acetate (8 mL) and 10% aqueous K$_2$CO$_3$ (6 mL). The aqueous layer was extracted with ethyl acetate (5×8 mL) and the combined extracts were dried over magnesium sulfate, filtered, and evaporated under vacuum. The crude product was purified by flash chromatography on silica gel (7.0×21 cm column; gradient elution starting with 70:30:2 hexane:acetone:saturated methanolic ammonia changing in steps to 60:40:2 to 50:50:2 to 100% acetone; collecting 50 mL fractions). Fractions 150–240 were combined and evaporated under vacuum to afford impure 8a-(3-benzyloxy-3-oxopropyl)-9-deoxo-8a-aza-8a-homoerythromycin A (448 mg). This material was further purified by flash chromatography on silica gel (4.0×20 cm column eluted with 95:5:1.5 chloroform:methanol:saturated methanolic ammonia, collecting 30 mL fractions). Fractions 13–14 were combined and evaporated to afford 8a-(3-benzyloxy-3-oxopropyl)-9-deoxo-8a-aza-8a-homoerythromycin A (101 mg) which still contained some impurities. This material was further purified by flash chromatography on silica gel (2.0×25 cm column eluted with 97:3:3 ethyl acetate:methanol:saturated methanolic ammonia, collecting 10 mL fractions). Fractions 43–67 were combined and evaporated to afford pure 8a-(3-benzyloxy-3-oxopropyl)-9-deoxo-8a-aza-8a-homoerythromycin A (74 mg) as an oil. An additional 16 mg of pure 8a-(3-benzyloxy-3-oxopropyl)-9-deoxo-8a-aza-8a-homoerythromycin A was obtained by rechromatography of mixed fractions (total 90 mg, 15% yield).

$^1$H NMR (400 MHz, CDCl$_3$): δ7.40–7.25 (5H, m, Ar—H), 5.12 & 5.08 (2×1H, 2 d, J=13 Hz, ArCH$_2$O), 3.27 (3H, s, OCH$_3$), 2.31 (6H, br s, N(CH$_3$)$_2$).

FAB-MS: m/z 903 (M+Li).

EXAMPLE 42

Synthesis of 8a-(2-carboxyethyl)-9-deoxo-8a-aza-8a-homoerythromycin A by hydrogenation of 8a-(3-benzyloxy-3-oxopropyl)-9-deoxo-8a-aza-8a-homoerythromycin A

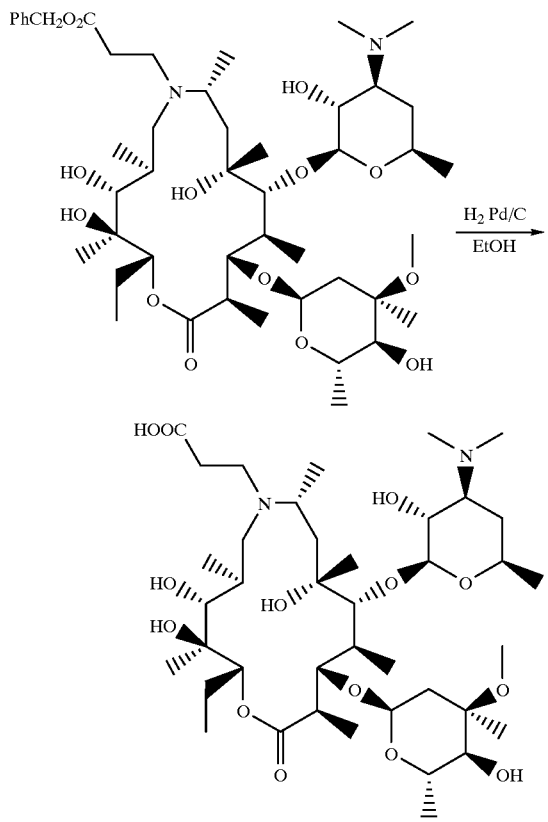

Palladium catalyst (80 mg, 10% Pd/C) was added to a solution of 8a-(3-benzyloxy-3-oxopropyl)-9-deoxo-8a-aza-8a-homoerythromycin A (74 mg, 0.082 mmol) in 0.8 mL of absolute ethanol. The reaction vessel was flushed and filled with nitrogen then flushed and filled with hydrogen. The reaction mixture was stirred at room temperature under one atmosphere (balloon) of hydrogen for 4.5 hours. The reaction mixture was filtered through Celite and the filtrate was evaporated under vacuum to a white powder. This crude product was triturated with ether to afford 8a-(2-carboxyethyl)-9-deoxo-8a-aza-8a-homoerythromycin A (27 mg, 40% yield) as a white powder.

$^1$H NMR (400 MHz, CD$_3$OD): δ3.33 (3H, s, OCH$_3$), 2.66 (6H, br s, N(CH$_3$)$_2$).

FAB-MS: m/z 808 (M+H).

EXAMPLE 43

Synthesis of 6-0.8a-N-methylene-8a-aza-9-deoxo-8a-homoerythromycin A by condensation of 8a-aza-9-deoxo-8a-homoerythromycin A with formaldehyde

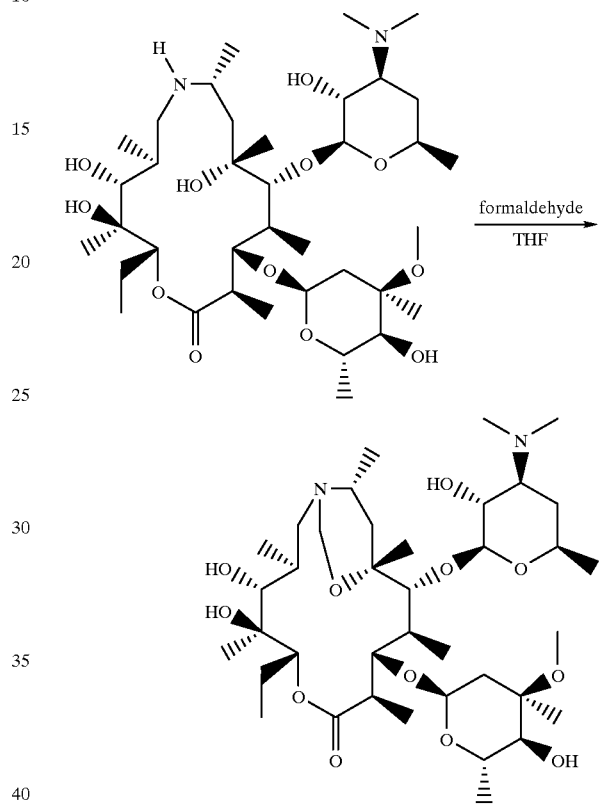

Paraformaldehyde (500 mg) was placed in a pear shaped flask with side arm. A solution of 8a-aza-9-deoxo-8a-homoerythromycin A (500 mg, 0.68 mmol) in 4 mL of dry THF was placed in a reaction vial then a layer of activated 3A sieves was added to the vial. The flask containing the paraformaldehyde was heated with a Bunsen burner and the formaldehyde gas thus generated was swept (with a stream of nitrogen) out of the flask through the side arm and bubbled into the reaction mixture. After a few minutes, all of the paraformaldehyde was gone so heating was stopped and the reaction vial was capped. The resulting reaction mixture was stirred at room temperature for 22 hours. The mixture was then diluted with THF (4 mL) and centrifuged. The supernatant was decanted and the solid residue was washed with TEF (3 mL) and recentrifuged. The combined supernatants were evaporated under vacuum to a colorless oil (571 mg). The crude product was purified by flash chromatography on silica gel (5.0×20 cm column eluted with 95.5:3:1.5 chloroform:methanol:saturated methanolic ammonia, collecting 50 mL fractions). Analytical TLC of the fractions indicated that fractions 30–66 contained the desired product (R$_f$ 0.18). These fractions were combined and evaporated under vacuum to afford 6-0,8a-N-methylene-8a-aza-9-deoxo-8a-homoerythromycin A as a white foam (289 mg, 57% yield)

¹H NMR (400 MHz, CDCl₃) δ4.79 (1H, d, J=4.5 Hz, H1"), 4.34 (1H, d, J=7 Hz, H1'), 4.00 & 3.84 (2×1H, 2 d, J=8 Hz, NCH₂O), 3.28 (3H, s, OCH₃), 2.24 (6H, s, N(CH₃)₂).

¹³C NMR (100 MHz, CDCl₃) δ179.5 (C-1), 103.4 (C-1'), 96.0 (C-1"), 79.6 (NCH₂O), 76.7 (C-6), 49.5 (OCH₃), 40.3 (N(CH₃)₂).

FAB-MS m/z 747 (M+H), 753 (M+Li).

EXAMPLE 44

Synthesis of 9-Deoxo-8a-aza-8a-cyanomethyl-8a-homoerythromycin A by Cyanomethylation of 9-Deoxo-8a-aza-8a-homoerythromycin A A suspension of 9-deoxo-8a-aza-8a-homoerythromycin A (10.14 g, 13.8 mmol) in anhydrous dimethylformamide (30 ml) was treated with p-nitrobenzyl iodide (3.83 g, 14.5 mmol). The mixture was heated to 75° C. for 90 minutes, then cooled to room temperature. Bromoacetonitrile (5 ml, 71.3 mmol) and powdered potassium carbonate (2 g, 14.5 mmol) were added and the resulting mixture was heated at 75/C. for 18 hours. The black suspension was poured into a fritted funnel and allowed to drip slowly into vigorously stirred ether (200 ml). The resulting suspension was filtered to afford a brown waxy solid (approximately 8 g). This crude product was partially dissolved in ethanol (50 ml) and acetic acid (3 ml) and 10% palladium on charcoal (4.7 g) was added. The suspension was hydrogenated on a Parr shaker at 50 p.s.i. for 4 hours, then filtered through Celite. The filtrate was partitioned between chloroform and water and the pH of the aqueous layer was adjusted to 10 by the addition of solid potassium carbonate. The organic layer was separated, washed with brine, dried through a plug of sodium sulfate and concentrated. This crude mixture was subjected to flash chromatography using a stepwise gradient of 5/10/20% methanol/methylene chloride to afford 9-deoxo-8a-aza-8a-cyanomethyl-8a-homoerythromycin A (2.4 g, 22% yield) as a tan solid. This solid was recrystallized from 80% aqueous methanol (20 ml) using decolorizing charcoal to afford 9-deoxo-8a-aza-8a-cyanomethyl-8a-homoerythromycin A (1.09 g) as an off white solid.

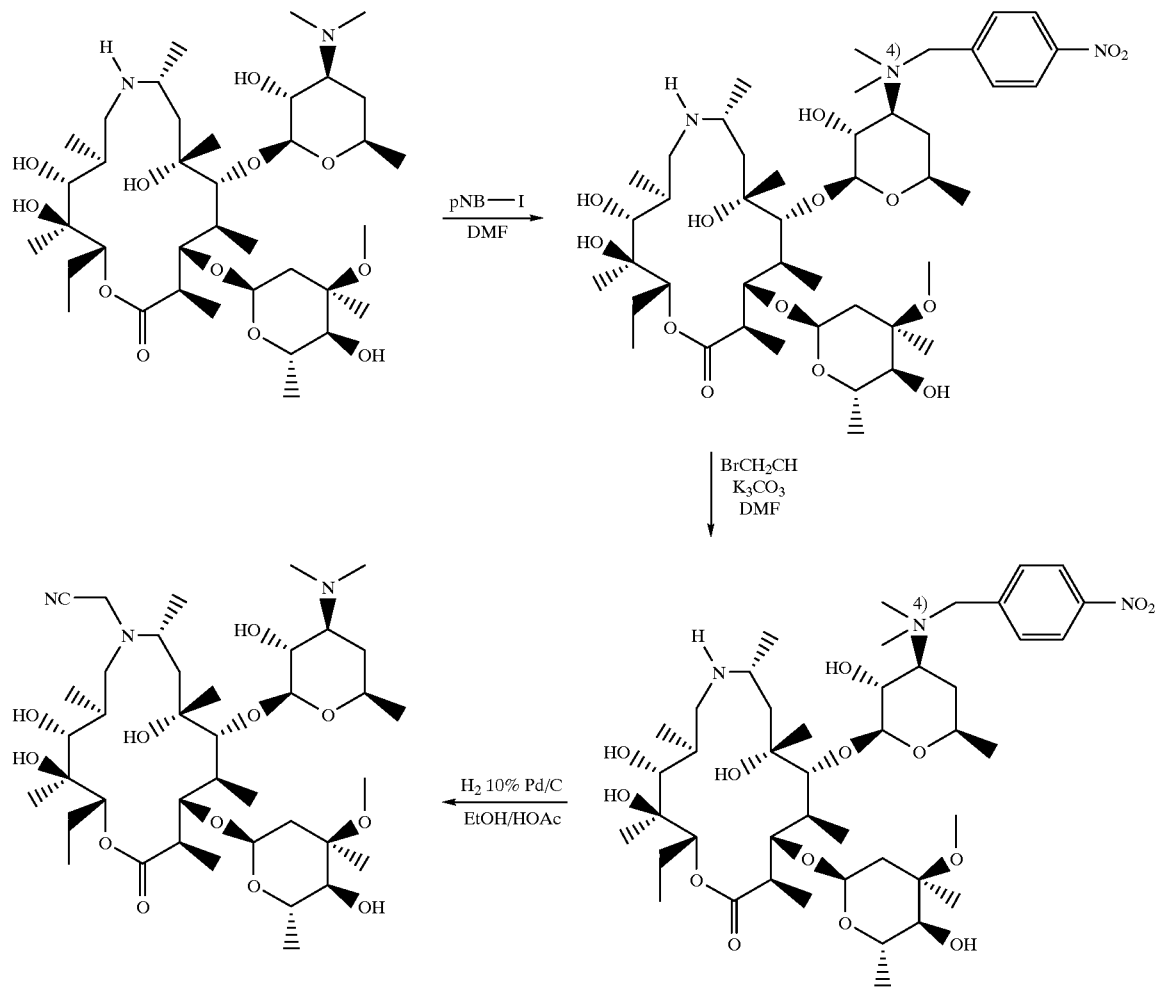

TLC R_f 0.62 (10% methanol/methylene chloride)

¹H NMR (400 MHz, CDCl₃) δ4.98 (d,H-1"), 4.78 (dd, H-13), 4.45 (d,H-1'), 3.97 (m,H-5"), 3.27 (s, OCH₃), 3.13 (dd,H-2'), 2.23 (s,N(CH₃)₂)

¹³C Mr (100.6 MHz, CDCl₃) δ178.53 (lactone), 117.40 (nitrile), 103.43 (C-1'), 94.71 (C-1").

FAB-MS m/z 774, 747, 589, 571, 432, 174, 158.

EXAMPLE 45

Synthesis of 9-Deoxo-8a-aza-8a-(2-aminoethyl)-8a-homoerythromycin A by Reduction of 9-Deoxo-8a-aza-8a-cyanomethyl-8a-homoerythromycin A

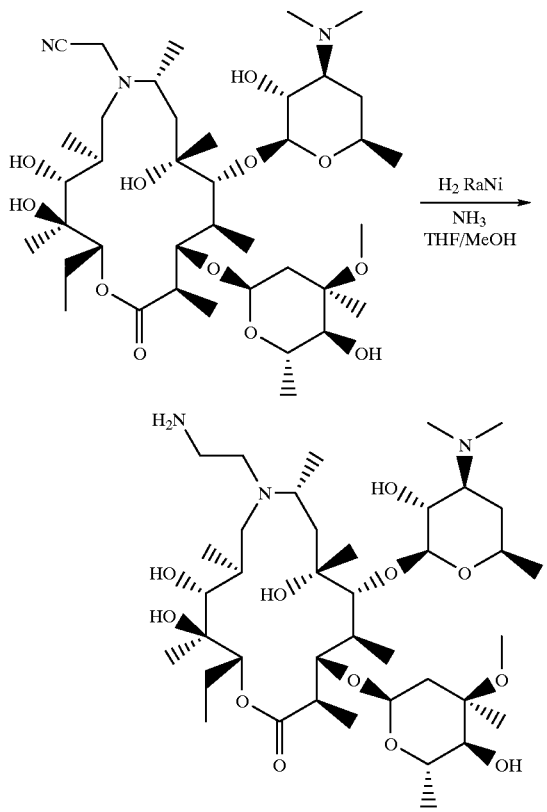

9-Deoxo-8a-aza-8a-cyanomethyl-8a-homoerythromycin A (2.13g, 2.75 mmol) was dissolved in tetrahydrofuran (3 ml) and ammonia-saturated methanol (3 ml). Freshly prepared W5 Raney nickel catalyst (approximately 2 g) was added and the suspension was hydrogenated on a Parr shaker at 48 p.s.i. for 24 hours. The suspension was filtered, concentrated and partitioned between chloroform and aqueous potassium carbonate. The organic layer was separated, washed with brine, dried through a plug of sodium sulfate, reduced by rotary evaporation and dried under vacuum to afford a chromatographically inseparable mixture of three products (1.1 g). This material was dissolved in methylene chloride (6 ml) and reacted with N-(9-fluorenylmethoxycarbonyloxy)succinimide (475 mg, 1.41 mmol) for 2 hours. The solution was partitioned between chloroform and aqueous potassium carbonate. The organic layer was separated, washed with brine, dried through a plug of sodium sulfate, concentrated and subjected to flash chromatography using a stepwise gradient of 5/10/20% methanol/methylene chloride to afford the FMOC derivative (900 mg). This derivative was dissolved in methylene chloride (1.5 ml) and piperazine (1.5 ml). After 90 minutes, the solution was diluted with chloroform and washed twice with brine, dried through a plug of sodium sulfate and concentrated. The crude amine was purified by flash chromatography using a stepwise gradient of 0.1/0.5/1% ammonium hydroxide in 20% methanol/methylene chloride. 9-Deoxo-8a-aza-8a-(2-aminoethyl)-8a-homoerythromycin A (501 mg, 23% yield) was obtained as a white solid.

$^1$H NMR (400 MHz, CDCl$_3$) δ4.96 (dd, H-13), 4.86 (d,H-1"), 3.20 (s,OCH$_3$), 2.20 (s,N(CH$_3$)$_2$).

$^{13}$C NMR (100.6 MHz, CDCl$_3$) δ176.78 (lactone), 103.62 (C-1), 96.41 (C-1").

FAB-MS m/z 778, 620, 445.

EXAMPLE 46

Synthesis of 9-Deoxo-8a-aza-8a-(2-dimethylaminoethyl)-8a-homoerythromycin A by Reductive Methylation of 9-Deoxo-8a-aza-8a-(2-aminoethyl)-8a-homoerythromycin A

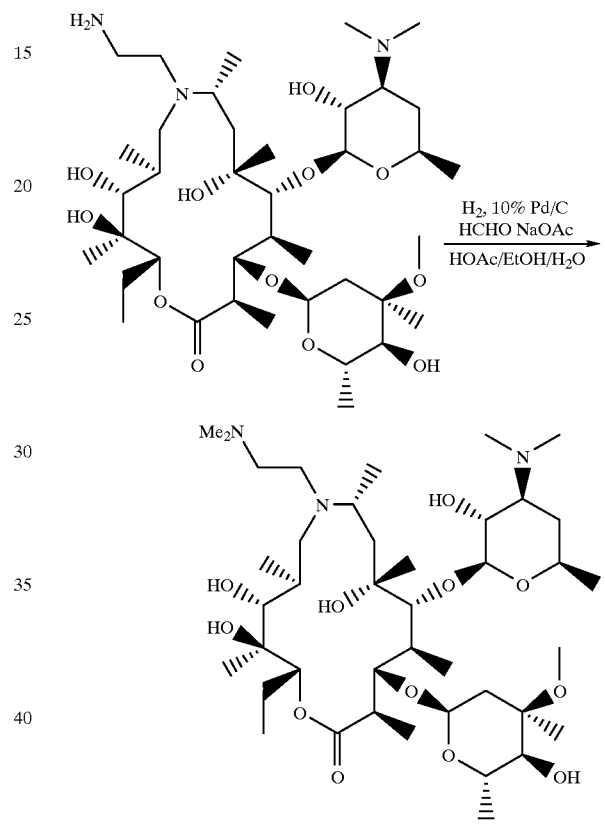

9-Deoxo-8a-aza-8a-(2-aminoethyl)-8a-homoerythromycin A (775 mg, 1 mmol), acetic acid (114 ml, 2 mmol), sodium acetate (104 mg, 2 mmol), 10% palladium on carbon (350 mg), and 37% formaldehyde (4.5 ml) were combined in ethanol (6 ml). Hydrogen was bubbled through the suspension for 6 hours, then a hydrogen-filled balloon was installed. After 23 hours, the suspension was filtered through Celite, concentrated and partitioned between chloroform and aqueous potassium carbonate. The organic layer was separated, washed with brine, dried through a plug of sodium sulfate, concentrated and subjected to flash chromatography using a stepwise gradient of 0.1/0.5/1% ammonia-saturated methanol in 20% methanol/methylene chloride to afford 9-deoxo-8a-aza-8a-(2-dimethylaminoethyl)-8a-homoerythromycin A (630 mg, 78% yield) as a white solid $^1$H NMR (400 MHz, CDCl$_3$, 60° C.) δ5.01 (dd, H-13), 4.96 (d,H-1"), 4.46 (d,H-1"), 3.99 (m,H-5'), 3.28 (s,OCH$_3$), 2.30 (s,N(CH$_3$)$_2$), 2.28 (s,N(CH$_3$)$_2$).

$^{13}$C NMR (100.6 MHz, CDCl$_3$) δ176.70 (lactone, 103.19 (C-1'), 96.08 (C-1").

FAB-MS (lithium spike) m/z 812, 648, 159.

EXAMPLE 47

Synthesis of 9-Deoxo-8a-aza-8a-(N-L-leucyl-2-aminoethyl)-8a-homoerythromycin A by Acylation of 9-Deoxo-8a-aza-8a-(2-aminoethyl)-8a-homoerythromycin A

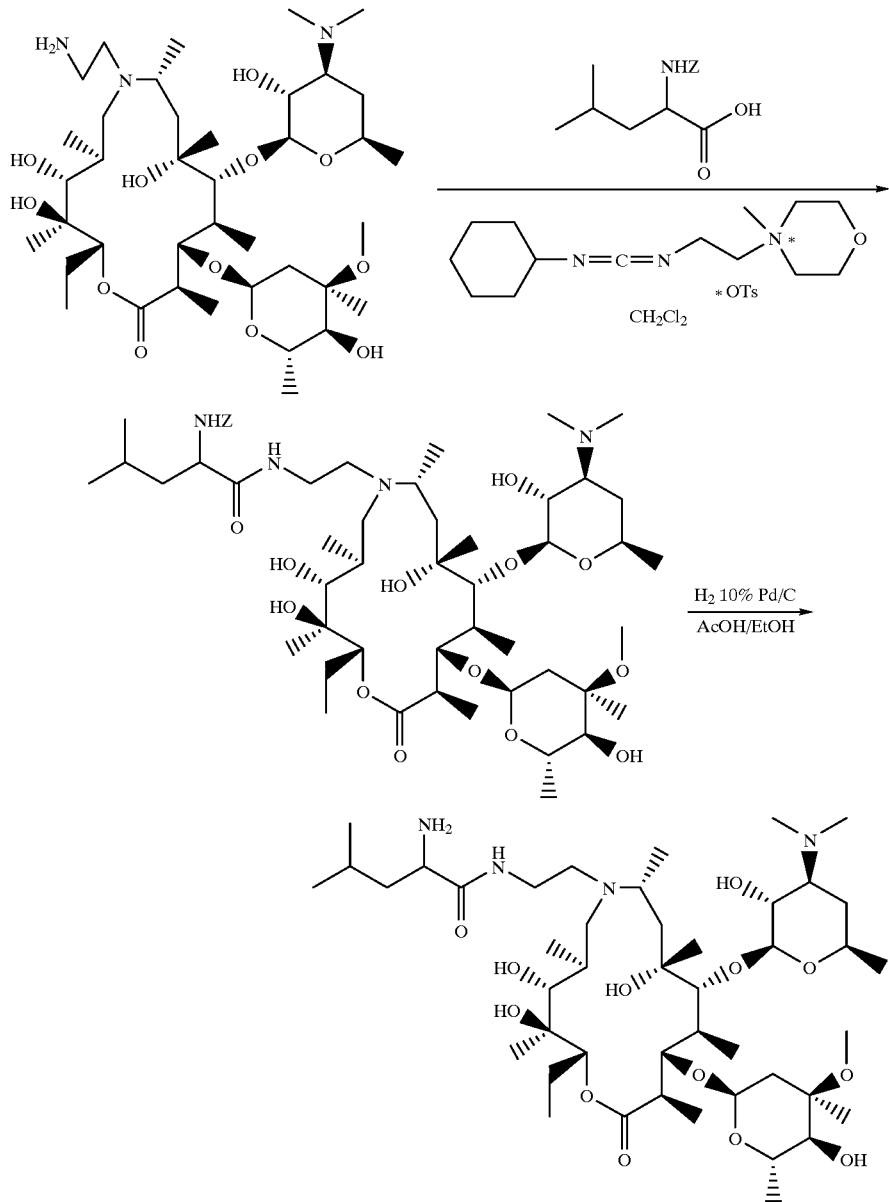

N-benzyloxycarbonyl-L-leucine (38 mg, 0.143 mmol), 1-cyclohexyl-3-(2-morpholinoethyl)carbodiimide methio-p-toluenesulfonate, (61 mg, 0.143 mmol) and 9-deoxo-8a-aza-8a-(2-aminoethyl)-8a-homoerythromycin A (106 mg, 0.136 mmol) were combined in anhydrous methylene chloride (1 ml). After 18 hours, the mixture was diluted with chloroform and sequentially washed with aqueous potassium carbonate, water, and brine. The organics were dried through a plug of sodium sulfate, concentrated and subjected o flash chromatography using a stepwise gradient of 0.1/0.5/1% ammonia-saturated methanol in 20% methanol/methylene chloride to afford the N-benzyloxycarbonyl derivative of the target compound. This material was dissolved in ethanol (3 ml) and acetic acd (100 ml); 10% palladium on carbon (50 mg) was added and hydrogen was bubbled through the mixture for 2 hours. A balloon of hydrogen was installed and the reaction proceeded for 16 hours. The mixture was filtered through Celite, concentrated, and parttioned between chloroform and aqueous potassium carbonate. The organic layer was washed twice with brine, dried through a plug of sodium sulfate, concentrated and subjected to flash chromatography using a stepwise gradient of 0.1/0.5/1% ammonia-saturate methanol in 20% methanol/methylene chloride to afford 9-deoxo-8a-aza-8a-(N-L-leucyl-2-aminoethyl)-8a-homoerythromycin A (73 mg, 60% yield).

$^1$H NMR (400 MHz, CDCl$_3$) δ5.03 (dd,H-13), 4.82 (d,H-1"), 3.24 (s,OCH$_3$), 2.29 (s,N(CH$_3$)$_2$).

$^{13}$C NMR (100.6 MH, CDCl$_3$) δ178.28, 178.08, 102.89 (C-1'), 98.88 (C-1").

EXAMPLE 48

Synthesis of 9-Deoxo-8a-aza-8a-(benzyloxycarbonylmethyl)-8a-homoerythromycin A by Alkylation of 9-Deoxo-8a-aza-8a-homoerythromycin A

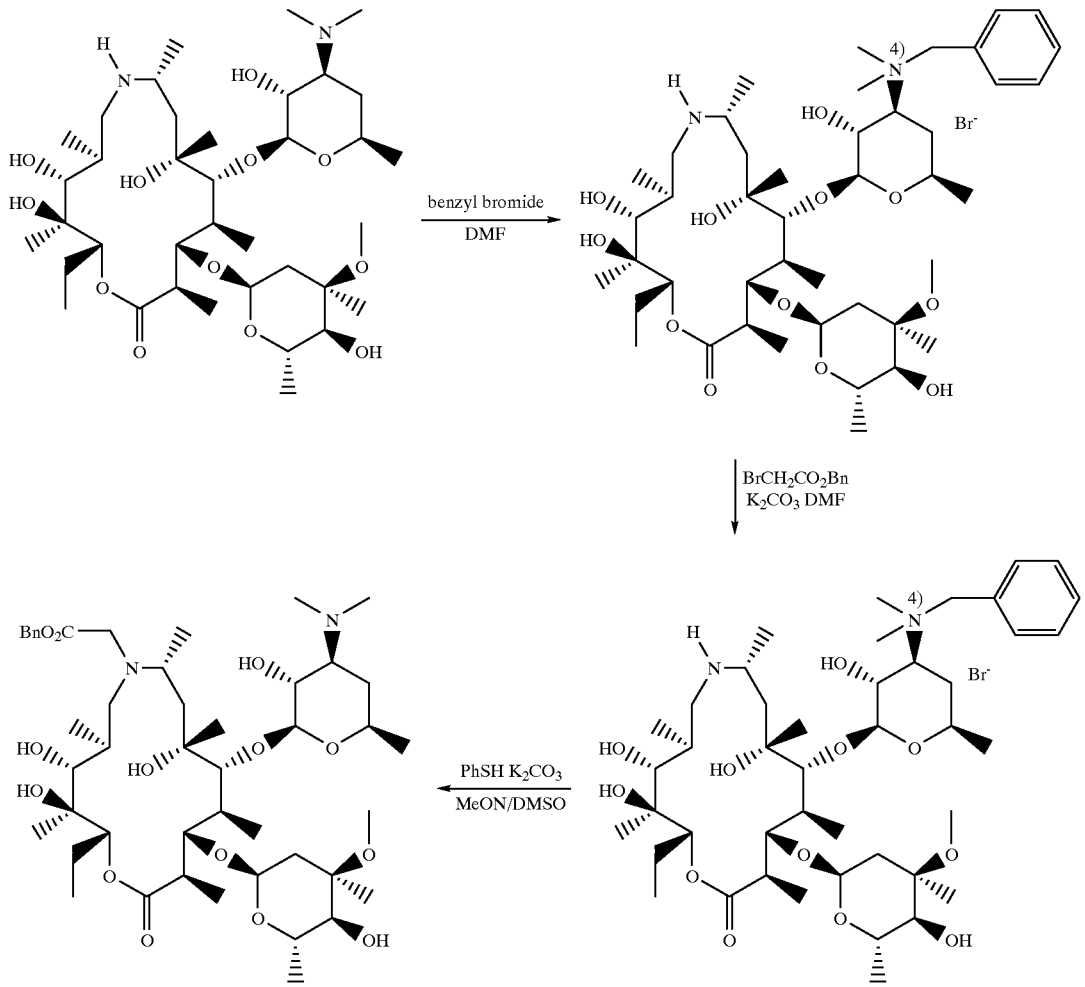

Benzyl bromide (1.56 ml, 13.1 mmol) was added to a suspension of 9-deoxo-8a-aza-8a-homoerythromycin A (9.61 g, 13.1 mmol) in dimethylformamide (13 ml). The suspension clarified as it was heated to 50/C. After 45 minutes, the solution was cooled to room temperature and benzyl bromoacetate (1.4 ml, 65.5 mmol) and powdered potassium carbonate (3.62 g, 26.2 mmol) were added. The suspension was heated at 50/C. for four days. The cooled suspension was poured into a fritted glass filter and allowed to slowly drip into vigorously stirred ether (40 ml). The solvent was decanted to afford an orange gum. This gum was briefly subjected to high vacuum before being dissolved in acetonitrile (20 ml) and dimethylsulfoxide (20 ml). Thiophenol (4.05 ml, 39.3 mmol) and powdered potassium carbonate (18 g 131 mmol) were added. After stirring at room temperature for 18 hours, the suspension was partitioned between ethyl acetate and water. The organic layer was separated and washed once with dilute aqueous potassium carbonate, twice with brine, then drie through a plug of sodium sulfate, concentrated and filtered through a plug of silica using a stepwise gradient of 5/10/30% methanol/methylene chloride to afford crude 9-deoxo-8a-aza-8a-(benzyloxycarbonylmethyl)-8a-homoerythromycin A (6 g) as a yellow soid. This crude product was subjected to flash chromatography using a stepwise gradient of 10/20% methanol/methylene chloride to afford 8a-(benzyloxycarbonylmethyl)-8a-homoerythromycin A (5.33 g, 46% yield) as a white solid.

$^1$H NMR (400 MHz, CDCl$_3$, 60° C.) δ5.08 (dd,PhCH$_2$) 4.99 (d,H-1"), 4.87 (dd,H-13), 4.39 (m,H-3), 4.35 (d,H-1'), 4.02 (m,H-5'), 3.18 (s,OCH3), 2.27 (s,N(CH$_3$)$_2$).

$^{13}$C NMR (100.6 MHz, CDCl$_3$, 60° C.) δ178.20, 172.27, 135.71, 128.31–128.60, 103.69 (C-1'), 95.20 (C-1").

FAB-MS m/z 883, 725, 708, 550, 158.

EXAMPLE 49

Synthesis of 9-Deoxo-8a-aza-8a-carboxymethyl-8a-homoerythromycin A by Catalytic Hydrogenation of 9-Deoxo-8a-aza-8a-(benzyloxycarbonylmethyl)-8a-homoerythromycin A

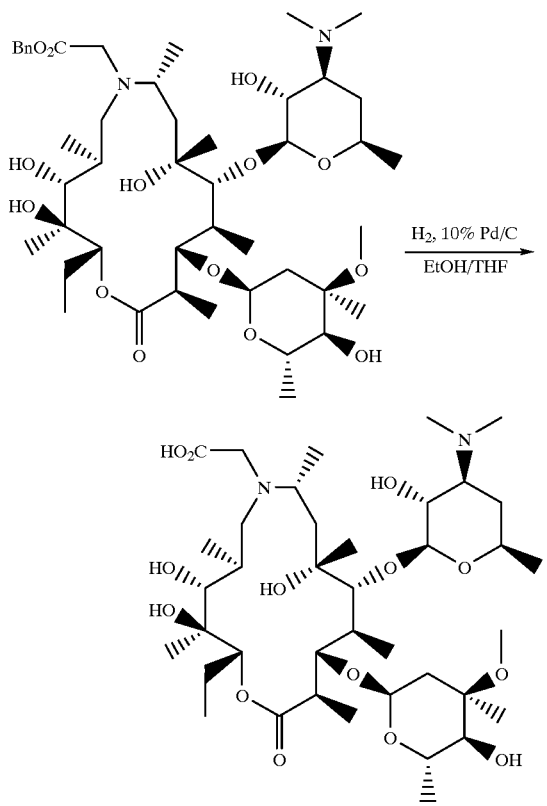

9-Deoxo-8a-aza-8a-(benzyloxycarbonylmethyl)-8a-homoerythromycin A (2.0 g, 2.27 mmol) and 10% palladium on charcoal (885 mg) were combined in ethanol (6 ml) and tetrahydrofuran (4 ml). Hydrogen was bubbled through the suspension for 90 minutes. The suspension was filtered through Celite into heptane evaporated to dryness and subjected to high vacuum for several hours to afford 9-deoxo-8a-aza-8a-carboxymethyl-8a-homoerythromycin A (1.66 g, 92% yield) as a white solid.

$^1$H NMR (400 MHz, CD$_3$OD, 60° C.) δ5.05 (d,H-1"), 4.97 (dd,H-13), 3.32 (s,OCH$_3$), 2.87 (s,N(CH$_3$)$_2$).

$^{13}$C NMR (100.6 MHz, CD$_3$OD, 60° C.) δ180.51, 170.49, 103.01 (C-1'), 96.25 (C-1").

FAB-MS m/z 794, 635, 479.

EXAMPLE 50

Synthesis of 9-Deoxo-8a-aza-8a-methoxycarbonylmethyl-8a-homoerythromycin A by Methylation of 9-Deoxo-8a-aza-8a-carboxymethyl-8a-homoerythromycin A

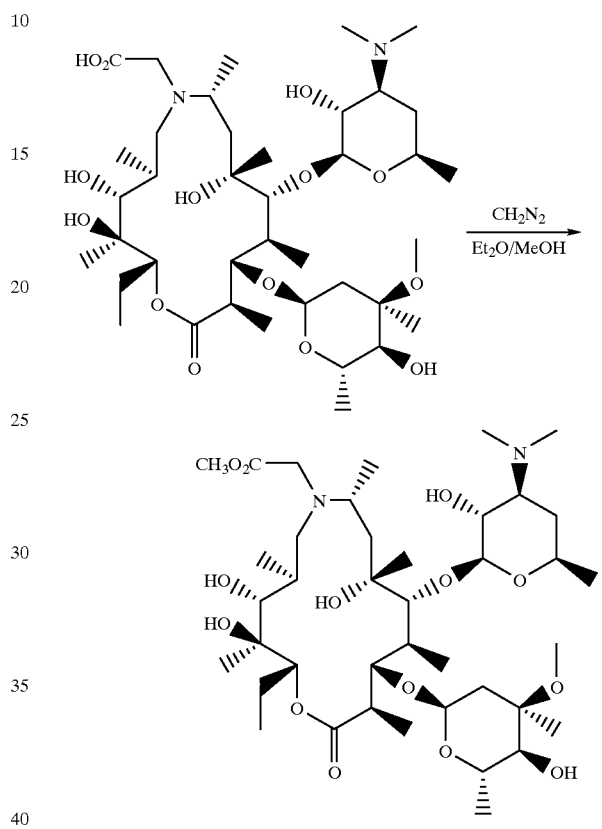

9-Deoxo-8a-aza-8a-carboxymethyl-8a-homoerythromycin A (217 mg, 0.274 mmol) was dissolved in methanol (5 ml) and an ethereal solution of diazomethane was added until a yellow tint persisted. After 30 minutes, the solution was evaporated to dryness and subjected to flash chromatography using a stepwise gradient of 10/20% methanol/methylene chloride to afford 9-deoxo-8a-aza-8a-methoxycarbonylmethyl-8a-homoerythromycin A (100 mg, 45% yield) as a white solid.

$^1$H NMR (400 MHz, CDCl$_3$, 60° C.) δ4.98 (br s,H-1"), 4.86 (br d,H-13), 3.65 (s,CO$_2$CH$_3$), 3.27 (s,OCH3), 2.38 (s,N(CH$_3$)$_2$).

$^{13}$C NMR (100.6 MHz, CDCl$_3$) δ172.68, 171.75, 103.34 (C-1'), 95.08 (C-1").

FAB-MS m/z (cesium spike) 808, 734.

EXAMPLE 51

Transesterification of 9-Deoxo-8a-aza-8a-methoxycarbonylmethyl-8a-homoerythromycin

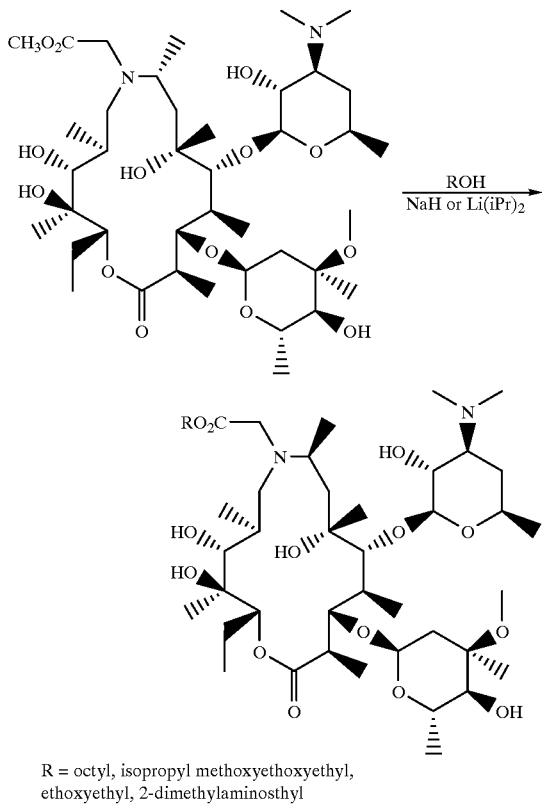

R = octyl, isopropyl methoxyethoxyethyl, ethoxyethyl, 2-dimethylaminoethyl

General Procedure

9-Deoxo-8a-aza-8a-methoxycarbonylmethyl-8a-homoerythromycin A (161 mg, 0.20 mmol) was dissolved in the appropriate alcohol (2 ml) and chilled in an ice bath. Sodium hydride or 1.5M lithium diisopropylamide (0.02 mmol) was added and the flask was allowed to warm to room temperature. After 18 hours, the solution was partitioned between chloroform and aqueous sodium bicarbonate, the pH of the aqeous layer was adjusted to 10 with solid potassium carbonate, the organic layer was separated and washed twice with brine, dried through a plug of sodium sulfate, reduced and subjected to flash chromatography to afford the title compounds. The followingesters were prepared.

Octyl ester $^1$H MR (400 MHz, CDCl$_3$, 60° C) δ4.97 (d,H-1"), 4.61 (dd,H-13), 3.26 (s,OCH3), 2.48 (s,N(CH$_3$)$_2$).

$^{13}$C NMR (100.6 MHz, CDCl$_3$, 60° C.) δ178.03, 172.41, 103.35 (C-1'), 95.36 (C-1").

FAB-MS m/z 905, 748, 730, 572

Isopropyl ester $^1$H NMR (400 MHz, CDCl$_3$, 60° C.) δ4.97 (d,H-1"), 4.87 (dd,H-13), 3.26 (s,OCH$_3$), 2.39 (s,N(CH$_3$)$_2$).

$^{13}$C NMR (100.6 MHz, CDCl$_3$, 60° C.) δ177.98, 171.83, 103.58 (C-1'), 95.33 (C-1").

FAB-MS m/z 836, 677, 659, 158.

Ethoxyethyl ester $^1$H NMR (400 MHz, CDCl$_3$, 60° C.) δ4.98 (d,H-1"), 4.88 (dd,H-13), 3.27 (s,OCH$_3$), 2.43 (s,N(CH$_3$)$_2$).

$^{13}$C NMR (100.6 MHz, CDCl$_3$, 60° C.) δ177.42, 171.74, 102.82 (C-1'), 94.70 (C-1").

FAB-MS m/z 866, 708, 690, 533.

Methoxyethoxyethyl ester $^1$H NMR (400 MHz, CDCl$_3$) δ4.98 (d,H-1"), 4.88 (dd,H-13), 3.32 (s,OCH$_3$), 3.28 (s,OCH$_3$), 2.44 (s,N(CH$_3$)$_2$).

$^{13}$C NMR (100.6 MHz, CDCl$_3$) δ172.01, 172.39, 103.47 (C-1'), 95.43 (C-1").

FAB-MS m/z 895, 720, 563.

2-Dimethylaminoethyl ester $^1$H NMR (400 MHz, CDCl$_3$, 60° C.) δ4.98 (d,H-1"), 4.83 (dd,H-13), 3.26 (s,OCH$_3$), 2.26 (s,N(CH$_3$)$_2$), 2.22 (s,N(CH$_3$)$_2$).

$^{13}$C NMR (100.6 MHz, CDCl$_3$, 60° C.) δ178.09, 172.34, 103.71 (C-1'), 95.21 (C-1").

FAB-MS m/z 865, 706, 158.

EXAMPLE 52

Synthesis of 9-Deoxo-8a-aza-3'-N-demethyl-8a-homoerythromycin A

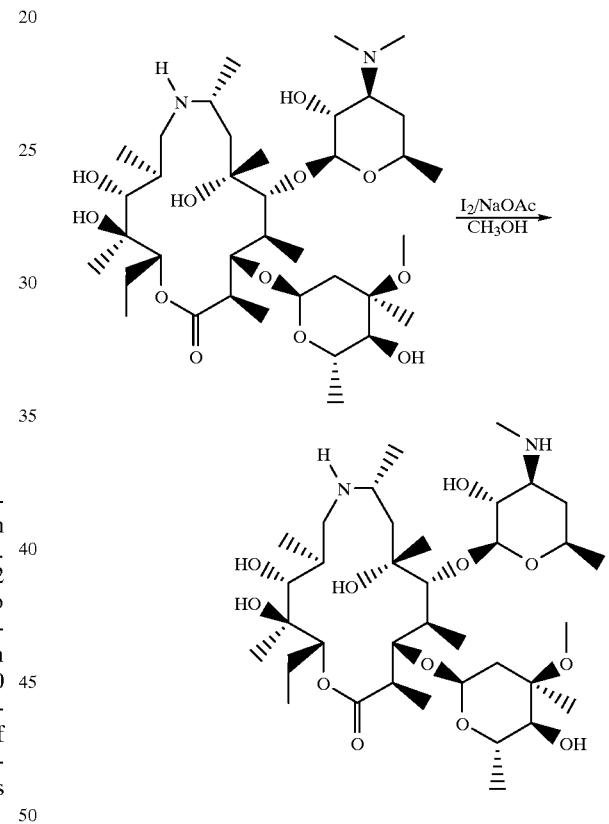

9-Deoxo-8a-aza-8a-homoerythromycin A (20 g, 27.2 mmol) and sodium acetate (12 g, 146 mmol) were dissolved in a mixture of methanol (160 mL) and water (40 mL). The solution was heated to 60° C. and iodine (20 g, 78.7 mmol) was added all at once. The pH was maintained between 9 and 9.5 by the addition of 5N sodium hydroxide. After 30 minutes the yellow solution was cooled to room temperature and most of the methanol was evaporated under vacuum. Methylene chloride (300 m) and water (300 ml), containing potassium carbonate (60 g) and sodium sulfite (60 g), were added and the mixture was stirred rapidly. The methylene chloride layer was removed and the aqueous layer was re-extracted twice with more methylene chloride (75 mL) The combined methylene chloride layers were added to water (150 ml), the mixture was rapidly stirred while the pH was adjusted to 4 with concentrated hydrochloric acid. The methylene chloride was removed and more methylene chloride (100 mL) was added. Te pH of the mixture was adjusted to 6 with 5N sodium hydroxide, the methylene chloride layer was removed and more methylene chloride was added. The pH of the mixture was adjusted to 6.5 with 5N sodium hydroxide, and the methylene chloride layer was remoed and more methylene chloride was added (100 mL). The pH of the mixture was adjusted to 10 with 5N sodium hydroxide, and the methylene chloride layer was removed and the aqueous layer was re-extracted twice with methylene chloride (100 mL). The combinedph 10 extracts were dried with anhydrous magnesium sulfate, were filtered and evaporated under vacuum to a give the title compound as a light yellow foam (17.4 g).

IR (CHCl$_3$) 3340, 2970, 2935, 2880, 2860, 2835, 2800, 1720, 1455, 1450, 1425, 1395, 1375,1345, 1320, 1300, 1275, 1260, 1240, 1165, 1160, 1120, 1085, 1050, 1045, 1030, 1005, 995, 955 cm$^{-1}$ $^1$H NMR (CDCl$_3$) δ(ppm) 4.93 (br d, H-1"), 4.74 (dd, H-13), 4.31 (d, H-1), 3.30 (s, OCH$_3$), 2.40 (s, N(CH$_3$)$_2$), 0.87 (t, CH$_2$CH$_3$)

FAB mass spectrum, m/z 721.4, 563.4, 547.2, 401.3, 143.9

EXAMPLE 53

Synthesis of 9-Deoxo-8a-aza-3'-N-demethyl-3'-N-phenyl-sulfonyl-8a-homoerythromycin A

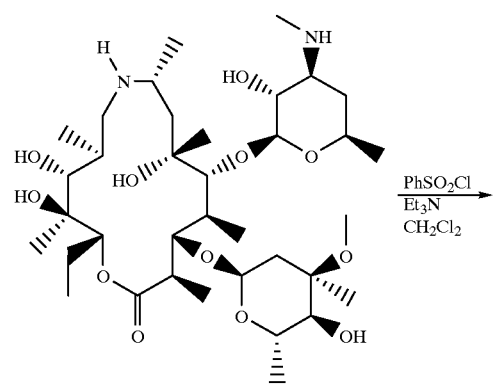

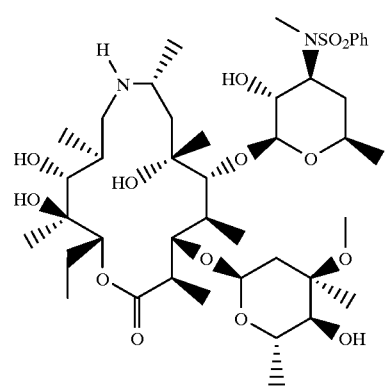

9-Deoxo-8a-aza-3'-N-demethyl-8a-homoerythromycin A (17.4 g, 24 mmol) was dissolved in methylene chloride (150 mL) and was cooled in an ice bath. Triethylamine (10 mL, 72 mmol) was added followed by the dropwise addition of phenylsulfonyl chloride (3.2 mL, 25. 2 mmol). After 2 hours, water (100 mL) was added to the mixture and the pH was adjusted to 6.5 with concentrated ydrochloric acid. The methylene chloride layer was removed and was washed with water (100 mL). The methylene chloride was dried with anhydrous magnesium sulfate, was filtered and evaporated to give the title compound as a foam (17 g).

The foam (16 g) wa dissolved in hot acetonitrile (50 mL), was cooled to rt and filtered after one hour. The solid was washed with acetonitrile (10 mL) and was dried under vacuum to give the title compound as a white crystalline solid (7.35 g).

MP 145–146° C.

IR (CHCl$_3$) 3530, 3370, 2965, 2935, 2875, 2860, 2835, 1720, 1455, 1445, 1425, 1395, 1370, 1345, 1325, 1305, 1275,1235,1175,1155, 1120, 1095, 1080, 1030, 1005, 990, 950, 945, 925 cm$^{-1}$ $^1$H NMR (CDCl$_3$) δ(ppm) 7.83 (d, ArH), 7.54 (dd, ArH), 7.48 (dd, ArH), 5.00 (d, H-1"), 4.94 (br d, 11-OH), 4.74 (dd, H-13), 4.37 (d, H-1'), 4.36 (br dd, H-3), 3.99 (dq, H-5"), 3.93 (m, H-3'), 3.52 (br d, H-11), 3.50 (m, H-5'), 3.48 (br d, H-5), 3.36 (s, OM e), 3.24 (ddd, H-2'), 3.05 (br s, 12-OH), 3.03 (t, H-4"), 2.76 (m, H-8), 2.73 (, N(Me)$_2$), 2.65 (p, H-2), 2.58 (dd, H-9a), 2.41 (m, H-9b), 2.31 (d, H-2"Eq.), 2.28 (d, 4"-OH), 1.92 (ddq, H-14a), 1.78 (m, H-4), 1.59 (m, H-10), 1.55 (dd, 2"ax), 1.33 (s, 6-CH$_3$), 1.28 (d, 5"-CH$_3$), 1.25 (s, 3"-CH$_3$), 1.18 (d, 2-CH$_3$), 1.13 (d, 5'-CH$_3$), 1.10(d, 8-CH$_3$), 1.06 (s, 12-CH$_3$), 0.98 (d, 4-CH$_3$), 0.94 (d, 10-CH$_3$), 0.86 (t, H-15)

$^{13}$C NMR (CDCl$_3$) δ(ppm) 178.8, 139.6, 132.6, 129.0, 128.9, 127.3, 103.4, 94.4, 84.3, 78.0, 77.8, 76.5, 75.0, 74.8, 73.0, 70.5, 68.2, 66.3, 65.4, 58.0, 49.7, 49.6, 49.5, 45.7, 43.5, 39.8, 36.0, 35.6, 34.6, 28.4, 27.5, 21.8, 21.7, 20.9, 18.1, 16.4, 14.9, 12. 0, 11.4, 9.95

FAB mass spectrum, m/z 861, 703, 685, 402, 266, 198, 127

EXAMPLE 54

Synthesis of 9-Deoxo-8a-aza-8a-(2-fluoroeth-1-yl)-3'-N-demethyl-3'-N-phenysulfonyl-8a-homoerythromycin A

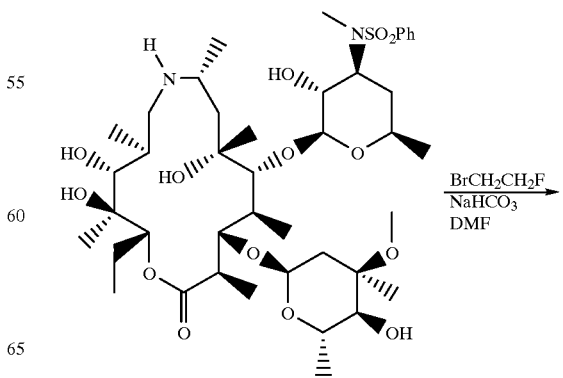

119

-continued

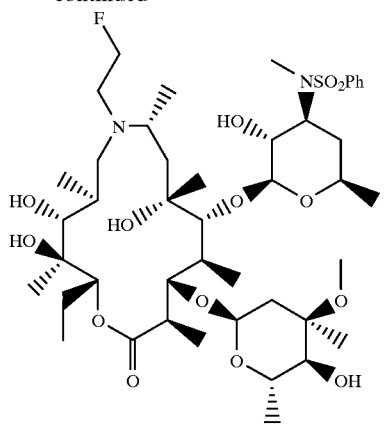

9-Deoxo-8a-aza-3'-N-demethyl-3'-N-phenylsulfonyl-8a-homoerythromycin A (0.2 g, 0.23 mmol), powdered sodium bicarbonate (0.06 g, 0.70 mmol) and 1-bromo-2-fluoroethane (0.05 mL, 0.67 mmol) were added to a 5 mL flask equipped with a magnetic stir bar. Dry dimethylformamide (0.2 ml) was added and the suspension was stirred at 100° C. for 68 hours. After cooling to room temperature, the mixture was partitioned between water (6 mL) and methylene chloride (6 mL), and the pH was adjuste to 10 with 2N sodium hydroxide. The methylene chloride layer was removed, was dried with anhydrous magnesium sulfate, was filtered and evaporated to a light yellow foam (0.234 g).

The foam was dissolved in 10% methylene chloride/methanol and was loadd onto a column of silica gel 60 (2.5×30 cm, 230–400 mesh, wet packed with 10% methylene chloride/methanol). The column was eluted with 10% methylene chloride/methanol and after a forerun of 40 mL, 3mL fractions were collected. Fractions 25–27 were ombined and evaporated to give 9-Deoxo-8a-aza-8a-(2-fluoroeth-1-yl)-3'-N-demethyl-3'-N-phenylsulfonyl-8a-homoerythromycin A as a foam (0.072 g). The forerun and tails, fractions 24, and 28–36, were combined and evaporated to a foam (0.051 g).

The combned forerun and tails was dissolved in methylene chloride and was placed on two 1000 micron silica preparative thin layer plates. The plates were developed with 10% methylene chloride/methanol and the title compound was removed, eluted with 10% methylee chloride/methanol, and evaporated to a foam (26 mg).

IR (CHCl$_3$) 3540, 3365, 2965, 2935, 2880, 2835, 1725, 1455, 1445, 1395, 1370, 1345, 1325, 1280, 1260, 1235, 1175, 1155, 1115, 1080, 1045, 1005, 995, 950, 945, 925 cm$^{-1}$ $^1$H NMR (CDCl$_3$) δ(ppm) 7.88 (d, ArH), 7.48 (dd, ArH), 7.43 (dd, ArH), 4.97 (dd, H-13), 4.93 (d, H-1"), 4.60–4.32 (m, CH$_2$F), 4.40 (d, H-1'), 3.27 (s, OMe), 2.73 (s, N(Me)$_2$), 0.89 (t, H-15)

$^{13}$C NMR (60° C. CDCl$_3$) δ(ppm) 177.1, 140.2, 132.0, 128.6, 127.5, 104.2, 96.1, 88.6, 83.4, 81.7, 78.1, 77.9, 77.0, 75.5, 74.2, 72.8, 70.0, 69.4, 68.6, 65.9, 59.7, 59.6, 58.2, 55.7, 55.6, 49.3, 46.3, 42.0, 41.9, 36.3, 35.1, 33.2, 28.4, 25.7, 22.0, 21.5, 20.6, 17.8, 16.1, 14.6, 14.2, 12.6, 12.4, 11.1

FNMR (60° C CDCl$_3$) δ(ppm) −218.1 (br m, CH$_2$F)

FAB mass spectrum Li spike, m/z 915.0, 907.9, 750.4, 732.4, 623.2, 607.2, 565.2, 477.1, 467.2, 449.0, 348.5, 322.3, 284.1, 266.2

EXAMPLE 55

Synthesis of 9-Deoxo-8a-aza-8a-(2-fluoroeth-1-yl)-3'-N-demethyl-8a-homoerythromycin A

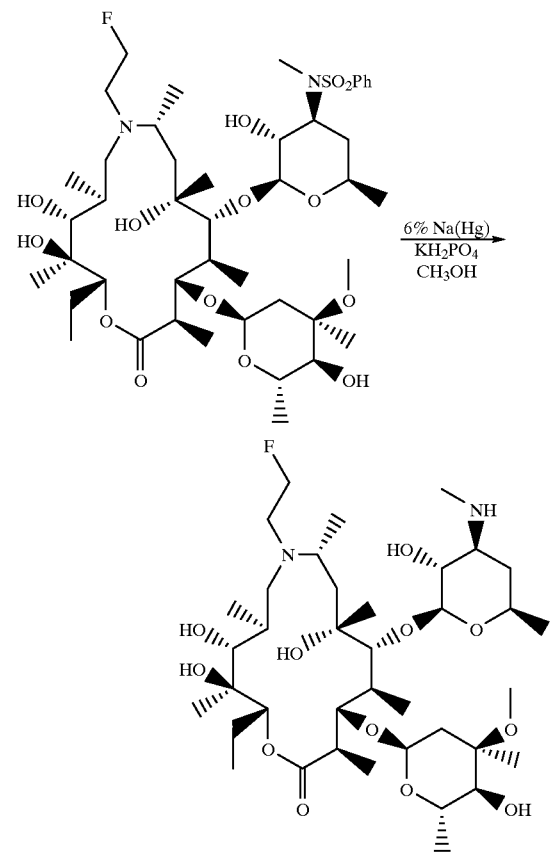

9-Deoxo-8a-aza-8a-(2-fluoroeth-1-yl)-3'-N-demethyl-3'-N-phenylsulfonyl-8a-homoerythromycin A (1.0 g, 1.10 mmol) was added to a well stirred suspension of potassium dihydrogen phosphate (5 g, 36.8 mmol) in methanol (20 mL). The mixture was cooled in a dry ice/ethylene lycol bath (bath temperature −20° C.), and finely ground 6% sodium amalgam (6.45 g, 16.8 mmol) was added in three batches. After 2 hours the suspension was added to a mixture of saturated potassium carbonate (100 mL) and ethyl acetate (40 mL). The ethyl acette layer was removed and the aqueous layer was re-extracted with more ethyl acetate (40 mL). The combined ethyl acetate extracts were washed with brine (40 mL), dried with magnesium sulfate, filtered and evaporated to a foam (0.88 g).

EXAMPLE 56

Synthesis of 9-Deoxo-8a-aza-8a-(2-fluoroeth-1-yl-8a-homoerythromycin A

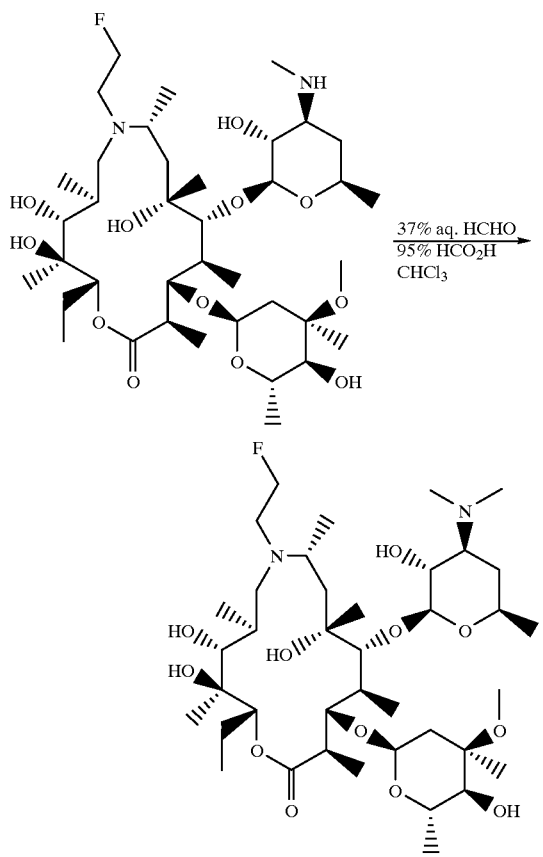

9-Deoxo-8a-aza-8a-(2-fluoroeth-1-yl)-3'-N-demethyl-8a-homoerythromycin A (0.88 g, 0.98 mmol) was dissolved in chloroform (20 mL) and was treated with 37% aqueous formaldehyde (0.1 mL, 1.33 mmol) and 96% formic acid (0.1 mL, 2.55 mmol). The mixture was heated at 60° C. for 20 hours and was then cooled to room temperature. Water (15 mL) and methylene chloride (10 mL) were added and the pH was adjusted to 4 with dilute hydrochloric acid. Te methylene chloride was removed and more methylene chloride (20 mL) was added. The pH of the mixture was adjusted to 5.5 with 5N sodium hydroxide, the methylene chloride layer was removed and more methylene chloride (20 mL) was added. The pH of the mixtre was adjusted to 11 and the methylene chloride layer was removed and the aqueous layer was re-extracted twice with methylene chloride (20 mL). The combined pH 11 extracts were dried with anhydrous magnesium sulfate, were filtered and evaporated under vcuum to a foam (0.64 g).

The foam was dissolved in 90:10:1 methylene chloride/methanol/conc. ammonium hydroxide and was loaded onto a column of silica gel 60 (4.5×16cm, 230–400 mesh, wet packed with 90:10:1 methylene chloride/methanol/conc. ammonium hydroxide). The column was eluted with 90:10:1 methylene chloride/methanol/conc. ammonium hydroxide and after a forerun of 75 mL, 4 mL fractions were collected. Fractions 12–20 were combined and evaporated to give the title compound as a foam (0.43 g).

The foam (0.25 g) was dissolved in hot isopropyl alcohol (2 mL), was cooled to rt and filtered after one hour. The solid was washed with isopropyl alcohol (1.5 mL) and was dried under vacuum to give the title compound as a white crystalline solid (0.15 g).

MP 198–201° C.

IR (CHCl$_3$) 3540, 3410, 2965, 2935, 2880, 2835, 2785, 1725, 1455, 1400, 1370, 1345, 1325, 1275, 1255, 1240, 1170, 1160, 1120, 1100, 1085, 1065, 1045, 1005, 995, 975, 950, 945 cm$^{-1}$ $^1$H NMR (60° C. CDCl$_3$) δ(ppm) 5.03 (d, H-1"), 4.92 (dd, H-13), 4.63–4.32 (m, CH$_2$F), 4.37 (d, H-1'), 3.28 (s, OMe), 2.32 (s, N(Me)$_2$), 0.88 (t, H-15)

FAB mass spectrum, m/z 781, 747, 652, 605, 589, 497, 448, 432, 348, 290, 204, 158, 116

EXAMPLE 57

Synthesis of 9-Deoxo-8a-aza-8a-(3-fluoroprop-1-yl)-3'-N-demethyl-3'-N-phenylsulfonyl-8a-homoerythromycin A

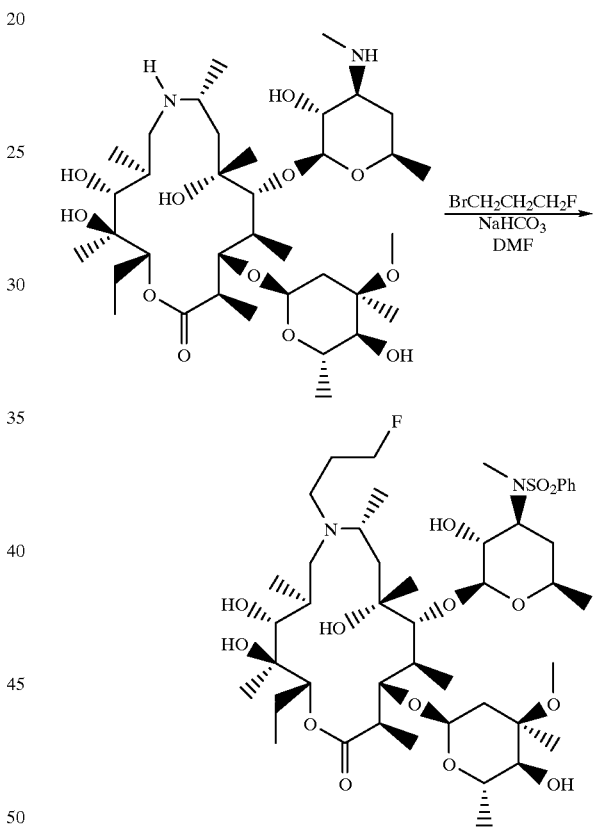

9-Deoxo-8a-aza-3'-N-demethyl-3'-N-phenylsulfonyl-8a-homoerythromycin A (0.2 g, 0.23 mmol), powdered sodium bicarbonate (0.06 g, 0.70 mmol) and 1-bromo-3-fluoropropane (0.03 mL, 0.35 mmol) were added to a 5 mL flask equipped with a magnetic stir bar. Dry dimethylformamide (0.2 ml) was added and the suspension was stirred at 100° C. for 92 hours, with an additional amount of 1-bromo-3-fluoropropane (0.015 mL, 0.17 mmol) and dimethylformamide (0.1 mL) beingadded at 68 hours. After cooling to room temperature, the suspension was partitioned between water (6 mL) and methylene chloride (6 mL), and the pH was adjusted to 10 with 2N sodium hydroxide. The methylene chloride layer was dried with anhydrous magnesim sulfate, was filtered, and was evaporated to a light yellow foam (0.265 g).

The foam was dissolved in 90:10:1 methylene chloride/methanol/concentrated ammonium hydroxide and was loaded onto a column of silica gel 60 (2.5×31.5 cm, 230–400 mesh, wet acked with 90:10:1 methylene chloride/methanol/concentrated ammonium hydroxide). The column was eluted with 90:10:1 methylene chloride/methanol/concentrated ammonium hydroxide and 8 mL fractions were collected. Fractions 12–14 were combined and evaprated to give the title compound as a foam (0.104 g).

IR (CHCl$_3$) 3540, 3400, 2965, 2935, 2880, 2835, 1725, 1455, 1445, 1395, 1370, 1340, 1325, 1280, 1260, 1240, 1155, 1115, 1080, 1045, 1010, 990, 950, 890 cm$^{-1}$ $^1$H NMR (CDCl$_3$) δ(ppm) 7.84 (d, ArH), 7.46 (dd, ArH), 7.41 (dd, ArH), 5.0 (dd, H-13), 4.83 (d, H-1"), 4.44+4.34 (dt, CH$_2$F), 4.38 (d, H-1'), 3.25 (s, OMe), 2.72 (s, N(Me)$_2$), 0.87 (t, H-15)

$^{13}$C NMR (60° C. CDCl$_3$) δ(ppm) 176.4, 140.2, 131.9, 128.4, 127.6, 104.9, 96.8, 90.1, 83.1, 81.5, 79.0, 77.8, 76.8, 75.2, 73.9, 72.8, 70.6, 69.9, 68.6, 66.0, 58.3, 58.1, 53.4, 49.3, 49.2, 42.5, 42.0, 36.4, 35.1, 32.8, 29.7, 29.5, 28.3, 25.2, 22.0, 21.5, 20.5, 17.7, 15.9, 15.3, 14.3, 12.9, 11.7, 11.2

FNMR (60° C. CDCl$_3$) δ(ppm) −220.5 (m, CH$_2$F)

FAB mass spetrum, m/z 921, 905, 781, 745, 636, 620, 462, 448, 318, 266

EXAMPLE 58

Synthesis of 9-Deoxo-8a-aza-8a-(3-fluoroprop-1-yl)-3'-N-demethyl-8a-homoerythromycin A

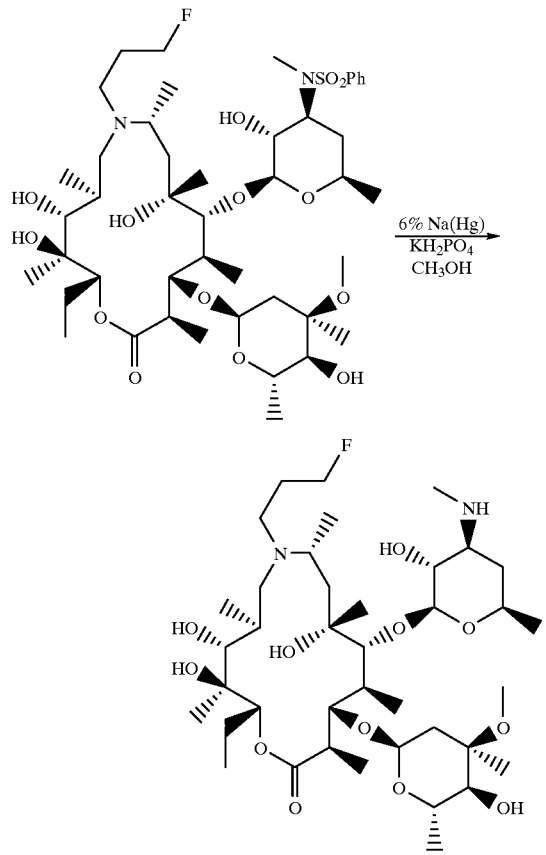

9-Deoxo-8a-aza-8a-(3-fluoroprop-1-yl)-3'-N-demethyl-3'-N-phenylsulfonyl-8a-homoerythromycin A (0.08 g, 0.087 mmol) was added to a well stirred suspension of potassium dihydrogen phosphate (0.55 g, 4.0 mmol) in methanol (1.5 mL). The mixture was cooled in a dry ice/ethylene glycol bath (bath temperature −20° C.), and finely ground 6% sodiu amalgam (0.57 g, 1.49 mmol) was added. After 2 hours the suspension was added to a mixture of saturated potassium carbonate (10 mL) and ethyl acetate (4 mL). The ethyl acetate layer was removed and the aqueous layer was re-extracted with more ethyl acetat (4 mL). The combined ethyl acetate extracts were washed with brine (4 mL), dried with magnesium sulfate, filtered and evaporated to a foam (0.087 g).

EXAMPLE 59

Synthesis of 9-Deoxo-8a-aza-8a-(3-fluoroprop-1-yl)-8a-homoerythromycin A

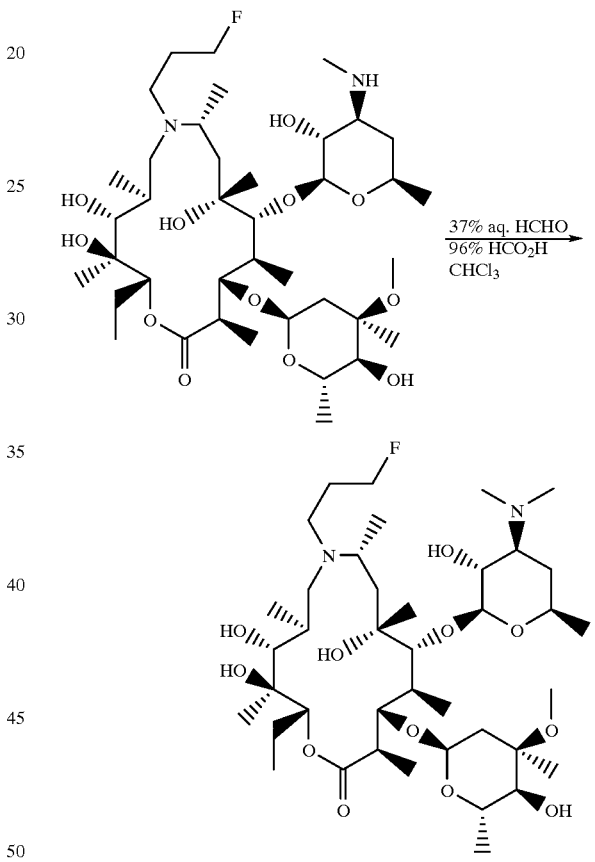

9-Deoxo-8a-aza-8a-(3-fluoroprop-1-yl)-3'-N-demethyl-8a-homoerythromycin A (0.88 g, 0.98 mmol) was dissolved in chloroform (2 mL) and was treated with 37% aqueous formaldehyde (0.01 mL, 0.13 mmol) and 96% formic acid (0.01 mL, 0.26 mmol). The mixture was heated at 60° C. for 20 hours and was then cooled to room temperature. Water (4 mL) and methylene chloride (6 mL) were added and the pH was adjusted to 11. The methylene chloride layer was removed and the aqueous layer was re-extracted twice with methylene chloride (4 m). The combined pH 11 extracts were dried with anhydrous magnesium sulfate, were filtered and evaporated under vacuum to a foam (0.068 g).

The foam was dissolved in 90:10:1 methylene chloride/methanol/conc. ammonium hydroxide and was loaded onto a column of silica gel 60 (2.5×24 cm, 230–400 mesh, wet packed with 90:10:1 methylene chloride/methanol/conc. ammonium hydroxide). The column was eluted with 90:10:1 methylene chloride/methanol/conc. ammonium hydroxide and after a forerun of 32 mL, 4 mL factions were collected. Fractions 17–24 were combined and evaporated to give the title compound as a foam (0.43 g).

IR (CHCl$_3$) 3540, 3410, 2965, 2935, 2875, 2835, 1725, 1455, 1395, 1370, 1345, 1325, 1275, 1260, 1240, 1160, 1115, 1105, 1085, 1045, 1010, 995, 975, 950, 890 cm$^{-1}$ $^1$H NMR (CDCl$_3$) δ(ppm) 5.0 (d, H-1'), 4.96 (dd, H-13), 4.48+4.36 (dt, CH$_2$F), 4.36 (d, H-1'), 3.27 (s, OMe), 2.31 (s, N(Me)$_2$), 0.88 (t, H-15)

$^{13}$C NMR (60° C. CDCl$_3$) δ(ppm) 177.6, 104.6, 96.1, 88.4, 83.2, 81.6, 78.2, 77.9, 76.9, 75.5, 74.3, 72.8, 70.5, 69.5, 65.7, 65.2, 58.7, 49.3, 46.6, 42.3, 41.4, 40.4, 35.0, 32.6, 29.8, 29.7, 29.5, 25.9, 22.0, 21.5, 21.0, 17.8, 16.1, 14.8, 14.6, 12.7, 12.0, 11.2

FAB mass spectrum, m/z 796, 637, 619, 510, 281, 158, 116

EXAMPLE 60

Synthesis of 9-Deoxo-8a-aza-8a-((4,4,4-trifluoro)-but-1-yl)-3'-N-demethyl-3'-N-phenylsulfonyl-8a-homoerythromycin A

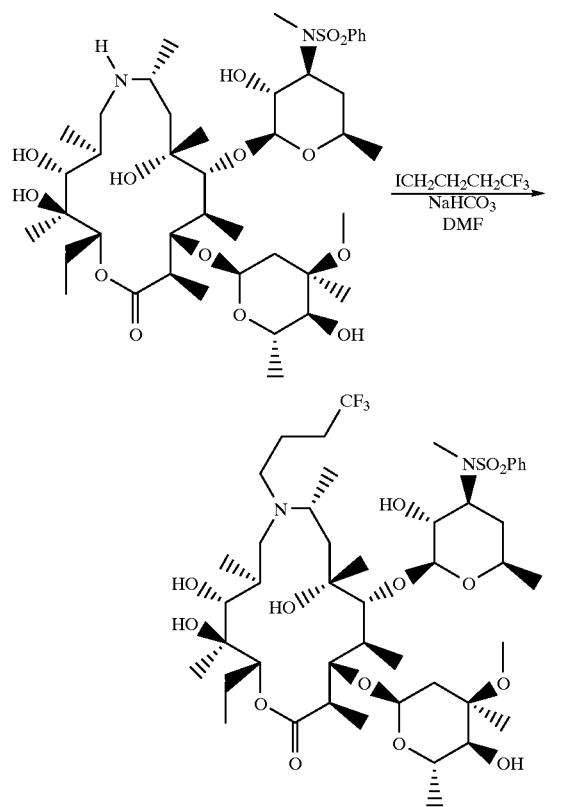

9-Deoxo-8a-aza-3'-N-demethyl-3'-N-phenylsulfonyl-8a-homoerythromycin A (0.2 g, 0.23 mmol), powdered sodium bicarbonate (0.07 g, 0.83 mmol) and 1-bromo-4,4,4-trifluorobutane (0.042 mL, 0.35 mmol) were added to a 5 mL flask equipped with a magnetic stir bar. Dry dimethylformamide (0.2 ml) was added and the suspension was stirred at 100° C. for 68 hours. 1-bromo-4,4,4-trifluorobutane (0.050 mL, 0.41 mmol) and dimethylformamide (0.05 mL) were then added and the mixture was stirred at 120° C. for 24 hours. After cooling to room temperature, the suspension was partitioned between water (8 mL) and methylene chloride (6 mL), and the pH was adjusted to 10 with 2N sodium hydroxide. The methylene chloride layer was dried with anhydrous magnesium sulfate, was filtered, and evaporated to a light yellow foam (0.220 g).

The foam was dissolved in 90:10:1 methylene chloride/methanol/concentrated ammonium hydrxide and was loaded onto a column of silica gel 60 (2.5×25.5 cm, 230–400 mesh, wet packed with 90:10:1 methylene chloride/methanol/concentrated ammonium hydroxide). The column was eluted with 90:10:1 methylene chloride/methanol/concentrated ammonium hydroxide and after a forerun of 48 mL, 8 mL fractions were collected. Fractions 12–14 were combined and evaporated to give the title compound as a foam (0.105 g).

IR (CHCl$_3$) 3540, 3410, 2970, 2935, 2880, 2835, 1725, 1455, 1445, 1395, 1375, 1335, 1325, 1280, 1250, 1240, 1150, 1115, 1080, 1045, 1010, 990, 950 cm$^{-1}$ $^1$H NMR (CDCl$_3$) δ(ppm) 7.86 (d, ArH), 7.47 (dd, ArH), 7.41 (dd, ArH), 5.03 (dd, H-13), 4.82 (d, H-1"), 4.42 (d, H-1'), 3.27 (s, OMe), 2.74 (s, N(Me)$_2$), 0.90 (t, H-15)

FNMR (60° C. CDCl$_3$) δ(ppm) –66.56 (t, CF$_3$)

FAB mass spectrum, m/z 971.5, 813.9, 796.0, 670.3, 512.8

EXAMPLE 61

Synthesis of 9-Deoxo-8a-aza-8a-((4,4,4-trifluoro)but-1-yl)-3'-N-demethyl-8a-homoerythromycin A

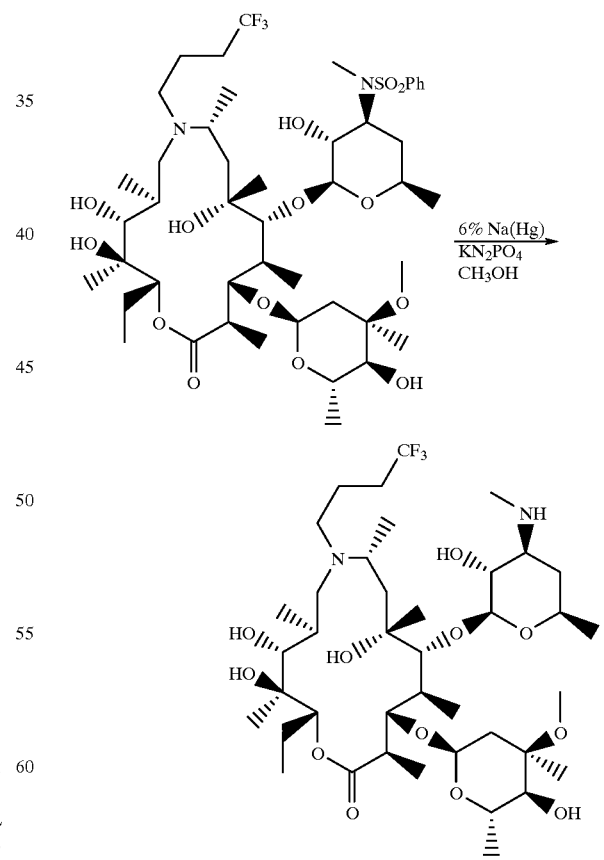

9-Deoxo-8a-aza-8a-((4,4,4-trifluoro)but-1-yl)-3'-N-demethyl-3'-N-phenylsulfonyl-8a-homoerythromycin A (0.09 g, 0.093 mmol) was added to a well stirred suspension of potassium dihydrogen phosphate (0.50 g, 3.7 mmol) in methanol (1.5 mL). The mixture was cooled in a dry ice/ethylene glycol bath (bath temperatue -20° C.), and finely ground 6% sodium amalgam (1.27 g, 3.3 mmol) was added in three portions. After 3 hours the suspension was added to a mixture of saturated potassium carbonate (8 mL) and ethyl acetate (12 mL). The ethyl acetate layer was removed and theaqueous layer was re-extracted with more ethyl acetate (4 mL). The combined ethyl acetate extracts were washed with brine (8 mL), dried with magnesium sulfate, filtered and evaporated to a foam (0.085 g). A sample of the foam was examined using thin layerchromatography and a significant amount of 9-Deoxo-8a-aza-8a-(4,4,4-trifluorobutyl)-3'-N-demethyl-3'-N-phenylsulfonyl-8a-homoerythromycin A was observed. Subsequently, the reaction was repeated using the above conditions.

The foam was added to a well stirred suspension of potassium dihydrogen phosphate (0.50 g, 3.7 mmol) in methanol (2 mL). The mixture was cooled in a dry ice/ethylene glycol bath (bath temperature -20° C.), and freshly ground 6% sodium amalgam (0.5 g, 1.3 mmol) was added. After 2 hours the suspension was added to a mixture of saturated potassium carbonate (8 mL) and ethyl acetate (8 mL). The ethyl acetate layer was removed and the aqueous layer was re-extracted with more ethyl acetate (4 mL). The combined ethyl acetate extracts were washedwith brine (8 mL), dried with magnesium sulfate, filtered and evaporated to a foam (0.079 g).

The foam was dissolved in 90:10:1 methylene chloride/methanol/conc. ammonium hydroxide and was loaded onto a column of silica gel 60 (2.5×18cm, 230–400 mesh, wet packed with 90:10:1 methylene chloride/methanol/conc. ammonium hydroxide). The column was eluted with 90:10:1 methylene chloride/methanol/conc. ammonium hydroxide and 4mL fractions were collected. Fractions 17–21 were combined and evaporated to give the title compound as a foam (0.028 g).

EXAMPLE 62

Synthesis of 9-Deoxo-8a-aza-8a-((4,4,4-trifluoro)but-1-yl)-8a-homoerythromycin A

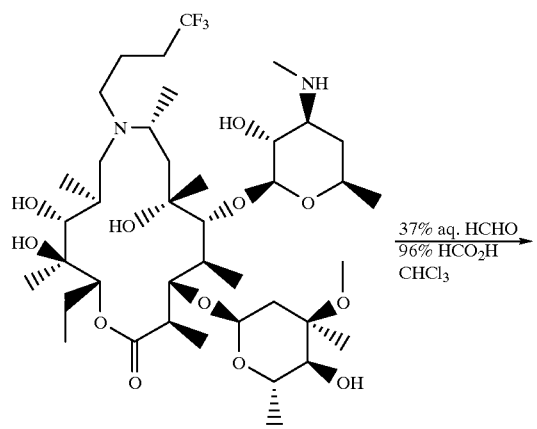

-continued

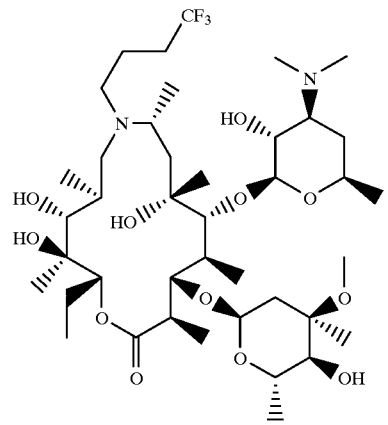

9-Deoxo-8a-aza-8a-((4,4,4-trifluoro)but-1-yl)-3'-N-demethyl-8a-homoerythromycin A (0.028 g, 0.034 mmol) was dissolved in chloroform (2 mL) and was treated with 37% aqueous formaldehyde (0.01 mL, 0.13mmol) and 96% formic acid (0.01 mL, 0.26 mmol). The mixture was heated at 60° C. for 16 hours and was then cooled to room temperature. Water (3 mL) and methylene chlride (5 mL) were added and the pH was adjusted to 11. The methylene chloride layer was removed and the aqueous layer was re-extracted twice with methylene chloride (4 mL). The combined pH 11 extracts were dried with anhydrous magnesium sulfate, were filtred and evaporated under vacuum to give the title compound as a foam (0.027 g).

IR (CHCl$_3$) 3540, 3410, 2965, 2935, 2875, 2830, 1725, 1455, 1395, 1375, 1345, 1280, 1250, 1160, 1105, 1085, 1045, 1010, 995, 975, 955, 890 cm$^{-1}$ $^1$H NMR (CDCl$_3$) δ(ppm) 4.98 (d, H-1'), 4.94 (dd, H-13), 4.38 (d, H-1'), 3.27 (s, OMe), 2.30 (s, N(Me)2), 0.89 (t, H-15)

FNMR (60° C. CDCl3) δ(ppm) -66.57 (t, CF$_3$)

FAB mass spectrum Li spike, m/z 846.3, 830.2, 687.5, 669.4, 513.1, 268.0, 223.7, 167.8, 157.9

EXAMPLE 63

Synthesis of 9-Deoxo-8a-aza-8a-(benzyl)-3'-N-demethyl-3'-N-phenylsulfonyl-8a-homoerythromycin A

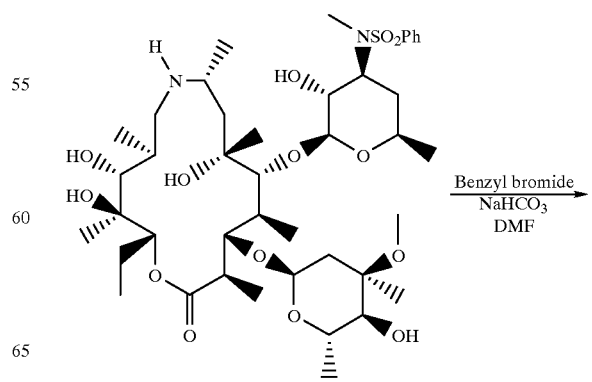

129
-continued

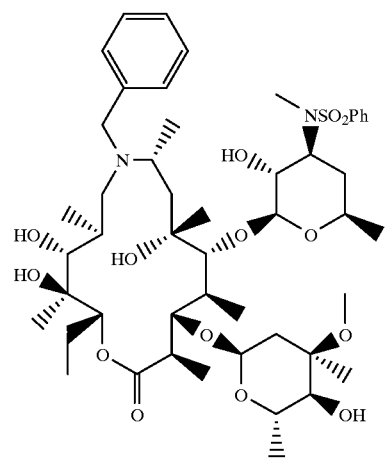

9-Deoxo-8a-aza-3'-N-demethyl-3'-N-phenylsulfonyl-8a-homoerythromycin A (0.2 g, 0.23 mmol), powdered sodium bicarbonate (0.06 g, 0.70 mmol) and benzylbromide (0.041 mL, 0.35 mmol) were added to a 5 mL flask equipped with a magnetic stir bar. Dry dimethylformamide (0.2 ml) was added and the suspension was stirred at 100° C. for 20 hours. The suspension was partitioned between water (8 mL) and methylene chloride (6 L), and the pH was adjusted to 10 with 2N sodium hydroxide. The methylene chloride layer was dried with anhydrous magnesium sulfate, was filtered, and evaporated to a light yellow foam (0.22 g).

The foam was dissolved in 90:10:1 methylene chloride/metanol/concentrated ammonium hydroxide and was loaded onto a column of silica gel 60 (2.5×25 cm, 230–400 mesh, wet packed with 90:10:1 methylene chloride/methanol/concentrated ammonium hydroxide). The column was eluted with 90:10:1 methylene chloride/methanol/concentrated ammonium hydroxide and 8 mL fractions were collected. Fractions 8–12 were combined and evaporated to give the title compound as a foam (0.2 g).

IR (CHCl$_3$) 3540, 3440, 2965, 2935, 2880, 2830, 1720, 1455, 1445, 1400, 1375, 1340, 1325, 1280, 1240, 1175, 1155, 1115, 1080, 1045, 1030, 1010, 995, 950, 940, 930 cm$^{-1}$ $^1$H NMR (CDCl$_3$) δ(ppm) 7.84 (d, ArH), 7.50–7.17 (ArH), 5.02 (dd, H-13), 4.93 (d, H-1"), 4.40 (d, H-1'), 3.31 (s, OMe), 2.59 (s, N(Me)2), 0.85 (t, H-15)

FAB mass spectrum, m/z 951.3, 935.3, 812.0, 794.0, 776.1, 696.7, 650.2, 492.9, 283.9, 266.0, 203.8,

130

EXAMPLE 64

Synthesis of 9-Deoxo-8a-aza-8a-(benzyl)-3'-N-demethyl-8a-homoerythromycin A

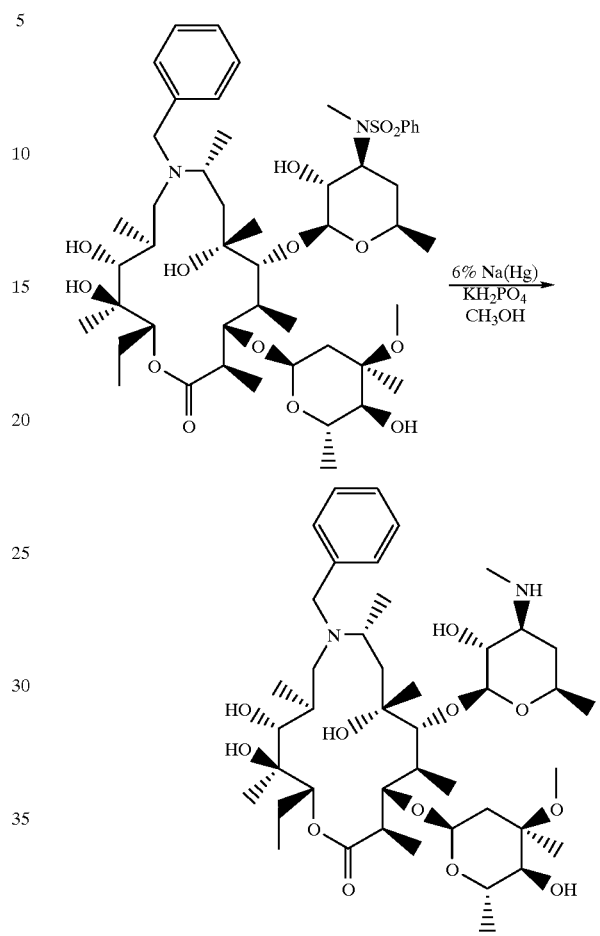

9-Deoxo-8a-aza-8a-(benzyl)-3'-N-demethyl-3'-N-phenylsulfonyl-8a-homoerythromycin A (0.10 g, 0.11 mmol) was added to a well stirred suspension of potassium dihydrogen phosphate (0.55 g, 4.0 mmol) in methanol (1.5 mL). The mixture was cooled in a dry ice/ethylene glycol bath (bath temperature –20° C.), and finely ground 6% sodim amalgam (0.77 g, 2.0 mmol) was added in three portions over 1.5 hours. After 3 hours the suspension was added to a mixture of saturated potassium carbonate (10 mL) and ethyl acetate (4 mL). The ethyl acetate layer was removed and the aqueous layer was reextracted with more ethyl acetate (4 mL). The combined ethyl acetate extracts were washed with brine (8 mL), dried with magnesium sulfate, filtered and evaporated to a foam (0.10 g).

The foam was dissolved in 90:10:1 methylene chloride/methanol/conc. ammonium hydroxide and was loaded onto a column of silica gel 60 (2.5×10 cm, 230–400 mesh, wet packed with 90:10:1 methylene chloride/methanol/conc. ammonium hydroxide). The column was eluted with 90:10:1 methylene chloride/methanol/conc. ammonium hyroxide and after a forerun of 16 mL, 4 mL fractions were collected. Fractions 8–14 were combined and evaporated to give the title compound as a foam (0.047 g).

$^1$H NMR (CDCl$_3$) δ(ppm) 7.34 (d, ArH), 7.27 (dd, ArH), 7.19 (dd, ArH), 5.02 (dd, H-13), 4.96 (d, H-1"), 4.38 (d, H-1'), 3.27 (s, OMe), 2.37 (s, N(Me)2), 0.87 (t, H-15)

EXAMPLE 65

Synthesis of 9-Deoxo-8a-aza-8a-(benzyl)-8a-homoerythromycin A

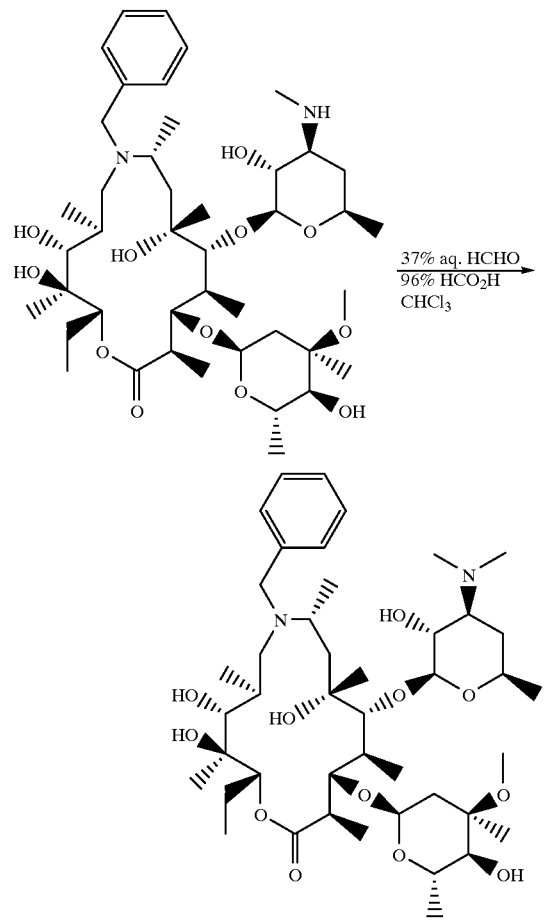

EXAMPLE 66

Synthesis of 9-Deoxo-8a-aza-8a-(4-methoxybenzyl)-3'-N-demethyl-3'-N-phenylsulfonyl-8a-homoerythromycin A

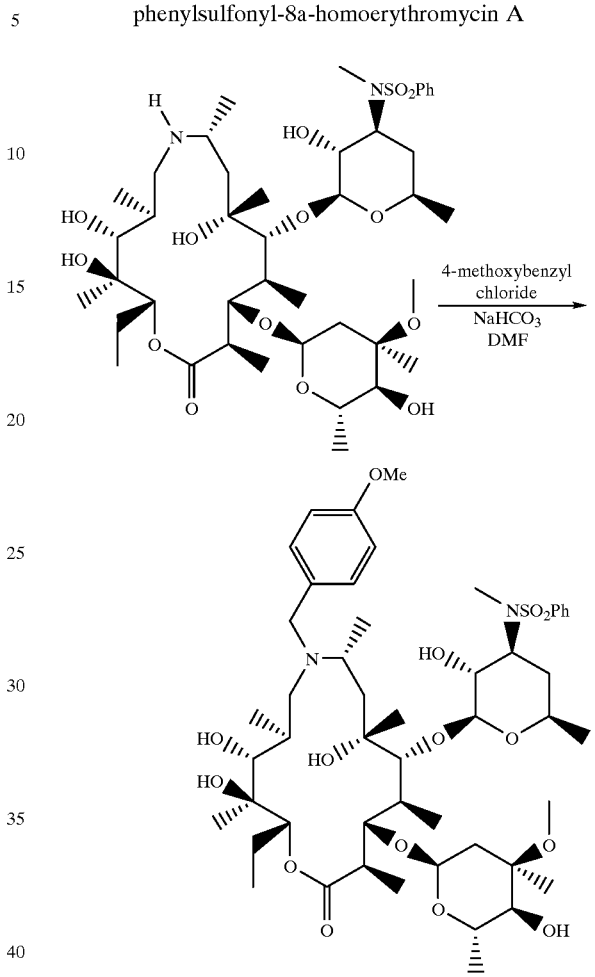

9-Deoxo-8a-aza-8a-(benzyl)-3'-N-demethyl-8a-homoerythromycin A (0.047 g, 0.058 mmol) was dissolved in chloroform (2 mL) and was treated with 37% aqueous formaldehyde (0.012 mL, 0.16 mmol) and 96% formic acid (0.012 mL, 0.30 mmol). The mixture was heated at 60° C. for 18 hours and was then cooled to room temperature. Water (3 mL) and methylene chloride (5 L) were added and the pH was adjusted to 11. The methylene chloride layer was removed and the aqueous layer was re-extracted twice with methylene chloride (4 mL). The combined pH 11 extracts were dried with anhydrous magnesium sulfate, were filtered and evaporated under vacuum to give the title compound as a foam (0.024 g).

IR (CHCl$_3$) 3540, 3420, 2965, 2935, 2875, 2830, 1720, 1455, 1400, 1375, 1345, 1330, 1280, 1260, 1240, 1165, 1160, 1105, 1085, 1065, 1045, 1010, 995, 975, 955, 890 cm$^{-1}$ $^1$H NMR (CDCl3) δ(ppm) 7.42 (d, ArH), 7.29 (dd, ArH), 7.24 (dd, ArH), 5.12 (d, H-1"), 4.87 (dd, H-13), 4.36 (d, H-1'), 3.29 (s, OMe), 2.18 (s, N(Me)2), 0.84 (t, H-15)

FAB mass spectrum Li spike, m/z 826.4, 681.7, 667.3, 649.3, 492.8, 247.8

9-Deoxo-8a-aza-3'-N-demethyl-3'-N-phenylsulfonyl-8a-homoerythromycin A (0.2 g, 0.23 mmol), powdered sodium bicarbonate (0.06 g, 0.70 mmol) and 4-methoxybenzyl chloride (0.047 mL, 0.35 mmol) were added to a 5 mL flask equipped with a magnetic stir bar. Dry dimethylformamide (0.2 ml) was added and the suspension was stirred at 100° C. for 20 hours. The suspension was partitioned between water (8 mL) and metylene chloride (6 mL), and the pH was adjusted to 10 with 2N sodium hydroxide. The methylene chloride layer was dried with anhydrous magnesium sulfate, was filtered, and evaporated to a light yellow foam.

The foam was dissolved in 90:10:1 methylene chlride/methanol/concentrated ammonium hydroxide and was loaded onto a column of silica gel 60 (2.5×30 cm, 230–400 mesh, wet packed with 90:10:1 methylene chloride/methanol/concentrated ammonium hydroxide). The column was eluted with 90:10:1 methylenechloride/methanol/concentrated ammonium hydroxide and 4mL fractions were collected. Fractions 16–18 were combined and evaporated to give the title compound as a foam (0.5 g).

IR (CHCl$_3$) 3540, 3440, 2965, 2935, 2875, 2835, 1725, 1610, 1510, 1455, 1445, 1400, 1375, 1340, 1325, 1280, 1245, 1155, 1115, 1080, 1045, 1030, 1010, 995, 950, 930 cm$^{-1}$

¹H NMR (CDCl₃) δ(ppm) 7.84 (d, ArH), 7.48 (dd, ArH), 7.44 (dd, ArH), 7.26 (d, ArH), 6.80 (d, ArH), 5.00 (d, H-1"), 4.94 (dd, H-13), 4.38 (d, H-1'), 3.73 (s, ArOMe), 3.29 (s, OCH₃), 2.60 (s, N(Me)₂), 0.86 (t, H-15)

¹³C NMR (60° C. CDCl₃) δ(ppm) 177.0, 140.1, 132.1, 130.1, 128.6, 127.4, 113.9, 103.9, 96.2, 88.6, 78.3, 77.9, 77.1, 75.4, 74.3, 72.9, 69.8, 69.3, 68.5, 65.9, 58.1, 55.8, 55.2, 49.3, 46.0, 42.2, 41.6, 36.2, 35.2, 33.0, 28.2, 25.7, 22.0, 21.6, 20.6, 17.8, 15. 6, 14.4, 13.8, 12.7, 11.0

FAB mass spectrum Li spike, m/z 981.8, 861.9, 842.1, 806.3, 121.2

EXAMPLE 67

Synthesis of 9-Deoxo-8a-aza-8a-(4-methoxybenzyl)-3'-N-demethyl-8a-homoerythroycin A

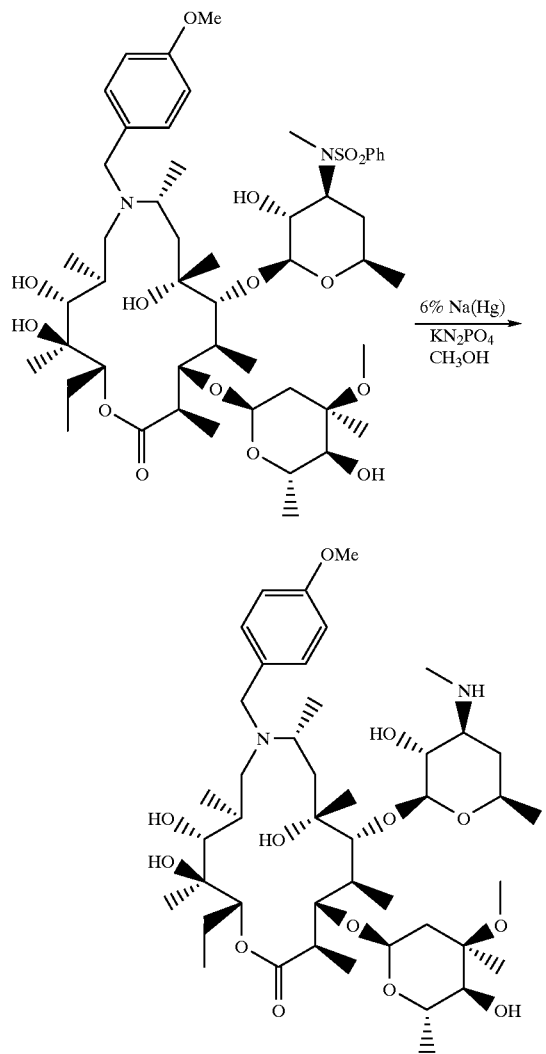

9-Deoxo-8a-aza-8a-(4-methoxybenzyl)-3'-N-demethyl-3'-N-phenylsulfonyl-8a-homoerythromycin A (0.12 g, 0.12 mmol) was added to a well stirred suspension of potassium dihydrogen phosphate (0.50 g, 3.7 mmol) in methanol (3.0 mL). Tetrahydrofuran (0.8 mL) was added to clear the cloudy suspension and the mixture was cooled in a dry ice/ethylene glycol bath (bath temperature –20° C.). Freshly ground 6% sodium amalgam (2.6 g, 6.8 mmol) was added in two portions over 1 hour. After 1.5 hours the suspension ws added to a mixture of saturated potassium carbonate (10 mL) and ethyl acetate (8 mL). The ethyl acetate layer was removed and the aqueous layer was re-extracted with more ethyl acetate (4 mL). The combined ethyl acetate extracts were washed with brine (mL), dried with magnesium sulfate, filtered and evaporated to a foam (0.12 g).

EXAMPLE 68

Synthesis of 9-Deoxo-8a-aza-8a-(4-methoxybenzyl-8a-homoerythromycin A

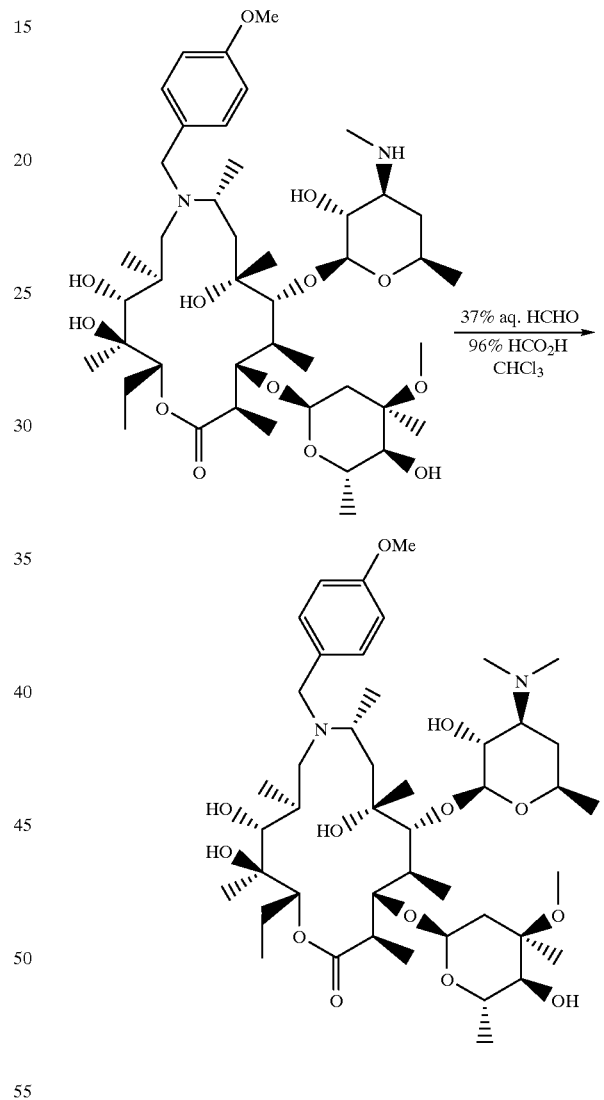

9-Deoxo-8a-aza-8a-(4-methoxybenzyl)-3'-N-demethyl-8a-homoerythromycin A (0.12 g 0.122 mmol) was dissolved in chloroform (5 mL) and was treated with 37% aqueous formaldehyde (0.014 mL, 0.18 mmol) and 96% formic acid (0.014 mL, 0.37 mmol). The mixture was heated at 60° C. for 18 hours and was then cooled to room temperature. Water (6 mL) an methylene chloride (6 mL) were added and the pH was adjusted to 11. The methylene chloride layer was removed and the aqueous layer was re-extracted twice with methylene chlorid e (4 mL). The combined pH 11 extracts were dried with anhydrous magnesium sulate, were filtered and evaporated under vacuum to give a foam.

The foam was dissolved in 90:10:1 methylene chloride/methanol/concentrated ammonium hydroxide and was loaded onto a column of silica gel 60 (2.5×24 cm, 230–400 mesh, wet packed with 90:10:1 methylene chloride/methanol/concentrated ammonium hydroxide). The column was eluted with 90:10:1 methylene chloride/methanol/concentrated ammonium hydroxide and 4 mL fractions were collected. Fractions 20–24 were combined and evaporated to give te title compound as a foam (0.067 g).

IR (CHCl$_3$) 3540, 3430, 2965, 2935, 2875, 2830, 1720, 1610, 1510, 1455, 1400, 1370, 1345, 1325, 1280, 1245, 1165, 1160, 1100, 1085, 1065, 1040, 1005, 995, 975, 950, 890 cm$^{-1}$ $^1$H NMR (CDCl$_3$) δ(ppm) 7.32 (d, ArH), 6.84 (d, ArH), 5.11 (d, H-1"), 4.88 (dd, H-13), 4.37 (d, H-1'), 3.76 (s, ArOMe), 3.29 (s, OCH3), 2.24 (s, N(Me)2), 0.85 (t, H-15)

FAB mass spectrum Li spike, m/z 855.9, 840.2, 726.9, 698.0, 679.7, 157.9, 121.3

EXAMPLE 69

Synthesis of 9-Deoxo-8a-aza-8a-(2-(2-ethoxyethoxy)eth-1-yl)-3'-N-demethyl-3'-N-phenylsulfonyl-8a-homoerythromycin A mamide (0.2 ml) was added and the suspension was stirred at 100° C. for 68 hours. The suspension was partitioned between water (8 mL) and methylne chloride (6 mL), and the pH was adjusted to 10 with 2N sodium hydroxide. The methylene chloride layer was dried with anhydrous magnesium sulfate, was filtered, and evaporated to a foam.

The foam was dissolved in 90:10:1 methylene chloride/methanol/concentrated ammonium hydroxide and was loaded onto a column of silica gel 60 (2.5×24 cm, 230–400 mesh, wet packed with 90:10:1 methylene chloride/methanol/concentrated ammonium hydroxide). The column was eluted with 90:10:1 methylene chloride/methaol/concentrated ammonium hydroxide and 4 mL fractions were collected. Fractions 18–22 were combined and evaporated to give the title compound as a foam (0.10 g).

IR (CHCl$_3$) 3540, 3410, 2970, 2935, 2875, 2835, 1725, 1455, 1445, 1400, 1370, 1340, 1325, 1280, 1240, 1155, 1115, 1080, 1045, 1030, 1010, 995, 950 cm$^{-1}$ $^1$H NMR (CDCl$_3$) δ(ppm) 7.85 (d, ArH), 7.47 (dd, ArH), 7.40 (dd, ArH), 4.97 (d, H-13), 4.87 (dd, H-1"), 4.40 (d, H-1'), 3.28 (s, OCH$_3$), 2.73 (8, N(Me)$_2$), 0.87 (t, H-15)

$^{13}$C NMR (60° C. CDCl$_3$) δ(ppm) 176.6, 140.2, 132.0, 128.5, 127.5, 104.5, 96.4, 88.6, 78.8, 77.8, 77.1, 75.3, 74.2, 72.8, 70.6, 70.4, 70.2, 68.5, 66.5, 65.9, 58.0, 54.7, 51.1, 49.3,

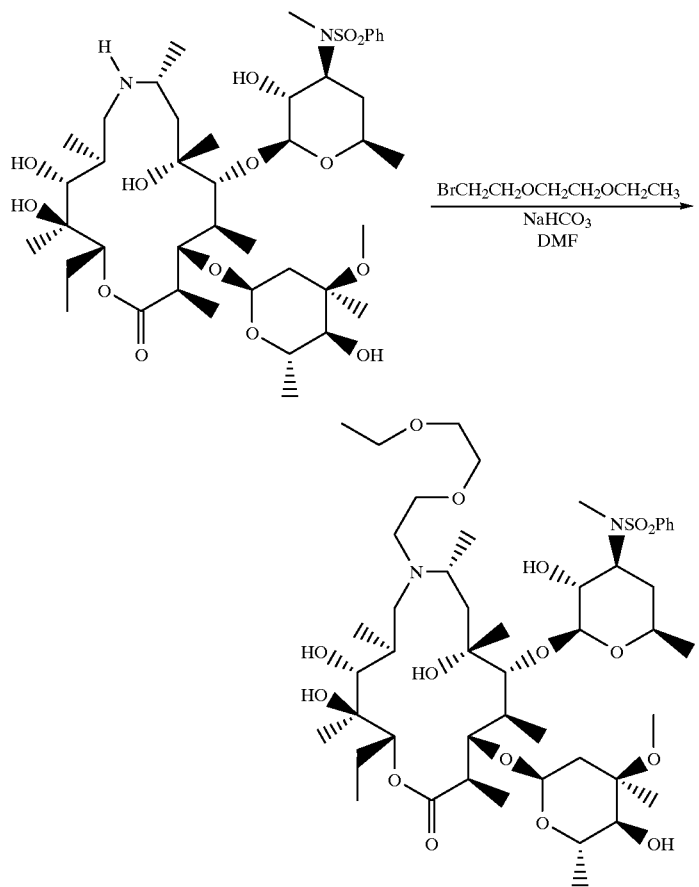

9-Deoxo-8a-aza-3'-N-demethyl-3'-N-phenylsulfonyl-8a-homoerythromycin A (0.2 g, 0.23 mmol), powdered sodium bicarbonate (0.06 g, 0.70 mmol) and 2-(2-ethoxyethoxy) ethyl bromide (0.05 mL, 0.35 mmol) were added to a 5 mL flask equipped with a magnetic stir bar. Dry dimethylfor- 46.9, 42.3, 36.4, 35.0, 33.0, 28.4, 25.5, 22.0, 21.5, 20.6, 17.8, 16.2, 15.2, 15.0, 14.4, 12.9, 1.8, 11.2, 11.0

FAB mass spectrum Li spike, m/z 977.7, 961.8, 838.1, 820.1, 722.9, 519.2, 284.0, 266.1, 197.6, 173.7, 115.4

EXAMPLE 70

Synthesis of 9-Deoxo-8a-aza-8a-(2-(2-ethoxyethoxy)eth-1-yl)-3'-N-demethyl-8a-homoerythromycin A

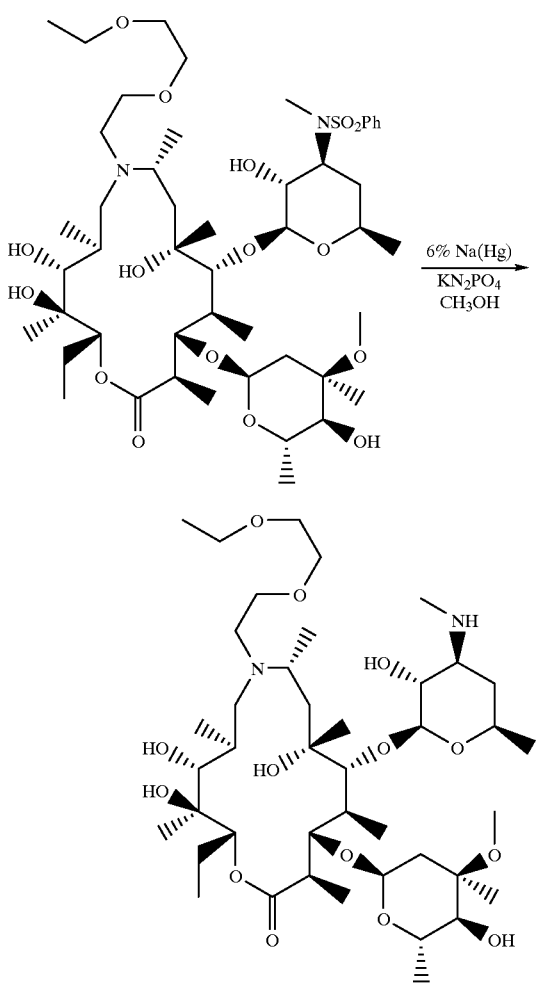

9-Deoxo-8a-aza-8a-(2-(2-ethoxyethoxy)eth-1-yl)-3'-N-demethyl-3'-N-phenylsulfonyl-8a-homoerythromycin A (0.05 g, 0.05 mmol) was added to a well stirred suspension of potassium dihydrogen phosphate (0.42 g, 3.1 mmol) in methanol (1.5 mL). The mixture was cooled in dry ice/ethylene glycol bath (bath temperature −20° C.) and freshly ground 6% sodium amalgam (0.42 g, 1.1 mmol) was added in two portions over 1 hour. After 1.5 hours the suspension was added to a mixture of saturated potassium carbonate (6 mL) and ethyl aetate (4 mL). The ethyl acetate layer was removed and the aqueous layer was re-extracted with more ethyl acetate (3 mL). The combined ethyl acetate extracts were washed with brine (8 mL), dried with magnesium sulfate, filtered and evaporated to a foam (0.49 g).

EXAMPLE 71

Synthesis of 9-Deoxo-8a-aza-8a-(2-(2-ethoxyethoxy)eth-1-yl)-8a-homoerythromycin A

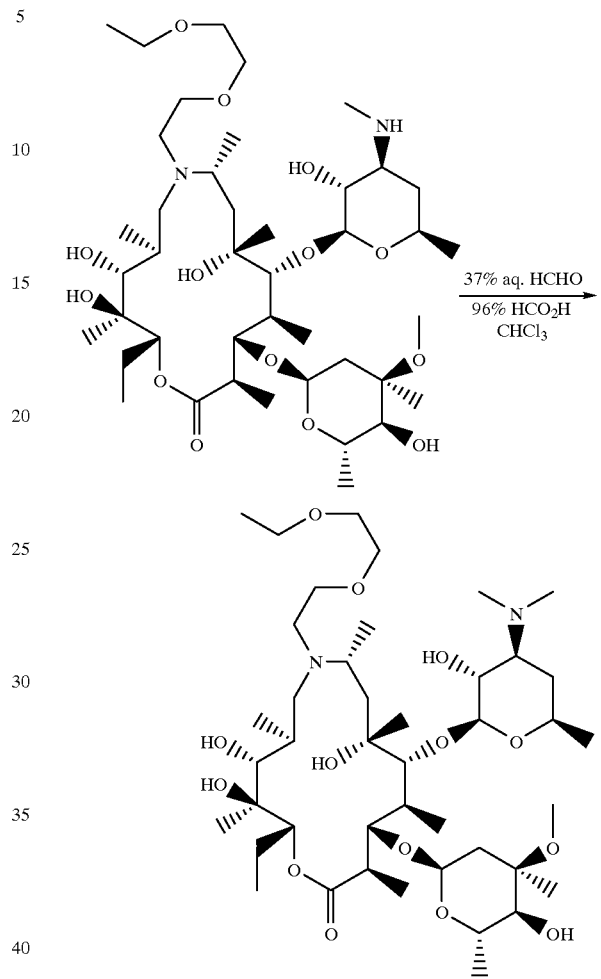

9-Deoxo-8a-aza-8a-(2-(2-ethoxyethoxy)eth-1-yl)-3'-N-demethyl-8a-homoerythromycin A (0.049 g, 0.05 mmol) was dissolved in chloroform (1.5 mL) and was treated with 37% aqueous formaldehyde (0.006 mL, 0.08 mmol) and 96% formic acid (0.006 mL, 0.15 mmol). The mixture was heated at 60° C. for 25 hours and was then cooled to room temperature. Water (6 mL) and methylene chloride (6 mL) were added and the pHwas adjusted to 11. The methylene chloride layer was removed and the aqueous layer was re-extracted twice with methylene chloride (4 mL). The combined pH 11 extracts were dried with anhydrous magnesium sulfate, were filtered and evaporated under vacuum to a foam (0.03 g).

The foam was dissolved in 90:10:1 methylene chloride/methanol/concentrated ammonium hydroxide and was loaded onto a column of silica gel 60 (2.5×12 cm, 230–400 mesh, wet packed with 90:10:1 methylene chloride/methanol/concentrated ammonium hydroxide). The column was eluted with 90:10:1 methylene chloride/methanol/concentrated ammonium hydroxide and 4 mL fractions were collected. Fractions 12+13 were combined and evaporated to give the title compound as a foam (0.014 g).

IR CHCl$_3$) 3420, 2970, 2940, 2880, 2820, 1725, 1455, 1400, 1372, 1345, 1165, 1120, 1105, 1085, 1045, 1010, 955 cm$^{-1}$ $^1$H NMR (CDCl$_3$) δ(ppm) 4.98 (d, H-1"), 4.97 (dd, H-13), 4.40 (d, H-1'), 3.29 (s, OCH3), 2.34 (s, N(Me)2), 0.89 (t, H-15)

FAB mass spectrum m/z 851, 747, 675, 563, 502, 459, 401, 355, 325, 281, 221, 158, 116

EXAMPLE 72

Synthesis of 9-Deoxo-8a-aza-8a-(2,2-difluoroeth-1-yl)-3'-N-demethyl-3'-N-phenylsulfonyl-8-a-homoerythromycin A

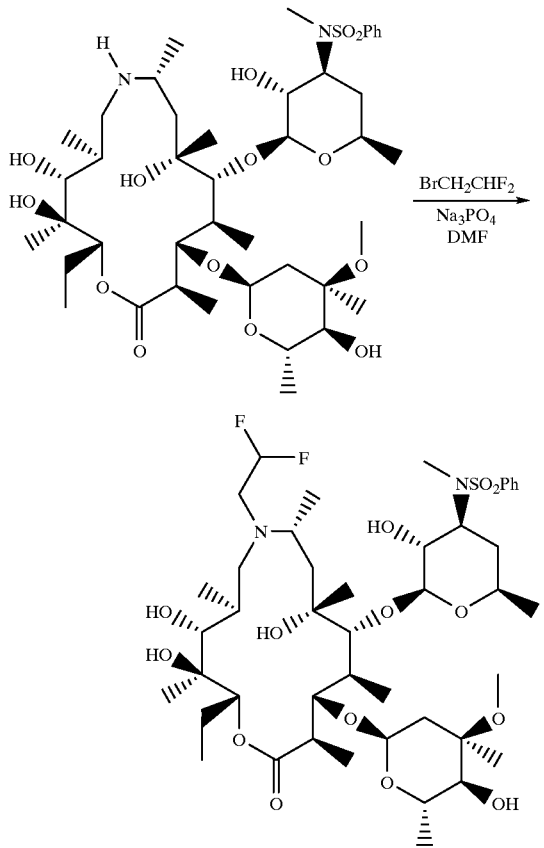

9-Deoxo-8a-aza-3'-N-demethyl-3'-N-phenylsulfonyl-8a-homoerythromycin A (0.2 g, 0.23 mmol), trisodiumphosphate (0.40 g, 2.4 mmol) and 1-bromo-2,2-difluoroethane (0.1 mL, 1.26 mmol) were added to a 5 mL flask equipped with a magnetic stir bar. Dry dimethylformamide (0.4 ml) was added and the suspension was stired at 100° C. for 44 hours, with a second addition of 1-bromo-2,2-difluoroethane (0.1 mL, 1.26 mmol) at 18 hours reaction time. After cooling to room temperature, the mixture was partitioned between water (6 mL) and methylene chloride (6 mL) and the pH was ajusted to 10 with 2N sodium hydroxide. The methylene chloride layer was dried with anhydrous magnesium sulfate, was filtered and evaporated to a light yellow foam (0.18 g).

The foam was dissolved in 90:10:1 methylene chloride/methanol/concentrated ammonium hydroxide and was loaded onto a column of silica gel 60 (2.5×25.5 cm, 230–400 mesh, wet packed with 90:10:1 methylene chloride/methanol/concentrated ammonium hydroxide). The column was eluted with 90:10:1 methylene chloride/methanol/concentraed ammonium hydroxide and 4mL fractions were collected. Fractions 11–13 were combined and evaporated to give a foam (0.038 g).

The foam was dissolved in methylene chloride and was placed on two 1000 micron silica preparative thin layer plates. The plates were developed with 90:10:1 methylene chloride/methanol/concentrated ammonium hydroxide and the title compound was removed, eluted with 90:10:1 methylene chloride/methanol/concentrated ammonium hydroxide, and evaporated to a foam (0.018 g).

IR (CHCl$_3$) 3540, 3365, 2965, 2935, 2880, 2835, 1725, 1455, 1445, 1395, 1370, 1345, 1325, 1280, 1260, 1235, 1175, 1155, 1115, 1080, 1045, 1005, 995, 950, 945, 925 cm$^{-1}$ $^1$H NMR (CDCl$_3$) δ(ppm) 7.86 (d, ArH), 7.48 (dd, ArH), 7.44 (dd, ArH), 5.96 (tt, CHF$_2$), 4.94 (H-13+H-1"), 4.44 (d, H-1'), 3.29 (s, OMe), 2.75 (s, N(Me)$_2$), 0.89 (t, H-15)

FNMR (60° C. CDCl$_3$) δ(ppm) –118.5 (m, CHF$_2$)

EXAMPLE 73

Synthesis of 9-Deoxo-8a-aza-8a-(2,2-difluoroeth-1-yl)-3'-N-demethyl-8a-homoerythromycin A

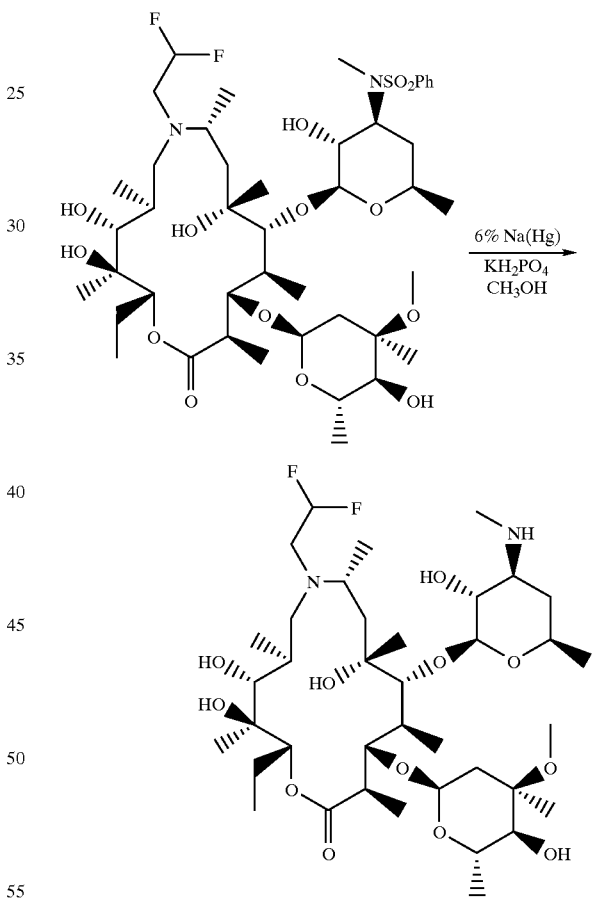

9-Deoxo-8a-aza-8a-(2,2-difluoroeth-1-yl)-3'-N-demethyl-3'-N-phenylsulfonyl-8a-homoerythromycin A (0.06 g, 0.06 mmol) was added to a well stirred suspension of potassium dihydrogen phosphate (0.2 g, 1.47 mmol) in methanol (2 mL). The mixture was cooled in a dry ice/ethylee glycol bath (bath temperature –20° C.), and finely ground 6% sodium amalgam (2.95 g, 7.7 mmol) was added all at once. After 2 hours the suspension was added to a mixture of saturated potassium carbonate (8 mL) and ethyl acetate (6 mL). The ethyl acetate layer was removed and the aqueous layer was re-extracted with more ethyl acetate (6 mL). The combined ethyl acetate extracts were washed with brine (10 mL), dried with magnesium sulfate, filtered and evaporated to a foam (0.06 g).

EXAMPLE 74

Synthesis of 9-Deoxo-8a-aza-8a-(2.2-difluoroeth-1-yl)-8a-homoerythromycin A

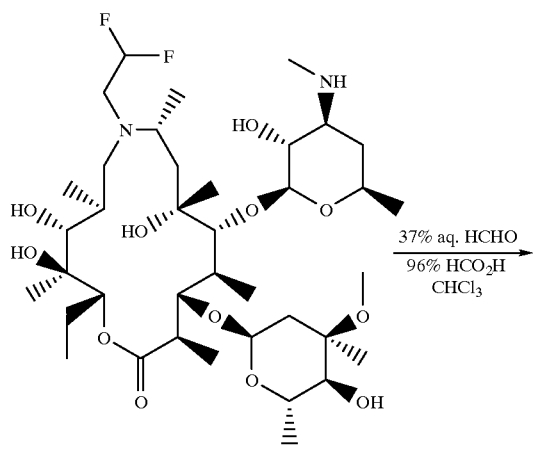

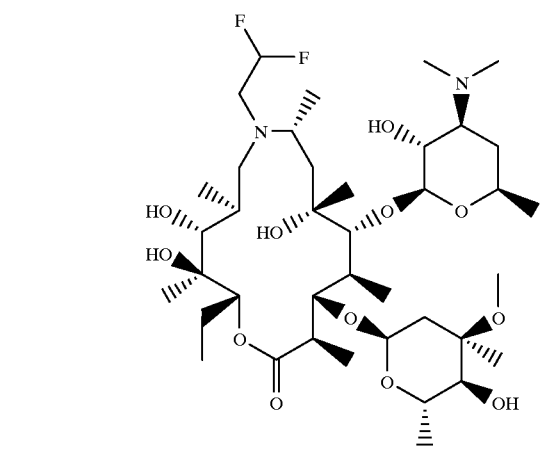

9-Deoxo-8a-aza-8a-(2,2-difluoroeth-1-yl)-3'-N-demethyl-8a-homoerythromycin A (0.06 g, 0.078 mmol) was dissolved in chloroform (3 mL) and was treated with 37% aqueous formaldehyde (0.01 mL, 0.13 mmol) and 96% formic acid (0.01 mL, 0.26 mmol). The mixture was heated at 60° C. for 20 hours and was then cooled to room temperature. After cooling to room temperature, water (6 mL) and methylene chloride (6 mL) were added and the pH was adjusted to 1. The methylene chloride layer was removed and the aqueous layer was re-extracted twice with methylene chloride (20 mL). The combined pH 11 extracts were dried with anhydrous magnesium sulfate, were filtered and evaporated under vacuum to a foam (0.04 g).

The foam was dissolved in 90:10:1 methylene chloride/methanol/conc. ammonium hydroxide and was loaded onto a column of silica gel 60 (2.5×12 cm, 230–400 mesh, wet packed with 90:10:1 methylene chloride/methanol/conc. ammonium hydroxide). The column was eluted with 90:10:1 methylene chloride/methanol/conc. ammonium hydroxide and 4 mL fractions were collected. Fractions 20–24 were combined and evaporated to give the title compound as a foam (0.02 g).

IR (CHCl$_3$) 3540, 3420, 2965, 2935, 2880, 285, 2785, 1720, 1455, 1400, 1375, 1345, 1325, 1275, 1255, 1240, 1175, 1160, 1120, 1100, 1085, 1065, 1045, 1005, 995, 975, 950, 890 cm$^{-1}$ $^1$H NMR (60° C. CDCl$_3$) δ(ppm) 6.00 (tt, CHF$_2$), 5.02 (d, H-1"), 4.91 (dd, H-13), 4.38 (d, H-1'), 3.28 (s, OMe), 2.32 (s, N(Me)$_2$), 0.88 (t, H-15)

$^{13}$C NMR (60° C. CDCl$_3$) δ(ppm) 178.0, 118.7, 116.3, 113.9, 103.9, 95.6, 86.8, 78.0, 77.3, 75.8, 74.4, 72.8, 70.3, 69.4, 68.6, 65.7, 65.5, 60.7, 57.4, 53.5, 49.3, 45.2, 42.0, 41.9, 40.3, 35.0, 32.9, 29.3, 26.0, 21.9, 21.5, 21.0, 17.9, 16.1, 14.6, 13.9, 13.2, 12.2, 11.1

FNMR (60° C. CDCl$_3$) δ(ppm) −118.5 (m, CHF2)

FAB mass spectrum, m/z 800.6, 641.7, 496.3, 157.9, 116.3

EXAMPLE 75

Synthesis of 9-Deoxo-8a-aza-8a-hydroxy-8a-homoerythromycin A and 9-Deoxo-8a-aza-8a-(propl-yl)-8-a-homoerythromycin A

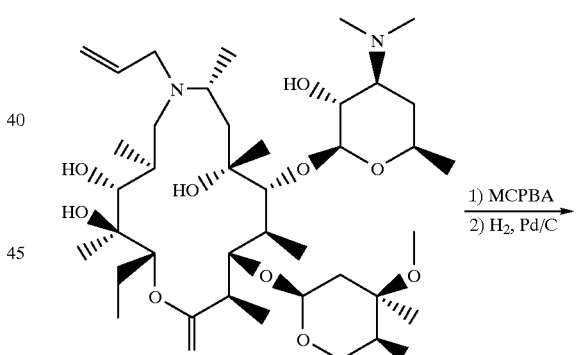

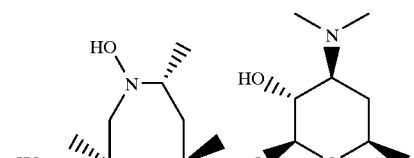

143
-continued

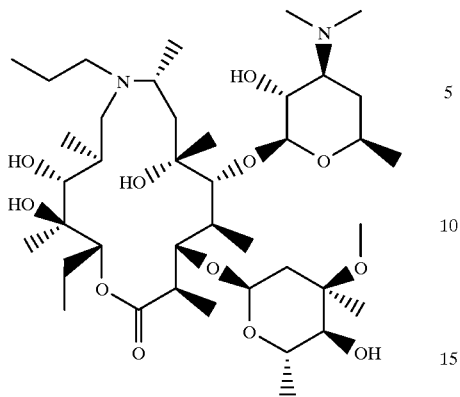

A methylene chloride (2 mL) suspension of 9-Deoxo-8a-aza-8a-(prop-2-en-1-yl)-8a-homoerythromycin A (0.2 g, 0.26 mmol) and sodium bicarbonate (0.065 g, 0.78 mmol) was cooled in an ice bath and was treated with 3-chloroperoxybenzoic acid (0.094 g, 0.542 mmol). The suspension was allowed to warm to room temperature after 30 minutes. After an additional 30 minutes the mixture was cooled in an ice bath and additional 3-chloroperoxybenzoic acid (0.045 g, 0.26 mmol) was added. After 30 minutes the suspension was washed with an aqueous solution of sodium bisulfite, and the methylene chloride was dried with magnesium sulfate, was filtered and evaporated to a foam.

The above foam was dissolved in ethanol (3 mL) and was hydrogenated at amospheric pressure for 45 minutes in the presence of 10% palladium on carbon (50 mg). The suspension was filtered through solka-floc and the filtrate was partitioned between water (4 mL) and methylene chloride (6 mL). The pH was adjusted from 2 to 10 withthe addition of potassium carbonate. The methylene chloride was removed and the aqueous layer was re-extracted with more methylene chloride (4 mL). The combined extracts were dried with magnesium sulfate, were filtered and evaporated to a foam (0.188 g).

The foam was dissolved in methylene chloride and was loaded onto a column of basic aluminum oxide (2.5×29cm, Brockmann 1, 150 mesh, wet packed with 1% methylene chloride/methanol). The column was eluted with 1% methylene chloride/methanol and 8 mL fractions were collected. Fractions 43–57 were combined and evaporated to give 9-Deoxo-8a-aza-8a-(prop-1-yl)-8a-homoerythromycin A as a foam (0.021 g). Fractions 64–68 were combined and evaporated to give 9-Deoxo-8a-aza-8a-hydroxy-8a-homoerythromycin A s a foam (0.041 g).

Data for 9-Deoxo-8a-aza-8a-hydroxy-8a-homoerythromycin A

IR (CHCl$_3$) 3420, 2970, 2935, 2880, 2835, 2785, 1720, 1455, 1420, 1400, 1375, 1345, 1325, 1280, 1240, 1180, 1160, 1140, 1120, 1100, 1080, 1045, 1005, 975, 955, 895 cm$^{-1}$ $^1$HNMR (CDCl$_3$) δ(ppm) 5.03 (d, H-1"), 4.76 (dd, H-13), 4.35 (d, H-1'), 3.24 (s, OCH$_3$), 2.25 (s, N(CH$_3$)$_2$), 0.84 (t, CH$_2$CH$_3$)

FAB mass spectrum, m/z 751.7, 735.6, 619.6, 593.8, 575.6, 559.8, 418.4, 158.2

144

EXAMPLE 76

Synthesis of 9-Deoxo-8a-aza-8a-acetyl-8a-homoerythromycin A by Acylation of 9-Deoxo-8a-aza-8a-homoerythromycin A

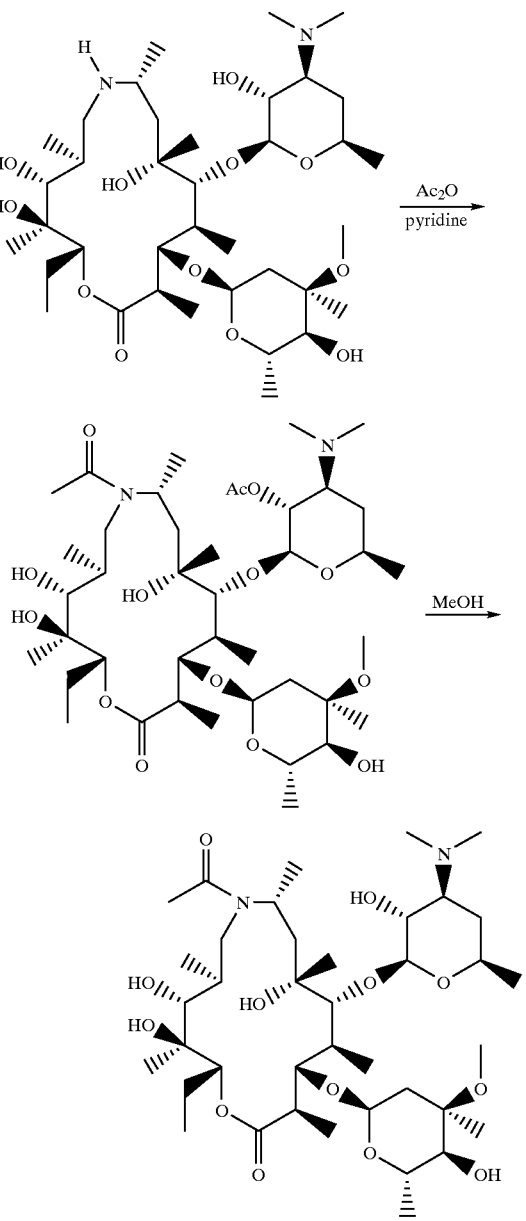

Acetic anhydride (540 μl, 5.72 mmol) and 9-deoxo-8a-aza-8a-homoerythromycin A (210 mg, 0.286 mmol) were combined in pyridine (1 ml) and stirred for two hours. The mixture was partitioned between chloroform and aqueous potassium carbonate. The organic layer was separated, washed with brine, dried through a plug of sodium sulfate and evaporated to dryness to yield an off white foam. The crude product was dissolved in methanol (3 ml) and aged 18 hours to methanolyze the 2'-ester. This solution was reduced and subjected to flash chromatography using a stepwise gradient of 0.1 to 0.5 to 1% ammonium hydroxide in 20% methanol/methylene chloride to afford 9-deoxo-8a-aza-8a-acetyl-8a-homoerythromycin A (193 mg, 87% yield) as a white solid.

$^1$H NMR (400 MHz, CDCl$_3$, 60° C.) δ5.34 (d, H-1"), 4.98 (dd, H-13), 3.23 (s, OCH$_3$), 2.23 (s,N(CH$_3$)$_2$).

$^{13}$C NMR (100.6 MHz, CDCl$_3$, 60° C.) d 176.14, 173.65, 103.66 (C-1'), 97.51 (C-1").

FAB-MS (lithium spike) m/z 783.

EXAMPLE 77

Synthesis of 9-Deoxo-8a-aza-8a-glycyl-8a-homoerythromycin A by Acylation of 9-Deoxo-8a-aza-8a-homoerythromycin A

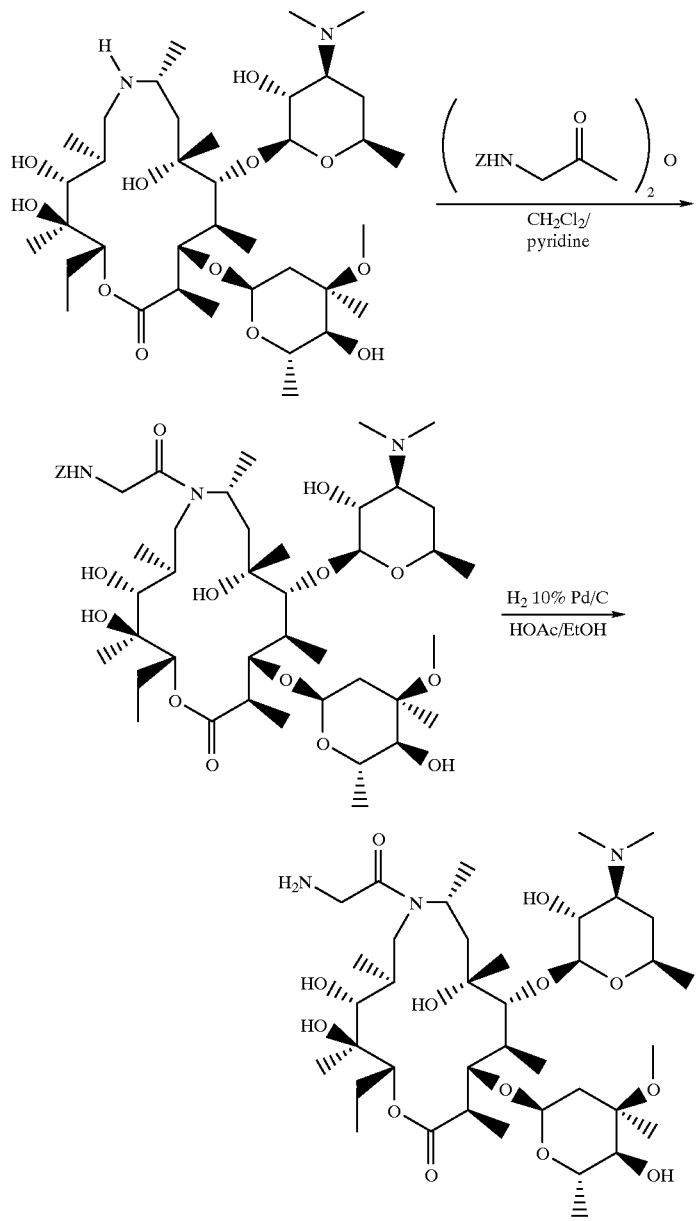

N-benzyloxycarbonyl glycine (627 mg, 3 mmol) was suspended in methylene chloride (20 ml) and 1-cyclohexyl-3-(2-morpholinoethyl)carbodiimide metho-p-toluenesulfonate (636 mg, 1.5 mmol) was added in one portion. The suspension clarified briefly. After one hour, the suspension was reduced in volume by rotary evaporation and partitioned between ethyl acetate and cold pH 4 phosphate buffer. The organic layer was separated and washed with chilled brine, chilled aqueous sodium bicarbonate, and chilled brine, then dried through a plug of sodium sulfate onto magnesium sulfate. The suspension was filtered into hexanes and evaporated to dryness. The solid was redissolved in methylene choride, hexane was added and the solution was evaporated to dryness and subjected to high vacuum for one hour to afford the crude anhydride (472 mg, 1.18 mmol, 79% yield). A solution of 9-deoxo-8a-aza-8a-homoerythromycin A (175 mg, 0.236 mmol) in pyridine (3 ml) was added in one portion to the crude anhydride. After 5 hours, the mixture was partitioned between chloroform and aqueous potassium carbonate. The organic layer was separated, washed twice with brine, dried through a plug of sodium sulfate and evaporated to dryness after removing pyridine by azeotroping twice with toluene. This crude product was subjected to flash chromatography using a stepwise gradient of 0.1 to 0.5 to 1% ammonium hydroxide in 20% methanolic methylene chloride to afford the N-benzyloxycarbonyl derivative of 9-deoxo-8a-aza-8a-glycyl-8a-homoerythromycin A (112 mg, 48% yield) as a white solid. This product was combined with 10% palladium on carbon (50 mg) in ethanol (3 ml) and acetic acid (50 ml) and hydrogen was bubbled through the suspension for 70 minutes. The suspension was filtered through Celite, reduced, and partitioned between chloroform and aqueous potassium carbonate. The organic layer was separated, washed twice with brine, dried through a plug of sodium sulfate and evaporated to dryness to afford 9-deoxo-8a-aza-8a-glycyl-8a-homoerythromycin A (77 mg, 90% yield) as a white solid.

$^1$H NMR (400 MHz, CDCl$_3$) δ4.98 (dd, H-13), 4.80 (d, H-1"), 3.21 (s, OCH$_3$), 2.23 (s, N(CH$_3$)$_2$).

$^{13}$C NMR (100.6 MHz, CDCl$_3$) δ176.22, 176.08, 104.01 (C-1'), 98.44 (C-1").

FAB-MS m/z 792, 634, 477, 158.

EXAMPLE 78

Synthesis of 9-Deoxo-8a-aza-8a-(Leu-Gly)-8a-homoerythromycin A by Acylation of 9-Deoxo-8a-aza-8a-glycyl-8a-homoerythromycin A

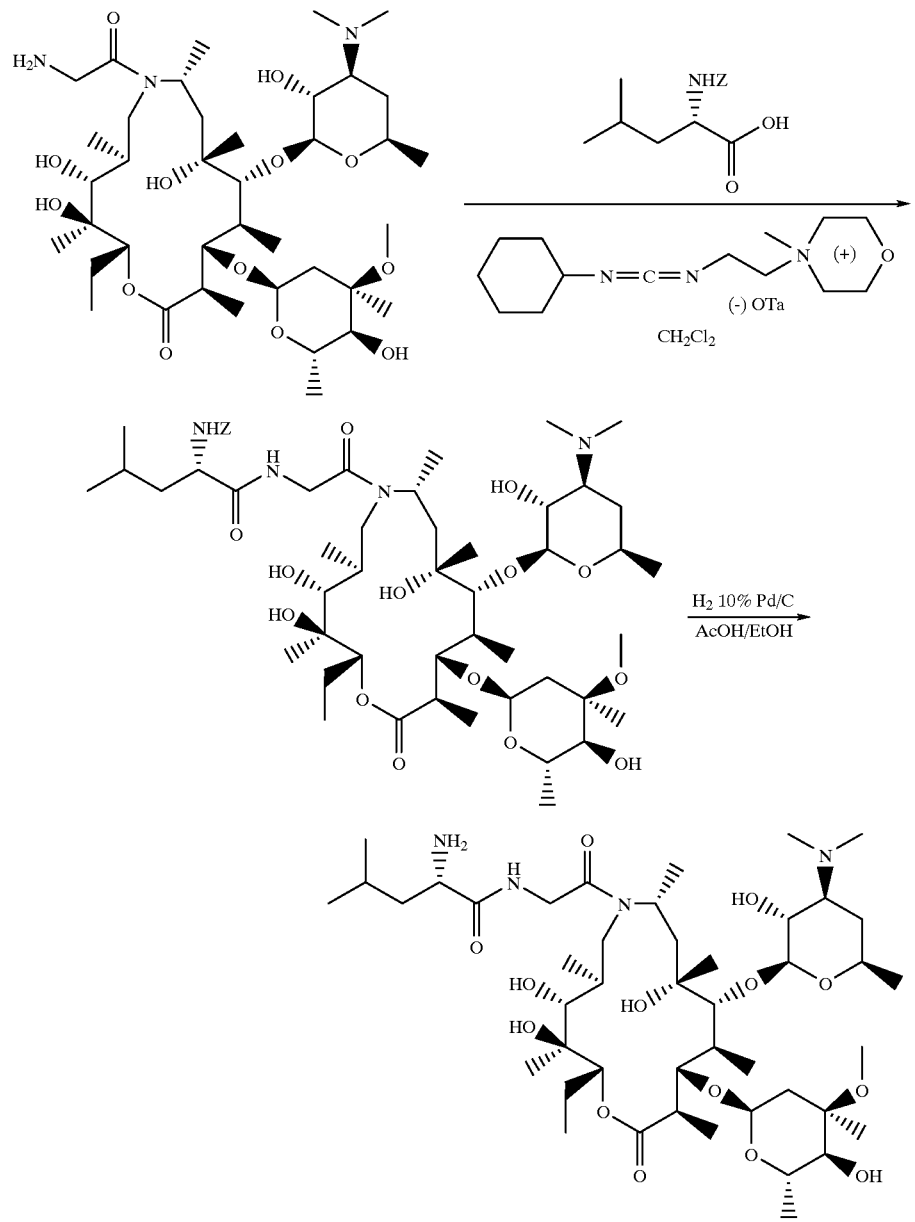

To a suspension of N-benzyloxycarbonyl leucine (45 mg, 0.17 mmol) and 9-deoxo-8a-aza-8a-glycyl-8a-homoerythromycin A (123 mg, 0.155 mmol) in methylene chloride (1 ml) was added in one portion 1-cyclohexyl-3-(2-morpholinoethyl)carbodiimide metho-p-toluenesulfonate (72 mg, 0.17 mmol). After 18 h, the suspension was partitioned between chloroform and aqueous potassium carbonate. The organic layer was separated and washed twice with brine, dried through a plug of sodium sulfate, concentrated and subjected to flash chromatography using acetone as eluent to afford the N-benzyloxycarbonyl derivative of 9-deoxo-8a-aza-8a-(Leu-Gly)-8a-homoerythromycin A (102 mg, 63% yield) as a white solid. This product was combined with 10% palladium on charcoal (83 mg) in ethanol (7.5 ml) and acetic acid (100 μl). Hydrogen was bubbled through the suspension for 2 hours before a hydrogen-filled balloon was installed. After 16 hours, the suspension was filtered through Celite, reduced, and partitioned between chloroform and aqueous potassium carbonate. The organic layer was separated, washed twice with brine, dried through a plug of sodium sulfate and evaporated to dryness to afford 9-deoxo-8a-aza-8a-(Leu-Gly)-8a-homoerythromycin A (73 mg, 82% yield) as a white solid.

$^1$H NMR (400 MHz, CDCl$_3$) δ4.96 (dd, H-13), 4.82 (d, H-1"), 3.21 (s, OCH$_3$), 2.21 (s, N(CH$_3$)$_2$).

$^{13}$C NMR (100.6 MHz, CDCl$_3$) δ176.08, 175.78, 171.05, 104.25 (C-1'), 98.63 (C-1").

FAB-MS m/z 905, 747, 555, 158.

EXAMPLE 79

9-Deoxo-8a-aza-8a-phenylsulfonyl-8a-homoerythromycin A

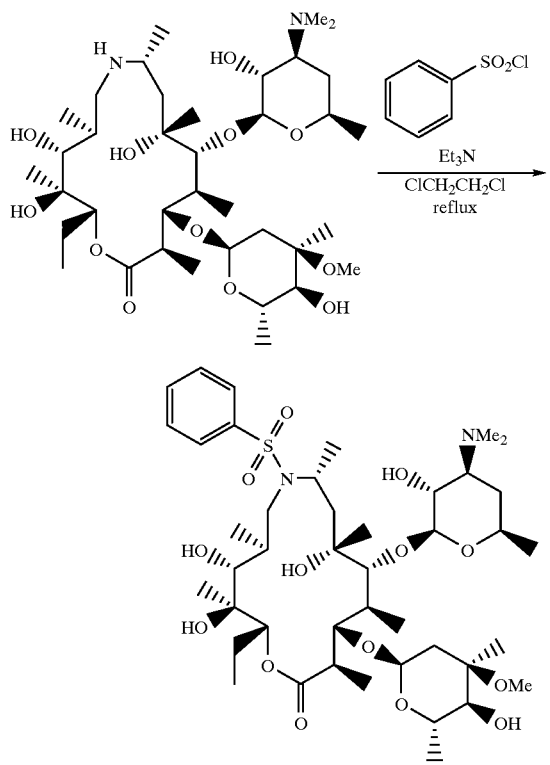

To 9-deoxo-8a-aza-8a-homoerythromycin A (12.5 g, 17.0 mmole, 1.0 eq.) in 1,2-dichloroethane (170 mL) as added triethylamine (7.6 mL, 54.5 mmole, 3.2 eq) and benzenesulfonyl chloride (2.4 mL, 18.8 mmole, 1.1 eq). The reaction mixture was refluxed for 18 hours, after which additional benzenesulfonyl chloride (0.5 mL, 0.3 eq) and triethylamine (1.8 mL, 0.8 eq) were added. After refluxing for an additional 150 minutes the reaction was quenched with aqueous NaHCO$_3$ and diluted with methylene chloride. After separating the aqueous and organic layers, the organic was washed twice more with aqueous NaHCO$_3$ (750 mL total volume). The organic layer was dried over MgSO$_4$, filtered and evaporated. The recovered foam was pumped on high vacuum overnight, giving the title compound (14.0 g, 94%).

$^1$H NMR (400 MHz, CDCl$_3$, 53° C.): δ7.80 (2H, d, ArH), 7.48 (3H, m, ArH), 5.03 (1H, dd, H-13), 4.97 (1H, d, H-1"), 4.51 (1H, d, H-1'), 4.37 (1H, m, H-8), 4.32 (1H, d, H-3), 4.06 (1H, m, H-5"), 3.71 (1H, d, H-5), 3.65 (1H, d, H-11), 3.57 (1H, m, H-5'), 3.35 (1H, m, H-9), 3.29 (3H, s, OCH$_3$), 3.24 (1H, m, H-2'), 3.04 (1H, t, H-4"), 2.81 (1H, t, H-2), 2.74 (1H, dd, H-7), 2.51 (1H, t, H-3'), 2.34 (1H, s, H-2"), 2.29 (6H, S, N(CH$_3$)$_2$), 1.93 (2H, m, H-4 & H-14), 1.65 (1H, d, H-4'), 1.59 (1H, dd, H-2") ppm.

FAB MS (Li spike): m/z 882 (M+Li)

EXAMPLE 80

2'-O-Acetyl-9-deoxo-8a-methyl-8a-aza-8a-homoerythromycin A

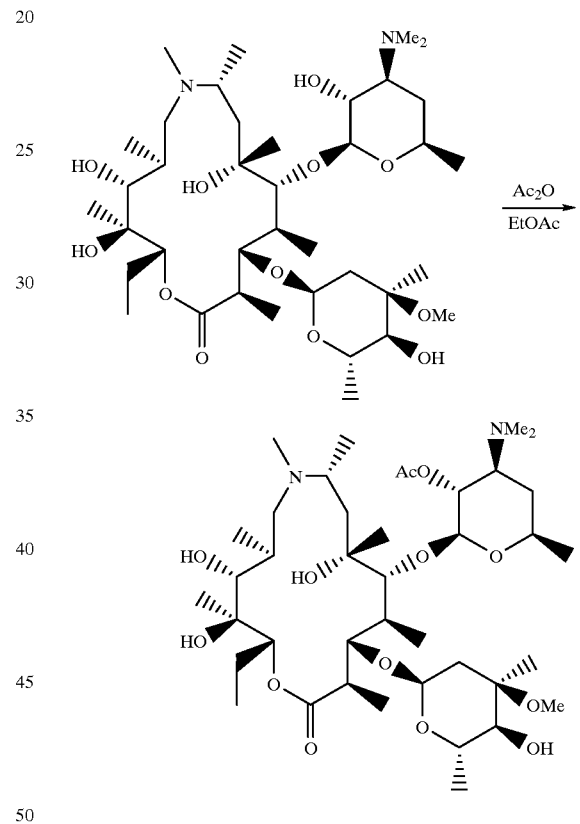

To 9-deoxo-8a-methyl-8a-aza-8a-homoerythromycin A (5.45 g, 7.32 mmole, 1.00 eq) was added ethyl acetate (45 mL) and acetic anhydride (1.04 mL, 11.10 mmole, 1.50 eq). The mixture was stirred for 18 hours at room temperature, after which water was added followed by ethyl acetate and enough HCl to reduce the pH to 2.5. The organic layer was discarded and the aqueous layer was basified to pH 9.5 with 2N NaOH. The aqueous layer was then extracted twice with ethyl acetate (100 mL) and dried over Na$_2$SO$_4$. After filtration of the drying agent the filtrate was evaporated and the resultant foam was pumped overnight on high vacuum to give 5.57 g (96%) of the title compound.

$^1$H NMR (400 MHz,CDCl$_3$, 20° C.): δ5.10 (1H, d, H-1"), 4.77 (1H, dd, H-13), 4.72 (1H,m, H-2'), 4.46 (1H, d, H-1'), 4.41 (1H, br s, H-3), 3.98 (1H, m, H-5"), 3.43 (3H, m, H-5, H-11, & H-5'), 3.31 (3H, s, OCH$_3$), 3.02 (1H, t, H-4"), 2.92

(1H, m, H-8), 2.73 (1H, m, H-2), 2.70 (1H, s, OH), 2.60 (1H, m, H-3'), 2.48 (1H, t, H-9), 2.23 (6H, s, N(CH$_3$)$_2$), 2.07 (3H, 8, 8a-CH$_3$), 2.03 (3H, s, OCOCH$_3$), 1.90 (1H, m, H-14), 1.54 (1H, dd, H-2''), 1.45 (1H, m, H-14) ppm.

EXAMPLE 81

2'-O-Acetyl-4''-O-carbobenzoxy-9-deoxo-8a-methyl-8a-aza-8a-homoerythromycin A

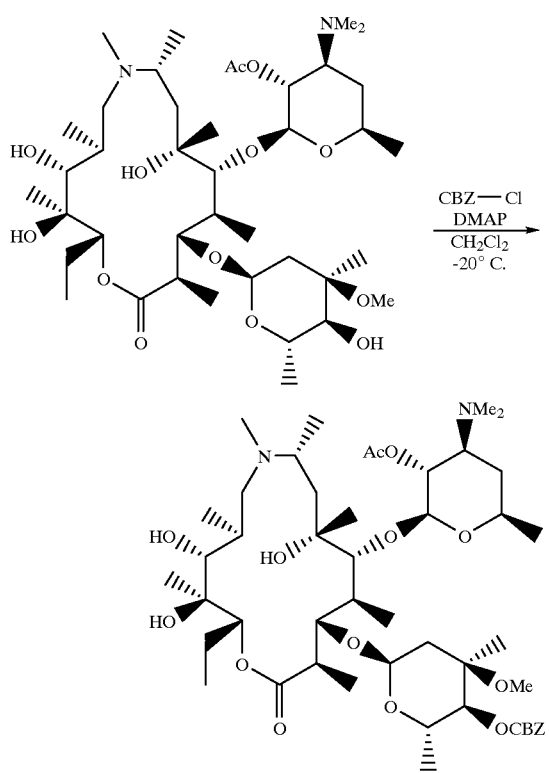

To 2'-O-acetyl-9-deoxo-8a-methyl-8a-aza-8a-homoerythromycin A (5.25 g, 6.65 mmole, 1.00 eq) in CH$_2$Cl$_2$ (65 mL) at −20° C., was added DMAP (3.24 g, 26.58 mmole, 4.00 eq) and benzyl chloroformate (2.84 mL, 19.95 mmole, 3.00 eq). The reaction mixture was stirred at −20° C. for 90 hours, then quenched with aqueous NaHCO$_3$, and extracted with CH$_2$Cl$_2$ The organic layer was washed a second time with aqueous NaHCO$_3$ and then dried over Na$_2$SO$_4$. Following filtration of the drying agent the filtrate was evaporated. Purification by silica gel chromatography (60% EtOAc/40% toluene) gave 4.27 g (70%) of the title compound.

$^1$H NMR (400 MHz, CDCl$_3$, 53° C.): δ7.32 (5H, s, ArH), 5.17 (2H, q, OCOOCH$_2$Ph) 5.11 (1H, 8, H-1''), 4.80 (1H, d, H-13), 4.71 (1H, br m, H-2'), 4.53 (1H, d, H-1'), 4.46 (2H, m, H-3 & H-4''), 4.35 (1H, m, H-5''), 3.57 (1H, m, H-5'), 3.43 (2H, m, H-5 & H-11), 3.29 (3H, s, OCH$_3$), 2.22 (6H, br s, N(CH$_3$)$_2$), 2.04 (3H, br s, 8a-CH$_3$), 1.98 (3H, br s, OCOCH$_3$), 1.88 (1H, m, H-14), 1.59 (1H, dd, H-2''), 1.45 (1H, m, H-14) ppm.

EXAMPLE 82

2'-O-Acetyl-4''-O-carbobenzoxy-(11-0,12-O-oxomethylene)-9-deoxo-8a-methyl-8a-aza-8a-homoerythromycin A

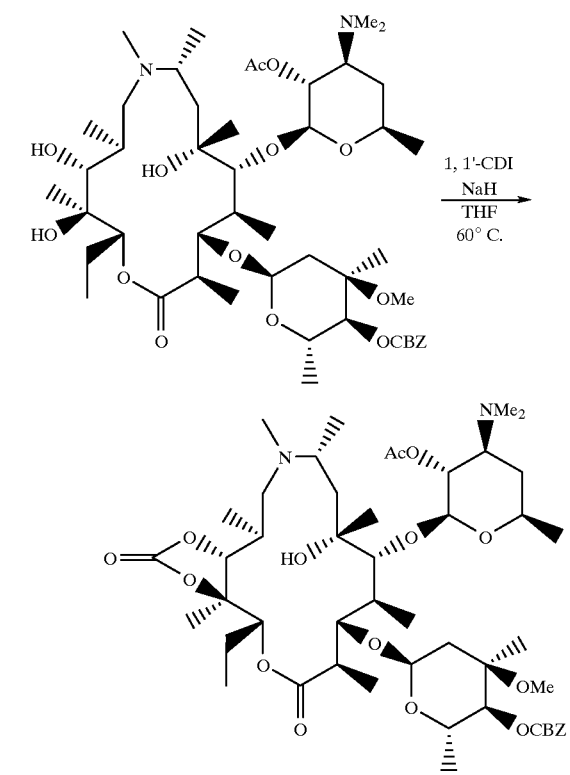

To 2'-O-acetyl-4''-O-carbobenzoxy-9-deoxo-8a-methyl-8a-aza-8a-homoerythromycin A (100 mg, 0.11. mmole, 1.00 eq) was added THF (700 μL), 1,1'-carbonyldiimidazole (83 mg, 0.51 mmole, 4.70 eq) and NaH (11 mg, 0.23 mmole, 2.10 eq; 50% wt. dispersion in oil). The reaction mixture was heated to 60° C. for 20 minutes, after which the reaction mixture was cooled and diluted with ethyl acetate. The organic layer was washed three times with water, dried over Na$_2$SO$_4$, filtered and the filtrate evaporated to give 90 mg of the title compound as a foam (88%).

IR(CH$_2$Cl$_2$): 1800 cm$^{-1}$ (carbonate) and 1735 cm$^{-1}$ (lactone). Polystyrene 1596 cm$^{-1}$.

FAB MS (Li spike): m/z 958 (M+Li).

EXAMPLE 83

(11-0,12-O-Oxomethylene)-9-deoxo-8a-methyl-8a-aza-8a-homoerythromycin A

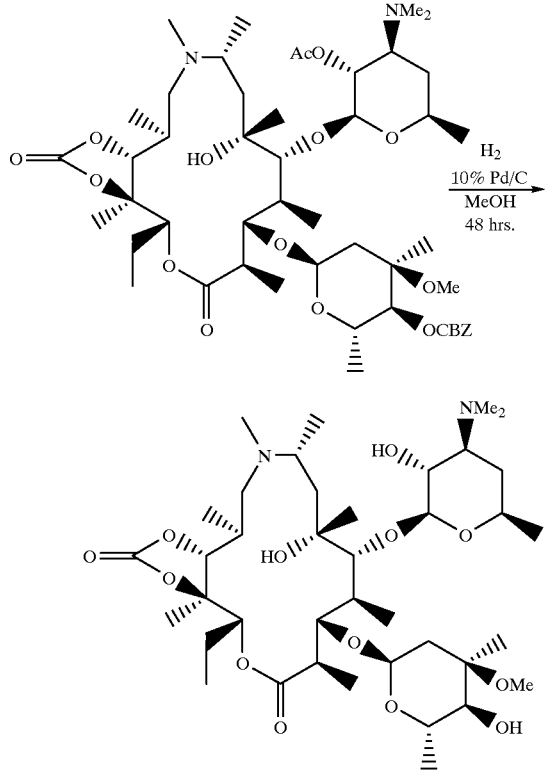

To 2'-O-acetyl-4"-O-carbobenzoxy-(11-0,12-O-oxomethylene)-9-deoxo-8a-methyl-8a-aza-8a-homoerythromycin A (29 mg, 0.03 mmole) was added methanol (1.25 mL) and 10% Pd/C (7.5 mg). The flask was evacuated and saturated with $H_2$. After 48 hours the reaction mixture was filtered through celite and the filtrate evaporated. The foam that was isolated was purified twice by silica gel chromatography (95% $CH_2Cl_2$/5% $CH_3OH$) to give 12.4 mg (53%) of the title compound.

$^1$H NMR (400 MHz, $CDCl_3$, 53° C.): δ5.18 (1H, d, H-1"), 4.92 (1H, dd, H-13), 4.75 (1H, br s, H-3), 4.51 (1H, d, H-1'), 4.24 (1H, m, H-11), 4.02 (1H, m, H-5"), 3.65 (1H, d, H-5), 3.57 (1H, m, H-5'), 3.31 (3H, s, $OCH_3$), 3.28 (1H, m, H-2'), 3.03 (2H, m, H-4"& H-8), 2.80 (1H, q, H-2), 2.57 (1H, br m, H-3'), 2.34 (6H, N($CH_3$)$_2$), 2.18 (3H, br s, 8a-$CH_3$) ppm.

FAB MS (Li-spike): m/z 781 (M+Li)

EXAMPLE 84

Synthesis of 4"-O-phenylacetyl-8a-aza-8a-methyl-9-deoxo-8a-homoerythromycin A by acylation of 8a-aza-8a-methyl-9-deoxo-8a-homoerythromycin A

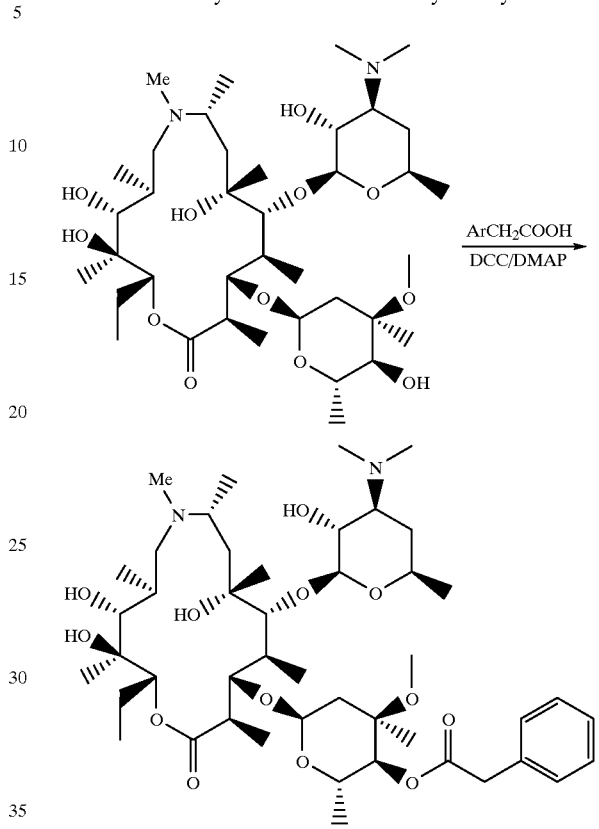

Phenylacetic acid (182 mg, 1.3 mmol) was added to a solution of 8a-aza-8a-methyl-9-deoxo-8a-homoerythromycin A (250 mg, 0.33 mmol) in 2 mL of dry dichloromethane then 1,3-dicyclohexylcarbodiimide (DCC, 276 mg, 1.3 mmol) was added followed by 4-dimethylaminopyridine (DMAP, 20 mg, 0.16 mmol). The resulting reaction mixture (white ppt) was stirred at room temperature for 22 hours. The mixture was then diluted with dichloromethane (4 mL) and filtered. The solid was washed with dichloromethane (3 mL). The combined filtrates were added to 5% aqueous $K_2CO_3$. The layers were separated and the aqueous layer was extracted with dichloromethane (2×2 mL). The combined extracts were dried over magnesium sulfate, filtered, and evaporated under vacuum to a light yellow foam. The crude product was dissolved in methanol and the resulting solution was stirred at room temperature for 18 hours (to cleave 2'-O-ester). The solvent was then evaporated and the residue was purified by flash chromatography on silica gel eluted with 95.5:3:1.5 chloroform-:methanol:saturated methanolic ammonia. The fractions containing the desired product ($R_f$ 0.20) were combined and evaporated under vacuum to afford 4"-O-phenylacetyl-8a-aza-8a-methyl-9-deoxo-8a-homoerythromycin A as an oil (116 mg, 40% yield).

$^1$H NMR (400 MHz, $CDCl_3$, 53° C.) δ7.34–7.18 (5H, m, Ar—H), 4.67 (1H, d, J=10 Hz, H-4"), 3.67 & 3.60 (2×1H, 2 d, J=14 Hz, $ArCH_2CO$), 3.28 (3H, s, $OCH_3$), 2.35 (6H, s, N($CH_3$)$_2$), 2.02 (3H, s, $NCH_3$).

EXAMPLE 85

Synthesis of 4"-O-(4-methoxyphenyl)-acetyl-8a-aza-8a-methyl-9-deoxo-8a-homoerythromycin A by acylation of 8a-aza-8a-methyl-9-deoxo-8a-homoerythromycin A

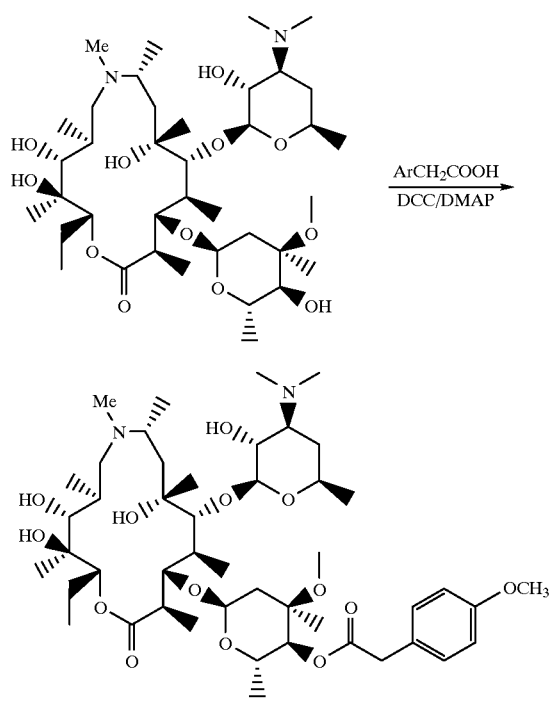

Substitution of 4-methoxyphenylacetic acid (222 mg, 1.3 mmol) for phenylacetic acid in the procedure described above for the synthesis of 4"-O-phenylacetyl-8a-aza-8a-methyl-9-deoxo-8 a-homoerythromycin A afforded 4"-O-(4-methoxyphenyl)-acetyl-8a-aza-8a-methyl-9-deoxo-8a-homoerythromycin A ($R_f$ 0.19) as a white foam (142 mg, 48% yield).

$^1$H NMR (400 MHz, $CD_3OD$, 53° C.) δ7.21 (2H, d, J=8 Hz, Ar—H), 6.86 (2H, d, J=8 Hz, Ar—H), 4.64 (1H, d, J=10 Hz, H-4"), 3.78 (3H, s, ArOCH$_3$), 3.64 & 3.56 (2×1H, 2 d, J=15 Hz, ArCH$_2$CO), 3.33 (3H, s, OCH$_3$), 2.44 (6H, s, N(CH$_3$)$_2$).

EXAMPLE 86

2'-O-Acetyl-9-deoxo-8a-aza-8a-methyl-8a-homoerythromycin A

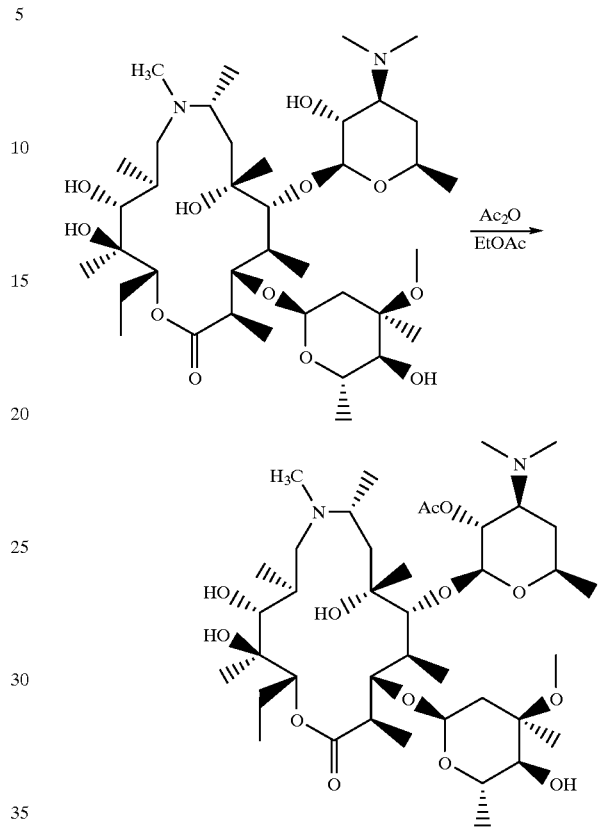

To a solution of 1.5 g (2.0 mmol) of 9-deoxo-8a-aza-8a-methyl-8a homoerythromycin A in 30 ml of ethyl acetate at room temperature was added 0.306 g (2.99 mmol) of acetic anhydride and the mixture was stirred for 24 hours. To the reaction was then added 30 ml of water and the mixture was stirred for an additional 30 minutes. The pH of the aqueous layer was adjusted to the 2-3 range with 1N hydrochloric acid and the organic and aqueous layer were separated. The pH of the aqueous layer was then adjusted to the 9–10 range with 1N sodium hydroxide solution and extracted with ethyl acetate. The ethyl acetate layer was washed with brine, dried (anhydrous sodium sulfate), and evaporated to yield 1.47 g (93% yield) of the title compound as a white foam.

TLC $R_f$ 0.37 ($CH_2Cl_2$—MeOH—$NH_4OH$, 9:1:0.1) MP softens at 100–2° C., melts at 114–117° C.

$^1$H NMR (400 MHz, $CDCl_3$) δ5.09 (d, H-1'), 4.81 (dd, H-13), 4.70 (dd, H-2'), 4.48 (br, H-3), 4.46 (d, H-1'), 3.30 (s, OCH$_3$), 2.22 (s, N(CH$_3$)$_2$), 2.03 (s,OCOCH$_3$), 1.99 (s, NCH$_3$).

$^{13}$C NMR (400 MHZ, CDCl$_3$) δ178.41, 169.89, 100.46, 94.17, 84.15, 78.16, 76.72, 75.95, 75.69, 74.75, 72.91, 71.49, 68.60, 66.53, 65.14, 63.69, 59.59, 56.41, 49.32, 45.26, 42.59, 40.66, 35.86, 34.70, 30.52, 30.28, 27.75, 21.98, 21.66, 21.48, 21.10, 18.14, 16.27, 14.21, 12.57, 11.89, 11.66, 11.38.

FAB Mass Spectrum (Li spike), m/z 797, 633, 574, 555.

EXAMPLE 87

2'-O-Acetyl-4'-deoxy-4"-oxo-9-deoxo-8a-aza-8a-methyl-8a-homoerythromycin A

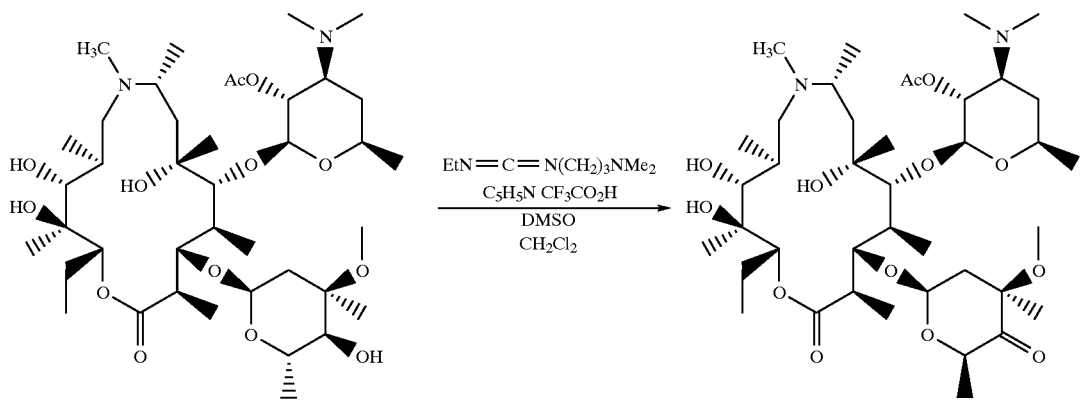

To a solution of 5.9 g (7.4 mmol) of 2'-O-Acetyl-9-deoxo-8a-aza-8a-methyl-8a-homoerythromycin A in 100 ml of dry methylene chloride under nitrogen at room temperature was successively added 5.3 ml (74.7 mmol) of dimethyl sulfoxide, 7.15 g (19.5 mmol) of 1-(3-dimethylaminopropyl)-3-ethylcarbodiimide hydrochloride and 7.15 g (37 mmol) of pyridinium trifluoroacetate. The reaction mixture was stirred for 2 hours, at which point 300 ml of ethyl acetate followed by 100 ml of water was added. The pH of the solution was adjusted to the range of 9–10 with 1N sodium hydroxide solution. The ethyl acetate layer was washed with brine, dried (anhydrous sodium sulfate) and evaporated. Silica chromatography with ethyl acetate-acetone-ammonium hydroxide (9:1:0.1) gave 4.8 g (82% yield) of the title compound as a white solid.

TLC R$_f$ 0.47 (EtOAc-Acetone-NH$_4$OH, 10:1:0.1) MP 68–70° C.

$^1$H NMR (400 MHz, CDCl$_3$) δ5.49 (t, H-1"), 4.85 (dd, H-13), 4.66 (dd, H-2'), 4.63 (br, H-3), 4.40 (q, H-5"), 4.36 (d, H-1'), 3.28 (s, OCH$_3$), 2.20 (s, N(CH$_3$)$_2$), 2.07 (s, OCOCH$_3$), 2.02 (s, NCH$_3$).

$^{13}$C NMR (400 MHZ, CDCl$_3$) δ212.19, 178.62, 169.82, 99.77, 95.53, 83.81, 77.47, 77.34, 77.02, 74.69, 71.52, 71.25, 69.06, 66.55, 63.59, 59.89, 56.67, 51.31, 44.43, 40.59, 40.46, 36,74, 36.62, 30.74, 30.70, 30.50, 30.10, 29.22, 27.64, 22.00, 21.46, 21.40, 21.08, 16.23, 15.71, 13.75, 12.48, 11.89, 11.30.

FAB Mass Spectrum, m/z 789, 630, 599, 575, 551.

EXAMPLE 88

4"-deoxy-4"-oxo-9-deoxo-8a-aza-8a-methyl-8a-homoerythromycin A

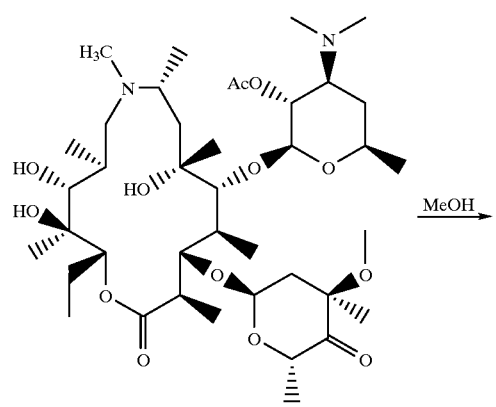

159
-continued

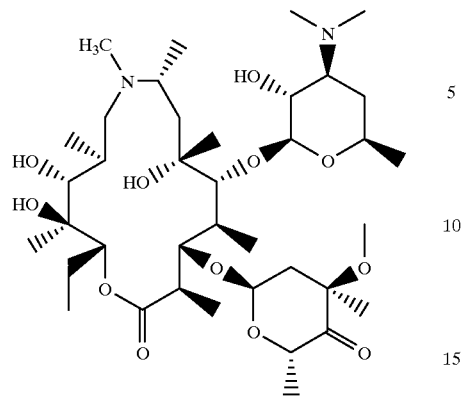

A solution of 4.8 g (6.1 mmol) of 2'-O-Acetyl-4"-deoxy-4"-oxo-9-deoxo-8a-aza-8a-methyl-8a-homoerythromycin A in 160 ml of methanol was stirred at room temperature for 48 hours. Evaporation of the solvent gave 4.52 g (99% yield) of the title compound.

TLC $R_f$ 0.44 ($CH_2Cl_2$—MeOH—$NH_4OH$, 9.3:0.7:0.1) MP softens at 73° C., melts at 86–89° C.

$^1$H NMR (400 MHz, $CDCl_3$) δ5.44 (t, H-1"), 4.82 (dd, H-13), 4.55 (br, H-3), 4.42 (q, H-5"), 4.22 (d, H-1'), 3.28 (s, $OCH_3$), 3.15 (dd, H-2'), 2.24 (s, $N(CH_3)_2$), 2.00 (s, $NCH_3$).

$^{13}$C NMR (400 MHZ, $CDCl_3$) δ212.19, 178.89, 103.61, 95.32, 85.37, 77.47, 77.35, 77.13, 75.45, 74.88, 71.53, 70.37, 69.38, 66.30, 65.40, 59.50, 56.44, 51.29, 45.08, 42.45, 40.24, 36,63, 36.38, 36.30, 30.49, 28.50, 27.69, 21.90, 21.41, 21.30, 16.35, 15.85, 14.15, 12.45, 11.91, 11.83, 11.30.

FAB Mass Spectrum (Li spike), m/z 753, 573, 398, 256.

EXAMPLE 89

4"-epi-9-deoxo-8a-aza-8a-methyl-8a-homoerythromycin A

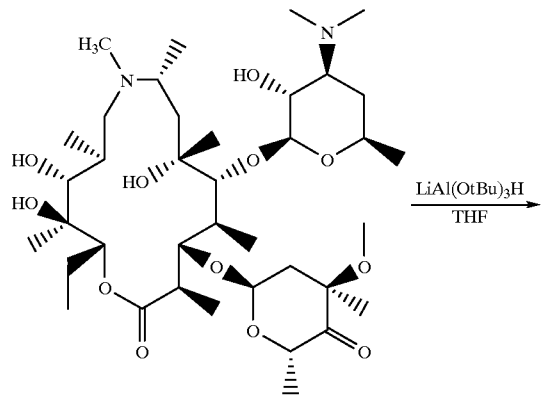

160
-continued

To 0.10 g (0.13 mmol) of 4"-deoxy-4"-oxo-9-deoxo-8a-aza-8a-methyl-8a-homoerythromycin A in 15 ml of dry tetrahydrofuran under nitrogen at room temperature was added 0.35 ml of lithium tri-tert-butoxy aluminohydride (1.0 M solution in THF). The reaction was judged to be complete by TLC after 15 minutes. The reaction mixture was quenched with 5 ml of water followed by 30 ml of ethyl acetate. The pH of the solution was adjusted to the range of 9–10 with 1N sodium hydroxide solution. The ethyl acetate layer was separated and washed with brine, dried (anhydrous sodium sulfate), and evaporated. The mixture of 9-deoxo-8a-aza-8a-methyl-8a-homoerythromycin A and the 4"-epimer was separated by preparative TLC. The plate was eluted with $CHCl_3$-acetone-$NH_4OH$, 6:4:0.2 and was developed twice to yield 35 mg (35% yield) of the title compound.

TLC $R_f$ 0.37 ($CHCl_3$-Acetone-$NH_4OH$, 3:3:0.2)

$^1$H NMR (400 MHz, $CDCl_3$) δ5.13 (br, H-1"), 4.77 (br, H-13), 4.55 (q, H-5"), 4.40 (br, H-3), 4.36 (d, H-1'), 3.27 (s, $OCH_3$), 3.14 (dd, H-2'), 2.24 (s, $N(CH_3)_2$), 1.92 (s, $NCH_3$).

FAB Mass Spectrum (Li spike), m/z 755, 591, 573, 159, 117.

EXAMPLE 90

Synthesis of 4"-methoximino-4"-deoxy-9-deoxo-8a-aza-8a-methyl-8a-homoerythromycin A by oximation of 4"-oxo-4"-deoxy-9-deoxo-8a-aza-8a-methyl-8a-homoerythromycin A

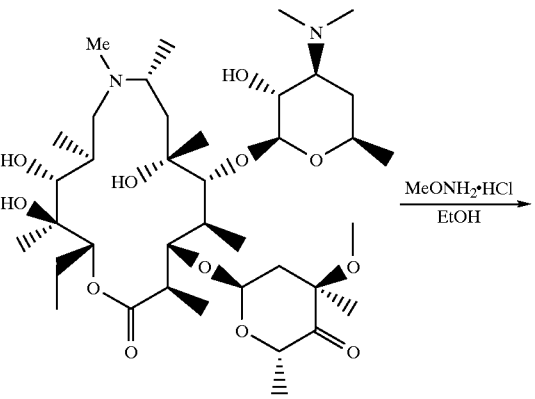

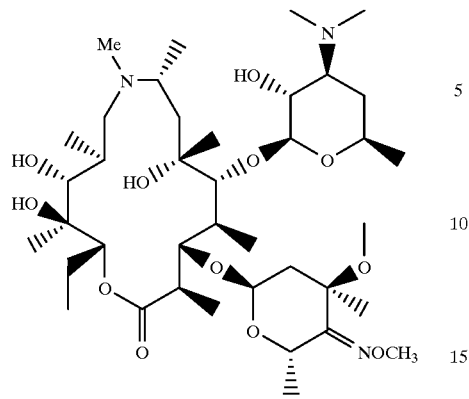

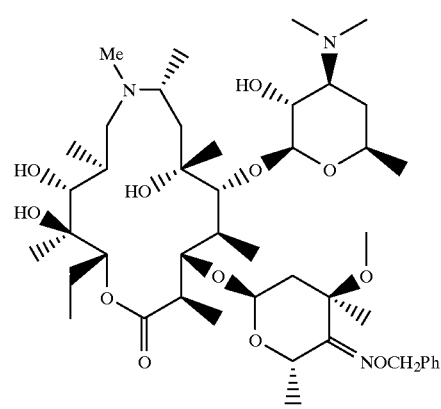

Pyridine (0.20 mL, 2.5 mmol) was added to a solution of 4"-oxo-4"-deoxy-9-deoxo-8a-aza-8a-methyl-8a-homoerythromycin A (200 mg, 0.27 mmol) in 2 mL of absolute ethanol then methoxylamine-hydrochloride (67 mg, 0.80 mmol) was added. The resulting solution was stirred at room temperature for 42 hours then the solvent was removed under vacuum. The residue was partitioned between dichloromethane (4 mL) and 5% aqueous potassium carbonate (4 mL). The aqueous layer was extracted with dichloromethane (2×3 mL) and the combined organic extracts were dried over magnesium sulfate, filtered, and evaporated to a colorless oil (265 mg). The crude product was purified by flash chromatography on silica gel (3.5×20 cm column eluted with 95.5:3:1.5 chloroform:methanol:saturated methanolic ammonia, collecting 50 mL fractions). Analytical TLC of the fractions indicated that fractions 6–12 contained the desired product ($R_f$ 0.27). These fractions were combined and evaporated under vacuum to afford 4"-methoximino-4'-deoxy-9-deoxo-8a-aza-8a-methyl-8a-homoerythromycin A as a colorless oil (195 mg, 94% yield, ca. 5:1 mixture of E and Z oxime isomers at C-4").

$^1$H NMR (400 MHz, CDCl$_3$) δ4.98 (1H, q, J=7 Hz, H-5"), 3.84 (3H, s, NOCH$_3$), 3.32 (3H, 8, OCH$_3$), 2.25 (6H, s, N(CH$_3$)$_2$), 1.97 (3H, s, NCH$_3$).

EXAMPLE 91

Synthesis of 4"-benzyloximino-4"-deoxy-9-deoxo-8a-aza-8a-methyl-8a-homoerythromycin A by oxidation of 4"-oxo-4"-deoxy-9-deoxo-8a-aza-8a-methyl-8a-homoerythromycin A

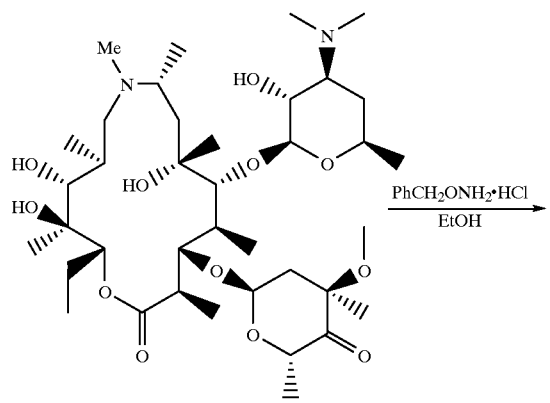

Substitution of 0-benzylhydroxylamine-hydrochloride (128 mg, 0.80 mmol) for methoxylamine-hydrochloride in the procedure described above for the preparation of 4"-methoximino-4"-deoxy-9-deoxo-8a-aza-8a-methyl-8a-homoerythromycin A afforded 4"-benzyloximino-4"-deoxy-9-deoxo-8a-aza-8a-methyl- 8a-homoerythromycin A as a colorless oil ($R_f$ 0.38, 202 mg, 90% yield, ca. 7:1 mixture of E and Z oxime isomers at C-4").

$^1$H NMR (400 MHz, CDCl$_3$) δ7.38–7.22 (5H, m, Ar—H), 5.14 & 5.07 (2×1H, 2 d, J=12 Hz, ArCH$_2$O), 4.96 (1H, q, J=7 Hz, H-5"), 3.27 (3H, s, OCH$_3$), 2.22 (6 H, s, N(CH$_3$)$_2$), 1.97 (3H, s, NCH$_3$).

EXAMPLE 92

4"-Deoxy-4"-hydrazono-9-deoxo-8a-aza-8a-methyl-8a-homoerythromycin A

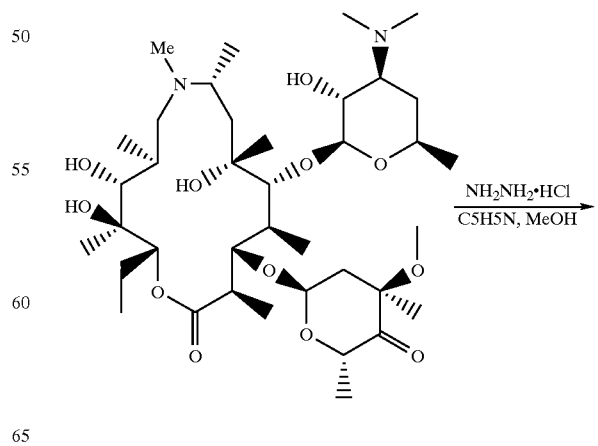

163

-continued

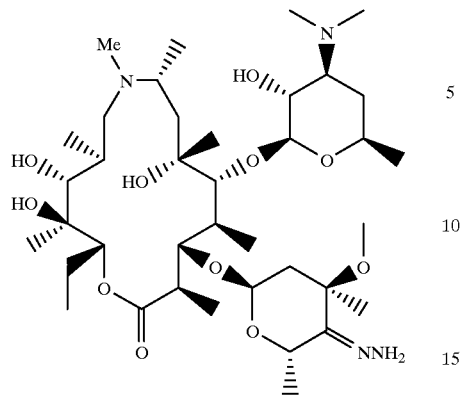

To a solution of 27.5 mg (0.036 mmol) of 4"-deoxy-4"-oxo-9-deoxo-8a-aza-8a-methyl-8a-homoerythromycin A in 1 ml of methanol was added 14.0 mg (0.20 mmol) of hydrazine hydrochloride followed by 31.6 mg (0. 40 mmol) of pyridine. The resulting mixture was stirred for 72 hours at room temperature. The methanol was then removed under vacuum and the residue was dissolved in 1 ml of water and 10 ml of ethyl acetate. The pH of the solution was adjusted to the range of 9–10 with 1N sodium hydroxide solution. The ethyl acetate layer was washed with brine, dried (anhydrous sodium sulfate), and evaporated. Silica chromatography with $CH_2Cl_2$-methanol-$NH_4OH$, 95:5:1 afforded 22.5 mg (80% yield) of the title compound as a mixture of E and Z isomers.

TLC $R_f$ 0.30 ($CH_2Cl_2$—MeOH—$NH_4OH$, 9.3:0.7:0.1) MP 115–118° C.

$^1$H NMR (400 MHz, at 60° C.,$CDCl_3$) δ6.09 (br, $NH_2$), 5.29 (dd, H-1"), 4.86 (dd, H-13), 4.56 (br, H-3), 4.51 (q, H-5"), 4.27 (d, H-1'), 3.20 (s, $OCH_3$), 2.27 (s, $N(CH_3)_2$), 2.03 (s, $NCH_3$).

FAB Mass Spectrum (Li spike), m/z 767.9, 591.7, 573.6.

EXAMPLE 93

4"-deoxy-4"-hydroxyimino-9-deoxo-8a-aza-8a-methyl-8a-homoerythromycin A

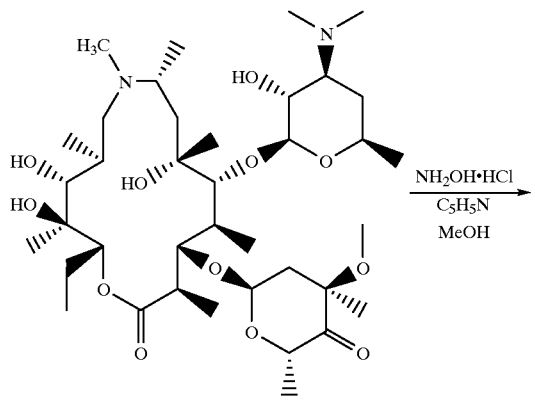

164

-continued

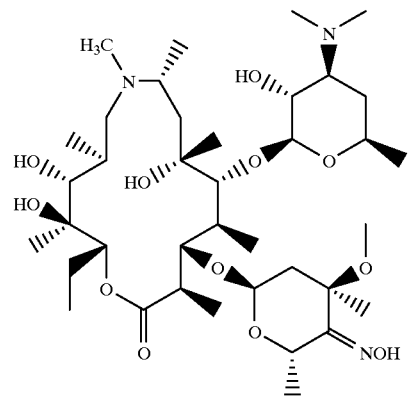

To 2.5 g (3.3 mmol) of 4"-deoxy-4"-oxo-9-deoxo-8a-aza-8a-methyl-8a-homoerythromycin A in 20 ml of methanol was added 2.7 ml (33 mmol) of pyridine followed by 1.2 g (16 mmol) of hydroxylamine hydrochloride. The resulting mixture was stirred for 48 hours at room temperature. Then the methanol was removed under vacuum and the residue was dissolved in 50 ml of water and 100 ml of ethyl acetate. The pH of the solution was adjusted to the range of 9–10 with 1N sodium hydroxide solution. The ethyl acetate layer was washed with brine, dried (anhydrous sodium sulfate), and evaporated. Silica chromatography with $CH_2Cl_2$-methanol-$NH_4OH$, 93:7:1 afforded 1.5 g (58% yield) of the title compound as a mixtures of E and Z isomers.

TLC $R_f$ 0.37 ($CHCl_3$-Acetone-$NH_4OH$, 3:3:0.2) MP softens at 122° C., melts at 131–136° C.

$^1$H NMR (400 MHz, $CDCl_3$) δ5.19 (t, H-1"), 5.06 (q, H-5"), 4.81 (dd, H-13), 4.38 (q, H-3), 4.23 (d, H-1'), 3.25 (s, $OCH_3$), 3.17 (dd, H-2'), 2.23 (s, $N(CH_3)_2$), 1.96 (s, $NCH_3$).

$^{13}$C NMR (400 MHZ, $CDCl_3$) δ178.58, 160.64, 103.16, 95.18, 84.95, 78.51, 77.35, 77.24, 77.04, 74.69, 70.66, 70.50, 69.38, 68.95, 66.62, 65.57, 65.40, 59.41, 56.24, 51.14, 50.45, 45.16, 42.03, 40.31, 39.45, 30.52, 28.95, 27.76, 25.27, 23.13, 21.87, 21.77, 21.33, 17.60, 16.98, 16.34, 14.84, 12.47, 12.05, 11.30, 11.05.

FAB Mass Spectrum (Li spike), m/z 768, 574, 416, 306

EXAMPLE 94

4"-Deoxy-4"-amino-9-deoxo-8a-aza-8a-methyl-8a-homoerythromycin A

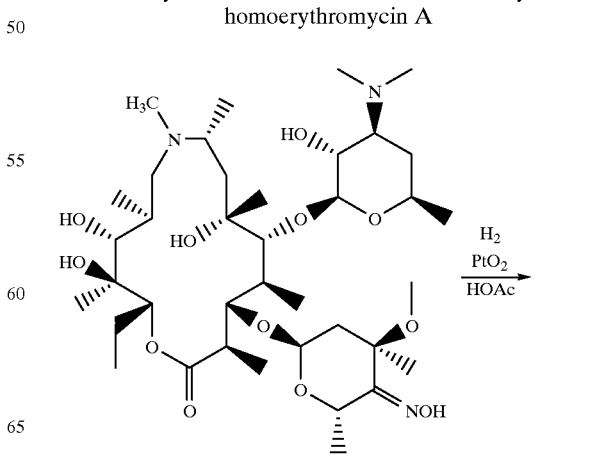

165
-continued

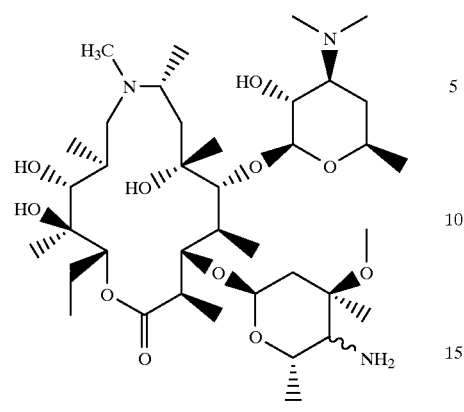

A solution of 0.50 g (0.65 mmol) of the oxime mixture (prepared as described in the previous example) in 5 ml of acetic acid was hydrogenated over 0.50 g of platinum oxide at 1000 psi at room temperature, initially for 48 hours. This was followed by a fresh addition of 0.20 g of platinum oxide and the reaction was continued for another 24 hours under 1000 psi. The reaction mixture was filtered and the acetic acid was removed under vacuum. The residue was dissolved in 10 ml of water and 50 ml of ethyl acetate. The pH of the solution was adjusted to the range of 9–10 with 1N sodium hydroxide solution. The ethyl acetate layer was separated and washed with brine, dried (anhydrous sodium sulfate), and evaporated to give 0.47 g (95% yield) of the title compound. The product was shown by proton NMR to be a mixture of 4"-(S) (δ4.61, q , H-5") and 4"-(R) (δ4.00, br, H-5") amines, approximately in the ratio of 2:1.

EXAMPLE 95

Separation of 4"-Deoxy-4"-(S) and 4"-(R)-amino-9-deoxo-8a-aza-8a-methyl-8a-homoerythromycin A

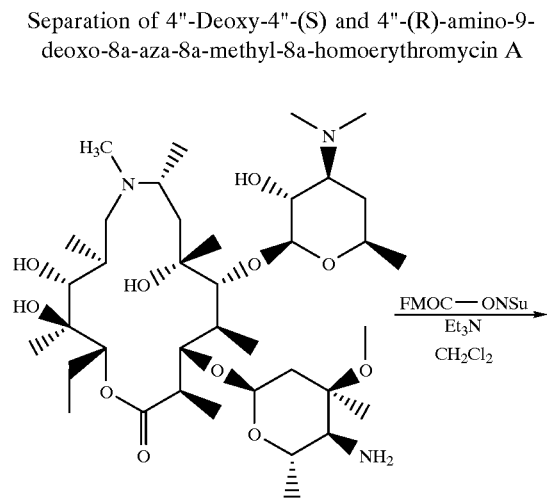

166
-continued

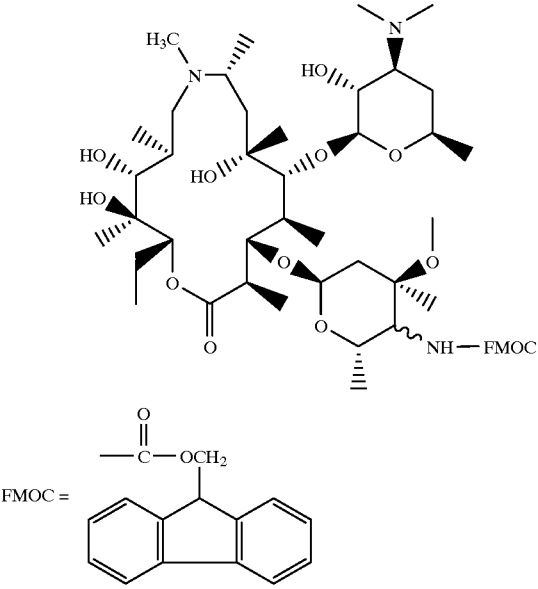

To a solution of 0.05 g (0.06 mmol) of the 4"-amino isomers, prepared as described in the previous example, in 1.5 ml methylene chloride at room temperature was added 0.027 g (0.080 mmol) of N-(9-fluorenylmethoxycarbonyloxy)succinimide (FMOC—ONSu) followed by 0.050 ml (0.33 mmol) of triethyl amine. The reaction mixture was stirred for 40 hours. The solvent was removed under vacuum and the residue was purified by preparative thin layer chromatography. The plate was developed with EtOAc-hexane-MeOH—NH$_4$OH (8:2:0.15:0.15). Two compounds were isolated and the NMR analysis revealed that the less polar component (R$_f$=0.48, δ4.05, m, H-5", 16.8 mg) was identified as an FMOC derivative of 4"-(S) amine (equatorial) and the slightly more polar component (R$_f$ 0.44, δ4.66, q, H-5", 6.6 mg) was identified as FMOC derivative of 4"-(R) amine (axial).

EXAMPLE 96

FMOC deprotection to give 4"-Deoxy-4"-(S)-amino-9-deoxo-8a-aza-8a-methyl-8a-homoerythromycin A

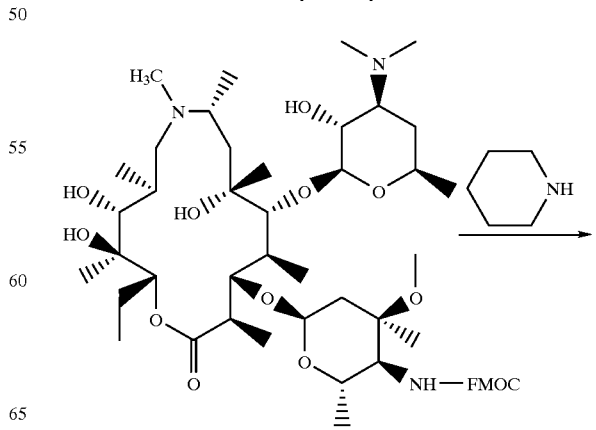

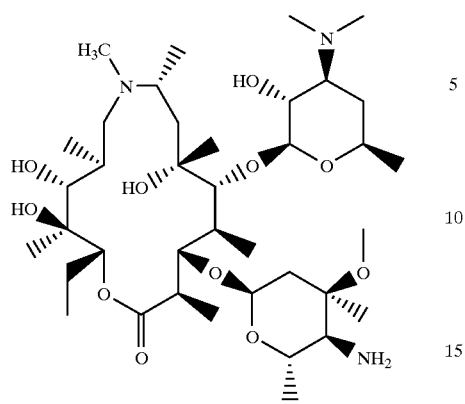

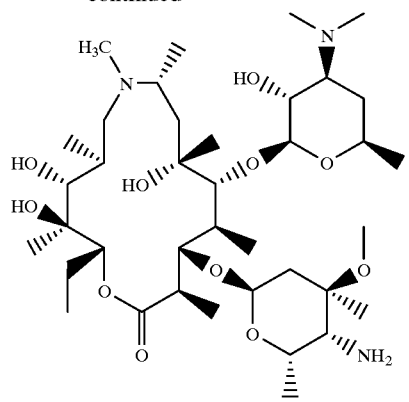

To 16.8 mg of the 4'-(S)-FMOC derivative was added 0.25 ml of piperidine and the mixture was stirred at room temperature. After 15 minutes TLC showed that the reaction was complete at which point piperidine was removed under vacuum and the residue purified by silica chromatography. Elution with $CH_2Cl_2$—MeOH—$NE_4OH$, 9.3:0.7:0.1 gave 8.2 mg of 4"-deoxy-4"-(S)-amino-9-deoxo-8a-aza-8a-methyl-8a-homoerythromycin A as a white solid.

$^1$H NMR (400 MHz, CDCl3, at 60° C.) δ5.10 (d, H-1"), 4.82 (dd, H-13), 4.46 (q, H-3), 4.39 (d, H-1'), 4.00 (br, H-5"), 3.27 (s, $OCH_3$), 2.38 (s, $N(CH_3)_2$), 2.03 (s, $NCH_3$).

EXAMPLE 97

FMOC deprotection to give 4"-Deoxy-4"-(R)-amino-9-deoxo-8a-aza-8a-methyl-8a-homoerythromycin A

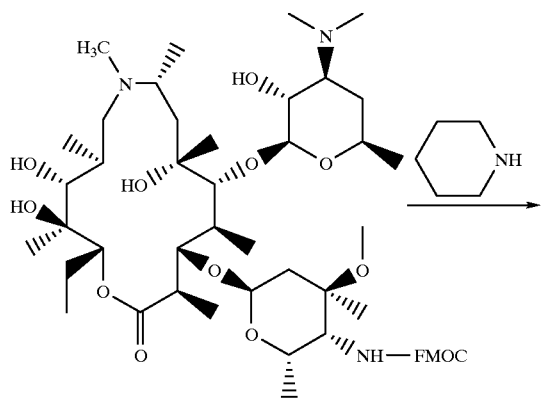

To 7.0 mg of the 4"-(R)-FMOC derivative was added 0.25 ml of piperidine and the mixture was stirred at room temperature. After 15 minutes TLC showed that the reaction was complete at which point piperidine was removed under vacuum and the residue purified by silica chromatography. Elution with $CH_2Cl_2$—MeOH—$NH_4OH$, 9.3:0.7:0.1 gave 4.3 mg of 4"-deoxy-4"-(R)-amino-9-deoxo-8a-aza-8a-methyl-8a-homoerythromycin A as a white solid.

EXAMPLE 98

4"-Deoxo-4"-(S)-acetylamino-9-deoxo-8a-aza-8a-methyl-8a-homoerythromycin-A

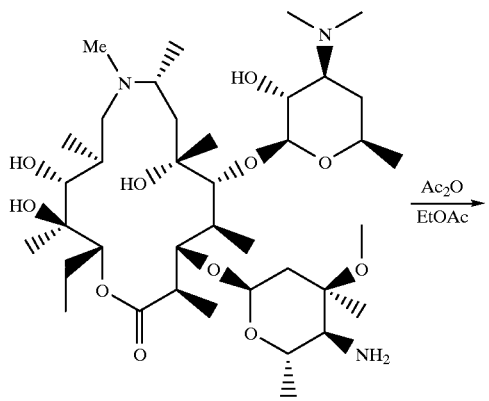

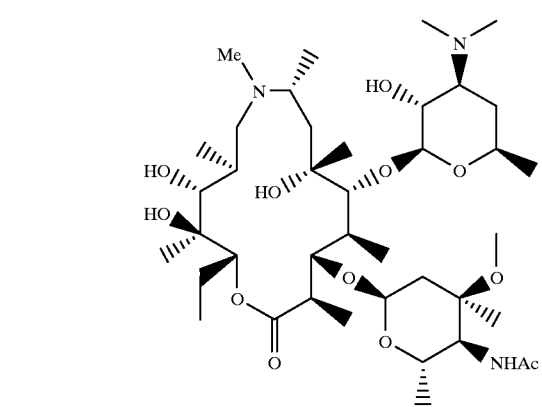

To a solution of 17.0 mg (0.022 mmol) of 4"-deoxy-4"-(S)-amino-9-deoxo-8a-aza-8a-methyl-8a- homoerythromycin A in 1.0 ml ethyl acetate was added 4.7 mg (0.046 mmol) of acetic anhydride and the mixture was stirred for 24 hours. To the reaction was then added 1.0 ml of water and the mixture was stirred for an additional 30 minutes. The pH of the aqueous layer was then adjusted to the 9–10 range with 1N sodium hydroxide solution and this layer was extracted with ethyl acetate. The ethyl acetate layer was washed with brine, dried (anhydrous sodium sulfate), and evaporated to yield crude product that was identified by NMR to be 2'-O-acetyl-4"-deoxo-4"-(S)-acetylamino-9-deoxo-8a-aza-8a-methyl-8a-homoerythromycin-A (diagnostic signals at δ4.72 dd, H-2' and at 3.70, t, H-4"). This product was not purified but was directly hydrolyzed by simply stirring in methanol at room temperature for 24 hours. Evaporation of methanol followed by silica chromatography and elution with $CH_2Cl_2$—MeOH—$NH_4OH$, 95:5:1 gave 16.2 mg of 4"-deoxy-4"-(S)-acetylamino-9-deoxo-8a-aza-8a-methyl-8a-homoerythromycin A as a white solid.

TLC $R_f$ 0.50 ($CH_2Cl_2$—MeOH—$NH_4OH$, 9.5:0.5:0.1) MP 131–135° C.

$^1$H NMR (400 MHz, at 60° C., $CDCl_3$) δ5.76 (d, NHAc), 5.13 (d, H-1"), 4.83 (dd, H-13), 4.49 (t, H-3), 4.30 (d, H-1'), 4.07 (m, H-5"), 3.70 (t, H-4"), 3.25 (s, $OCH_3$), 2.29 (br, N($CH_3$)$_2$), 3.01 (s, NHCOCH$_3$), 1.96 (s, $NCH_3$).

FAB mass spectrum (Li spike), m/z 796, 579, 374, 306, 161.

EXAMPLE 99

4"-Deoxo-4"-(R)-acetylamino-9-deoxo-8a-aza-8a-methyl-8a-homoerythromycin A

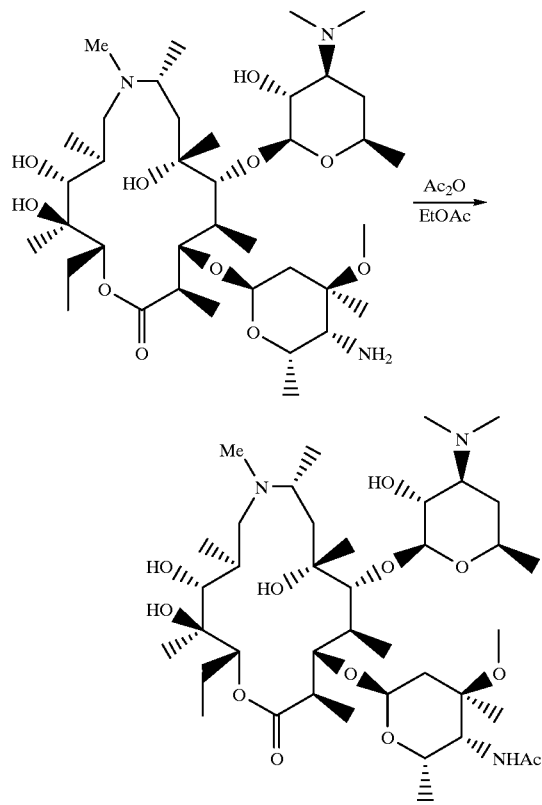

To a solution of 20.0 mg (0.026 mol) of 4"-deoxy-4"-(R)-amino-9-deoxo-8a-aza-8a-methyl-8a-homoerythromycin A in 1.0 ml ethyl acetate was added 5.8 mg (0.056 mmol) of acetic anhydride and the mixture was stirred for 24 hours. To the reaction was then added 1.0 ml of water and the mixture was stirred for an additional 30 minutes. The pH of the aqueous layer was then adjusted to the 9–10 range with 1N sodium hydroxide solution and this layer was extracted with ethyl acetate. The ethyl acetate layer was washed with brine, dried (anhydrous sodium sulfate), and evaporated to yield crude product that was identified by NMR to be 2'-O-acetyl-4"-deoxo-4"-(R)-acetylamino-9-deoxo-8a-aza-8a-methyl-8a-homoerythromycin-A (diagnostic signals at δ4.70 dd, H-2' and at 3.66, d, H-4"). This product was not purified but was directly hydrolyzed by simply stirring in methanol at room temperature for 24 hours. Evaporation of methanol followed by silica chromatography and elution with $CH_2Cl_2$—MeOH—$NH_4OH$, 95:5:1 gave 17.6 mg of 4"-deoxy-4"-(R)-acetylamino-9-deoxo-8a-aza-8a-methyl-8a-homoerythromycin A as a white solid.

TLC $R_f$ 0.60 ($CH_2Cl_2$—MeOH—$NH_4OH$, 9.0:1.0:0.1) MP 153–156° C.

$^1$H NMR (400 MHz, at 60° C., $CDCl_3$) δ5.75 (d, NHAc), 5.17 (d, H-1"), 4.83 (dd, H-13), 4.68 (q, H-5"), 4.48 (br, H-3), 4.39 (d, H-1'), 3.74 (d, H-4"), 3.29 (s, $OCH_3$), 2.27 (br, N($CH_3$)$_2$), 2.01 (s, NHCOCH$_3$), 1.99 (s, $NCH_3$).

FAB mass spectrum (Li spike), m/z 796, 597, 579, 366, 306.

EXAMPLE 100

Synthesis of 4"-(4-methoxyphenylacetyl)amino-4"-deoxy-9-deoxo-8a-aza-8a-methyl-8a-homoerythromycin A by acylation of 4"-amino-4"-deoxy-9-deoxo-8a-aza-8a-methyl-8a-homoerythromycin A

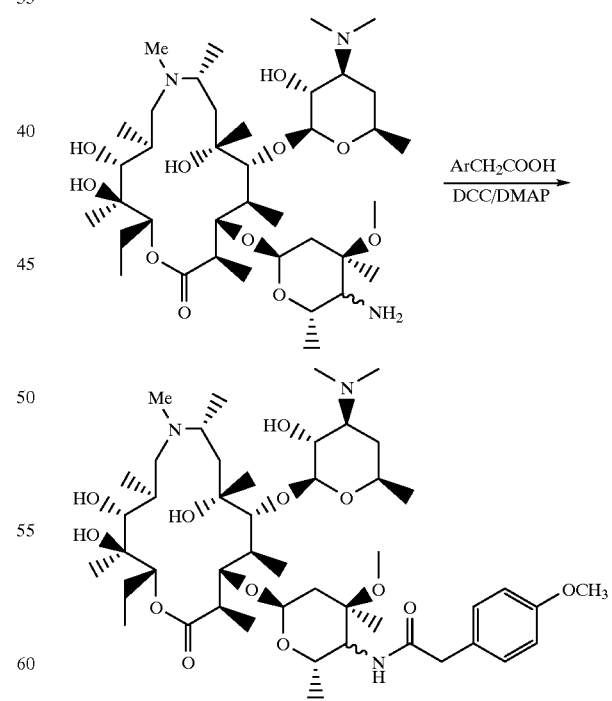

4"-Amino-4"-deoxy-9-deoxo-8a-aza-8a-methyl-8a-homoerythromycin A (150 mg, 0.20 mmol, mixture of epimers at C-4") was added to a solution of 1,3-dicyclohexylcarbodiimide (83 mg, 0.40 mmol) in 2 mL of dry dichloromethane. 4-Methoxyphenylacetic acid (37 mg, 0.22 mmol) was then added followed by 4-dimethylaminopyridine (10 mg, 0.08 mmol). The mixture (white precipitate) was stirred at room temperature for 15 hours then filtered. The filtrate was partitioned between dichloromethane (3 mL) and 5% aqueous $K_2CO_3$ (3 mL). The layers were separated and the aqueous layer was extracted with dichloromethane (3×3 mL). The combined organic layers were dried over $MgSO_4$, filtered, and evaporated. The crude product was purified by flash chromatography on silica gel (3.5×20 cm column eluted with 95:5:1 chloroform:methanol:saturated methanolic ammonia collecting 50 mL fractions). Fractions 5–8 were combined and evaporated under vacuum to afford 4"-(4-methoxyphenylacetyl)-amino-4"-deoxy-9-deoxo-8a-aza-8a-methyl-8a-homoerythromycin A (190 mg) as a colorless oil (mixture of epimers at C-4"). The epimers were separated by repeated flash chromatography as described below. The mixture was first purified by flash chromatography on silica gel (3.0×22 cm column eluted with 94:4.5:1.5 ethyl acetate-:methanol:saturated methanolic ammonia collecting 50 mL fractions). Fractions 11–17 were combined and evaporated under vacuum to afford pure 4"-(S)-(4-methoxyphenylacetyl)-amino-4"-deoxy-9-deoxo-8a-aza-8a-methyl-8a-homoerythromycin A (81 mg) as a colorless oil. Fractions 18–26 contained a mixture of both epimers by TlC (enriched in the 4"-(R) epimer) and were combined and evaporated to a colorless oil (74 mg). This mixture was then repurified by flash chromatography on silica gel (3.0×24 cm column eluted with 95.5:3:1.5 chloroform:methanol:saturated methanolic ammonia collecting 50 mL fractions). Fraction 4 was evaporated under vacuum to afford pure 4"-(R)-(4-methoxyphenylacetyl)-amino-4"-deoxy-9-deoxo-8a-aza-8a-methyl-8a-homoerythromycin A (15 mg) as a colorless oil. Evaporation of fractions 5–8 provided an additional 50 mg of material which consisted of a mixture of the 4"-(S) and 4"-(R) epimers.

DATA FOR 4"-(S)-EPIMER:

$^1$H NMR (400 MHz, CDCl$_3$, 53° C.): δ7.15 (2H, d, J=9 Hz, Ar—H), 6.84 (2H, d, J=9 Hz, Ar—H), 3.77 (3H, s, ArOCH$_3$), 3.68 (1H, t, J=9 Hz, H$_{4"}$), 3.15 (3H, s, OCH$_3$), 2.32 (6H, br s, N(CH$_3$)$_2$), 2.01 (3H, br s, NCH$_3$).

DATA FOR 4"-(R)-EPIMER:

$^1$H NMR (400 MHz, CDCl$_3$, 53° C.): δ7.17 (2H, d, J=9 Hz, Ar—H), 6.87 (2H, d, J=9 Hz, Ar—H), 3.80 (3H, s, ArOCH$_3$), 3.27 (3H, 8, OCH$_3$), 2.32 (6H, br s, N(CH$_3$)$_2$), 2.02 (3H, br s, NCH$_3$).

EXAMPLE 101

General Procedure for the Coupling of N-Fluorenylmethoxycarbonyl Amino Acid Pentafluorophenyl Esters to 4"-Deoxy-4"-amino-9-deoxo-8a-aza-8a-methyl-8a-homoerythromycin A

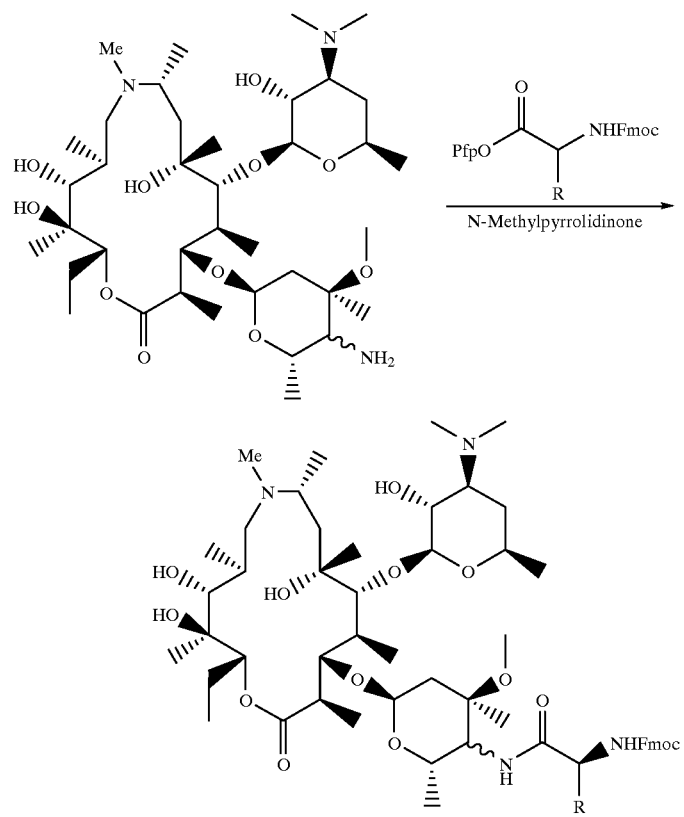

(4"R,S)-4"-Deoxy-4"-(N-Fmoc-L-alanyl)amino-9-deoxo-8a-aza-8a-methyl-8a-homoerythromycin A (R=Methyl)

To a solution of 50 mg (0.06 mmol) of (4"R,S)-4"-deoxy-4"-amino-9-deoxo-8a-aza-8a-methyl-8a-homoerythromycin A in 2 ml N-methylpyrrolidone was added 35 mg (0.07 mmol) of N-Fmoc-L-alanine pentaflurophenyl ester and the resulting mixture was stirred for 2 hours at room temperature. The reaction mixture was diluted with 2 ml of water and extracted with ethyl acetate. The ethyl acetate layer was washed with brine, dried (anhydrous sodium sulfate), and evaporated. Silica chromatography with $CH_2Cl_2$-methanol-$NH_4OH$, 95:5:1, afforded 48.8 mg (78% yield) of the title compound.

$^1$H NMR (400 MHz, at 60° C., $CDCl_3$) δ7.74–7.27 (m, aromatic protons), 5.19 (d, H-1"), 5.07 (d, H-1"), 4.87–4.81 (br, H-13), 4,69 (q, H-5"), 4.49 (br, H-3), 4.42 (br, H-3), 4.14 (m, H-5"), 3,72 (d, H-4"), 3.67 (t, H-4"), 3.27 (s, $OCH_3$), 3.15 (s, $OCH_3$), 2.28 (s, $N(CH_3)_2$), 2.25 (s, $N(CH_3)_2$), 2.03 (s, $NCH_3$).

FAB Mass Spectrum (Li spike), m/z 1047.5, 782.8, 591.6, 573.6, 422.4.

EXAMPLE 102

The following derivatives were prepared using the procedure of Example 101 by substituting the appropriate N-Fmoc amino acid pentafluorophenyl ester for N-Fmoc-L-alanine pentafluorophenyl ester.

(4"R,S)-4"-Deoxy-4"-(N-Fmoc-L-valyl)amino-9-deoxo-8a-aza-8a-methyl-8a-homoerythromycin A (R=Isopropyl)

Yield 63%

$^1$H NMR (400 MHz, at 60° C., $CDCl_3$) δ7.72–7.28 (m, aromatic protons), 5.18 (d, H-1"), 5.13 (d, H-1"), 4.88–4.82 (br, H-13), 4,70 (q, H-5"), 4.48 (br, H-3), 4.12 (m, H-5"), 3,73 (t, H-4"), 3.69 (d, H-4"), 3.25 (s, $OCH_3$), 3.21 (s, $OCH_3$), 2.29 (br, $N(CH_3)_2$), 2.00 (8, $NCH_3$).

FAB Mass Spectrum (Li spike), m/z 1076.3, 1070.6, 783.7, 592.1, 574.1.

(4"R,S)-4"-Deoxy-4"-(N-Fmoc-L-leucyl)amino-9-deoxo-8a-aza-8a-methyl-8a-homoerythromycin A (R=2-Methyl propyl)

Yield 88%

$^1$H NMR (400 MHz, at 60° C., $CDCl_3$) δ7.73–7.27 (m, aromatic protons), 5.17 (d, H-1"), 5.08 (d, H-1"), 4.87–4.82 (br, H-13), 4,69 (q, H-5"), 4.50 (br, H-3), 4.48 (br, H-3), 3,68 (t, H-4"), 3.48 (d, H-4"), 3.27 (s, $OCH_3$), 3.15 (s, $OCH_3$), 2.30 (s, $N(CH_3)_2$), 2.25 (s, $N(CH_3)_2$), 2.00 (s, $NCH_3$).

(4"R,S)-4"-Deoxy-4"-(N-Fmoc-L-phenylalanyl) amino-9-deoxo-8a-aza-8a-methyl-8a-homoerythromycin A (R=Benzyl)

TLC $R_f$ 0.47 ($CH_2Cl_2$—MeOH—$NH_4OH$, 9.3:0.7:0.1) Yield 90%

$^1$H NMR (400 MHz, at 60° C., $CDCl_3$) δ7.72–7.20 (m, aromatic protons), 5.12–5.09 (br, H-1"), 4.86–4.81 (br, H-13), 4.60 (q, H-5"), 4.06 (m, H-5"), 3.67 (d, H-4"), 3.63 (t, H-4"), 3.26 (s, $OCH_3$), 3.10 (s, $OCH_3$), 2.31–2.22 (br, $N(CH_3)_2$), 2.01 (s, $NCH_3$).

(4"R,S)-4"-Deoxy-4"-(N-Fmoc-O-tert-butyl-L-tyrosyl)amino-9-deoxo-8a-aza-8a-methyl-8a-homoerythromycin A (R=4-t-Butoxy benzyl)

TLC $R_f$ 0.33 ($CH_2Cl_2$—MeOH—$NH_4OH$, 9.3:0.7:0.1) Yield 89% $^1$H NMR (400 MHz, at 60° C., $CDCl_3$) d 7.72–6.85 (m, aromatic protons), 5.12 (d, H-1"), 5.10 (br, H-1"), 4.85–4.82 (br, H-13), 4.65 (q, H-5"), 4.06 (m, H-5"), 3.68 (d, H-4"), 3.64 (t, H-4"), 3.27 (s, $OCH_3$), 3.12 (s, $OCH_3$), 2.29 (s, $N(CH_3)_2$ ), 2.25 (br, $N(CH_3)_2$), 2.03 (s, $NCH_3$).

FAB Mass Spectrum (Li spike), m/z 1196.1, 1189.9, 783.8, 592.1, 574.1.

EXAMPLE 103

General Procedure for the Deprotection of 4"-Deoxy-4"-(N-Fmoc-aminoacyl)amino-9-deoxo-8a-aza-8a-methyl-8a-homoerythromycin Derivatives

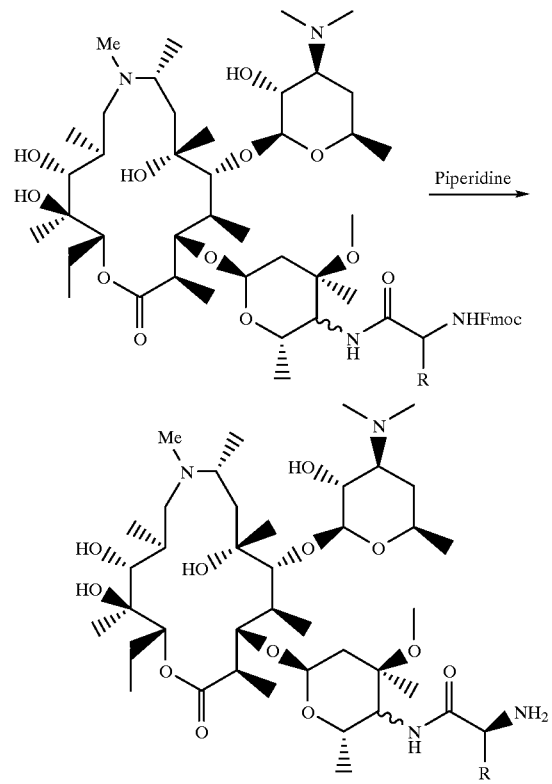

(4"R,S)-4"-Deoxy-4"-(L-alanyl)amino-9-deoxo-8a-aza-8a-methyl-8a-homoerythromycin A (R=Methyl)

To 40 mg (0.038 mmol) of (4"R,S)-4"-deoxy-4"-(N-Fmoc-L-alanyl) amino-9-deoxo-8a-aza-8a-methyl-8a-homoerythromycin A in 1 ml of methylene chloride was added 0.5 ml of piperidine and the reaction was stirred for 2 hours at room temperature. After verifying completion of the reaction by TLC, the mixture was evaporated. Silica chromatography with $CH_2Cl_2$-methanol-$NH_4OH$, 95:5:1 afforded 26.2 mg (85% yield) of the title compound.

TLC $R_f$ 0.44 ($CH_2Cl_2$—MeOH—$NH_4OH$, 9:1:0.1)

$^1$H NMR (400 MHz, at 60° C., $CDCl_3$) δ5.21 (d, H-1"), 5.15 (d, H-1"), 4.84–4.79 (m, H-13), 4.68 (q, H-5"), 4.46–4.44 (m, H-3), 4.41 (d, H-1'), 4.38 (d, H-1'), 4.13 (m, H-5"), 3.70 (d, H-4"), 3.66 (d, H-4"), 3.30 (s, $OCH_3$), 3.28 ((s, $OCH_3$), 2.29 (s, $N(CH_3)_2$ ), 2.27 (s, $N(CH_3)_2$), 2.01 (8, $NCH_3$), 2.00 (s, $NCH_3$).

FAB Mass Spectrum (Li spike), m/z 826.5, 756.4, 573.9, 229.

EXAMPLE 104

The following derivatives were prepared by the procedure of Example 103 by substituting the appropriate precursors for 4"-deoxy-4"-(N-Fmoc-L-alanyl)amino-9-deoxo-8a-aza-8a-methyl-8a-homoerythromycin A.

(4"R,S)-4"-Deoxy-4"-(L-valyl) amino-9-deoxo-8a-aza-8a-methyl-8a-homoerythromycin A (R= Isopropyl)

Yield 94%

¹H NMR (400 MHz, at 60° C., CDCl₃) δ5.20 (d, H-1"), 5.15 (d, H-1"), 4.84–4.80 (br, H-13), 4.68 (q, H-5"), 4.46 (br, H-3), 4.41 (d, H-1"), 4.37 (d, H-1"), 4.14 (m, H-5"), 3,72 (t, H-4"), 3.70 (d, H-4"), 3.30 (s, OCH₃), 3.27 (s, OCH₃), 2.29 (s, N(CH₃)₂), 2.27 (s, N(CH₃)₂), 2.01 (s, NCH₃).

FAB Mass Spectrum (Li spike), m/z 854.3, 848,6, 783.7, 574.1

(4"R,S)-4"-Deoxy-4"-(L-leucyl) amino-9-deoxo-8a-aza-8a-methyl-8a-homoerythromycin A (R=2-Methyl propyl)

Yield 88%

¹H NMR (400 MHz, at 60° C., CDCl₃) δ5.21 (d, H-1"), 5.16 (d, H-1"), 4.85–4.80 (br, H-13), 4,68 (q, H-5"), 4.48 (br, H-3), 4.40 (d, H-1'), 4,38 (d, H-1'), 3,71 (t, H-4"), 3.68 (d, H-4"), 3.29 (s, OCH₃), 3.27 (s, OCH₃), 2.30 (s, N(CH₃)₂), 2.29 (s, N(CH₃)₂), 2.02 (s, NCH₃).

FAB Mass Spectrum (Li spike), m/z 868.2, 862.2, 592, 574.

(4"R,S)-4"-Deoxy-4"-(O-tert-butyl-L-tyrosyl)amino-9-deoxo-8a-aza-8a-methyl-8a-homoerythromycin A (R=4-t-Butoxy benzyl)

Yield 93%

¹H NMR (400 MHz, at 60° C., CDCl₃) δ7.10–6.89 (m, aromatic Protons), 5.18 (d, H-1"), 5.15 (d, H-1"), 4.84–4.80 (br, H-13), 4.68 (q, H-5'), 4.45 (br, H-3), 4.41 (d, H-1'), 4.39 (d, H-1"), 4. 23 (m, H-5"), 3.30 (s, OCH₃), 3.28 (s, OCH₃), 2.30 (br, N(CH₃)₂), 2.01 (s, NCH₃).

FAB Mass Spectrum (Li spike), m/z 974.1, 783.8, 592.1, 574.1, 416.3.

EXAMPLE 105

(4"R,S)-4"-Deoxy-4"-(N-Fmoc-L-prolyl)amino-9-deoxo-8a-aza-8a-methyl-8a-homoerythromycin A

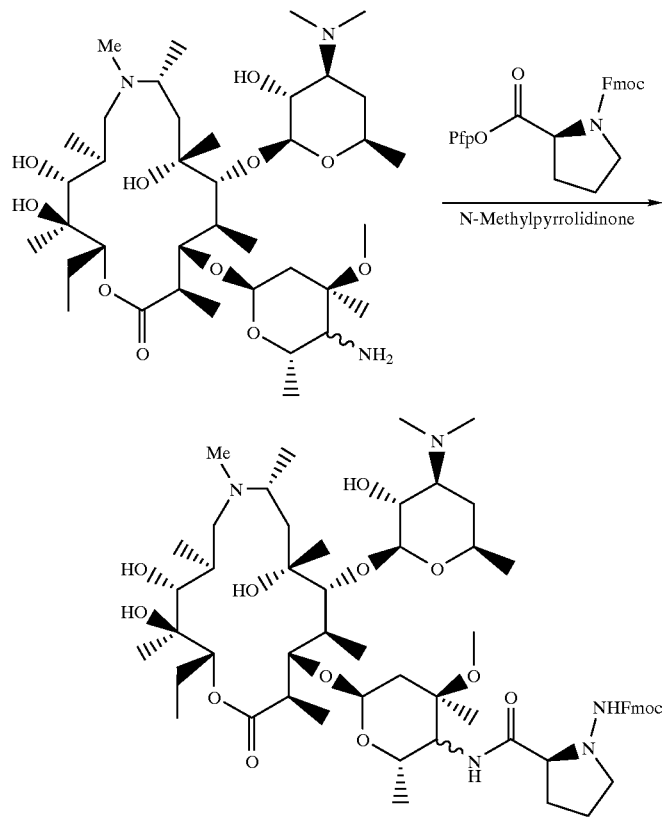

Pfp = Pentafluorophenyl
Fmoc = Fluorenylmethoxycarbonyl (4"R,S)-4"-Deoxy-4"-(L-phenylalanyl)amino-9-deoxo-8a-aza-8a-methyl-8a-homoerythromycin A (R=Benzyl)

Yield 65%

¹H NMR (400 MHz, at 60° C., CDCl₃) δ7.30–7.18 (m, aromatic Protons), 5.19 (d, H-1"), 5.17 (br, H-1"), 4.84–4.79 (br, H-13), 4.67 (q, H-5"), 4.44 (br, H-3), 4.41 (d, H-1'), 4.37 (d, H-1"), 4. 13 (m, H-5"), 3.71 (t, H-4'), 3.30 (s, OCH₃), 3.27 (s, OCH₃), 2.29 (br, N(CH₃)₂), 2.01 (s, NCH₃).

To a solution of 50 mg (0.06 mmol) of (4"R,S)-4"-deoxy-4"-amino-9-deoxo-8a-aza-8a-methyl-8a-homoerythromycin A in 1 ml N-methylpyrrolidone was added 40 mg (0.07 mmol) of N-Fmoc-L-prolyl pentafluorophenyl ester and the resulting mixture was stirred overnight at room temperature. The reaction mixture was diluted with water and extracted with ethyl acetate. The ethyl acetate layer was washed with brine, dried (anhydrous sodium sulfate), and evaporated. Silica chromatography with CH₂Cl₂-methanol-NH₄OH, 93:7:1, afforded 55.5 mg (77% yield) of title compound.

$^1$H NMR (400 MHz, at 60° C, CDCl$_3$) δ7.73–7.26 (m, aromatic Protons), 5.17(d, H-1"), 5.08 (br d, H-1"), 4.88–4.82 (br, H-13), 4.64 (q, H-5"), 4.10 (m, H-5"), 3.70 (d, H-4"), 3.66 (t, H-4"), 3.28 (s, OCH$_3$), 3.15 (s, OCH$_3$), 2.40 (s, N(CH$_3$)$_2$ ), 2.35 (br, N(CH$_3$)$_2$), 2.09 (s, NCH$_3$), 2.05 (s, NCH$_3$).

FAB Mass Spectrum (Li spike), m/z 1073.5, 1067.8, 573.6.

EXAMPLE 106

(4"R,S)-4"-Deoxy-4"-(L-prolyl)amino-9-deoxo-8a-aza-8a-methyl-8a-homoerythromycin A

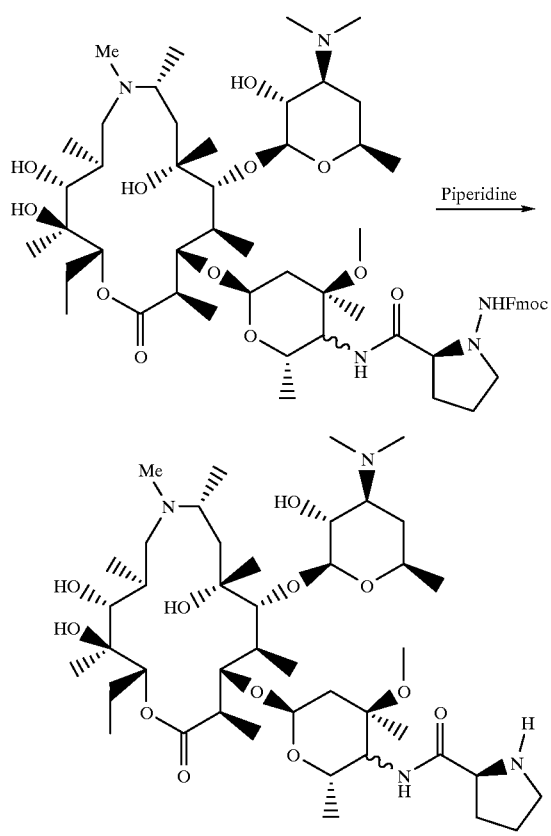

To 45 mg (0.042 mmol) of (4"R,S)-4"-deoxy-4"-(N-Fmoc-L-prolyl)amino-9-deoxo-8a-aza-8a-methyl-8a-homoerythromycin A in 2 ml of methylene chloride was added 0.5 ml of piperidine and the resulting mixture was stirred for one hour at room temperature. After verifying the completion of reaction by TLC, the mixture was evaporated. Silica chromatography with CH$_2$Cl$_2$-methanol-NH$_4$OH, 95:5:1 afforded 27.8 mg (78% yield) of the title compound.

$^1$H NMR (400 MHz, at 60° C., CDCl$_3$) δ5.20 (d, H-1"), 5.14 (d, H-1"), 4.85–4.80 (br, H-13), 4.66 (q, H-5"), 4.46 (br, H-3), 4.40 (d, H-1'), 4.35 (d, H-1"), 4. 12 (m, H-5"), 3.67 (d, H-4"), 3.65 (t, H-4"), 3.29 (s, OCH$_3$), 3.26 (s, OCH$_3$), 2.28 (s, N(CH$_3$)$_2$), 2.26 (s, N(CH$_3$)$_2$), 2.01 (s, NCH$_3$), 2.00 (s, NCH$_3$).

FAB Mass Spectrum (Li spike), m/z 851.8, 755.9, 722.8, 573.7.

EXAMPLE 107

(4"R,S)-4"-Deoxy-4"-(L-aspartyl-β-benzyl ester)-amino-9-deoxo-8a-aza-8a-methyl-8a-homoerythromycin A

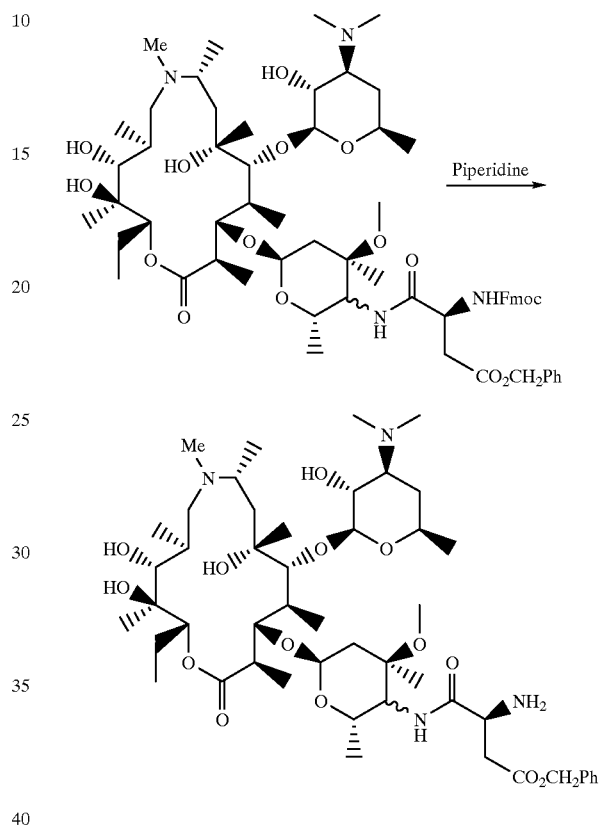

To 89 mg (0.038 mmol) of (4"R,S)-4"-deoxy-4"-(N-Fmoc-L-aspartyl-b-benzylester)amino-9-deoxo-8a-aza-8a-methyl-8a-homoerythromycin A (prepared from (4"R,S)-4"-deoxo-4"-amino-9-deoxo-8a-aza-8a-methyl-8a-homoerythromycin A and Fmoc-L-aspartic acid-b-benzyl ester by DCC/DMAP coupling ) in 2.5 ml of methylene chloride was added 0.5 ml of piperidine and stirred for 2 hours at room temperature. The mixture was evaporated. Silica chromatography with CH$_2$Cl$_2$-methanol-NH$_4$OH, 95:5:1 afforded 47.4 mg (85% yield) of the title compound.

$^1$H NMR (400 MHz, at 60° C., CDCl$_3$) δ7.31 (m aromatic protons), 5.16 (s, CH$_2$—Ar), 5.13 (s, CH$_2$—Ar), 4.85–4.81 (br, H-13), 4.80 (q, H-5"), 4.46 (br, H-3), 4.41 (d, H-1"), 4.37 (d, H-1"), 4. 14 (m, H-5"), 3.30 (s, OCH$_3$), 3.28 (s, OCH$_3$), 2.29 (br s, N(CH$_3$)$_2$), 2.05 (s, NCH$_3$).

FAB Mass Spectrum (Li spike), m/z 953.7, 928.5, 591.8, 574.

EXAMPLE 108

(4"R,S)-4"-Deoxy-4"-(L-aspartyl)amino-9-deoxo-8a-aza-8a-methyl-8a-homoerythromycin A

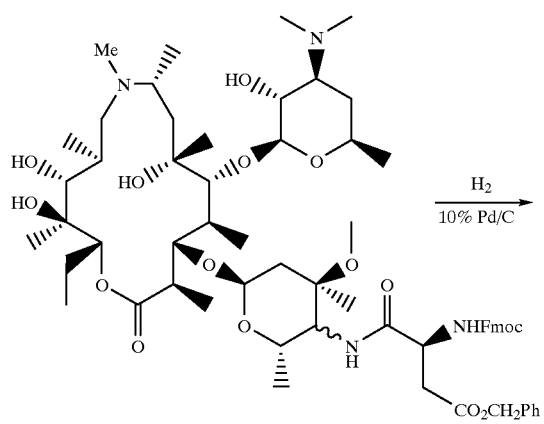

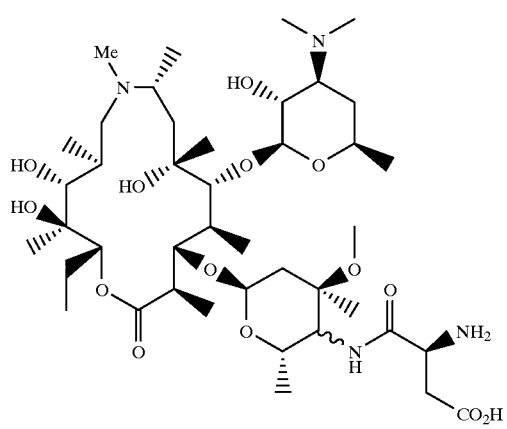

A mixture of 34 mg (0.035 mmol) of (4"R,S)-4"-deoxo-4"-(L-aspartyl -b-benzyl ester)amino-9-deoxo-8a-aza-8a-methyl-8a-homoerythromycin A and 10 mg of 10% Pd/C in 2 ml methanol was stirred under hydrogen at room temperature for 18 hours. The reaction mixture was filtered and the filtrate was evaporated under vacuum to give 26.4 mg (86% yield ) of the title compound.

$^1$H NMR (400 MHz, at 60° C., CDCl$_3$) δ5.18 (br, H-1"), 5.10 (d, H-1'), 4.87–4.80 (br, H-13), 4.67 (q, H-5"), 4.40 (br, H-3), 4.34 (d, H-1'), 4. 12 (m, H-5'), 3.67 (t, H-4"), 3.28 (s, OCH$_3$), 3.25 (s, OCH$_3$), 2.30 (br, N(CH$_3$)$_2$), 2.01 (br, NCH$_3$).

FAB Mass Spectrum (Li spike), m/z 870, 755.1, 591.8, 573.8.

EXAMPLE 109

(4"R,S)-4"-Deoxy-4"-(L-pyroglutamyl)amino-9-deoxo-8a-aza-8a-methyl-8a-homoerythromycin A

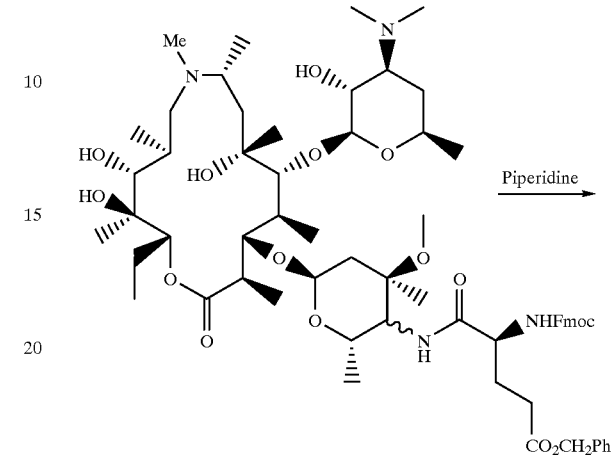

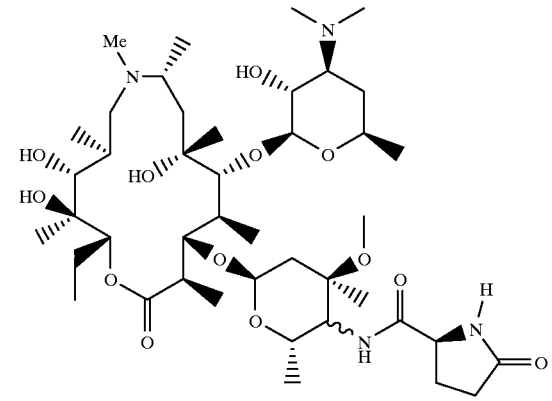

To 48 mg (0.040 mmol) of (4"R,S)-4"-deoxy-4"-(N-Fmoc-L-glutamyl-g-benzylester)amino-9-deoxo-8a-aza-8a-methyl-8a-homoerythromycin A (prepared from (4"R,S)-4"-deoxo-4"-amino-9-deoxo-8a-aza-8a-methyl-8a-homoerythromycin A and Fmoc-L-glutamyl-g-benzyl ester by DCC/DMAP coupling) in 2 ml of methylene chloride was added 0.5 ml of piperidine and stirred for 2 hours at room temperature. After verifying completion of the reaction by TLC, the mixture was evaporated. Silica chromatography with CH$_2$Cl$_2$-methanol-NH$_4$OH, 95:5:1 afforded 13.2 mg (39% yield) of the title compound.

$^1$H NMR (400 MHz, at 60° C., CDCl$_3$) δ5.15 (d, H-1"), 5.12 (d, H-1'), 5.00 (dd, H-13), 4.87 (dd, H-13), 4.80 (q, H-5"), 4.52 (br s, H-3), 4.49 (d, H-1'), 4.30 (d, H-1'), 4. 19 (m, H-5'), 4.14 (m, CO—CH—NH—), 3.80 (d, H-4"), 3.75 (t, H-4"), 3.30 (s, OCH$_3$), 3.28 (s, OCH$_3$), 2.32 (s, N(CH$_3$)$_2$), 2.26 (s, N(CH$_3$)$_2$), 2.01 (s, NCH$_3$).

FAB Mass Spectrum (Li spike), m/z 866, 859.9, 591.8, 573.9.

EXAMPLE 110

(4"R,S)-4"-Deoxy-4"-(N-Fmoc-L-glutamyl)amino-9-deoxo-8a-aza-8a-methyl-8a-homoerythromycin A

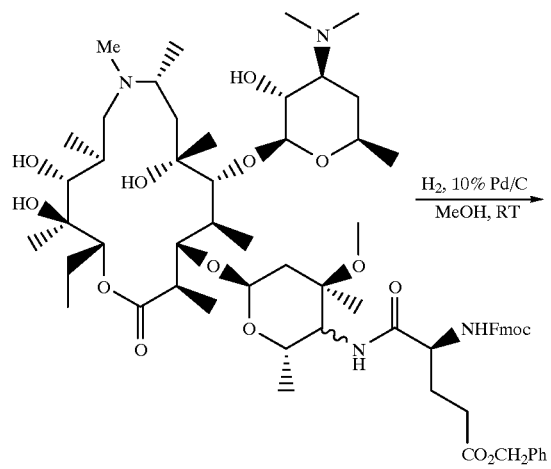

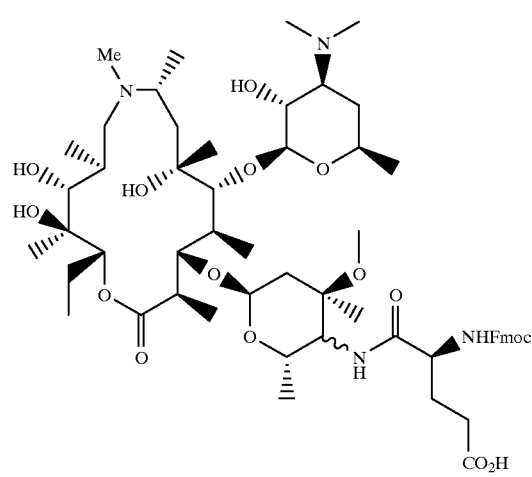

A mixture of 58 mg (0.048 mmol) of (4"R,S)-4"-deoxo-4"-(N-Fmoc-L-glutamyl-g-benzylester) amino-9-deoxo-8a-aza-8a-methyl-8a-homoerythromycin A (prepared from (4"R,S)-4"-deoxy-4"-amino-9-deoxo-8a-aza-8a-methyl-8a-homoerythromycin A and Fmoc-L-glutamic acid-g-benzyl ester by DCC/DMAP coupling) and 10 mg of 10% Pd/C in 2.5 ml methanol was stirred under hydrogen at room temperature for 18 hours. The reaction mixture was filtered and the filtrate was evaporated under vacuum to give 39 mg (75% yield) of the title compound.

$^1$H NMR (400 MHz, at 60° C., CDCl$_3$) δ7.70–7.27 (m, aromatic protons), 5.15(br d, H-1"), 5.07 (d, H-1'), 4.88–4.81 (br, H-13), 4.70 (q, H-5"), 3.75 (d, H-4"), 3.69 (t, H-4"), 3.29 (s, OCH$_3$), 3.23 (s, OCH$_3$), 2.67 (s, N(CH$_3$)$_2$ ), 2.34 (s, N(CH$_3$)$_2$), 2.02 (s, NCH$_3$), 2.00 (s, NCH$_3$).

FAB Mass Spectrum, m/z 1099.8, 873.9, 859.9.

EXAMPLE 111

(4"R,S)-4"-Deoxy-4"-(L-glutamyl)amino-9-deoxo-8a-aza-8a-methyl-8a-homoerythromycin A

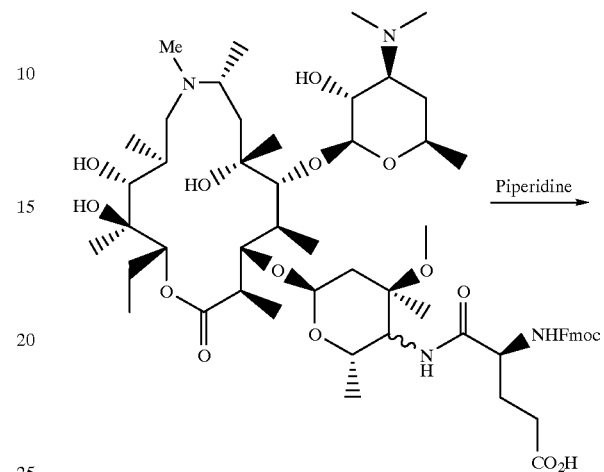

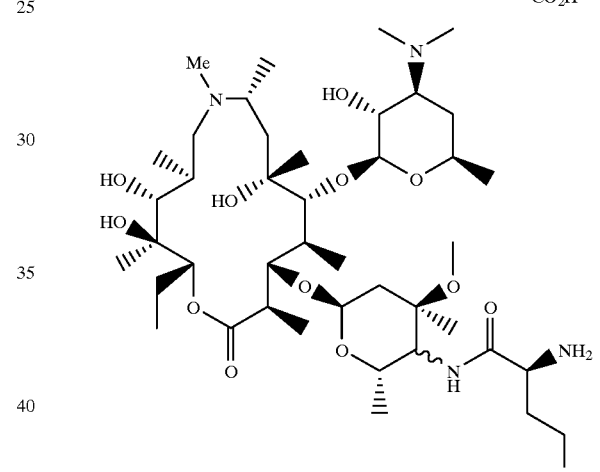

To 39 mg (0.035 mmol) of (4"R,S)-4"-deoxo-4"-(N-Fmoc-L-glutamyl)amino-9-deoxo-8a-aza-8a-methyl-8a-homoerythromycin A in 2 ml of methylenechloride was added 0.5 ml of piperidine and stirred for one hour at room temperature. After verifying completion of the reaction by TLC, the mixture was evaporated to dryness and the residue was repeatedly washed with hexane (to remove by product fluorenene/piperidine adduct) leaving behind 21 mg (69% yield) of the title compound.

1H NMR (400 MHz, at 60° C., CDCl$_3$) δ5.18 (d, H-1"), 5.10 (d, H-1'), 4.88–4.84 (br, H-13), 4.70 (q, H-5"), 4.41 (d, H-1"), 4.40 (br, H-3), 4.34 (d, H-1'), 4. 17 (m, H-5"), 3.30 (s, OCH$_3$), 3.26 (s, OCH$_3$), 2.50 (s, N(CH$_3$)$_2$), 2.28 (s, N(CH$_3$)$_2$), 2.01 (s, NCH$_3$).

FAB Mass Spectrum (Li spike), m/z 883.7, 820.2, 591.8, 573.9, 416.3.

EXAMPLE 112

2'-O-Acetyl-9-deoxo-8a-aza-8a-allyl-8a-homoerythromycin A

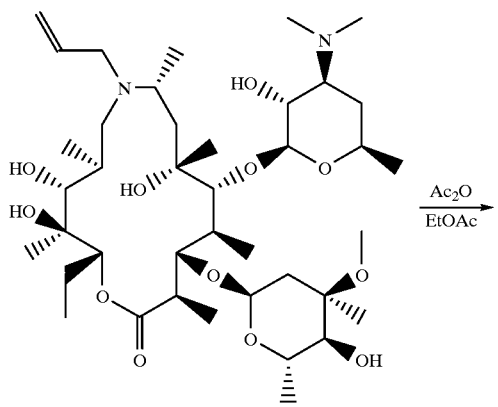

A solution of 9-deoxo-8a-aza-8a-allyl-8a-homoerythromycin A (8.65 g, 11.16 mmol) in ethyl acetate (65 mL) was treated with acetic anhydride (1.6 mL, 16.7 mmol) then stirred at room temperature for 30 minutes. The reaction mixture was diluted with water (60 mL) and stirred while the pH was adjusted from 6.2 to 4.0 by addition of 2N hydrochloric acid. The aqueous phase was separated, layered with dichloromethane (60 mL), and the mixture stirred while the pH was brought to 10 with 5N sodium hydroxide solution. The phases were separated and the aqueous portion was extracted with more dichloromethane (2×40 mL). The combined dichloromethane extracts were dried with magnesium sulfate, filtered and evaporated under vacuum to provide 2'-O-acetyl-9-deoxo-8a-aza-8a-allyl-8a-homoerythromycin A (8.08 g) as a foam.

FAB-MS m/z 824 (M+Li), 818 (M+H), 658, 642.

EXAMPLE 113

4"-Deoxy-4"-oxo-9-deoxo-8a-aza-8a-allyl-8a-homoerythromycin A

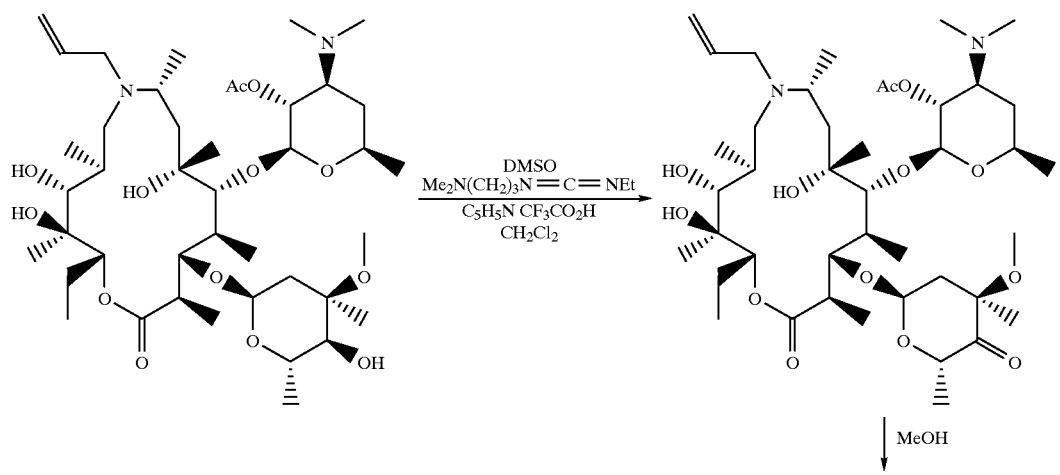

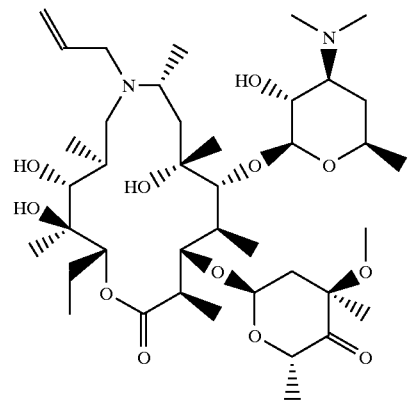

A solution of 2'-O-acetyl-9-deoxo-8a-aza-8a-allyl-8a-homoerythromycin A (8.0 g, 9.79 mmol) in dichloromethane (75 mL) and dimethylsulfoxide (7 mL, 97.9 mmol) was treated over two minutes with 1-(3-dimethylaminopropyl)-3-ethylcarbodiimide hydrochloride (5.64 g, 29.4 mmol) and then over three minutes with pyridinium trifluoroacetate (5.7 g, 29.4 mmol). The resulting mixture was stirred at room temperature for 2.5 hours, then diluted with water (75 mL) and stirred vigorously while the pH of the aqueous phase was adjusted from 4.6 to 9.5 by addition of 5N sodium hydroxide solution. The phases were separated and the aqueous portion was extracted with more dichloromethane (2×50 mL). The combined dichloromethane extracts were washed with aqueous 5% sodium bicarbonate (3×50 mL), dried over magnesium sulfate, filtered and evaporated under vacuum to afford crude 2'-O-acetyl-4"-deoxy-4"-oxo-9-deoxo-8a-aza-8a-allyl-8a-homoerythromycin A (8.4 g) as a foam.

The crude product was dissolved in methanol (50 mL) and the solution was stirred at room temperature overnight followed by one hour at 50° C. After cooling to room temperature, the mixture was evaporated under vacuum to afford 4"-deoxy-4"-oxo-9-deoxo-8a-aza-8a-allyl-8a-homoerythromycin A (7.7 g) as a foam.

FAB-MS m/z 780 (M +Li), 774 (M +H), 616, 600.

EXAMPLE 114

4"-Deoxy-4"-hydroxyimino-9-deoxo-8a-aza-8a-allyl-8a-homoerythromycin A

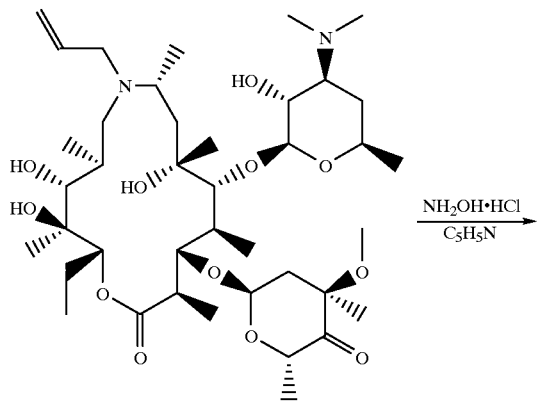

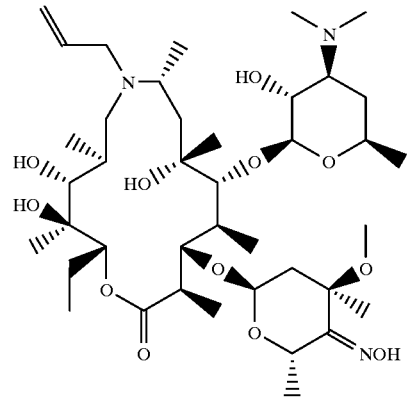

Hydroxylamine hydrochloride (3.4 g, 49 mmol) was added to a solution of 4"-deoxy-4"-oxo-9-deoxo-8a-aza-8a-allyl-8a-homoerythromycin A (4.0 g, 4.9 mmol) in pyridine (12 mL). The resulting mixture was stirred at room temperature for 16 hours, then evaporated under vacuum to remove the pyridine. The residue was stirred with dichloromethane (100 mL) and water (100 mL, pH of aqueous phase was 5.9) and the layers separated. The aqueous portion was stirred with additional dichloromethane (100 mL) while adjusting the pH to 6.0 with 5N sodium hydroxide solution. The extraction process was repeated with three additional 100 mL portions of dichloromethane with adjustment of the pH of the aqueous phase to values of 6.5, 7.0 and 11.0. The pH 7.0 and 11.0 extracts were combined and evaporated under vacuum to provide 4"-deoxy-4"-hydroxyimino-9-deoxo-8a-aza-8a-allyl-8a-homoerythromycin A (2.36 g) as a mixture of oxime isomers.

$^1$H NMR (CDCl$_3$, 60° C.) δ5.95 (br m, C$\underline{H}$=CH$_2$), 5.32 (t, H-1"), 5.14 (m, CH=C$\underline{H}_2$), 5.05 (m, H-5"), 4.92 (dd, H-13), 4.42 (d, H-1'), 4.38 (m, H-3), 3.63 (br s, H-11), 3.31 (s, OCH$_3$), 2.48 (br s, N(CH$_3$)$_2$), 0.90 (t, CH$_2$C$\underline{H}_3$).

FAB-MS m/z 795 (M+Li), 789 (M+H), 630, 616, 600.

EXAMPLE 115

4"-Deoxy-4"-amino-9-deoxo-8a-aza-8a-allyl-8a-homoerythromycin A

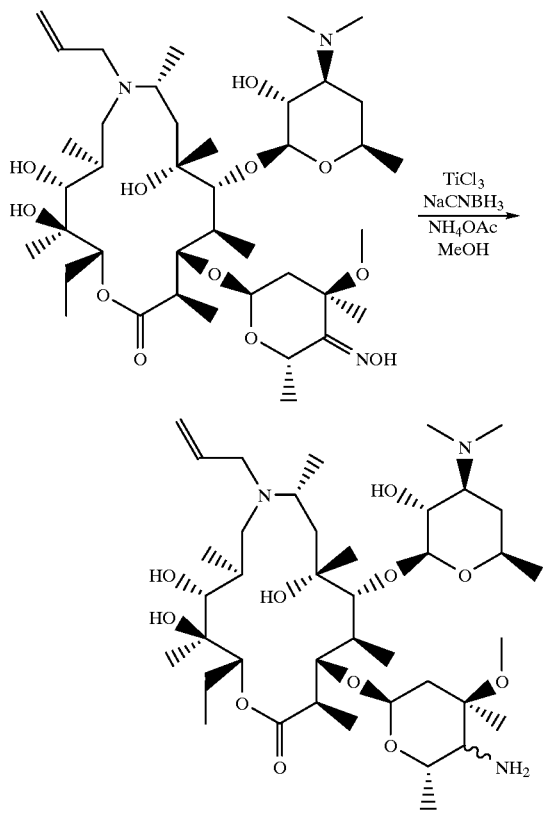

A solution of 4"-deoxy-4"-hydroxyimino-9-deoxo-8a-aza-8a-allyl-8a-homoerythromycin A (2.0 g, 2.4 mmol) in methanol (50 mL) was treated sequentially with ammonium acetate (4.5 g, 58 mmol), sodium cyanoborohydride (0.5 g, 95% pure, 7.6 mmol), and titanium(III)chloride (5.0 mL of a 15% solution in 20% hydrochloric acid, 5.8 mmol). The resulting mixture was stirred at room temperature for 27 hours, then treated with nitromethane (40 drops) and stirred an additional 15 minutes to reduce excess oxidant. The apparent pH of the mixture was adjusted from 6.05 to 7.0 with 5N sodium hydroxide before evaporating the solvent under vacuum. The residue was stirred with dichloromethane (200 mL) and water (200 mL) while adjusting the pH of the aqueous portion to 9.5 with 5N sodium hydroxide. The layers were separated and the aqueous portion extracted with additional dichloromethane (2×100 mL). The combined dichloromethane extracts were dried over magnesium sulfate, filtered and evaporated under vacuum to afford the crude 4"-amino derivative (1.88 g).

A portion (1.6 g) of the crude product was purified by column chromatography on EM silica gel 60 (4.5×23 cm, 230–400 mesh, packed under 90:10:1 dichloromethane-methanol-conc. ammonium hydroxide). The column was eluted with 90:10:1 dichloromethane-methanol-conc. ammonium hydroxide, collecting 25 mL fractions. Fractions 15–24 were combined, evaporated under vacuum, and the residue lyophilized from benzene to afford 4"-deoxy-4"-amino-9-deoxo-8a-aza-8a-allyl-8a-homoerythromycin A (1.02 g) as a 3:2 (4"R):(4"S) mixture of isomers.

$^1$H NMR (CDCl$_3$, 60° C.) δ5.94 (m, C$\underline{H}$=CH$_2$), 5.08 (m, CH=C$\underline{H}_2$ and H-1"), 4.93 (m, H-13), 4.64 (q, H-5" of the 4"R-isomer), 4.39 (m, H-1' and H-3), 4.06 (dq, H-5"of the 4"S-isomer), 3.65 (s, H-11), 3.54 (m, H-5 and H-5'), 3.28 (s, OCH$_3$ of the 4"R-isomer), 3.26 (s, OCH$_3$ of the 4"S-isomer), 2.36 (br s, N(CH$_3$)$_2$).

FAB-MS m/z 781 (M+Li), 775 (M+H), 617, 616, 600.

EXAMPLE 116

4"-Deoxy-4"-amino-9-deoxo-8a-aza-8a-propyl-8a-homoerythromycin A

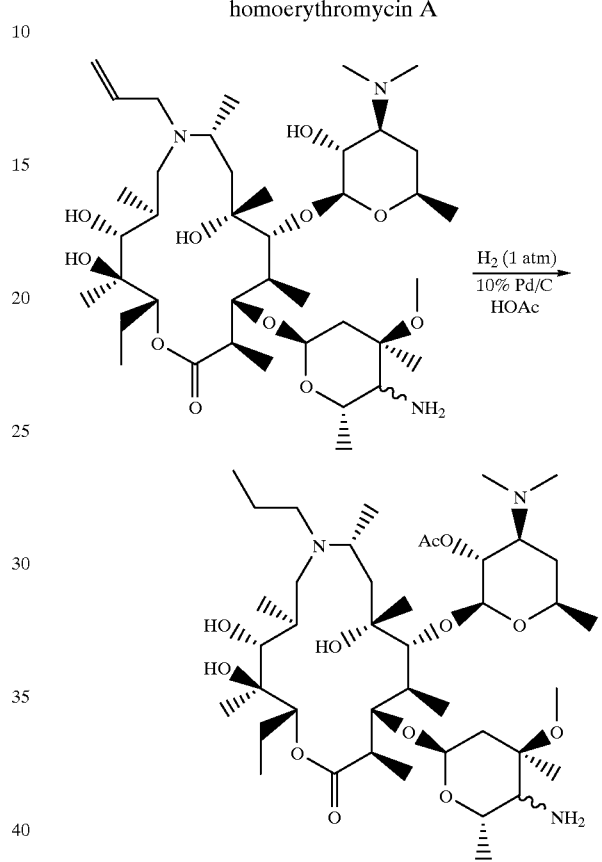

A mixture of 4"-deoxy-4"-amino-9-deoxo-8a-aza-8a-allyl-8a-homoerythromycin A (ca. 150 mg of a mixture of 4"-isomers), 10% palladium on carbon (120 mg) and acetic acid (5 mL) was stirred under a hydrogen atmosphere at room temperature for 5 hours. The mixture was filtered and the filtrate evaporated under vacuum. The residue was stirred with dichloromethane (6 mL) and water (4 mL) while adjusting the pH to 10 with dilute aqueous sodium hydroxide. The layers were separated and the aqueous portion was extracted with more dichloromethane (4 mL). The combined extracts were dried over magnesium sulfate, filtered and evaporated under vacuum to provide crude product.

The crude product was purified by chromatography on a column of EM silica gel 60 (4.5×14 cm, 230–400 mesh). The column was packed and eluted with 90:10:1 dichloromethane-methanol-conc. ammonium hydroxide, collecting 8 mL fractions. Fractions 25–30 were combined and evaporated under vacuum to provide 4"-deoxy-4"-amino-9-deoxo-8a-aza-8a-propyl-8a-homoerythromycin A (121 mg) as a mixture of 4"-isomers (ca. 2:1 R:S).

$^1$H NMR (CDCl$_3$, 60° C.) δ4.66 (q, H-5" of the 4"R-isomer), 4.03 (m, H-5"of the 4"S-isomer), 3.27 (s, OCH$_3$ of the 4"R-isomer), 3.25 (s, OCH$_3$ of the 4"S-isomer), 2.40 (br s, N(CH$_3$)$_2$).

FAB-MS m/z 777 (M+H), 619, 618, 602, 158.

EXAMPLE 117

2'-O-Acetyl-9-deoxo-8a-aza-8a-methoxycarbonethyl-8a-homoerythromycin A

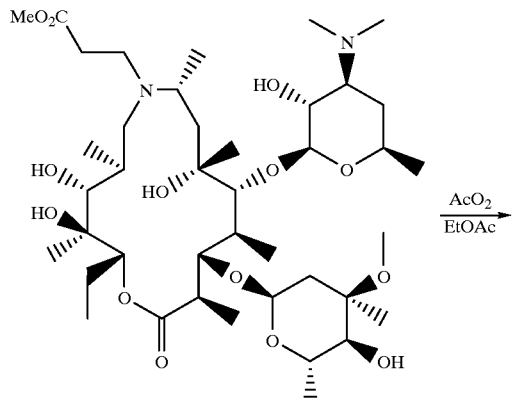

Acetic anhydride (0.062 mL, 0.66 mmol) was added to a solution of 9-deoxo-8a-aza-8a-(3-methoxy-3-oxopropyl)-8a-homoerythromycin A (355 mg, 0.43 mmol) in dry ethyl acetate (2.7 mL). The resulting solution was stirred at room temperature for 3.5 hours. Water (2 mL) was then added and the two-phase mixture was stirred at room temperature for 2 hours. The pH of the aqueous phase was adjusted to 2.5 by addition of 1N hydrochloric acid. The layers were separated and the organic phase was discarded. Fresh ethyl acetate was added and the pH of the aqueous layer was adjusted to 9.5 by addition of 1N sodium hydroxide. The layers were separated and the aqueous layer was extracted three times with ethyl acetate. The combined ethyl acetate extracts were dried over magnesium sulfate, filtered and evaporated under vacuum to afford 2'-O-acetyl-9-deoxo-8a-aza-8a-(3-methoxy-3-oxopropyl)-8a-homoerythromycin A (299 mg) as a clear colorless oil. The crude product was essentially pure and was used without further purification in the next step.

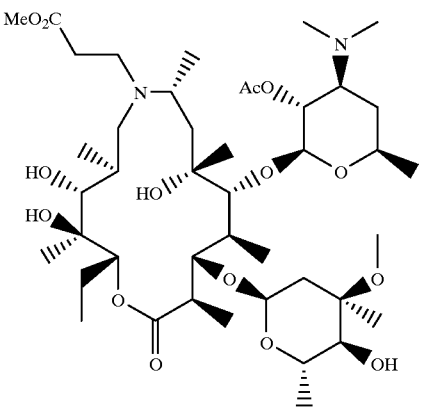

$^1$H NMR (400 MHz, CD$_3$OD) δ5.11 (br s, H-$^{1"}$), 4.75 (dd, H-2'), 4.65 (d, H-1'), 4.29 (br s, H-3), 4.15 (m, H-5"), 3.71 (m, H-5'), 3.67 (s, CO$_2$CH$_3$), 3.56 (d, H-5), 3.48 (br s, H-11), 3.35 (s, OCH$_3$), 3.03 (d, H-4"), 2.27 (s, (N(CH$_3$)$_2$), 2.08 (s, OCOCH$_3$), 1.33 (br s, 6-CH$_3$), 1.11 (s, 12-CH$_3$), 0.91 (t, CH$_2$C$\underline{H}_3$).

EXAMPLE 118

2'-O-Acetyl-4"-deoxy-4"-oxo-9-deoxo-8a-aza-8a-(3-methoxy-3-oxo-propyl)-8a-homoerythromycin A

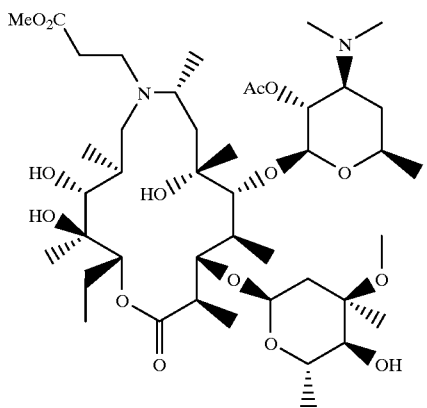 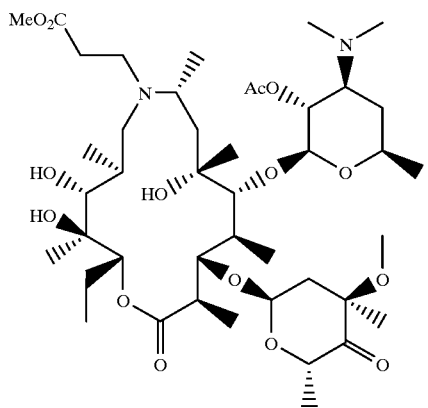

1-(3-Dimethylaminopropyl)-3-ethylcarbodiimide hydrochloride (200 mg, 1.04 mmol) was added to a solution of 2'-O-acetyl-9-deoxo-8a-aza-8a (3-methoxy-3-oxopropyl)-8a-homoerythromycin A (299 mg, 0.35 mmol) in dry dichloromethane (2.1 mL). Methyl sulfoxide (0.246 mL, 3.5 mmol) was then added dropwise followed by dropwise addition of a solution of pyridinium trifluoroacetate (204 mg, 1.06 mol) in dry dichloromethane (0.7 mL). The reaction mixture was then stirred at room temperature for 110 minutes. Aqueous potassium carbonate (5%) was added and the pH of the aqueous layer was adjusted to 10 by addition of solid potassium carbonate. The layers were separated and the aqueous layer was extracted four times with ethyl acetate. The combined organic layers were dried over magnesium sulfate, filtered and evaporated under vacuum to afford 2'-O-acetyl-4"-deoxy-4"-oxo-9-deoxo-8a-aza-8a-(3-methoxy-3-oxopropyl) -8a-homoerythromycin A as a clear yellow oil (746 mg). The crude product contains some residual DMSO and other reagent derived impurities. However, it was used without further purification in the next step.

$^1$H NMR (400 MHz, CD$_3$OD) δ5.56 (m, H-1"), 5.03 (dd, H-13), 4.79 (dd, H-2'), 4.58 (br s, H-3), 4.56 (d, H-1'), 4.53 (q, H-5"), 3.66 (8, CO$_2$CH$_3$), 3.58 (d, H-5), 3.55 (m, H-5'), 3.41 (br s, H-11), 3.26 (s, OCH$_3$), 2.26 (s, N(CH$_3$)$_2$), 2.10 (s, OCOCH$_3$), 0.90 (t, CH$_2$CH$_3$).

EXAMPLE 119

4"-Deoxy-4"-hydroxyimino-9-deoxo-8a-aza-8a-(3-methoxy-3-oxopropyl)-8a-homoerythromycin A

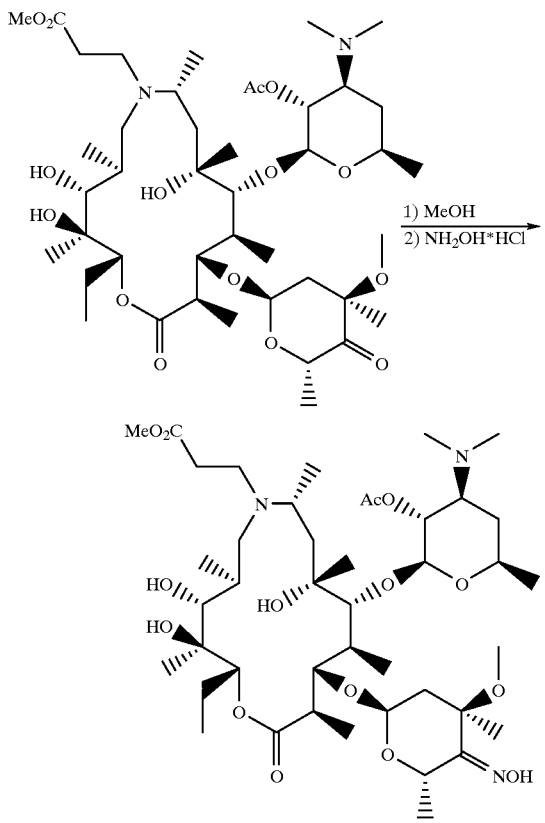

A solution of crude 2'O-acetyl-4"-deoxy-4"-oxo-9-deoxo-8a-aza-8a-(3-methoxy-3-oxopropyl)-8a-homoerythromycin A (746 mg) in methanol (4 mL) was stirred at room temperature for 19 hours. Analytical TLC showed complete deacetylation. Hydroxylamine hydrochloride (121 mg) was then added. The reaction mixture was stirred at room temperature for 1.5 hours then evaporated under vacuum. The residue was partitioned between ethyl acetate and aqueous potassium carbonate (pH of aqueous layer was adjusted to 10 by addition of solid potassium carbonate). The aqueous layer was extracted four times with ethyl acetate and the combined organic layers were dried over magensium sulfate, filtered and evaporated under vacuum to afford a clear colorless oil (294 mg). The crude product was purified by flash chromatography on EN silica gel 60 (4.0×48 cm column eluted with 95:5:1 chloroform:methanol:aqueous ammonia collecting 30 mL fractions). Fractions 23–34 were combined and evaporated under vacuum to afford 4"-deoxy-4"-hydroxyimino-8a-aza-8a-(3-methoxy-3-oxopropyl)-8a-homoerythromycin A (169 mg) as a foam.

$^1$H NMR (400 MHz, CD$_3$OD) δ5.33 (dd,H-1"), 5.16 (q, H-5"), 5.05 (dd, H-13), 4.42 (d, H-1'), 4.31 (br s, H-3), 3.71 (br s, H-11), 3.66 (br s, CO$_2$CH$_3$), 3.65 (d, H-5), 3.58 (m, H-5'), 3.28 (s, OCH$_3$), 3.25 (dd, H-2'), 2,32 (s, N(CH$_3$)$_2$), 1.31 (br s, 6-CH$_3$), 1.10 (s, 12-CH$_3$), 1.09 (d, 8-CH$_3$), 1.03 (d, 4-CH$_3$), 0.96 (d, 10-CH$_3$), 0.90 (t, CH$_2$CH$_3$).

EXAMPLE 120

4"-Deoxy-4"-amino-9-deoxo-8a-aza-8a-(3-methoxy-3-oxo-propyl)-8a-homoerythromycin A

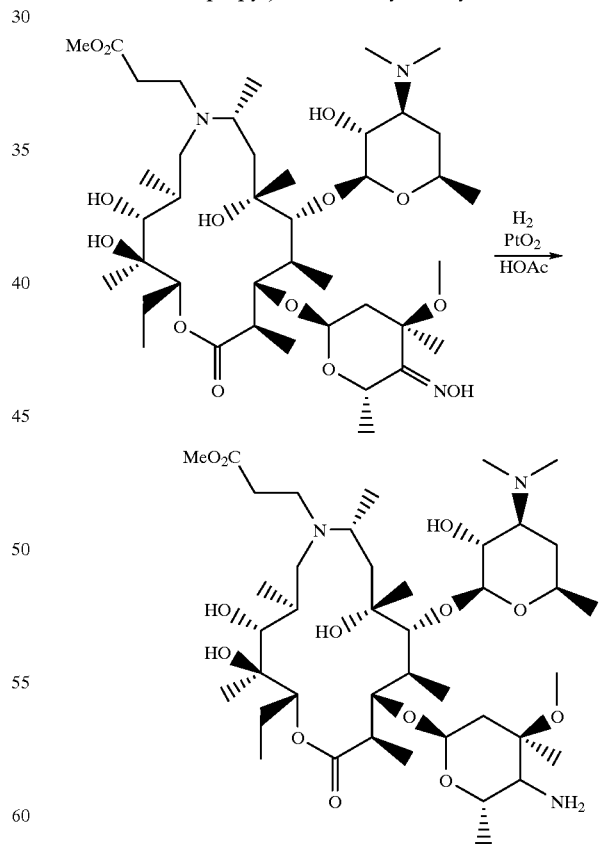

A solution of 4"-deoxy-4"-hydroxyimino-9-deoxo-8a-aza-8a-(3-methoxy-3-oxopropyl)-8a-homoerythromycin A (169 mg, 0.19 mmol) in absolute ethanol was stirred with Raney nickel for 2 hours at room temperature to remove potential catalyst poisons. The Raney nickel was premoved by filtration and the filtrate was evaported under vacuum. The residue was dissolved in acetic acid (4 mL) then platinum oxide (123 mg, 0.54 mmol) was added. The reaction mixture was shaken under a hydrogen atmosphere (1000 psi) at room temperature for 48 hours. The mixture was then filtered through Celite® and the filtrate was evaporated under vacuum. The residue was partitioned between 10% aqueous sodium bicarbonate and ethyl acetate. The aqueous layer was extracted six times with ethyl acetate. The combined organic layers were dried over magnesim sulfate, filtered and evaporated under vacuum to afford a colorless oil (116 mg). Analytical TLC indicated that no reaction had occurred. The crude material was therefore redissolved in acetic acid (4 mL) and platinum oxide (115 mg, 0.50 mmol, different batch) was added. The mixture was shaken under an atmosphere of hydrogen (1000 psi) at room temperature for 72 hours. Workup as before afforded 4"-deoxy-4"-amino-9-deoxo-8a-aza-8a-(3-methoxy-3-oxopropyl)-8a-homoerythromycin A (ca. 1:1 mixture of epimers at C-4") as a white solid (73 mg).

$^1$H NMR (400 MHz, CD$_3$OD) δ5.23 and 5.19 (two br s, H-1"), 5.02 and 4.98 (two dd, H-B), 4.44 and 4.37 (two d, H-1'), 3.58 (s, CO$_2$CH$_3$), 2.55 and 2.51 (two s, N(CH$_3$)$_2$).

FAB-MS, m/z 826 (M+Li).

EXAMPLE 121

2'-O-Acetyl-8a-aza-8a-homoerythromycin

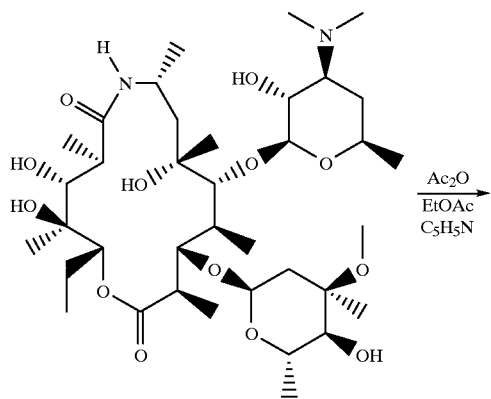

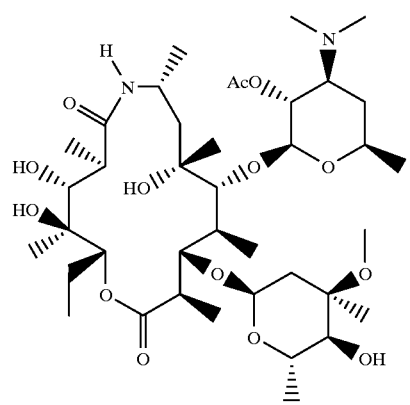

A solution of 8a-aza-8a-homoerythromycin A (1.37 g, 1.83 mmol) and acetic anhydride (0.26 mL, 2.75 mmol) in ethyl acetate (12 mL) was stirred at room temperature for 27 minutes, then treated with pyridine (0.15 mL, 1.83 mmol) and stirred an additional 18 minutes. The mixture was evaporated under vacuum to remove most of the ethyl acetate. The residue was stirred with dichloromethane (12 mL) and water (12 mL) while the pH of the aqueous phase was carefully adjusted to 11 by addition of aqueous sodium hydroxide. The layers were separated and the aqueous portion was extracted with more dichloromethane (12 mL). The combined extracts were dried with magnesium sulfate, filtered and evaporated under vacuum to provide 2'-O-acetyl-8a-aza-8a-homoerythromycin A (1.45 g) as a foam. This material was used in the next step without further purification.

EXAMPLE 35

4"-Deoxy-4"-oxo-8a-aza-8a-homoerythromycin A

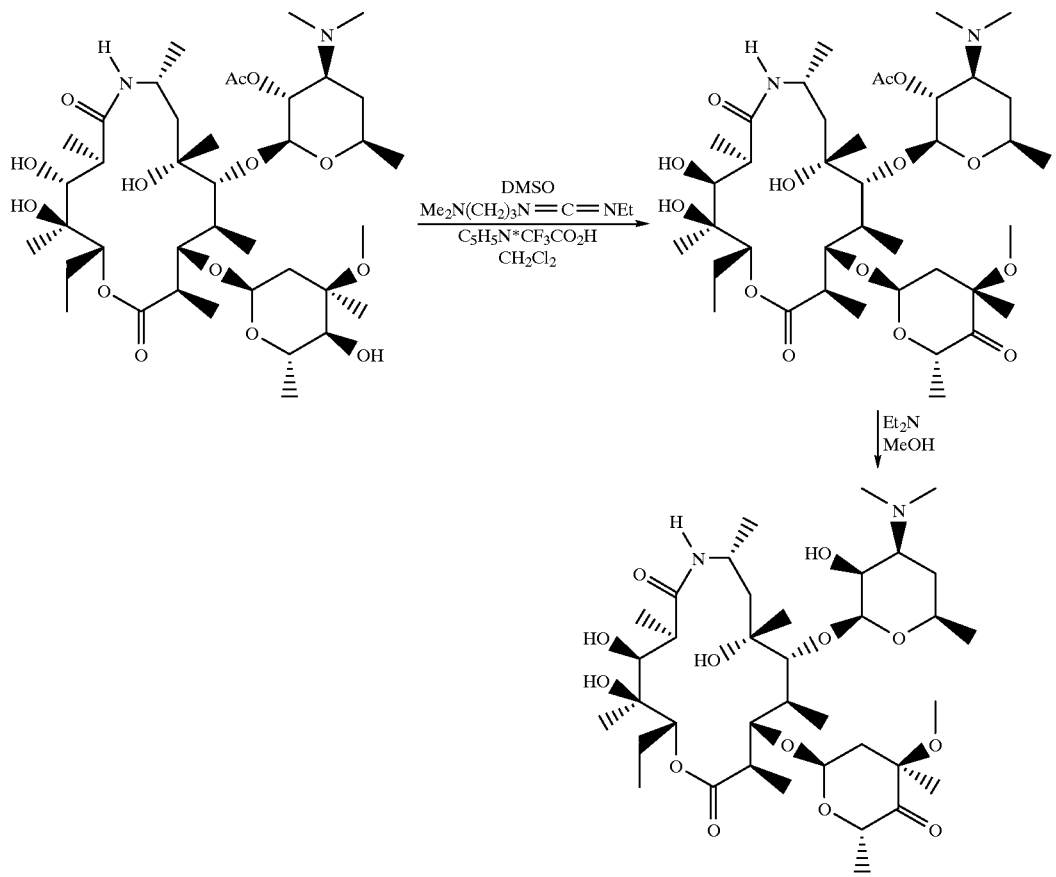

A solution of 2'-O-acetyl-8a-aza-8a-homoerythromycin A (1.45 g, 1.83 mmol) in dichloromethane (20 mL) was treated sequentially with dimethyl sulfoxide (1.3 mL, 18.4 mmol), 1-(3-dimethylaminopropyl)-3-ethylcarbodiimide (1.06 g, 5.52 mmol) and pyridinium trifluoroacetate (1.06 g, 5.52 mmol). The resulting solution was stirred at room temperature for 3.5 hours, then diluted with water (12 mL) and stirred while the pH of-the aqueous phase was brought to 9.5 with aqueous sodium hydroxide. The layers were separated and the aqueous portion extracted with more dichloromethane (3×35 mL). The combined dichloromethane extracts were washed with 5% aqueous sodium bicarbonate, dried over magnesium sulfate, filtered and evaporated under vacuum to provide crude 2'-O-acetyl-4"-deoxy-4"-oxo-8a-aza-8a-homoerythromycin A as a foam.

$^1$H NMR (CDCl$_3$) δ5.52 (d, NH), 5.35 (t, H-1"), 4.94 (dd, H-13), 4.72 (dd, H-2'), 4.37 (m, H-3 and H-5"), 4.31 (d, H-1'), 4.17 (m, H-8), 3.47 (d, H-5), 3.37 (m, H-5'), 3.43 (s, H-11), 3.32 (s, OCH$_3$), 2.58 (m, H-2), 2.27 (br s, N(CH$_3$)$_2$), 2.06 (s, OCOCH$_3$), 0.89 (t, CR$_2$C$\underline{H}_3$).

Deacetylation was accomplished by dissolving the above product in methanol (12 mL), adding triethylamine (ca. 0.2 mL), and stirring the resulting solution at room temperature for 3 days. The solvent was removed under vacuum and the residue was chromatographed on EM silica gel 60 (230–400 mesh, 1.5×4.5 cm column packed under and eluted with 90:10:1 dichloromethane-ethanol-conc. ammonium hydroxide, collecting six 25 mL fractions followed by 8 mL fractions). Fractions 11–15 were pooled and evaporated under vacuum to provide 4"-deoxy-4"-oxo-8a-aza-8a-homoerythromycin A (0.95 g) as a foam.

$^1$H NMR (CDCl$_3$) δ6.06 (br d, NH), 5.37 (t, H-1"), 4.92 (dd, H-13), 4.43 (m, H-3), 4.41 (q, H-5"), 4.21 (d, H-1'), 4.16 (m, H-8), 3.50 (d, H-5), 3.44 (s, H-11), 3.36 (m, H-5), 3.29 (s, OCH$_3$), 3.12 (dd, H-2'), 2.60 (dq, H-2), 2.42 (m, H-3'), 2.23 (s, N(CH$_3$)$_2$), 1.87 (m, H-4 and H-14a), 1.63 (m, H-4'eq), 0.87 (t, CH$_2$C$\underline{H}_3$)

$^{13}$C NMR (CDCl$_3$) δ212.1, 177.8, 176.6, 103.7, 95.4, 83.2, 77.4, 77.3, 77.0, 76.8, 76.7, 74.7, 74.1, 71.6, 70.4, 70.0, 69.3, 65.4, 51.2, 45.5, 42.7, 42.6, 41.6, 40.5, 40.2, 36.8, 28.4, 27.6, 23.4, 21.6, 21.4, 20.8, 16.2, 16.1, 14.8, 11.3, 9.2.

FAB-MS m/z 748 (M+H), 591, 158.

EXAMPLE 123

4"-Deoxy-4"-hydroxyimino-8a-aza-8a-homoerythromycin A

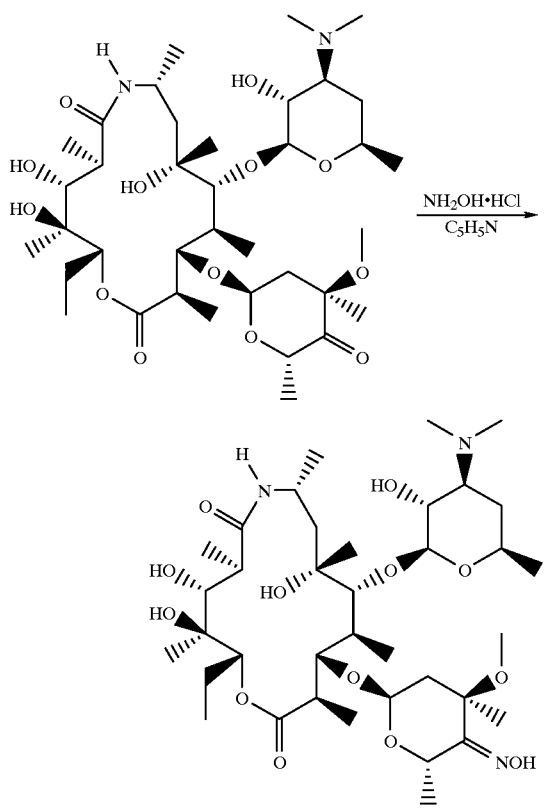

A mixture of 4"-deoxy-4"-oxo-8a-aza-8a-homoerythromycin A (0.90 g, 1.2 mmol), hydroxylamine hydrochloride (0.85 g, 12 mmol) and pyridine (4 mL) was stirred at room temperature for 24 hours, then evaporated under vacuum. The residue was stirred with water (25 mL) and dichloromethane (25 mL) while adjusting the pH of the aqueous phase from 5 to 11 with aqueous sodium hydroxide. The phases were separated and the aqueous portion was extracted with more dichloromethane (6 mL). The combined dichloromethane extracts were dried with magnesium sulfate, filtered, evaporated under vacuum, and three times dissolved in warm toluene (20 mL) and evaporated under vacuum to afford crude 4"-deoxy-4"-hydroxyimino-8a-aza-8a-homoerythromycin A (0.90 g) as a 3:1 mixture of oxime isomers.

$^1$H NMR (CDCl$_3$) δ5.97 (br d, NH), 5.22 (t, H-1" of minor isomer), 5.14 (t, H-1" of major isomer), 5.07 (q, H-5" of major isomer), 4.95 (br d, H-13 of major isomer), 4.92 (br d, H-13 of minor isomer), 4.54 (q, H-5" of minor isomer), 4.38 (d, H-1), 4.24 (m, H-3), 4.15 (m, H-8), 3.74 (d, H-5), 3.56 (m, H-5'), 3.45 (br s, H-11), 3.27 (s, OCH$_3$), 3.16 (dd, H-2'), 3.47 (m, H-3'), 2.34 (8, N(CH$_3$)$_2$), 0.87 (t, CH$_2$CH$_3$).

$^{13}$C NMR (CDCl$_3$) δ177.6, 176.3, 160.4, 157.4, 104.1, 102.9, 95.6, 95.4, 83.8, 83.2, 79.9, 76.9, 76.6, 75.0, 74.9, 74.2, 74.0, 70.6, 70.3, 69.4, 68.9, 66.8, 65.8, 65.5, 65.4, 51.1, 50.3, 45.3, 42.8, 42.4, 41.7, 41.6, 41.4, 40.7, 39.4, 35.3, 29.0, 28.9, 27.4, 27.3, 25.2, 23.4, 23.0, 21.7, 21.5, 21.4, 21.3, 17.5, 17.3, 16.5, 15.4, 14.8, 11.2, 11.1, 9.4.

FAB-MS m/z 785 (M+Na), 769 (M+Li), 763 (M+H), 592, 417, 158.

EXAMPLE 124

4"-Deoxy-4"-amino-8a-aza-8a-homoerythromycin A

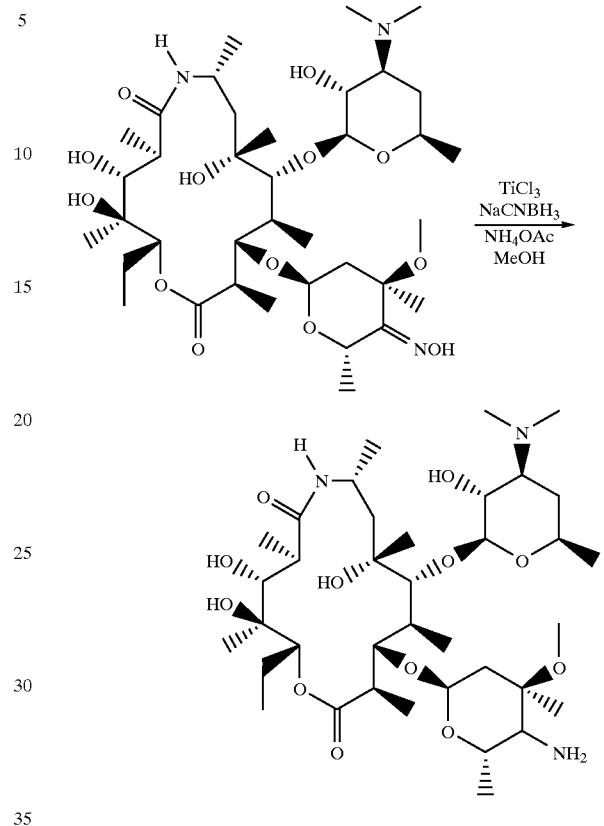

A solution of 4"-deoxy-4"-hydroxyimino-8a-aza-8a-homoerythromycin A (200 mg, 0.26 mol) in methanol (4 mL) was treated sequentially with ammonium acetate (450 mg, 5.78 mmol), sodium cyanoborohydride (48 mg, 95% pure, 0.73 mmol) and titanium(III)chloride (0.50 mL of a 15% solution in 20% hydrochloric acid, 0.58 mmol). The resulting mixture was stirred at room temperature for 24.5 hours, then treated with nitromethane (8 drops) and stirred a few minutes. Evaporation of the solvent under vacuum left a residue which was stirred with dichloromethane and water while adjusting the pH of the aqueous phase to 9.5 with sodium hydroxide. The layers were separated and the aqueous portion was extracted with more dichloromethane. The combined organic extracts were dried with magnesium sulfate, filtered and evaporated under vacuum to a foam (163 mg).

The crude product was purified by chromatography on EM silica gel 60 (230–400 mesh, 1.5×30.5 cm column packed under and eluted with 90:10:1 dichloromethane-methanol-conc. ammonium hydroxide, collecting 7×8 mL fractions then 43×3 mL fractions followed by 8 mL fractions). Fractions 53–62 were combined, evaporated under vacuum, and the residue was lyophilyzed from warm benzene (8 mL) containing a few drops of dichloromethane to afford 4"-deoxy-4"-amino-8a-aza-8a-homorythromycin A (76 mg) as a mixture of 4"-isomers (ca. 55:45 (4"R):(4"S) as determined by $^1$H NMR).

$^1$H NMR (CDCl$_3$) δ6.69 and 6.54 (two br d$^{1s}$, NE), 5.08 and 5.06 (two overlapping d$^{1s}$, H-1"), 4.87 (dd, H-13), 4.56 (q, H-5"of 4"R-isomer), 4.50 (d, H-1' of 4"R-isomer), 4.44 (d, H-1' of 4"S-isomer), 4.30 (m, H-3), 4.13 (m, H-8), 3.99

(dq, H-5" of 4"S-isomer), 3.55 and 3.53 (two overlapping d'$^s$, H-5), 3.46 and 3.45 (two s'$^s$, H-11), 3.26 (s, OCH$_3$ of 4"R-isomer), 3.24 (s, OCH$_3$ of 4"S-isomer), 3.16 and 3.13 (two overlapping dd'$^s$, H-21), 2.31 (br s, N(CH$_3$)$_2$ of 4"S-isomer), 2.77 (br s, N(CH$_3$)$_2$ of 4"R-isomer), 1.67 (m, H-4'eq), 1.48 (s, 6-CH$_3$), 0.86 (t, CH$_2$C$\underline{H}_3$).

$^{13}$C NMR (CDCl$_3$, 60° C.) δ177.6, 177.5, 176.5, 176.3, 103.0, 102.6, 95.1, 94.9, 83.4, 83.0, 77.3, 77.2, 77.0, 76.8, 76.6, 75.1, 74.8, 74.1, 74.0, 72.7, 70.5, 70.2, 68.6, 68.4, 66.1, 65.8, 65.7, 62.8, 61.9, 57.9, 49.2, 45.7, 43.2, 43.0, 42.6, 42.5, 41.6, 41.5, 40.6, 40.5, 40.1, 35.1, 29.1, 29.0, 27.7, 23.2, 22.0, 21.7, 21.2, 18.7, 17.8, 16.2, 16.1, 14.6, 14.5, 11.0, 9.7, 9.6, 9.2, 9.1.

FAB-MS m/z 771 (M=Na), 592, 158.

EXAMPLE 125

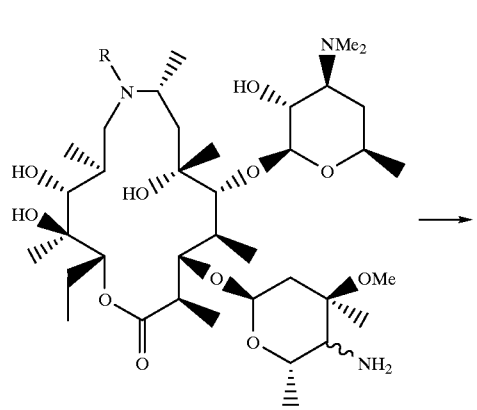

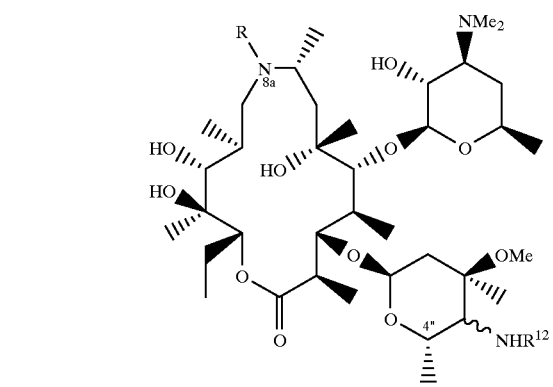

By using variations of the procedures described in Examples 98–101 and the 4"-amino derivatives of Examples 94, 96, 97, 115, 116 and 120, the following 4"-acylamino analogs were prepared.

| R | R$^{12}$ | 4"-configuration |
|---|---|---|
| CH$_3$ | SO$_2$CH$_3$ | R + S |
| CH$_3$ | SO$_2$—C$_6$H$_4$—CH$_3$ (p-tolyl) | R |
| CH$_3$ | SO$_2$—C$_6$H$_4$—CH$_3$ (p-tolyl) | S |
| CH$_3$ | COCH$_2$CH(CH$_3$)$_2$ | R |
| CH$_3$ | COCH$_2$CH(CH$_3$)$_2$ | S |
| CH$_3$ | CO—C$_6$H$_5$ | R + S |
| CH$_3$ | CO—C$_6$H$_4$—Cl (m-Cl) | R + S |
| CH$_3$ | CO$_2$CH$_2$—C$_6$H$_5$ | R + S |
| CH$_3$ | CO-naphthyl | R + S |
| CH$_3$ | CO-(2-thienyl) | R + S |
| CH$_3$ | CO-(3-pyridyl) | R + S |
| CH$_2$CH=CH$_2$ | SO$_2$—C$_6$H$_4$—CH$_3$ (p-tolyl) | R + S |
| CH$_2$CH=CH$_2$ | COCH$_2$CH$_3$ | R + S |
| CH$_2$CH=CH$_2$ | COCH$_2$CH(CH$_3$)$_2$ | R + S |
| CH$_2$CH=CH$_2$ | COCH$_2$—C$_6$H$_4$—CH$_3$ (p-tolyl) | R + S |
| CH$_2$CH=CH$_2$ | COCH$_2$-(2-thienyl) | R + S |

-continued

| R | R$^{12}$ | | 4"-configuration |
|---|---|---|---|
| CH$_2$CH=CH$_2$ | 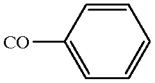 CO—⌬ | | R + S |
| CH$_2$CH=CH$_2$ | CO$_2$CH$_2$CH=CH$_2$ | | R + S |
| CH$_2$CH=CH$_2$ | 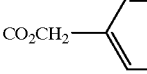 CO$_2$CH$_2$—⌬—NO$_2$ | | R + S |
| CH$_3$CH$_2$CH$_2$ | COCH$_2$CH(CH$_3$)$_2$ | | R + S |
| CH$_3$CH$_2$CH$_2$ | 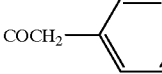 COCH$_2$—⌬—OCH$_3$ | | R + S |
| CH$_3$O$_2$CCH$_2$CH$_2$ | 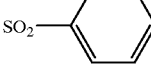 SO$_2$—⌬—CH$_3$ | | R + S |
| CH$_3$O$_2$CCH$_2$CH$_2$ | COCH$_2$CH$_3$ | | R + S |
| CH$_3$O$_2$CCH$_2$CH$_2$ | 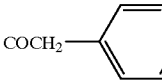 COCH$_2$—⌬—OCH$_3$ | | R + S |

EXAMPLE 126

The antibacterial activities of the compounds of Examples 8 and 10 against a panel of aerobic Gram positive and negative bacteria is shown in Table I. Similarly, the antibacterial activities of the compounds of Examples 89, 94, 96, and 97 are presented in Table II. The assay employs a liquid turbidimetric microtiter method for the determination of the minimum inhibitory concentration (MIC) in broth media. The MIC endpoint in mcg/ml is defined as the lowest concentration of test compound that completely inhibits the growth (absence of turbidity) of bacteria. The MIC is generally not an absolute value but rather a concentration range that falls within a two-fold dilution limit. Generally twelve two-fold dilutions of the test compound are employed with the initial concentration set at 128 mcg/ml.

TABLE I

In Vitro Activity of Compounds of Examples 8 and 10.

| Microorganism | | MIC Values (mcg/ml) | |
|---|---|---|---|
| | | 8 | 10 |
| Enterococcus faecalis | MB 5407 | 8 | 4 |
| Enterococcus faecium | MB 5416 | 0.25 | 0.25 |
| Streptococcus agalactiae | CL 1343 | ≦0.06 | ≦0.06 |
| Staphylococcus aureus | MB 2865 | 0.5 | 0.5 |
| Staphylococcus epidermidis | MB 5414 | 1 | 1 |
| Staphylococcus haemolyticus | MB 5412 | 0.5 | 0.5 |

TABLE I-continued

In Vitro Activity of Compounds of Examples 8 and 10.

| Microorganism | | MIC Values (mcg/ml) | |
|---|---|---|---|
| | | 8 | 10 |
| Streptococcus pneumoniae | CL 2883 | ≦0.06 | ≦0.06 |
| Streptococcus pyogenes | MB 2874 | ≦0.06 | ≦0.06 |
| Streptococcus pyogenes | MB 54061 | 128 | 128 |
| Streptococcus viridans | CL 2943 | 8 | 1 |
| Escherichia coli | MB 2884 | 4 | 1 |
| Escherichia coli | MB 4926 | 2 | 0.06 |
| Klebsiella pneumoniae | MB 4005 | 8 | 2 |
| Pseudomonas stutzeri | MB 1231 | ≦0.06 | ≦0.06 |

Example 8 9-Deoxo-8a-aza-8a-homoerythromycin A
Example 10 9-Deoxo-8a-methyl-8a-aza-8a-homoery-thromycin A

TABLE II

In vitro Activity of Compounds of Examples 89, 94, 96, and 97

| Microorganism | | 89 | 94 | 96 | 97 | Erythromycin A |
|---|---|---|---|---|---|---|
| Enterococcus faecalis | MB 5407 | 1 | 4 | 2 | 2 | 1 |
| Staphylococcus aureus | MB 2865 | 0.5 | 1 | 1 | 1 | 0.12 |
| Staphylococcus epidermidis | MB 5414 | 0.25 | 0.5 | 0.51 | 0.5 | 0.12 |
| Streptococcus pneumoniae | CL 2883 | ≦0.06 | ≦0.06 | ≦0.06 | ≦0.06 | ≦0.06 |
| Streptococcus pyogenes | MB 2874 | ≦0.06 | ≦0.06 | ≦0.06 | ≦0.06 | ≦0.06 |
| Enterobacter cloacae | CL 4298 | 0.5 | ≦0.06 | ≦0.06 | 0.12 | 16 |
| Escherichia coli | MB 2884 | 1 | 0.12 | 0.12 | 0.25 | 16 |
| Klebsiella pneumoniae | MB 4005 | 1 | 0.12 | 0.12 | 0.25 | 32 |
| Haemophilus influenzae | MB 5363 | 0.5 | 0.5 | 0.25 | 0.5 | 2 |
| Haemophilus influenzae | AT 43163 | 0.5 | 0.25 | 0.25 | 0.25 | 2 |

Example 89 4"-Epi-9-deoxo-8a-aza-8a-methyl-8a-homoerythromycin A
Example 94 4"-Deoxy-4"-amino-9-deoxo-8a-aza-8a-methyl-8a-homoerythromycin A (2:1 mixture of 4"-isomers)
Example 96 4"-Deoxy-4"(S)-amino-9-deoxo-8a-aza-8a-methyl-8a-homoerythromycin A
Example 97 4"-Deoxy-4"(R)-amino-9-deoxo-8a-aza-8a-methyl-8a-homoerythromycin A The compounds of formula (II) are useful as antibacterial agents both in vitro and in vivo, and their spectrum of activity is similar to that of erythromycin A. Consequently, they can be used for the same purposes, and, in the same manner as erythromycin A. In general, the antibacterial compounds of formula II and salts thereof, exhibit in vitro activity against a variety of Gram-positive microorganisms, e.g. *Streptococcus pyogenes*, and against certain Gram-negative microogranisms such as those of spherical or ellipsoidal shape (cocci). Their activity is readily demonstrated by in vitro tests against various micro-organisms. Their in vitro activity renders them useful for topical application; for sterilization purposes, e.g., sick-room utensils; and as industrial antimicrobials, for example, in water treatment, slime control, and preservation of paint and wood. The extrapolation of such in vitro tests to support for such utilities for macrolide compounds is taught in U.S. Pat. No. 4,518,590, cited above.

While the invention has been described, exemplified and illustrated in reference to certain preferred embodiments

What is claimed is:

1. A compound of the formula:

or a pharmaceutically acceptable salt, ester or metal complex thereof, where said metal complex is taken from the group consisting of copper, zinc, cobalt, nickel and cadmium; wherein:

$R^1$ is selected from the group consisting of:
hydrogen, hydroxy, C1–4 alkoxy, formyl, C1–10 alkylcarbonyl, C1–10 alkoxycarbonyl, Ar-oxycarbonyl, Ar-C1–10 alkoxycarbonyl, C1–10 alkylsulfonyl or Ar-sulfonyl wherein said C1–10 alkyl group or Ar group is substituted by 1–3 F, Cl, Br, I, hydroxy, amino, C1–5 acylamino or C1–4 alkyl groups; and unsubstituted or substituted C1–10 alkyl, C2–10 alkenyl or C2–10 alkynyl wherein said alkyl chain, if more than 2 carbons in length, can have inserted therein 1 to 2 oxa, thia or aza of the formula —NR— where R is hydrogen or C1–3 alkyl, and wherein said substituents are independently 1–3 of a substituent selected from the group consisting of:
  (a) Ar or Het optionally substituted by 1–3 of F, Cl, Br, I, C1-4 alkyl, C1–3 alkoxy, amino, C1–4 alkylamino, di(C1–4 alkyl) amino, or hydroxy;
  (b) HetCy unsubstituted or substituted by hydroxy, amino, C1–4 alkylamino, di(C1–4 alkyl)amino, C1–4 alkylcarbonyloxy or C1–4 alkylcarbonylamino;
  (c) F, Cl, Br or I;
  (d) hydroxy that is non-acylated or acylated by $R^aCO$ or $R^bS(O)_2$ wherein $R^a$ is hydrogen, C1–6 alkyl, Ar, Het, Ar-alkyl, or Het-alkyl and $R^b$ is C1–6 alkyl or Ar;
  (e) C1–10 alkoxy;
  (f) Ar-oxy or Het-oxy unsubstituted or substituted by 1–3 F, Br, Cl, I, hydroxy, amino or C1–4 alkyl groups;
  (g) amino or C1–10 alkylamino non-acylated or acylated by $R^aCO$, $R^a$—O—CO or $R^bSO_2$ where $R^a$ and $R^b$ as are as defined above;
  (h) di(C1–10 alkyl) amino;
  (i) Ar-amino, Het-amino or Het-C1–10 alkylamino wherein said Ar or Het group is unsubstituted or substituted by 1–3 F, Cl, Br, I, hydroxy, amino or C1–4 alkyl groups;
  mercapto;
  (k) C1–10 alkylthio, C1–10 alkylsulfinyl, C1–10 alkylsulfonyl, Ar-thio, Ar-sulfinyl or Ar-sulfonyl wherein said Ar group is unsubstituted or substituted by 1–3 F, Cl, I, Br, hydroxy, amino or C1–4 alkyl groups;
  (l) formyl;
  (m) C1–10 alkylcarbonyl;
  (n) Ar-carbonyl, Het-carbonyl, Ar-C1–10 alkylcarbonyl or Het-C1–10 alkylcarbonyl wherein said Ar or Het group is unsubstituted or substituted by 1–3 F, Cl, I, Br, hydroxy, amino or C1–4 alkyl groups;
  (o) carboxy;
  (p) C1–10 alkoxycarbonyl;
  (q) Ar-oxycarbonyl, Het-oxycarbonyl, Ar-C1–10 alkoxycarbonyl or Het-C1–10 alkoxycarbonyl wherein said Ar or Het group is unsubstituted or substituted by 1–3 F, Cl, Br, I, hydroxy, amino or C1–4 alkyl groups;
  (r) carbamoxy or sulfamoyl wherein the N-atom is unsubstituted or substituted by 1–2 C1–6 alkyl groups or by a C4–6 alkylene chain;
  (s) cyano;
  (t) isonitrilo;
  (u) nitro;
  (v) azido;
  (w) iminomethyl unsubstituted or substituted on nitrogen or carbon with C1–10 alkyl;
  (x) oxo and
  (y) thiono;

R1 and R10 together are C1–3 alkylene unsubstituted or substituted by an oxo group;

$R^1$ and $R^4$ together are C1–3 alkylene unsubstituted or substituted by an oxo group;

$R^2$ and $R^3$ are selected from the group consisting of hydrogen, C1–10 alkyl and Ar; with the proviso that $R^2$ and $R^3$ can together be double bonded to an oxygen or sulfur atom to form an oxo or thiono substituent respectively;

$R^4$ and $R^5$ are independently hydrogen or C1–10 alkylcarbonyl with the proviso that $R^4$ and $R^5$ can together be double bonded to a carbon atom to form a carbonyl group;

$R^6$ and $R^7$ are both hydrogen or one of $R^6$ and $R^7$ is hydrogen and the other is hydroxy, or an acyloxy derivative taken from the group consisting of formyloxy, C1–10 alkylcarbonyloxy, Ar-carbonyloxy, Ar-C1–10 alkylcarbonyloxy and —NHR$^{12}$;

$R^6$ and $R^7$ are together selected from the group consisting of oxo, hydroxyimino, C1–10 alkoxyimino, Ar—C1–10 alkoxyimino and aminoimino;

$R^8$ is selected from the group consisting of methyl, Ar—C1–10 alkoxycarbonyl, and Ar-sulfonyl;

$R^9$ is selected from the group consisting of hydrogen, formyl, C1–10 alkyolcarbonyl, C1–10 alkoxycarbonyl , and Ar—C1–10 alkoxycarbonyl;

$R^{10}$ is hydrogen or C1–3 alkyl;

$R^{11}$ is a substituent selected from the group consisting of 1–3 F, Cl, Br and C1–3 alkyl;

$R^{12}$ is hydrogen, arylsulfonyl or heteroarylsulfonyl unsubstituted or substituted by 1–3 halo or $C_{1-3}$ alkyl groups, alkylsulfonyl, or —C(O)—X—A—R$^{13}$;

X is a valence bond, O or NH;

A is a valence bond or C1–3 alkylene;

$R^{13}$ is selected from the group consisting of hydrogen, C1–10 alkyl, Ar, Ar—C1–10 alkyl, Het, HetCy, and C3–7 cycloalkyl, any of which $R^{13}$ groups other than hydrogen can be substituted by one to three substituents selected from the group consisting of F, Cl, Br, I, hydroxyl, C1–3 alkoxy, cyano, isonitrilo, nitro, amino, mono- or di- (C1–3) alkylamino, mercapto C1–3 alkylthio, C1–3 alkylsulfinyl, Ar-thio, Ar-sulfinyl, carboxyl, carbamoyl, C1–3 alkylcarbonyl and C1–3 alkoxycarbonyl;

Ar is selected from the group consisting of phenyl, fluorenyl and naphthyl; Het is selected from the group consisting of 5 to 6 membered aromatic heterocyclic rings containing 1 to 3 ring nitrogen atoms, 5 membered aromatic heterocyclic rings containing 1 oxygen ring atom, 5 membered aromatic heterocyclic rings containing 1 sulfur ring atom, 5 membered aromatic heterocyclic rings containing 1 sulfur and 1 nitrogen ring atom, and 5 membered aromatic heterocyclic rings containing 1 oxygen and 1 nitrogen ring atom HetCy is selected from the group consisting of 4 to 6 membered saturated heterocyclic rings containing 1 nitrogen ring atom, 3 to 6 membered saturated heterocyclic rings containing 1 oxygen ring atom, and 6 membered saturated heterocyclic rings contains 1 nitrogen and 1 oxygen ring atom and m and n are independently integers of zero or one.

2. The compound as claimed in claim 1, wherein $R^1$ is hydrogen.

3. The compound as claimed is claim 1, wherein $R^1$ is methyl.

4. The compound as claimed in claim 1, wherein $R^1$ is ethyl.

5. The compound as claimed in claim 1, wherein $R^1$ is n-propyl.

6. The compound as claimed in claim 1, wherein $R^1$ is n-butyl.

7. The compound as claimed in claim 1, wherein $R^1$ is isopropyl.

8. The compound as claimed in claim 1, wherein $R^1$ is propenyl.

9. The compound as claimed in claim 1, wherein $R^1$ is methoxycarbonylethyl.

10. The compound as claimed in claim 1, wherein n is 0.

11. The compound as claimed in claim 1, wherein n is 1.

12. The compound as claimed in claim 1, wherein $R^6$ and $R^7$ are oxo.

13. The compound as claimed in claim 1, wherein $R^6$ and $R^7$ are hydroxyimino.

14. The compound as claimed in claim 1, wherein $R^6$ is hydroxyl and $R^7$ is hydrogen and the configuration at the 4"-position is (S).

15. The compound as claimed in claim 1, wherein $R^6$ is hydrogen and $R^7$ is hydroxyl and the configuration at the 4"-position is (R).

16. The compound as claimed in claim 1, wherein $R^6$ is hydrogen and $R^7$ is amino, respectively, or $R^6$ is amino and $R^7$ is hydrogen, respectively.

17. The compound as claimed in claim 1, wherein $R^6$ is hydrogen and $R^7$ is amino substituted by methylcarbonyl, respectively, or $R^6$ is amino substituted by methylcarbonyl and $R^7$ is hydrogen, respectively.

18. The compound as claimed in claim 1, wherein $R^6$ is hydrogen and $R^7$ is amino substituted by methoxycarbonyl, respectively or $R^6$ is amino substituted by methoxycarbonyl and $R^7$ is hydrogen, respectively.

19. The compound as claimed in claim 1, wherein $R^6$ is hydrogen and $R^7$ is amino substituted by aralkoxycarbonyl, respectively or $R^6$ is amino substituted by aralkoxycarbonyl and $R^7$ is hydrogen, respectively.

20. The compound as claimed in claim 1, wherein $R^6$ is hydrogen and $R^7$ is amino substituted by fluorenylmethoxycarbonyl, respectively or $R^6$ is amino substituted by fluorenylmethoxycarbonyl and $R^7$ is hydrogen, respectively.

21. The compound as claimed in claim wherein $R^1$ is $CH_2=CFCH_2$.

22. The compound as claimed in claim 1, wherein $R^1$ is $FCH_2CH_2$.

23. A pharmaceutical composition comprising a pharmaceutically acceptable carrier and an antibiotically effective amount of the compound as claimed in claim 1.

24. A method of treating a bacterial infection in a mammal in need thereof, comprising the step of administering to said mammal a pharmacologically effective amount of the compound as claimed in claim 1.

25. A pharmaceutical composition comprising a pharmaceutically acceptable carrier and an antibiotically effective amount of the compound as claimed in claim 15.

26. A method of treating a bacterial infection in a mammal in need thereof, comprising the step of administering to said mammal a pharmacologically effective amount of the compound as claimed in claim 13.

27. A pharmaceutical composition comprising a pharmaceutically acceptable carrier and an antibiotically effective amount of the compound as claimed in claim 1.

28. A method of treating a bacterial infection in a mammal in need thereof, comprising the step of administering to said mammal a pharmacologically effective amount of the compound as claimed in claim 1.

29. A compound of the formula:

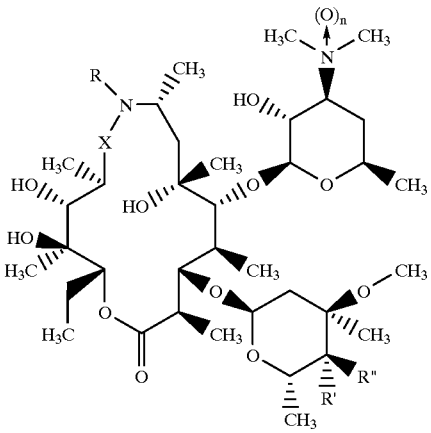

or a pharmaceutically acceptable salt, ester or metal complex thereof, wherein said metal complex is taken from the group consisting of copper, cobalt, zinc, nickel and cadmium, wherein X is —$CH_2$— or

R is taken from the group consisting of hydrogen, hydroxyl, C1–10 alkylcarbonyl, C1–10 alkoxycarbonyl, Ar-oxycarbonyl, Ar—C1–10 alkoxycarbonyl, Ar-sulfonyl and unsubstituted or substituted C1–10 alkyl or C2–10 alkenyl wherein said substituent is taken from the group consisting of amino, C1–10 alkylamino, di(C1–10 alkyl)amino, hydroxyl, C1–10 alkoxy, Ar-oxy, C1–10 alkylthio, Ar-thio, C1–10 alkylsulfonyl, Ar-sulfonyl, carboxyl, cyano, amido, C1–10 alkoxycarbonyl, bromo, chloro, fluoro, Ar, Het, HetCy, carbamoyl, oxo, sulfamoyl, C1–10 alkylcarbonyloxy, C1–10 alkylcarbonyl, C1–10 alkylcarbonylamino and Ar—C1–10 alkyloxycarbonyl; R' and R" are independently selected from the group consisting of hydrogen, hydroxyl, C1–10 alkylcarbonyloxy, Ar—C1–10 alkylcarbonyloxy and —NHR²;

R² is taken from the group consisting of hydrogen, C1–10 alkylcarbonyl, Ar-sulfonyl, Ar-sulfonyl substituted by halogen, Het-sulfonyl and —CO—X—A—R³;

X is a valence bond, O or NH;

A is a valence bond or C1–3 alkyl;

R³ is selected from the group consisting of hydrogen, C1–10 alkyl, Ar, Ar—C1–10 alkyl, Het, HetCy and C3–7 cycloalkyl, any of which R³ groups other than hydrogen can be substituted by one to three substituents selected from the group consisting of fluoro, chloro, bromo, hydroxyl, C1–3 alkoxy, carbonyl, cyano, isonitrilo, nitro, amino, mono- or di(C1–3 alkyl)amino, mercapto, C1–3 alkylthio, C1–3 alkylsulfinyl, C1–3 alkylsulfonyl, Ar-thio, Ar-sulfinyl, sulfamoyl, Ar-sulfonyl, carbamoyl, C1–3 alkylcarbonyl, C1–3 alkoxycarbonyl, Ar—C1–10 alkoxycarbonylamino, and C1–10 alkylamido;

R' and R" together can form an oxo or hydroxyimino group;

Ar is selected from the group consisting of phenyl, fluorenyl and naphthyl;

Het is a member selected from the group consisting of 5 to 6 membered aromatic heterocyclic rings containing 1 to 3 ring nitrogen atoms, 5 membered aromatic heterocyclic rings containing 1 oxygen ring atom, 5 membered aromatic heterocyclic rings containing 1 sulfur ring atom, 5 membered aromatic heterocyclic rings containing 1 sulfur and 1 nitrogen ring atom, and 5 membered aromatic heterocyclic rings containing 1 oxygen and 1 nitrogen ring atom; and HetCy is selected from the group consisting of 4 to 6 membered saturated heterocyclic rings containing 1 nitrogen ring atom, 3 to 6 membered saturated heterocyclic rings containing 1 oxygen ring atom, and 6 membered saturated heterocyclic rings containing 1 nitrogen and 1 oxygen ring atom.

30. A pharmaceutical composition comprising a pharmaceutically acceptable carrier and an antiobiotically effective amount of the compound as claimed in claim 29.

31. A method of treating a bacterial infection in a mammal in need thereof, comprising the step of administering to said mammal a pharmacologically effective amount of the compound as claimed in claim 24.

32. A compound of the formula:

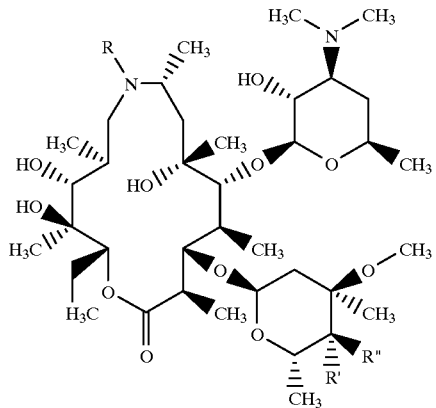

or a pharmaceutically acceptable salt or ester thereof, wherein:

R is selected from the group consisting of hydrogen, C1–10 alkyl, C2–10 alkenyl and Ar-sulfonyl;

R' and R" together are oxo or hydroxyimino;

R' and R" are independently selected from the group consisting of hydrogen, hydroxyl, C1–10 alkylcarbonyloxy, Ar—C1–10 alkylcarbonyloxy, amino and amino substituted by a substituent selected from the group consisting of C1–10 alkylcarbonyl, Ar-carbonyl, Ar—C1–10 alkylcarbonyl, C1–10 alkoxycarbonyl, Ar—C1–10 alkoxycarbonyl, Het-carbonyl, Het-C1–10 alkylcarbonyl and Ar-sulfonyl;

Ar is selected from the group consisting of phenyl, fluorenyl and naphthyl;

Het is selected from the group consisting of 5 to 6 membered aromatic heterocyclic rings containing 1 to 3 ring nitrogen atoms, 5 membered aromatic heterocyclic rings containing 1 oxygen ring atom, 5 membered aromatic heterocyclic rings containing 1 sulfur ring atom, 5 membered aromatic heterocyclic rings containing 1 sulfur and 1 nitrogen ring atom, and 5 membered aromatic heterocyclic rings containing 1 oxygen and 1 nitrogen ring atom.

33. A pharmaceutical composition comprising a pharmaceutically acceptable carrier and an antiobiotically effective amount of the compound as claimed in claim 32.

34. A method of treating a bacterial infection in a mammal in need thereof, comprising the step of administering to said mammal a pharmacologically effective amount of the compound as claimed in claim 32.

35. A compound of the formula:

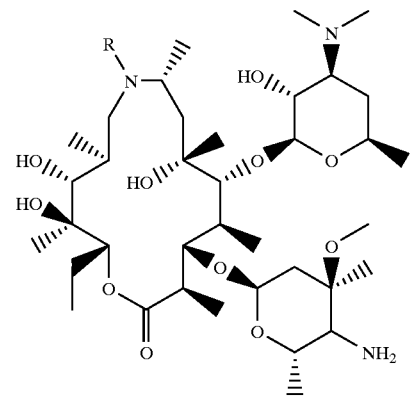

or a pharmaceutically acceptable salt, ester or metal complex thereof, wherein the configuration at 4" is (R) or (S) or a mixture thereof, wherein R is selceted from the group consisting of
CH₃, CH₃CH₂, CH₃CH₂CH₂, (CH₃)₂CH, CH₂=CHCH₂, CH=CCH₂, HOCH₂CH₂, HOCH₂CH₂CH₂, CH₃O₂CCH₂CH₂, C₆H₅CH₂O₂CCH₂CH₂, NCCH₂, H₂NCH₂CH₂, (CH₃)₂NCH₂CH₂, or CH₂=CFCH₂, C₆H₅CH₂ and

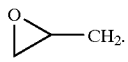

36. A compound of the formula:

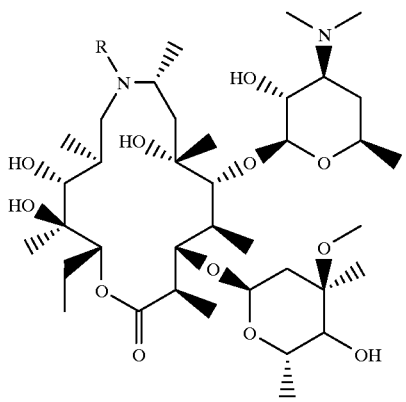

or a pharmaceutically acceptable salt, ester or metal complex thereof, wherein the configuration at 4" is (R) or (S) or a mixture thereof, wherein R is selected from the group consisting of
CH$_3$, CH$_3$CH$_2$, CH$_3$CH$_2$CH$_2$, (CH$_3$)$_2$CH, CH$_2$=CHCH$_2$, CH=CCH$_2$, HOCH$_2$CH$_2$, HOCH$_2$CH$_2$CH$_2$, CH$_3$O$_2$CCH$_2$CH$_2$, C$_6$H$_5$CH$_2$O$_2$CCH$_2$CH$_2$, NCCH$_2$, H$_2$NCH$_2$CH$_2$, (CH$_3$)$_2$NCH$_2$CH$_2$, or CH$_2$=CFCH$_2$, C$_6$H$_5$CH$_2$ and

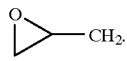

37. A compound of the formula

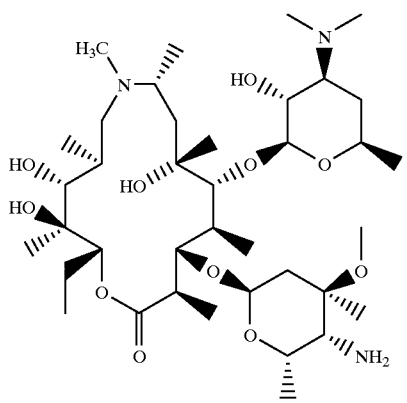

or a pharmaceutically acceptable salt thereof.

38. A compound of the formula

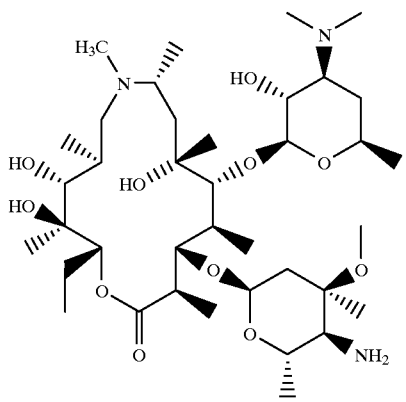

or a pharmaceutically acceptable salt thereof.

39. A compound of the formula

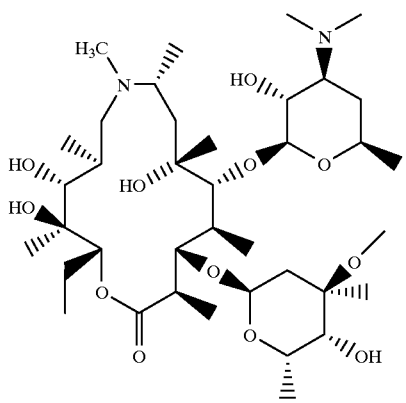

or a pharmaceutically acceptable salt thereof.

40. A pharmaceutical composition comprising a pharmaceutically acceptable carrier and an antibiotically effective amount of the compound as claimed in claim 37.

41. A pharmaceutical composition comprising a pharmaceutically acceptable carrier and an antibiotically effective amount of the compound as claimed in claim 38.

42. A method of treating a bacterial infection in a mammal in need thereof, comprising the step of administering to said mammal a pharmacologically effective amount of the compound as claimed in claim 37.

43. A method of treating a bacterial infection in a mammal in need thereof, comprising the step of administering to said mammal a pharmacologically effective ammount of the compound as claimed in claim 38.

44. A compound represented by one of the following structural formulas:

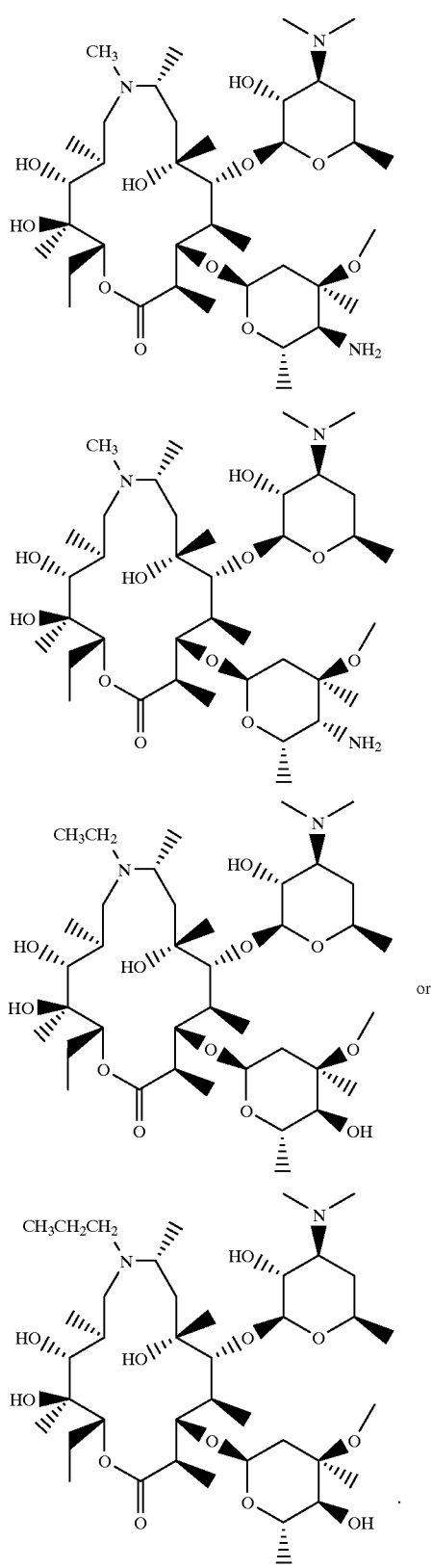
or
45. A compound according to claim 44 represented by the structural formula:
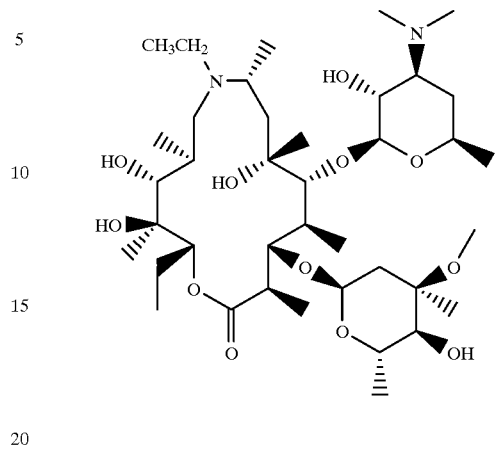
46. A compound according to claim 44 represented by the structural formula:
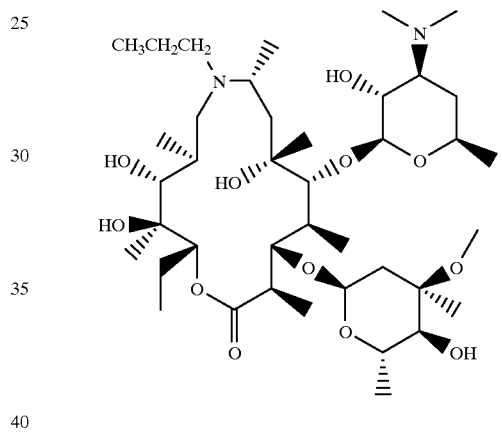
47. A compound in accordance with claim 44 represented by the formula:
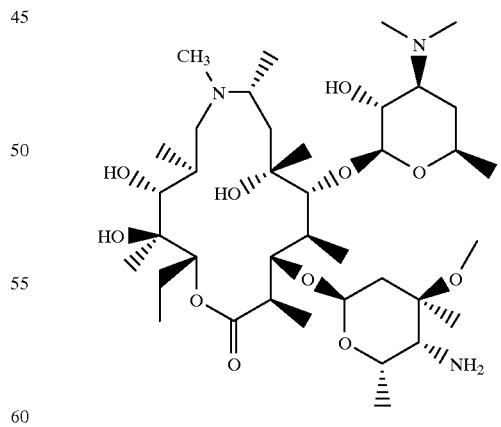
48. A compound in accordance with claim 44 represented by the formula:

213
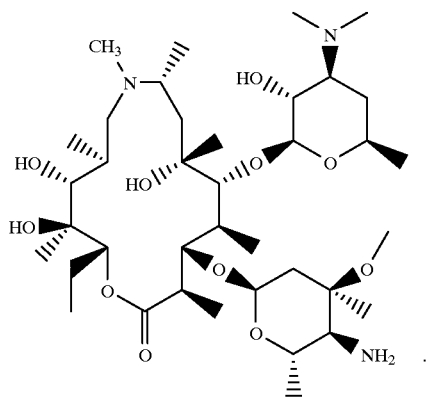
214
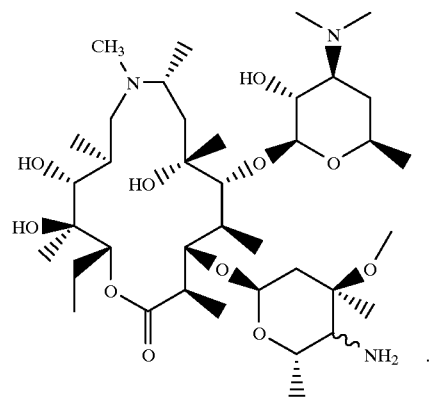
49. A mixture of compounds represented by the structural formula:
* * * * *